(12) United States Patent
Laberge et al.

(10) Patent No.: US 10,413,542 B2
(45) Date of Patent: *Sep. 17, 2019

(54) METHODS AND COMPOSITIONS FOR KILLING SENESCENT CELLS AND FOR TREATING SENESCENCE-ASSOCIATED DISEASES AND DISORDERS USING AN INHIBITOR OF AKT KINASE

(71) Applicants: Buck Institute for Research on Aging, Novato, CA (US); Unity Biotechnology, Inc., Brisbane, CA (US); Mayo Foundation for Medical Education and Research, Rochester, MN (US)

(72) Inventors: Remi-Martin Laberge, San Francisco, CA (US); Nathaniel David, Brisbane, CA (US); Alain Philippe Vasserot, Carlsbad, CA (US); Darren J. Baker, Rochester, MN (US); Bennett G. Childs, Rochester, MN (US); James L. Kirkland, Rochester, MN (US); Tamar Tchkonia, Rochester, MN (US); Jan M. A. van Deursen, Rochester, MN (US); Yi Zhu, Rochester, MN (US)

(73) Assignees: Buck Institute for Research on Aging, Novato, CA (US); Unity Biotechnology, Inc., Brisbane, CA (US); Mayo Foundation for Medical Education and Research, Rochester, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/950,965

(22) Filed: Apr. 11, 2018

(65) Prior Publication Data

US 2018/0256568 A1    Sep. 13, 2018

Related U.S. Application Data

(63) Continuation of application No. 15/114,762, filed as application No. PCT/US2015/013387 on Jan. 28, 2015, now Pat. No. 9,993,472.
(Continued)

(51) Int. Cl.
| | | |
|---|---|---|
| A61K 31/4375 | (2006.01) |
| A61P 11/00 | (2006.01) |
| A61P 9/10 | (2006.01) |
| A61P 19/02 | (2006.01) |
| A61K 31/496 | (2006.01) |
| A61P 27/02 | (2006.01) |
| A61K 31/428 | (2006.01) |
| A61K 31/495 | (2006.01) |
| A61K 31/5377 | (2006.01) |
| A61K 31/404 | (2006.01) |
| A61K 45/06 | (2006.01) |
| A61K 31/4178 | (2006.01) |
| A61K 31/728 | (2006.01) |

(Continued)

(52) U.S. Cl.
CPC .......... *A61K 31/496* (2013.01); *A61K 9/0048* (2013.01); *A61K 9/0073* (2013.01); *A61K 31/404* (2013.01); *A61K 31/4178* (2013.01); *A61K 31/428* (2013.01); *A61K 31/4375* (2013.01); *A61K 31/495* (2013.01); *A61K 31/5377* (2013.01); *A61K 31/728* (2013.01); *A61K 45/06* (2013.01); *A61K 47/36* (2013.01); *A61P 9/10* (2018.01); *A61P 11/00* (2018.01); *A61P 27/02* (2018.01); *C12N 5/0081* (2013.01); *C12N 2501/999* (2013.01); *C12N 2503/02* (2013.01); *C12Q 1/485* (2013.01)

(58) Field of Classification Search
CPC .......................... A61K 9/0073; A61P 9/0073
See application file for complete search history.

(56) References Cited

U.S. PATENT DOCUMENTS

| | | |
|---|---|---|
| 6,617,346 B1 | 9/2003 | Kong et al. |
| 6,734,302 B2 | 5/2004 | Kong et al. |

(Continued)

FOREIGN PATENT DOCUMENTS

| | | |
|---|---|---|
| KR | 20130139512 A | 12/2013 |
| WO | WO-03028443 A1 | 4/2003 |

(Continued)

OTHER PUBLICATIONS

Markman B, Dienstnnann R, Tabernero J., Targeting the PI3K/Akt/mTOR pathway—beyond rapalogs. Oncotarget. Nov. 2010; 1(7): 530. PMID: 21317449. (Year: 2010).*

Jakubsick, Claudia et. al. Human Pulmonary Fibroblasts Exhibit Altered Interleukin-4 and Interleukin-13 Receptor Subunit Expression in Idiopathic Interstitial Pneumonia. Am J Pathol. Jun. 2004; 164(6): 1989-2001.

U.S. Appl. No. 15/955,542 First Action Interview Pilot Program Pre-Interview Communication, dated Jun. 13, 2018.

(Continued)

*Primary Examiner* — Theodore R. West
(74) *Attorney, Agent, or Firm* — Michael Schiff; Janet Martineau; Wilson, Sonsini, Goodrich & Rosati

(57) ABSTRACT

Methods are provided herein for selectively killing senescent cells and for treating senescence-associated diseases and disorders by administering a senolytic agent. Senescence-associated diseases and disorders treatable by the methods using the senolytic agents described herein include cardiovascular diseases and disorders associated with or caused by arteriosclerosis, such as atherosclerosis; idiopathic pulmonary fibrosis; chronic obstructive pulmonary disease; osteoarthritis; senescence-associated ophthalmic diseases and disorders; and senescence-associated dermatological diseases and disorders.

12 Claims, 72 Drawing Sheets

Specification includes a Sequence Listing.

Related U.S. Application Data

(60) Provisional application No. 61/932,704, filed on Jan. 28, 2014, provisional application No. 61/932,711, filed on Jan. 28, 2014, provisional application No. 61/979,911, filed on Apr. 15, 2014, provisional application No. 62/002,709, filed on May 23, 2014, provisional application No. 62/042,708, filed on Aug. 27, 2014, provisional application No. 62/044,664, filed on Sep. 2, 2014, provisional application No. 62/057,820, filed on Sep. 30, 2014, provisional application No. 62/057,825, filed on Sep. 30, 2014, provisional application No. 62/057,828, filed on Sep. 30, 2014, provisional application No. 62/061,627, filed on Oct. 8, 2014, provisional application No. 62/061,629, filed on Oct. 8, 2014.

(51) Int. Cl.
*C12N 5/00* (2006.01)
*A61K 47/36* (2006.01)
*A61K 9/00* (2006.01)
*C12Q 1/48* (2006.01)

(56) References Cited

U.S. PATENT DOCUMENTS

| | | | |
|---|---|---|---|
| 7,482,134 B2 | 1/2009 | Jang et al. | |
| 7,705,007 B2 | 4/2010 | Fotouhi et al. | |
| 7,767,684 B2 | 8/2010 | Bruncko et al. | |
| 7,842,681 B2 | 11/2010 | Elmore et al. | |
| 7,851,626 B2 | 12/2010 | Ding et al. | |
| 7,893,278 B2 | 2/2011 | Haley et al. | |
| 8,114,893 B2 | 2/2012 | Baell et al. | |
| 8,168,645 B2 | 5/2012 | Baell et al. | |
| 8,168,784 B2 | 5/2012 | Franczyk, II et al. | |
| 8,343,967 B2 | 1/2013 | Ding et al. | |
| 8,426,422 B2 | 4/2013 | Hexamer et al. | |
| 8,563,735 B2 | 10/2013 | Bruncko et al. | |
| 8,586,754 B2 | 11/2013 | Bruncko et al. | |
| 8,691,184 B2 | 4/2014 | Wang et al. | |
| 9,018,381 B2 | 4/2015 | Diebold et al. | |
| 9,248,140 B2 | 2/2016 | Diebold et al. | |
| 9,266,860 B2 | 2/2016 | Guy et al. | |
| 9,360,471 B2 | 6/2016 | Qi | |
| 9,527,847 B2 | 12/2016 | Palombella et al. | |
| 9,630,990 B2 | 4/2017 | Shetty et al. | |
| 9,849,128 B2 | 12/2017 | Laberge et al. | |
| 9,855,266 B2 | 1/2018 | Laberge et al. | |
| 10,213,426 B2 * | 2/2019 | Laberge | A61P 9/10 |
| 2002/0054915 A1 | 5/2002 | Goldenheim et al. | |
| 2002/0197602 A1 | 12/2002 | Burmer et al. | |
| 2003/0086916 A1 | 5/2003 | Goligorsky et al. | |
| 2004/0242545 A1 | 12/2004 | Otsuka et al. | |
| 2005/0019865 A1 | 1/2005 | Kihm et al. | |
| 2005/0181076 A1 | 8/2005 | Ziegler | |
| 2005/0282803 A1 | 12/2005 | Haley et al. | |
| 2006/0122150 A1 | 6/2006 | Argentieri et al. | |
| 2007/0129416 A1 | 6/2007 | Ding et al. | |
| 2008/0221132 A1 | 9/2008 | Cai et al. | |
| 2008/0234362 A1 | 9/2008 | Chandler | |
| 2009/0105319 A1 | 4/2009 | Pellecchia et al. | |
| 2010/0016218 A1 | 1/2010 | Lichter et al. | |
| 2010/0292200 A1 | 11/2010 | Kile et al. | |
| 2010/0310504 A1 | 12/2010 | Lowe et al. | |
| 2011/0028437 A1 | 2/2011 | Robbins et al. | |
| 2011/0212909 A1 | 9/2011 | Wen et al. | |
| 2011/0218206 A1 | 9/2011 | Chan | |
| 2012/0028925 A1 | 2/2012 | Tao et al. | |
| 2012/0035134 A1 | 2/2012 | Diebold et al. | |
| 2012/0046333 A1 * | 2/2012 | Hardie | A61K 31/35 514/422 |
| 2012/0108590 A1 | 5/2012 | Birtalan et al. | |
| 2012/0115880 A1 | 5/2012 | Dyer et al. | |
| 2012/0129853 A1 | 5/2012 | Elmore et al. | |
| 2012/0156134 A1 | 6/2012 | Squires | |
| 2012/0183534 A1 | 7/2012 | Gruber | |
| 2012/0276093 A1 | 11/2012 | Ballinari et al. | |
| 2012/0277210 A1 | 11/2012 | Catron et al. | |
| 2012/0283269 A1 | 11/2012 | Blagosklonny et al. | |
| 2013/0096121 A1 | 4/2013 | Wang et al. | |
| 2013/0149314 A1 | 6/2013 | Bullerdiek et al. | |
| 2013/0225603 A1 | 8/2013 | Chavala et al. | |
| 2013/0267534 A1 | 10/2013 | Bruncko et al. | |
| 2013/0287763 A1 | 10/2013 | Sathyanarayanan et al. | |
| 2013/0302283 A1 | 11/2013 | Kihm | |
| 2013/0317043 A1 | 11/2013 | Wagner et al. | |
| 2014/0005190 A1 | 1/2014 | Baell et al. | |
| 2014/0017341 A1 | 1/2014 | Gourlaouen | |
| 2014/0018302 A1 | 1/2014 | Walensky et al. | |
| 2014/0073640 A1 | 3/2014 | Judd et al. | |
| 2014/0134163 A1 | 5/2014 | Errico et al. | |
| 2014/0220111 A1 | 8/2014 | Hayes et al. | |
| 2014/0242545 A1 | 8/2014 | Brun et al. | |
| 2014/0256721 A1 | 9/2014 | Hamblin et al. | |
| 2014/0272947 A1 | 9/2014 | Zhang et al. | |
| 2014/0275082 A1 | 9/2014 | Tao et al. | |
| 2014/0328893 A1 | 11/2014 | Adnot | |
| 2015/0051215 A1 | 2/2015 | Wooster et al. | |
| 2015/0126573 A1 | 5/2015 | Boczkowski et al. | |
| 2015/0140036 A1 | 5/2015 | Mannick et al. | |
| 2015/0231136 A1 | 8/2015 | Chavala et al. | |
| 2016/0000744 A1 | 1/2016 | Day et al. | |
| 2016/0022720 A1 | 1/2016 | Jordan | |
| 2016/0122758 A1 | 5/2016 | Krizhanovsky et al. | |
| 2017/0056421 A1 | 3/2017 | Zhou et al. | |
| 2017/0119789 A1 | 5/2017 | Campisi et al. | |
| 2017/0196858 A1 | 7/2017 | Laberge et al. | |
| 2017/0198253 A1 | 7/2017 | Laberge et al. | |
| 2017/0348307 A1 | 12/2017 | Laberge et al. | |
| 2018/0104222 A1 | 4/2018 | Childs | |

FOREIGN PATENT DOCUMENTS

| | | |
|---|---|---|
| WO | WO-03051359 A1 | 6/2003 |
| WO | WO-2006018632 A2 | 2/2006 |
| WO | WO-2006039704 A2 | 4/2006 |
| WO | WO-2008113131 A1 | 9/2008 |
| WO | WO-2008125487 A1 | 10/2008 |
| WO | WO-2009039553 A1 | 4/2009 |
| WO | WO-2009105234 A2 | 8/2009 |
| WO | WO-2010080478 A1 | 7/2010 |
| WO | WO-2010148447 A1 | 12/2010 |
| WO | WO-2011068560 A1 | 6/2011 |
| WO | WO-2011083150 A2 | 7/2011 |
| WO | WO-2014186878 A1 | 11/2014 |
| WO | WO-2015051252 A1 | 4/2015 |
| WO | WO-2015066442 A1 | 5/2015 |
| WO | WO-2015116735 A1 | 8/2015 |
| WO | WO-2015116740 A1 | 8/2015 |
| WO | WO-2015181526 A1 | 12/2015 |

OTHER PUBLICATIONS

Co-pending U.S. Application: Laberge, Remi-Martin et al. Use of Sulfonamide Inhibitors of BCL-2 and BCL-XL to Treat Ophthalmic Disease by Selectively Removing Senescent Cells. U.S. Appl. No. 16/054,667, filed Aug. 3, 2018, pp. 1-248.

No Author. Glossary of medical education terms, institute of International Medical Education. pp. 1-23. http://www.iime.ogr/glossary.htm [Accessed Mar. 2013].

U.S. Appl. No. 15/113,723 Non-Final Office Action dated Jul. 26, 2018.

Wilson C., Sweep Away Senile Cells. Life Extension Magazine, Mar. 2015, pp. 1-17.

Anderson, et al. Why is Osteoarthritis an Age-Related Disease? Best Pract Res Clin Rheumatol. Feb. 2010; 24(1): 15.

Arya, et al. Nutlin-3, the small-molecule inhibitor of MDM2, promotes senescence and radiosensitises laryngeal carcinoma cells harbouring wild-type p53. Br J Cancer. Jul. 13, 2010;103(2):186-95. doi: 10.1038/sj.bjc.6605739. Epub Jun. 29, 2010.

(56) References Cited

OTHER PUBLICATIONS

Bajwa, et al. Inhibitors of the anti-apoptotic Bcl-2 proteins: a patent review. Expert Opin Ther Pat. Jan. 2012;22(1):37-55. doi: 10.1517/13543776.2012.644274. Epub Dec. 23, 2011.
Baker, et al. Clearance of p16lnk4a-positive senescent cells delays ageing-associated disorders. Nature 479(7372):232-236 (2011).
Barak, et al. mdm2 expression is induced by wild type p53 activity. EMBO J. Feb. 1993;12(2):461-8.
Brenkman, et al. Mdm2 induces mono-ubiquitination of FOXO4. PLoS One. Jul. 30, 2008;3(7):e2819. doi: 10.1371/journal.pone.0002819.
Campisi, et al. Cell senescence: role in aging and age-related diseases. Interdiscip Top Gerontol. 2014;39:45-61. doi: 10.1159/000358899. Epub May 13, 2014.
Campisi, J. Cellular senescence as a tumor-suppressor mechanism. Trends Cell Biol. Nov. 2001;11(11):527-31.
Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.
Campisi, J. Senescent cells, tumor suppression, and organismal aging: good citizens, bad neighbors. Cell. Feb. 25, 2005;120(4):513-22.
Caruso, et al. Apoptotic-like tumor cells and apoptotic neutrophils in mitochondrion-rich gastric adenocarcinomas: a comparative study with light and electron microscopy between these two forms of cell death. Rare Tumors. Jun. 7, 2013;5(2):68-71. doi: 10.4081/rt.2013.e18. Print Apr. 15, 2013.
Chang, et al. Clearance of senescent cells by ABT263 rejuvenates aged hematopoietic stem cells in mice. Nat Med. Dec. 14, 2015. doi: 10.1038/nm.4010.
Co-pending U.S. Appl. No. 15/481,129, filed Apr. 6, 2017.
Co-pending U.S. Appl. No. 15/827,539, filed Nov. 30, 2017.
Coppe, et al. A Human-Like Senescence-Associated Secretory Phenotype Is Conserved in Mouse Cells Dependent on Physiological Oxygen. PLoS One 5:e9188 (2010).
Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.
Doroshevskaya, et al. Apoptosis Regulator Proteins: Basis for the Development of Innovation Strategies for the Treatment of Rheumatoid Arthritis in Patients of Different Age. Bulletin of Experimental Biology and Medicine. Jan. 2014, vol. 156, Issue 3, pp. 377-380.
Efeyan, et al. Induction of p53-dependent senescence by the MDM2 antagonist nutlin-3a in mouse cells of fibroblast origin. Cancer Res. Aug. 1, 2007;67(15):7350-7.
Extended European Search Report and Search Opinion dated Aug. 28, 2017 for European Patent Application No. EP15743068.7.
First Action Interview Pilot Program Pre-Interview Communication dated May 16, 2017 for U.S. Appl. No. 15/455,575.
Freund, et al. p38MAPK is a novel DNA damage response-independent regulator of the senescence-associated secretory phenotype. EMBO J. Apr. 20, 2011;30(8):1536-48. doi: 10.1038/emboj.2011.69. Epub Mar. 11, 2011.
Gagarina, et al. SirT1 enhances survival of human osteoarthritic chondrocytes by repressing protein tyrosine phosphatase 1B and activating the insulin-like growth factor receptor pathway. Arthritis Rheum. May 2010;62(5):1383-92.
Gannon et al., Mdm2-p53 signaling regulates epidermal stem cell senescence and premature aging phenotypes in mouse skin. Developmental Biology, 353:1-9, 2011.
Golstein, et al. Cell death by necrosis: towards a molecular definition. Trends in Biochemical Sciences. vol. 32, Issue 1, p. 37-43, Jan. 2007.
Guan, et al. Imidazoline derivatives: a patent review (2006-present). Expert Opin Ther Pat. Nov. 2012;22(11):1353-65. doi: 10.1517/13543776.2012.727397. Epub Sep. 24, 2012.
Hashimoto, et al. Role of p53 in human chondrocyte apoptosis in response to shear strain. Arthritis Rheum. Aug. 2009;60(8):2340-9.
Haupt, et al. Mdm2 promotes the rapid degradation of p53. Nature. May 15, 1997;387(6630):296-9.
Holford et al., Phannacokinetics and Phannacodynamics: Dose Selection & the Time Course of Drug Action, In: Katzung B.G., ed. Basic & Clinical Pharmacology (7th ed.), Appleton & Lange, Stamford, CT, 1998: 34-49.
Honda, et al. Oncoprotein MDM2 is a ubiquitin ligase E3 for tumor suppressor p53. FEBS Lett. Dec. 22, 1997;420(1):25-7.
Huang, et al. Reduced transcriptional activity in the p53 pathway of senescent cells revealed by the MDM2 antagonist nutlin-3. Aging (Albany NY). Oct. 2009; 1(10): 845-854. Published online Sep. 25, 2009. doi: 10.18632/aging.100091.
Ianitti, et al. Intra-articular injections for the treatment of osteoarthritis: focus on the clinical use of hyaluronic acid. Drugs R D. 2011;11(1):13-27.
International Preliminary Report on Patentability dated Aug. 2, 2016 for International PCT Patent Application No. PCT/US2015/013376.
International Preliminary Report on Patentability dated Aug. 2, 2016 for International PCT Patent Application No. PCT/US2015/013387.
Jeon, et al. Local clearance of senescent cells attenuates the development of post-traumatic osteoarthritis and creates a pro-regenerative environment. Nat Med. Jun. 2017;23(6):775-781. doi: 10.1038/nm.4324. Epub Apr. 24, 2017.
Juven, et al. Wild type p53 can mediate sequence-specific transactivation of an internal promoter within the mdm2 gene. Oncogene. Dec. 1993;8(12):3411-6.
Kerr, et al. Apoptosis: a basic biological phenomenon with wide-ranging implications in tissue kinetics. Br J Cancer. Aug. 1972;26(4):239-57.
Kroemer, et al. Classification of cell death: recommendations of the Nomenclature Committee on Cell Death 2009. Cell Death Differ. Jan. 2009; 16(1): 3-11.
Kubbutat, et al. Regulation of p53 stability by Mdm2. Nature. May 15, 1997;387(6630):299-303.
Laberge, et al. Glucocorticoids suppress selected components of the senescence-associated secretory phenotype. Aging Cell 11(4):569-578, 2012.
Laberge, et al. Mitochondrial DNA damage induces apoptosis in senescent cells. Cell Death Dis. Jul. 18, 2013;4:e727. doi: 10.1038/cddis.2013.199.
Lahav, Galit. Oscillations by the p53-Mdm2 feedback loop. Adv Exp Med Biol. 2008;641:28-38.
Leist, et al. Four deaths and a funeral: from caspases to alternative mechanisms. Nat Rev Mol Cell Biol. Aug. 2001;2(8):589-98.
Lessene; et al., Structure-guided design of a selective BCL-X(L) inhibitor., Nat Chem Biol., Jun. 2013, 9(6), 390-7.
Loeser, Richard F. Aging and Osteoarthritis: The Role of Chondrocyte Senescence and Aging Changes in the Cartilage Matrix. Osteoarthritis Cartilage. Aug. 2009; 17(8): 971-979. Published online Mar. 12, 2009. doi: 10.1016/j.joca.2009.03.002.
Manfredi, James. The Mdm2-p53 relationship evolves: Mdm2 swings both ways as an oncogene and a tumor suppressor. Genes Dev. Aug. 1, 2010;24(15):1580-9. doi: 10.1101/gad.1941710.
Martin, et al. Chondrocyte senescence, joint loading and osteoarthritis. Clin Orthop Relat Res. Oct. 2004;(427 Suppl):S96-103.
Momand, et al. The mdm-2 oncogene product forms a complex with the p53 protein and inhibits p53-mediated transactivation. Cell. Jun. 26, 1992;69(7):1237-45.
Notice of Allowance dated Aug. 3, 2017 and corresponding allowed claims for U.S. Appl. No. 15/467,129.
Notice of Allowance dated Aug. 18, 2017 and corresponding allowed claims for U.S. Appl. No. 15/455,575.
Office Action dated May 17, 2017 for U.S. Appl. No. 15/069,769.
Office Communication dated Jul. 21, 2017 for U.S. Appl. No. 15/467,129.
Office Communication dated Sep. 14, 2017 for U.S. Appl. No. 15/114,762.
Office Communication dated Sep. 27, 2017 for U.S. Appl. No. 15/481,129.
Oliner, et al. Oncoprotein MDM2 conceals the activation domain of tumour suppressor p53. Nature. Apr. 29, 1993;362(6423):857-60.

(56) References Cited

OTHER PUBLICATIONS

Perry, et al. The mdm-2 gene is induced in response to UV light in a p53-dependent manner. Proc Natl Acad Sci U S A. Dec. 15, 1993;90(24):11623-7.
Prieur, et al. Cellular senescence in vivo: a barrier to tumorigenesis. Curr Opin Cell Biol. Apr. 2008;20(2):150-5. doi: 10.1016/j.ceb. 2008.01.007. Epub Mar. 18, 2008.
Rodier, et al. Persistent DNA damage signalling triggers senescence-associated inflammatory cytokine secretion. Nat Cell Biol. Aug. 2009;11(8):973-9. doi: 10.1038/ncb1909. Epub Jul. 13, 2009.
Sączewski, et al. Imidazoline Scaffold in Medicinal Chemistry: A Patent Review (2012-2015). Expert Opin Ther Pat 26 (9), 1031-1048. Jul. 20, 2016.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Taranto, et al. Detection of the p53 regulator murine double-minute protein 2 in rheumatoid arthritis. J Rheumatol. Mar. 2005;32(3):424-9.
Thomasova, et al. p53-Independent Roles of MDM2 in NF-κB Signaling: Implications for Cancer Therapy, Wound Healing, and Autoimmune Diseases. Neoplasia. Dec. 2012; 14(12): 1097-1101.
Tovar, et al. MDM2 small-molecule antagonist RG7112 activates p53 signaling and regresses human tumors in preclinical cancer models. Cancer Res. Apr. 15, 2013;73(8):2587-97. doi: 10.1158/0008-5472.CAN-12-2807. Epub Feb. 11, 2013.
UAMS News Bureau. UAMS Research Findings Show Radiation, Aging Effects Can Be Cleared with Drug; Findings Published in Nature Medicine. www.uamshealth.com/news. Dec. 14, 2015. 2 pages.
Uraoka, et al. Loss of bcl-2 during the senescence exacerbates the impaired angiogenic functions in endothelial cells by deteriorating the mitochondrial redox state. Hypertension. Aug. 2011;58(2):254-63. doi: 10.1161/HYPERTENSIONAHA.111.176701. Epub Jul. 5, 2011.
U.S. Appl. No. 15/455,630 Non-Final Office Action dated Nov. 28, 2017.
U.S. Appl. No. 15/481,129 First Action Interview dated Nov. 20, 2017.
U.S. Appl. No. 15/455,684 First Action Interview Pilot Program, Pre-Interview Communication, dated Dec. 15, 2017.
Van Deursen, Jan M. The role of senescent cells in ageing. Nature. May 22, 2014;509(7501):439-46. doi: 10.1038/nature13193.
Vassilev, et al. In vivo activation of the p53 pathway by small-molecule antagonists of MDM2. Science. Feb. 6, 2004;303(5659):844-8. Epub Jan. 2, 2004.
Wang. Senescent human fibroblasts resist programmed cell death, and failure to suppress bcl2 is involved. Cancer Res. Jun. 1, 1995;55(11):2284-92.
Zauli, et al. Dasatinib plus Nutlin-3 shows synergistic antileukemic activity in both p53 wild-type and p53 mutated B chronic lymphocytic leukemias by inhibiting the Akt pathway. Clin Cancer Res. Feb. 15, 2011;17(4):762-70. doi: 10.1158/1078-0432.CCR-10-2572. Epub Nov. 24, 2010.
Zhang, et al. MDM2 Promotes Rheumatoid Arthritis via Activation of MAPK and NF-κB. Int Immunopharmacol 30, 69-73. Dec. 2, 2015.
Zhao, et al. Small molecule inhibitors of MDM2-p53 and MDMX-p53 interactions as new cancer therapeutics. BioDiscovery, 8. 2013; 8(4).15 pages.
Zhu, et al. Identification of a novel senolytic agent, navitoclax, targeting the Bcl-2 family of anti-apoptotic factors. Aging Cell. Jun. 2016;15(3):428-35. Epub Mar. 18, 2016.
Co-Pending U.S. Appl. No. 15/981,696, filed May 16, 2018.
Co-Pending U.S. Appl. No. 15/955,542, filed Apr. 17, 2018.
Axanova, Linara S. et al. 1,25-Dihydroxyvitamin D3 and PI3K/AKT Inhibitors Synergistically Inhibit Growth and Iduce Senescence in Prostate Cancer Cells. Prostate. 70(15):1658-1671 (Nov. 1, 2010).
Chappell, William H. Ras/Raf/MEK/ERK and PI3K/PTEN/Akt/mTOR inhibitors: rationale and importance to inhibiting these pathways in human health. Oncotarget. Mar. 2011;2(3):135-64.
Dienstmann, Rodrigo et al. Picking the point of inhibition: a comparative review of PI3K/AKT/mTOR pathway inhibitors. Mol Cancer Ther. May 2014;13(5):1021-31. Epub Apr. 18, 2014.
Kegel, Magdalena. Cancer Drug Candidate to Be Tested on Lung Fibrosis in Phase 1 Clinical Trial. Pulmonary Fribrosis News. pp. 1-2 (May 2, 2016).
Le Cras, Timothy D. et al. Inhibition of PI3K by PX-866 Prevents Transforming Growth Factor-Induced Pulmonary Fibrosis. Am J Pathol. Feb. 2010;176(2):679-86. Epub Dec. 30, 2009.
Liu, Shuang et al. The PI3K-Akt pathway inhibits senescence and promotes self-renewal of human skin-derived precursors in vitro. Aging Cell. Aug. 2011;10(4):661-74. Epub May 3, 2011.
U.S. Appl. No. 15/455,684 First Action Interview Office Action Summary dated Apr. 12, 2018.
Zhu, Yi et al. The Achilles' heel of senescent cells: from transcriptome to senolytic drugs. Aging Cell. Aug. 2015;14(4):644-58. Epub Apr. 22, 2015.
U.S. Appl. No. 15/069,769 Office Action dated May 17, 2017.
No Author. Form S-1 Registration Statement As Filed with the Securities and Exchange Commission on Apr. 23, 2018, pp. 1-243.
U.S. Appl. No. 15/455,630 Non-Final Office Action dated May 22, 2018.

* cited by examiner

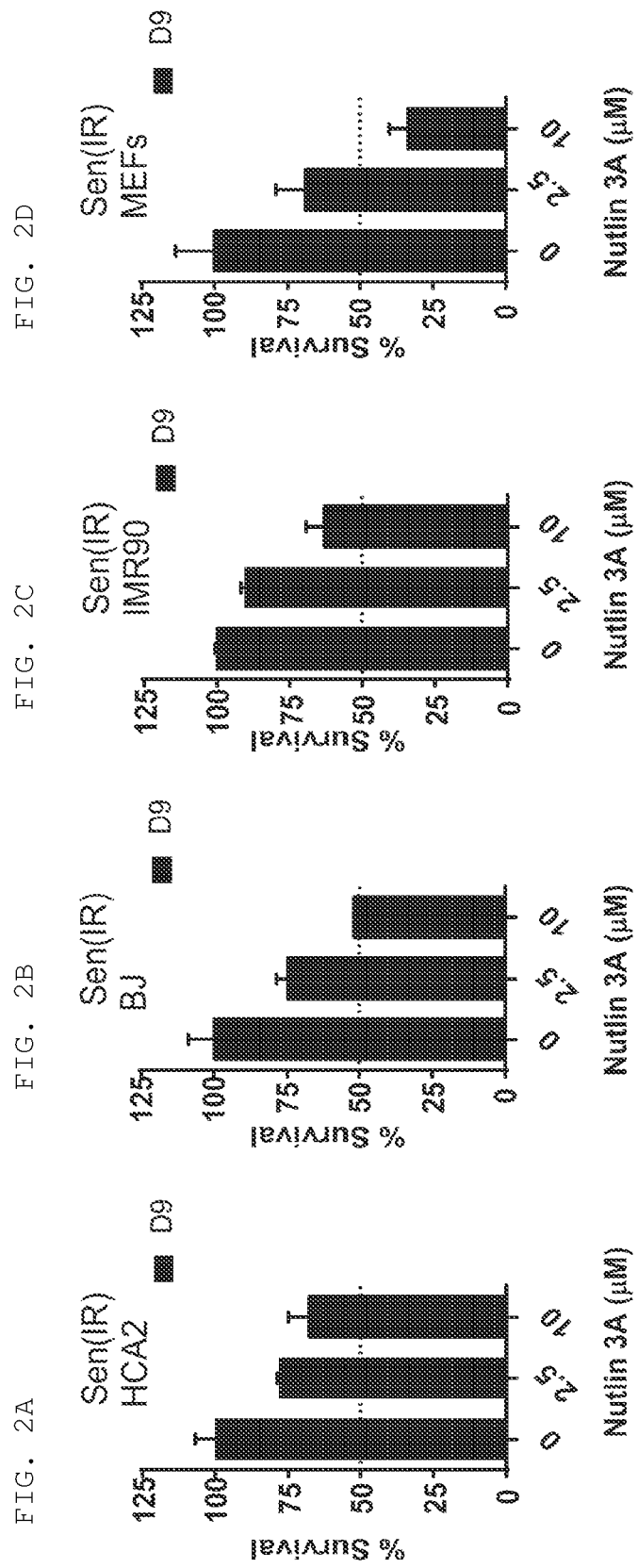

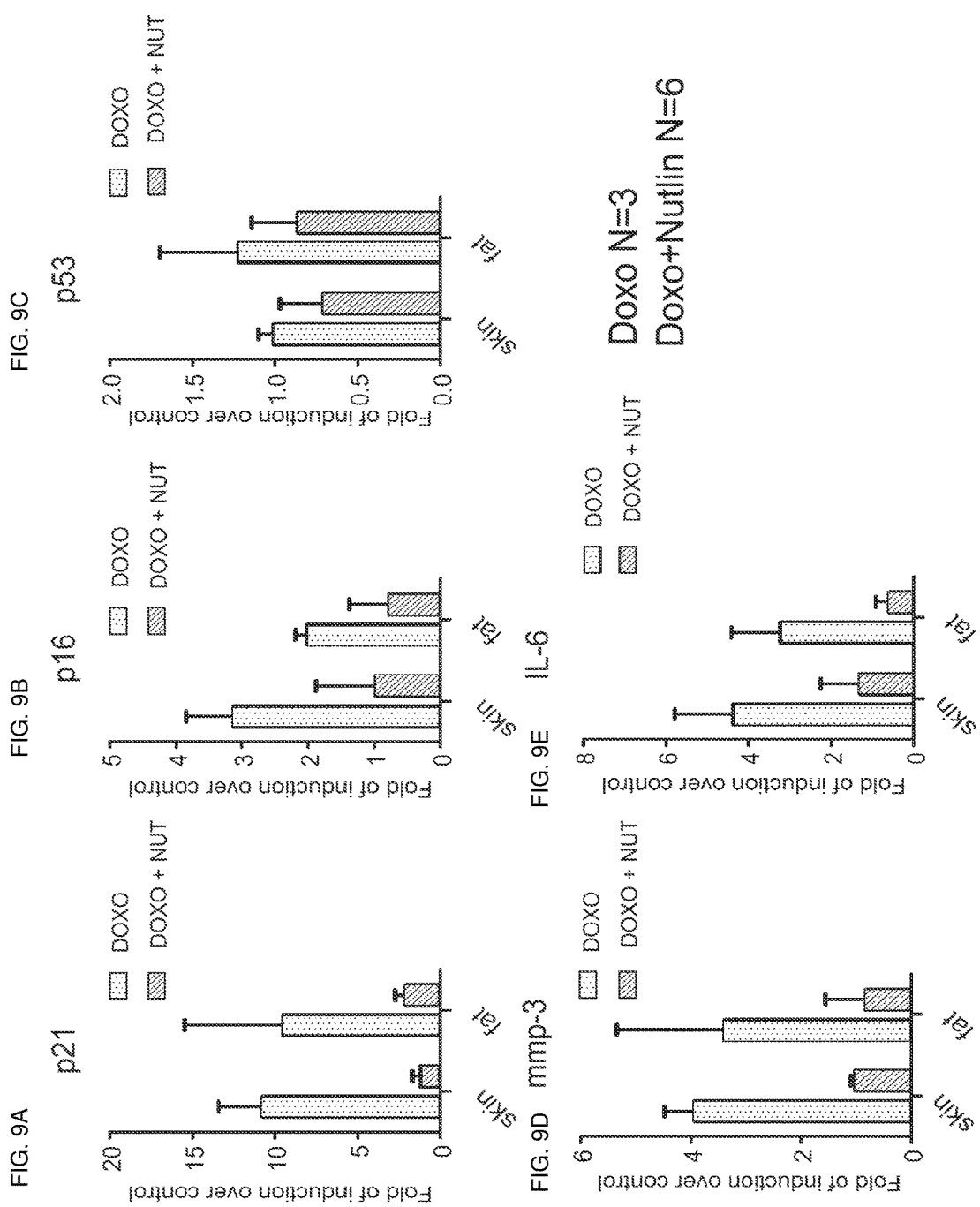

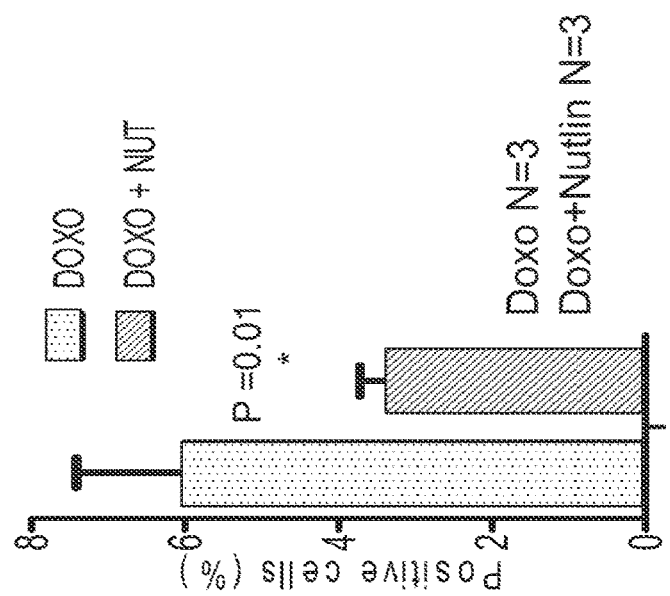
FIG. 10B γH2AX
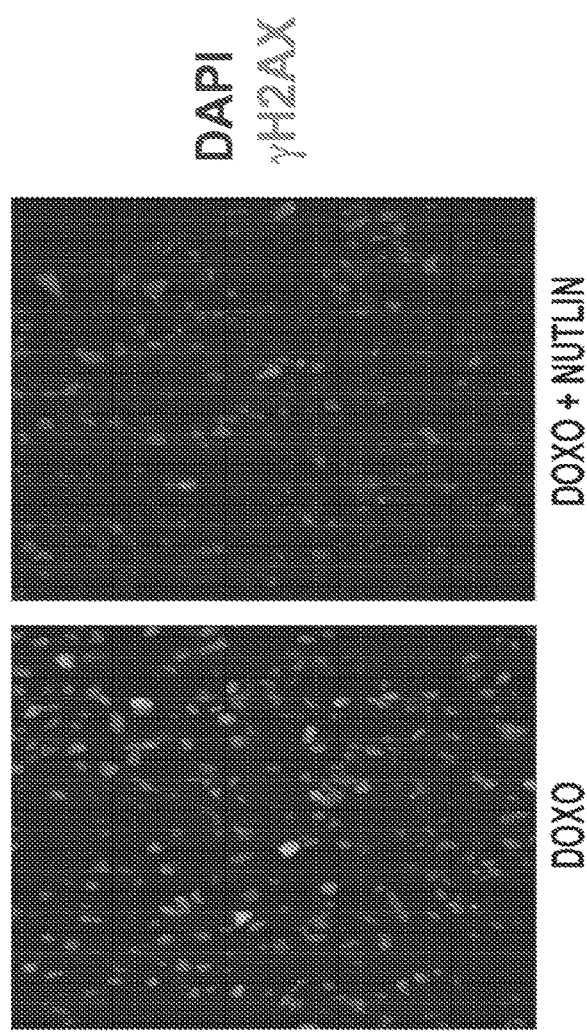
FIG. 10A

Sen(IR)
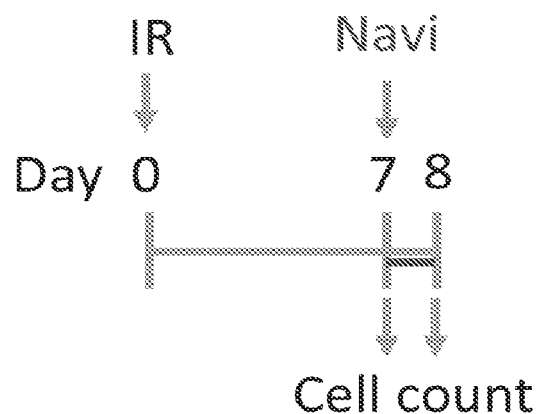
Non Sen
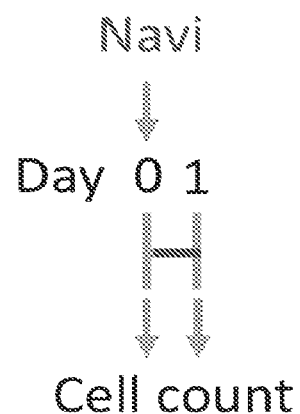
*FIG. 15*

| | Groups | Animals | Procedure | Treatment | Readout |
|---|---|---|---|---|---|
| 1 | ACL Control | 16 x C57Blk<br>1 x 3MR | ACL surgery<br>Vehicle IA injections to parallel GCV group<br>[Control group for GCV treatment] | Vehicle (10 μl) qd for 5 days, optional second cycle | qPCR & histology |
| 2 | GCV | 3 x 3MR | ACL surgery<br>IA injection of GCV | GCV (2.5 μg per knee injection) qd for 5 days, optional second cycle | Luminescence<br>qPCR & histology |
| 3 | Nutlin | 12 C57Blk | ACL surgery<br>IA injection of nutlin-3a | Nutlin-3a (5.8 μg per knee injection) qod for 2 weeks | qPCR & histology |
| 4 | Sham Control | 4 C57Blk<br>(n=3 PCR, n=1 histology) | Sham surgery<br>Vehicle IA injections to parallel GCV group<br>[Control group for knee injections] | Vehicle (10 μl) qd for 5 days, optional second cycle | qPCR & histology |

*FIG. 35*

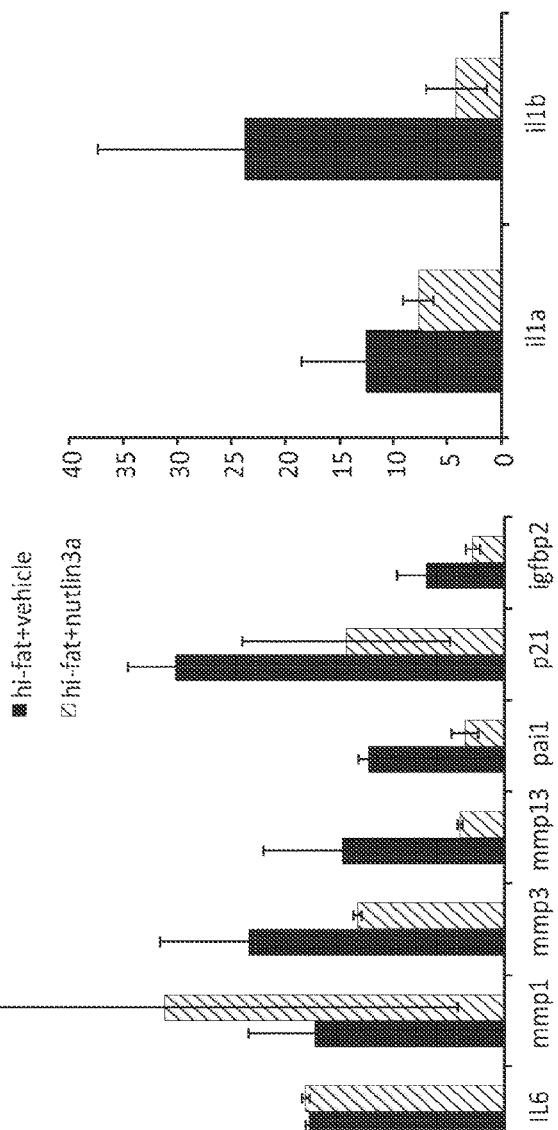
FIG. 45A
FIG. 45B
FIG. 45C
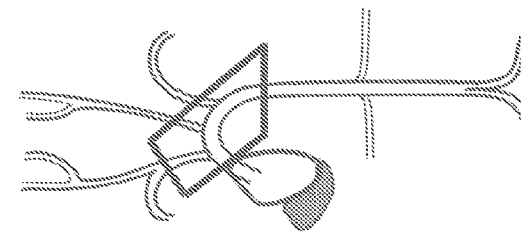
FIG. 45D
| Group | | iL6 | mmp1 | mmp3 | mmp13 | pai1 | p21 | igfbp2 | il1a | il1b |
|---|---|---|---|---|---|---|---|---|---|---|
| hi-fat+nutlin3a | versus hi-fat + vehicle | 0.055 | 0.632 | 0.448 | 0.064 | 0.129 | 0.902 | 0.158 | 0.041 | 0.379 |
| | versus chow + vehicle | 0.532 | 0.664 | 0.348 | 0.270 | 0.005 | 0.238 | 0.244 | 0.505 | 0.290 |
| hi-fat+vehicle | versus chow + vehicle | 0.077 | 0.878 | 0.455 | 0.914 | 0.575 | 0.072 | 0.279 | 0.193 | 0.241 |

+ Vehicle     + Nutlin-3a miD    3704    3686

% plaque    2.85%    1.46%

Atherosclerosis, % of aorta

*, $p<0.05$

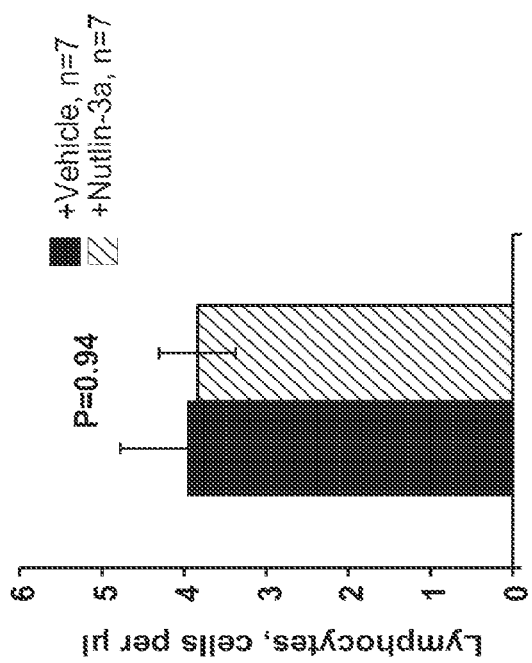
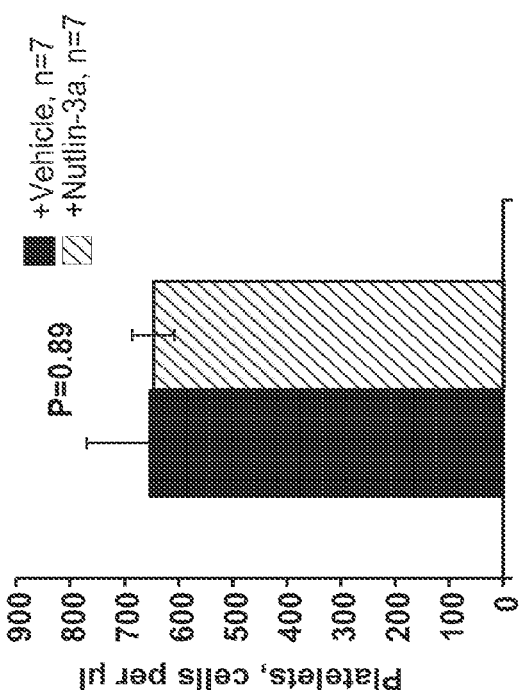
FIG. 48A
FIG. 48B

LDLr-/- descending aortas

LDLr-/- descending aortas

○ Plaques that were harvested are marked with dashed circles marks fat on outside of aorta

"Lipid pockets"

Senescent (lipid-bearing) smooth muscle foam cells

METHODS AND COMPOSITIONS FOR KILLING SENESCENT CELLS AND FOR TREATING SENESCENCE-ASSOCIATED DISEASES AND DISORDERS USING AN INHIBITOR OF AKT KINASE

CROSS-REFERENCE TO RELATED APPLICATION

This application is a continuation of U.S. patent application Ser. No. 15/114,762, filed Jul. 27, 2016, which is the U.S. National Stage of PCT/US2015/013387, filed Jan. 28, 2015; which claims the priority benefit of U.S. Provisional Application 62/061,629, filed Oct. 8, 2014, U.S. Provisional Application 62/061,627, filed Oct. 8, 2014, U.S. Provisional Application 62/057,828, filed Sep. 30, 2014, U.S. Provisional Application 62/057,825, filed Sep. 30, 2014, U.S. Provisional Application 62/057,820, filed Sep. 30, 2014, U.S. Provisional Application 62/044,664, filed Sep. 2, 2014, U.S. Provisional Application 62/042,708, filed Aug. 27, 2014, U.S. Provisional Application 62/002,709, filed May 23, 2014, U.S. Provisional Application 61/979,911, filed Apr. 15, 2014, U.S. Provisional Application 61/932,711, filed Jan. 28, 2014, U.S. Provisional Application 61/932,704, filed Jan. 28, 2014. U.S. application Ser. No. 15/114,762 and PCT/US2015/013387 are hereby incorporated herein by reference in their entirety for all purposes.

STATEMENT OF GOVERNMENT INTEREST

This invention was made with government support under AG009909, AG017242, AG041122 and AG046061 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 44237-721-308-Sequence-Listing.txt. The text file is 8 KB, was created on Apr. 9, 2018, and is being submitted electronically via EFS-Web.

BACKGROUND

Technical Field

The disclosure herein relates generally to methods for treatment and prophylaxis of senescent cell-associated diseases and disorders.

Description of the Related Art

Senescent cells accumulate in tissues and organs of individuals as they age and are found at sites of age-related pathologies. Senescent cells are believed important to inhibiting proliferation of dysfunctional or damaged cells and particularly to constraining development of malignancy (see, e.g., Campisi, *Curr. Opin. Genet. Dev.* 21:107-12 (2011); Campisi, *Trends Cell Biol.* 11:S27-31 (2001); Prieur et al., *Curr. Opin. Cell Biol.* 20:150-55 (2008)); nevertheless, the presence of senescent cells in an individual may contribute to aging and aging-related dysfunction (see, e.g., Campisi, *Cell* 120:513-22 (2005)). Given that senescent cells have been causally implicated in certain aspects of age-related decline in health and may contribute to certain diseases, and are also induced as a result of necessary life-preserving chemotherapeutic and radiation treatments, the presence of senescent cells may have deleterious effects to millions of patients worldwide. However, identifying and developing treatments of such diseases and conditions by selective elimination of senescent cells has been an arduous undertaking. The present disclosure addresses these needs and offers related advantages.

BRIEF SUMMARY

Provided herein are methods for treating senescence-associated diseases by administering a senolytic agent. The following are certain embodiments described in greater detail herein. As described herein the senolytic agent is administered for a time sufficient and in an amount sufficient that selectively kills senescent cells. Also provided herein are methods for selectively killing senescent cells in a subject who has a senescence associated disease or disorder, which in certain embodiments is not a cancer, and which senolytic agents described herein are administered to the subject in need thereof according to the administration methods described herein.

In one embodiment, a method is provided for treating a senescence-associated disease or disorder comprising administering to a subject in need thereof a therapeutically-effective amount of a small molecule senolytic agent that selectively kills senescent cells over non-senescent cells; wherein the senescence-associated disease or disorder is not a cancer, wherein the senolytic agent is administered in at least two treatment cycles, wherein each treatment cycle independently comprises a treatment course of from 1 day to 3 months followed by a non-treatment interval of at least 2 weeks; provided that if the senolytic agent is an MDM2 inhibitor, the MDM2 inhibitor is administered as a monotherapy, and each treatment course is at least 5 days long during which the MDM2 inhibitor is administered on at least 5 days. In certain embodiments, the senolytic agent is selected from an MDM2 inhibitor; an inhibitor of one or more BCL-2 anti-apoptotic protein family members wherein the inhibitor inhibits at least BCL-xL; and an Akt specific inhibitor. In a specific embodiment, the MDM2 inhibitor is a cis-imidazoline compound, a spiro-oxindole compound, or a benzodiazepine compound. In a specific embodiment, the cis-imidazoline compound is a nutlin compound. In a specific embodiment, the senolytic agent is an MDM2 inhibitor and is Nutlin-3a or RG-1172. In a specific embodiment, the nutlin compound is Nutlin-3a. In a specific embodiment, the cis-imidazoline compound is RG-7112, RG7388, RO5503781, or is a dihydroimidazothiazole compound. In a specific embodiment, the dihydroimidazothiazole compound is DS-3032b. In a specific embodiment, the MDM2 inhibitor is a spiro-oxindole compound selected from MI-63, MI-126, MI-122, MI-142, MI-147, MI-18, MI-219, MI-220, MI-221, MI-773, and 3-(4-chlorophenyl)-3-((1-(hydroxymethyl)cyclopropyl)methoxy)-2-(4-nitrobenzyl)isoindolin-1-one. In a specific embodiment, the MDM2 inhibitor is Serdemetan; a piperidinone compound; CGM097; or an MDM2 inhibitor that also inhibits MDMX and which is selected from RO-2443 and RO-5963. In a specific embodiment, the piperidinone compound is AM-8553. In a specific embodiment, the inhibitor of one or more BCL-2 anti-apoptotic protein family members is a BCL-2/BCL-xL inhibitor; a BCL-2/BCL-xL/BCL-w inhibitor; or a BCL-xL selective inhibitor. In a specific embodiment, the senolytic agent is an inhibitor of one or more BCL-2 anti-apoptotic protein family members wherein the inhibitor inhibits at least Bcl-xL and is selected from ABT-263, ABT-737, WEHI-539, and A-1155463. In a specific embodiment, the BCL-xL selective inhibitor is a benzothiazole-hydrazone compound, an aminopyridine compound, a benzimidazole compound, a tetrahydroquinolin compound, or a phenoxyl compound. In a specific embodiment, the benzothiazole-hydrazone compound is a WEHI-539. In a specific embodiment, the inhibitor of the one or more BCL-2 anti-apoptotic protein family members is A-1155463, ABT-263, or ABT-737. In a specific embodiment, the Akt inhibitor is MK-2206. In a specific embodiment, the senolytic agent is an MDM2 inhibitor or is an inhibitor of one or more BCL-2 anti-apoptotic protein family members wherein the inhibitor inhibits at least BCL-xL and is cytotoxic to cancer cells, the total dose of the senolytic agent administered during each treatment cycle is an amount ineffective for treating a cancer. In a specific embodiment, the senolytic agent is an MDM2 inhibitor or is an inhibitor of one or more BCL-2 anti-apoptotic protein family members wherein the inhibitor inhibits at least BCL-xL and is cytotoxic to cancer cells and wherein the senolytic agent is administered in two or more treatment cycles, the total dose of the senolytic agent administered during the two or more treatment cycles is an amount less than the amount effective for a cancer treatment. In a specific embodiment, the MDM2 inhibitor is Nutlin-3a; RG-7112; RG7388; RO5503781; DS-3032b; MI-63; MI-126; MI-122; MI-142; MI-147; MI-18; MI-219; MI-220; MI-221; MI-773; and 3-(4-chlorophenyl)-3-((1-(hydroxymethyl)cyclopropyl)methoxy)-2-(4-nitrobenzyl) isoindolin-1-one; Serdemetan; AM-8553; CGM097; or an MDM2 inhibitor that also inhibits MDMX and which is selected from RO-2443 and RO-5963. In a specific embodiment, the inhibitor of one or more BCL-2 anti-apoptotic protein family members is ABT-263, ABT-737, A-1155463, or WEHI-539. In another embodiment, the subject has a cancer and wherein the senescence-associated disease or disorder is a chemotherapy side effect or radiotherapy side effect, wherein the senolytic agent is administered to the subject on one or more days beginning on at least the sixth day subsequent to an administration cycle of the chemotherapy or radiotherapy and not concurrent with the chemotherapy or radiotherapy, and wherein the senolytic agent is not a chemotherapeutic agent for treating the cancer, and wherein the senolytic agent is a small molecule and is selected from an MDM2 inhibitor; an inhibitor of one or more BCL-2 anti-apoptotic protein family members wherein the inhibitor inhibits at least BCL-xL selected from a BCL-2/BCL-xL inhibitor; a BCL-2/BCL-xL/BCL-w inhibitor; and a BCL-xL selective inhibitor; and an Akt specific inhibitor. In another specific embodiment, the chemotherapeutic side effect is selected from gastrointestinal toxicity, peripheral neuropathy, fatigue, malaise, low physical activity, hematological toxicity, hepatotoxicity, alopecia, pain, mucositis, fluid retention, and dermatological toxicity. In another specific embodiment, the chemotherapeutic side effect is fatigue. In another specific embodiment, the chemotherapeutic side effect comprises cardiotoxicity. In another specific embodiment, the senescence-associated disease or disorder is osteoarthritis, atherosclerosis, chronic obstructive pulmonary disease, or idiopathic pulmonary fibrosis. In another specific embodiment, administration of the senolytic agent comprises three or more treatment cycles. In another specific embodiment, the senolytic agent is administered on one day, two days, three days, or four days with the proviso that the senolytic agent is not the MDM2 inhibitor. In another specific embodiment, the senolytic agent is administered as a monotherapy.

In another embodiment, a method is provided for treating a senescence-associated disease or disorder that is not a cancer, comprising administering to a subject in need thereof a therapeutically-effective amount of a small molecule senolytic agent that selectively kills senescent cells over non-senescent cells and which agent is cytotoxic to cancer cells, wherein the senolytic agent is administered as a monotherapy within at least one treatment cycle, which treatment cycle comprises a treatment course followed by a non-treatment interval; and wherein the total dose of the senolytic agent administered during the treatment cycle is an amount less than the amount effective for a cancer treatment, wherein the senolytic agent is (a) an inhibitor of a Bcl-2 anti-apoptotic protein family member that inhibits at least Bcl-xL; (b) an MDM2 inhibitor; or (c) an Akt specific inhibitor. In certain embodiments, the senolytic agent is administered during two or more treatment cycles, and wherein the total dose of the senolytic agent administered during the two or more treatment cycles is an amount less than the amount effective for a cancer treatment.

In other specific embodiments of the methods described above and herein, each treatment course is no longer than (a) one month, or (b) no longer than two months, or (c) no longer than 3 months. In a specific embodiment, each treatment course is no longer than (a) 5 days, (b) 7 days, (c) 10 days, (d) 14 days, or (e) 21 days. In a specific embodiment, the senolytic agent is administered every $2^{nd}$ day or every $3^{rd}$ day of each treatment course. In a specific embodiment, the treatment course is one day, two days, three days, or four days. In another specific embodiment, the senolytic agent is administered daily during each treatment course. In another specific embodiment, the non-treatment interval is at least two weeks, at least one month, at least 2 months, at least 3 months, at least 6 months, at least 9 months, or at least 1 year. In another specific embodiment, the treatment course is one In another specific embodiment, the senescence-associated disease or disorder is a cardiovascular disease selected from atherosclerosis, angina, arrhythmia, cardiomyopathy, congestive heart failure, coronary artery disease, carotid artery disease, endocarditis, coronary thrombosis, myocardial infarction, hypertension, aortic aneurysm, cardiac diastolic dysfunction, hypercholesterolemia, hyperlipidemia, mitral valve prolapsed, peripheral vascular disease, cardiac stress resistance, cardiac fibrosis, brain aneurysm, and stroke. In another specific embodiment, the senescence-associated disease or disorder is an inflammatory or autoimmune disease or disorder selected from osteoarthritis, osteoporosis, oral mucositis, inflammatory bowel disease, kyphosis, and herniated intervertebral disc. In another specific embodiment, the senescence-associated disease or disorder is a neurodegenerative disease selected from Alzheimer's disease, Parkinson's disease, Huntington's disease, dementia, mild cognitive impairment, and motor neuron dysfunction. In another specific embodiment, the senescence-associated disease or disorder is a metabolic disease selected from diabetes, diabetic ulcer, metabolic syndrome, and obesity. In another specific embodiment, the senescence-associated disease or disorder is a pulmonary disease selected from pulmonary fibrosis, chronic obstructive pulmonary disease, asthma, cystic fibrosis, emphysema, bronchiectasis, and age-related loss of pulmonary function. In another specific embodiment, the senescence-associated disease or disorder is an eye disease or disorder selected from macular degeneration, glaucoma, cataracts, presbyopia, and vision loss. In another specific embodiment, the senescence-associated disease or disorder is an age-related disorder selected from renal disease, renal failure, frailty, hearing loss, muscle fatigue, skin conditions, skin wound healing, liver fibrosis, pancreatic fibrosis, oral submucosa fibrosis, and sarcopenia. In another specific embodiment, the senescence-associated disease or disorder is a dermatological disease or disorder is selected from eczema, psoriasis, hyperpigmentation, nevi, rashes, atopic dermatitis, urticaria, diseases and disorders related to photosensitivity or photoaging, rhytides; pruritis; dysesthesia; eczematous eruptions; eosinophilic dermatosis; reactive neutrophilic dermatosis; pemphigus; pemphigoid; immunobullous dermatosis; fibrohistocytic proliferations of skin; cutaneous lymphomas; and cutaneous lupus. In another specific embodiment, the senescence-associated disease or disorder is atherosclerosis; osteoarthritis; pulmonary fibrosis; hypertension, or chronic obstructive pulmonary disease. In another specific embodiment, the senolytic agent is administered directly to an organ or tissue that comprises the senolytic cells. In another specific embodiment, the senolytic agent is combined with at least one pharmaceutically acceptable excipient to formulate a pharmaceutically acceptable composition to provide timed-release of the senolytic agent. In another specific embodiment, the senolytic agent is administered as a bolus infusion. In another specific embodiment, the senescence-associated disease or disorder is osteoarthritis and the senolytic agent is administered directly into the osteoarthritic joint. In another specific embodiment, the senolytic agent is administered intra-articularly to the osteoarthritic joint. In another specific embodiment, the senolytic agent is administered topically, transdermally, or intradermally. In another specific embodiment, the senescence-associated disease or disorder is osteoarthritis and the senolytic agent induces production of Type II collagen in a joint. In another specific embodiment, the senescence-associated disease or disorder is osteoarthritis and the senolytic agent inhibits erosion of a proteoglycan layer in a joint. In another specific embodiment, the senescence-associated disease or disorder is osteoarthritis and the senolytic agent inhibits erosion of a bone of a joint. In another specific embodiment, pulmonary fibrosis is idiopathic pulmonary fibrosis. In another specific embodiment, the senolytic agent reduces the amount of fibrotic pulmonary tissue in the lung. In another specific embodiment, the senolytic agent is administered intranasally, by inhalation, intratracheally, or by intubation. In another specific embodiment, the senescence associated disease or disorder is atherosclerosis, and wherein the senolytic agent increases the stability of atherosclerotic plaque. In another specific embodiment, the senescence associated disease or disorder is atherosclerosis, and wherein the senolytic agent inhibits formation of atherosclerotic plaque in a blood vessel of the subject. In another specific embodiment, the senescence associated disease or disorder is atherosclerosis, and wherein the senolytic agent reduces the lipid content of an atherosclerotic plaque in a blood vessel of the subject. In another specific embodiment, the senescence associated disease or disorder is atherosclerosis, and wherein the senolytic agent increases the fibrous cap thickness of the plaque. In another specific embodiment, the senescent cells are senescent preadipocytes, senescent endothelial cells, senescent fibroblasts, senescent neurons, senescent epithelial cells, senescent mesenchymal cells, senescent smooth muscle cells, senescent macrophages, or senescent chondrocytes. In another specific embodiment, the senolytic agent kills at least 20% of the senescent cells and kills no more than 5% of non-senescent cells in an organ or tissue comprising the senescent cells associated with the senescence associated disease or disorder. In another specific embodiment, the senolytic agent kills at least 25% of the senescent cells in an organ or tissue comprising the senescent cells associated with the senescence associated disease or disorder.

In one embodiment, a method is provided for treating osteoarthritis in a subject comprising administering to the subject a therapeutically-effective amount of a small molecule senolytic agent that selectively kills senescent cells over non-senescent cells, wherein (a) the senolytic agent is administered in at least two treatment cycles wherein each treatment cycle independently comprises a treatment course of from 1 day to 3 months followed by a non-treatment interval, and wherein the non-treatment interval is at least two weeks; or (b) the senolytic agent is administered directly to the osteoarthritic joint. In another specific embodiment, the senolytic agent induces collagen Type II production in the osteoarthritic joint. In another specific embodiment, senolytic agent inhibits erosion of a proteoglycan layer in the osteoarthritic joint. In another specific embodiment, the senolytic agent inhibits erosion of a bone of the osteoarthritic joint. Also provided herein in an embodiment, is a method for inducing production of collagen Type II comprising administering to a subject in need thereof a therapeutically-effective amount of a senolytic agent, which selectively kills senescent cells over non-senescent cells, wherein (a) the senolytic agent is administered in at least two treatment cycles wherein each treatment cycle independently comprises a treatment course of from 1 day to 3 months followed by a non-treatment interval, wherein the non-treatment interval is at least two weeks; or (b) the senolytic agent is administered directly to the osteoarthritic joint. In another specific embodiment, the senolytic agent is administered intra-articularly In another specific embodiment, the senolytic agent is administered topically, transdermally, or intradermally. In another specific embodiment, the senolytic agent is administered as a bolus infusion. In another specific embodiment, the senolytic agent is combined with at least one pharmaceutical excipient to formulate a pharmaceutical composition that provides timed release of the senolytic agent. In another specific embodiment, the senolytic agent inhibits erosion of a proteoglycan layer in the osteoarthritic joint. In another specific embodiment, the senolytic agent inhibits erosion of a bone of the osteoarthritic joint. In another specific embodiment, the senolytic agent kills at least 20% of the senescent cells and kills no more than 5% of non-senescent cells in the osteoarthritic joint. In another specific embodiment, the senolytic agent kills at least 25% of the senescent cells in the osteoarthritic joint.

In one embodiment, a method is provided for treating a senescence-associated pulmonary disease or disorder in a subject comprising administering to the subject a therapeutically effective amount of a small molecule senolytic agent that selectively kills senescent cells over non-senescent cells, wherein the senolytic agent is administered as a monotherapy in at least two treatment cycles wherein each treatment cycle independently comprises a treatment course of from 1 day to 3 months followed by a non-treatment interval wherein the non-treatment interval is at least 2 weeks. In another specific embodiment, a method is provided for treating a senescence-associated pulmonary disease or disorder in a subject comprising administering to the subject a senolytic agent, which senolytic agent is a small molecule compound that selectively kills senescent cells, wherein the senolytic agent is administered in at least two treatment cycles, each cycle comprising a treatment course and a non-treatment interval, and wherein the non-treatment interval is at least 2 months. In a specific embodiment, the senescence-associated pulmonary disease or disorder is pulmonary fibrosis. In another specific embodiment, pulmonary fibrosis is idiopathic pulmonary fibrosis. In another specific embodiment, the senescence-associated pulmonary disease or disorder is chronic obstructive pulmonary disease (COPD). In another specific embodiment, the senescence-associated pulmonary disease or disorder is selected from age-related loss of pulmonary function, cystic fibrosis, bronchiectasis, emphysema, and asthma. In another specific embodiment, the senolytic agent is administered directly to an affected pulmonary tissue that comprises the senescent cells. In another specific embodiment, the senolytic agent is administered by inhalation, intranasally, intratracheally, or by intubation In another specific embodiment, the senolytic agent is administered as a bolus infusion. In another specific embodiment, the senolytic agent is combined with at least one pharmaceutical excipient to formulate a pharmaceutical composition that provides timed release of the senolytic agent. In another specific embodiment, the senolytic agent kills at least 20% of the senescent cells and kills no more than 5% of non-senescent cells in a lung of the subject. In another specific embodiment, the senolytic agent kills at least 25% of the senescent cells in a lung of the subject.

In one embodiment, a method is provided for treating a cardiovascular disease or disorder caused by or associated with arteriosclerosis in a subject comprising administering to the subject a therapeutically-effective amount of a small molecule senolytic agent that selectively kills senescent cells over non-senescent cells, wherein the senolytic agent is administered in at least two treatment cycles wherein each treatment cycle independently comprises a treatment course from 1 day to 3 months followed by a non-treatment interval, wherein the non-treatment interval is at least 2 weeks. In a specific embodiment, the subject has atherosclerosis, congestive heart failure, peripheral vascular disease, hypertension, or coronary artery disease. In another specific embodiment, the cardiovascular disease or disorder is atherosclerosis. In another specific embodiment, the senolytic agent increases the stability of atherosclerotic plaque. In another specific embodiment, the senolytic agent reduces the lipid content of an atherosclerotic plaque in a blood vessel of the subject. In another specific embodiment, the senolytic agent increases the fibrous cap thickness of the plaque. In another specific embodiment, the senolytic agent inhibits formation of atherosclerotic plaque in a blood vessel of the subject. In another specific embodiment, the likelihood of occurrence of myocardial infarction, angina, stroke, carotid thrombosis, or coronary thrombosis is reduced. In another embodiment, a method is provided for increasing the stability of atherosclerotic plaque present in a blood vessel of a subject comprising administering to the subject a therapeutically-effective amount of a small molecule senolytic agent that selectively kills senescent cells over non-senescent cells, wherein the senolytic agent is administered in at least two treatment cycles wherein each treatment cycle independently comprises a treatment course of from 1 day to 3 months followed by a non-treatment interval, wherein the non-treatment interval is at least 2 weeks. In a specific embodiment, the subject has a cardiovascular disease selected from atherosclerosis, congestive heart failure, peripheral vascular disease, hypertension, or coronary artery disease. In another specific embodiment, the cardiovascular disease or disorder is atherosclerosis. In another specific embodiment, the senolytic agent reduces the lipid content of an atherosclerotic plaque in a blood vessel of the subject. In another specific embodiment, the senolytic agent increases the fibrous cap thickness of the plaque. In another specific embodiment, the senolytic agent inhibits formation of atherosclerotic plaque in a blood vessel of the subject. In another specific embodiment, the senolytic agent reduces the amount of atherosclerotic plaque in a blood vessel of the subject. In another specific embodiment, the senolytic agent is administered parenterally or orally. In another specific embodiment, the senolytic agent is administered directly to an artery that comprises the senescent cells. In another specific embodiment, the senolytic agent is administered as a bolus infusion. In another specific embodiment, the senolytic agent is combined with at least one pharmaceutical excipient to formulate a pharmaceutical composition that provides timed release of the senolytic agent. In another specific embodiment, the senolytic agent kills at least 20% of the senescent cells and kills no more than 5% of non-senescent cells in an arteriosclerotic artery of the subject. In another specific embodiment, the senolytic agent kills at least 25% of the senescent cells in an arteriosclerotic artery of the subject.

In certain embodiments of the methods described herein and above, the treatment course is no longer than one month or no longer than two months. In another specific embodiment, the treatment course is (a) no longer than 5 days, (b) no longer than 7 days, (c) no longer than 10 days, (d) no longer than 14 days, or (e) no longer than 21 days. In another specific embodiment, the senolytic agent is administered every $2^{nd}$ day or every $3^{rd}$ day of the treatment course. In another specific embodiment, the treatment course is one day, two days, three days, or four days. In another specific embodiment, the senolytic agent is administered daily during the treatment course. In another specific embodiment, the non-treatment interval is (a) at least one month, (b) at least 2 months, (c) at least 3 months, (d) at least 6 months, (e) at least 9 months, or (f) at least 1 year. In another specific embodiment, the treatment course is one day and the non-treatment interval is between 0.5-12 months. In other particular embodiments, when an MDM2 inhibitor is administered, the treatment course is at least 5 days. In another specific embodiment, the senolytic agent is administered as a monotherapy. In another specific embodiment, the senolytic agent is administered in three or more treatment cycles.

In certain embodiments related to the methods described above and herein the senolytic agent is selected from an MDM2 inhibitor; an inhibitor of one or more BCL-2 anti-apoptotic protein family members wherein the inhibitor inhibits at least BCL-xL; and an Akt specific inhibitor. In another specific embodiment, the MDM2 inhibitor is a cis-imidazoline compound, a spiro-oxindole compound, or a benzodiazepine compound. In another specific embodiment, the cis-imidazoline compound is a nutlin compound. In another specific embodiment, the nutlin compound is Nutlin-3a. In another specific embodiment, the cis-imidazoline compound is RG-7112, RG7388, RO5503781, or is a dihydroimidazothiazole compound. In another specific embodiment, the dihydroimidazothiazole compound is DS-3032b. In another specific embodiment, the MDM2 inhibitor is a spiro-oxindole compound selected from MI-63, MI-126, MI-122, MI-142, MI-147, MI-18, MI-219, MI-220, MI-221, MI-773, and 3-(4-chlorophenyl)-3-((1-(hydroxymethyl)cyclopropyl)methoxy)-2-(4-nitrobenzyl)isoindolin-1-one. In another specific embodiment, the MDM2 inhibitor is Serdemetan; a piperidinone compound; CGM097; or an MDM2 inhibitor that also inhibits MDMX and which is selected from RO-2443 and RO-5963. In another specific embodiment, the piperidinone compound is AM-8553. In another specific embodiment, the inhibitor of one or more BCL-2 anti-apoptotic protein family members is a BCL-2/BCL-xL inhibitor; a BCL-2/BCL-xL/BCL-w inhibitor; or a BCL-xL selective inhibitor. In another specific embodiment, the BCL-xL selective inhibitor is a benzothiazole-hydrazone compound, an aminopyridine compound, a benzimidazole compound, a tetrahydroquinolin compound, or a phenoxyl compound. In another specific embodiment, the benzothiazole-hydrazone compound is a WEHI-539. In another specific embodiment, the inhibitor of the one or more BCL-2 anti-apoptotic protein family members is A-1155463, ABT-263, or ABT-737. In another specific embodiment, the Akt inhibitor is MK-2206. In another specific embodiment, the senolytic agent is an MDM2 inhibitor or is an inhibitor of one or more BCL-2 anti-apoptotic protein family members wherein the inhibitor inhibits at least BCL-xL and is cytotoxic to cancer cells, the total dose of the senolytic agent administered during each treatment cycle is an amount ineffective for treating a cancer. In another specific embodiment, the MDM2 inhibitor is Nutlin-3a; RG-7112; RG7388; RO5503781; DS-3032b; MI-63; MI-126; MI-122; MI-142; MI-147; MI-18; MI-219; MI-220; MI-221; MI-773; and 3-(4-chlorophenyl)-3-((1-(hydroxymethyl)cyclopropyl) methoxy)-2-(4-nitrobenzyl)isoindolin-1-one; Serdemetan; AM-8553; CGM097; or an MDM2 inhibitor that also inhibits MDMX and which is selected from RO-2443 and RO-5963. In another specific embodiment, the inhibitor of one or more BCL-2 anti-apoptotic protein family members is ABT-263, ABT-737, A-1155463, or WEHI-539.

Also provided herein in another embodiment, is a method for treating a senescence-associated disease or disorder in a subject comprising administering to the subject a senolytic agent that is a small molecule MDM2 inhibitor that selectively kills senescent cells over non-senescent cells, wherein the senolytic agent is administered as a monotherapy, wherein the senolytic agent is administered in at least two treatment cycles wherein each treatment cycle independently comprises a treatment course followed by a non-treatment interval, wherein the treatment course is at least 5 days long and no longer than three months, during which treatment course the MDM2 inhibitor is administered on at least 5 days, and wherein the senescence-associated disease or disorder is not a cancer. In a specific embodiment, the treatment course is at least 9 days long. In another specific embodiment, the treatment course is no longer than one month or no longer than two months. In another specific embodiment, the treatment course is no longer than 10, 14, or 21 days. In another specific embodiment, the MDM2 inhibitor is administered daily. In another specific embodiment, the MDM2 inhibitor is administered every $2^{nd}$ day or every $3^{rd}$ day of the treatment course. In another specific embodiment, the non-treatment interval is at least 2 weeks, at least one month, at least 2 months, at least 6 months, at least 9 months, or at least 1 year. In another specific embodiment, the MDM2 inhibitor to the subject comprises three or more treatment cycles. In another specific embodiment, the MDM2 inhibitor is a cis-imidazoline compound, a spiro-oxindole compound, or a benzodiazepine compound. In another specific embodiment, the cis-imidazoline compound is a nutlin compound. In another specific embodiment, the nutlin compound is Nutlin-3a. In another specific embodiment, the cis-imidazoline compound is RG-7112, RG7388, or RO5503781, or a dihydroimidazothiazole compound. In another specific embodiment, the dihydroimidazothiazole compound is DS-3032b. In another specific embodiment, the MDM2 inhibitor is a spiro-oxindole compound selected from MI-63, MI-126; MI-122, MI-142, MI-147, MI-18, MI-219, MI-220, MI-221, MI-773, and 3-(4-chlorophenyl)-3-((1-(hydroxymethyl)cyclopropyl) methoxy)-2-(4-nitrobenzyl)isoindolin-1-one. In another specific embodiment, the MDM2 inhibitor is Serdemetan; a piperidinone compound; an MDM2 inhibitor that also inhibits MDMX and is selected from RO-2443 and RO-5963; or CGM097. In another specific embodiment, the piperidinone compound is AM-8553. In another specific embodiment, the method further comprises administering to the subject a small molecule inhibitor of one or more of mTOR, NFκB, PI3-k, and AKT pathways. In another specific embodiment, the method further comprises administering to the subject an Akt specific inhibitor. In another specific embodiment, the method further comprises the AKT inhibitor is MK-2206.

In one embodiment, a method is provided for treating a senescence-associated disease or disorder in a subject comprising administering to the subject a senolytic agent that is a small molecule inhibitor of one or more BCL-2 anti-apoptotic protein family members wherein the inhibitor inhibits at least BCL-XL, wherein the senolytic agent selectively kills senescent cells over non-senescent cells, wherein the senolytic agent is administered in at least two treatment cycles, wherein each treatment cycle independently comprises a treatment course of from 1 day to 3 months followed by a non-treatment interval of at least 2 weeks, and wherein the senescence-associated disease or disorder is not a cancer. In another specific embodiment, the inhibitor of one or more BCL-2 anti-apoptotic protein family members is a BCL-2/BCL-xL inhibitor; a BCL-2/BCL-xL/BCL-w inhibitor; or a BCL-xL selective inhibitor. In another specific embodiment, the inhibitor of the one or more BCL-2 anti-apoptotic protein family members is a benzothiazole-hydrazone compound, an aminopyridine compound, a benzimidazole compound, a tetrahydroquinolin compound, or a phenoxyl compound. In another specific embodiment, the benzothiazole-hydrazone compound is a WEHI-539. In another specific embodiment, the inhibitor of the one or more BCL-2 anti-apoptotic protein family members is A-1155463, ABT-263, or ABT-737. In another specific embodiment, the method further comprises administering to the subject a small molecule inhibitor of one or more of mTOR, NFκB, PI3-k, and AKT pathways. In another specific embodiment, the method further comprises administering to the subject an Akt specific inhibitor. In another specific embodiment, the method further comprises the AKT inhibitor is MK-2206.

In one embodiment, a method is provided for treating a senescence-associated disease or disorder in a subject comprising administering to the subject a senolytic agent that is a small molecule specific inhibitor of AKT, wherein the senolytic agent wherein the senolytic agent selectively kills senescent cells over non-senescent cells, wherein the senolytic agent is administered as a monotherapy in at least two treatment cycles, wherein each treatment cycle independently comprises a treatment course of from 1 day to 3 months followed by a non-treatment interval of at least 2 weeks, and wherein the senescence-associated disease or disorder is not a cancer. In another specific embodiment, the AKT inhibitor is MK-2206. In another specific embodiment, the method further comprises administering to the subject a small molecule inhibitor of one or more of mTOR, NFκB, and PI3-k, pathways.

In other specific embodiments of the methods described above and herein, each treatment course is no longer than one month or no longer than two months. In another specific embodiment, each treatment course is (a) no longer than 5 days, is (b) no longer than 7 days, is (c) no longer than 10 days, is (d) no longer than 14 days, or is (e) no longer than 21 days. In another specific embodiment, the senolytic agent is administered every $2^{nd}$ day or every $3^{rd}$ day of the treatment course. In another specific embodiment, each treatment course is one day, two days, three days, or four days. In another specific embodiment, the senolytic agent is administered daily during the treatment course. In another specific embodiment, the non-treatment interval is at least two weeks, one month, at least 2 months, at least 6 months, at least 9 months, or at least 1 year. In another specific embodiment, the senolytic agent to the subject comprises three or more treatment cycles. In another specific embodiment, the senolytic agent is administered as a monotherapy. In another specific embodiment, the senescence-associated disease or disorder is a cardiovascular disease selected from atherosclerosis, angina, arrhythmia, cardiomyopathy, congestive heart failure, coronary artery disease, carotid artery disease, endocarditis, coronary thrombosis, myocardial infarction, hypertension, aortic aneurysm, cardiac diastolic dysfunction, hypercholesterolemia, hyperlipidemia, mitral valve prolapsed, peripheral vascular disease, cardiac stress resistance, cardiac fibrosis, brain aneurysm, and stroke. In another specific embodiment, the subject has a cardiovascular disease selected from atherosclerosis, congestive heart failure, peripheral vascular disease, hypertension, or coronary artery disease. In another specific embodiment, the senescence-associated disease or disorder is inflammatory or autoimmune disease or disorder selected from osteoarthritis, osteoporosis, oral mucositis, inflammatory bowel disease, kyphosis, and herniated intervertebral disc In another specific embodiment, the senescence-associated disease or disorder is a neurodegenerative disease selected from Alzheimer's disease, Parkinson's disease, Huntington's disease, dementia, mild cognitive impairment, and motor neuron dysfunction. In another specific embodiment, the senescence-associated disease or disorder is a metabolic disease selected from diabetes, diabetic ulcer, metabolic syndrome, and obesity. In another specific embodiment, the senescence-associated disease or disorder is a pulmonary disease selected from idiopathic pulmonary fibrosis, chronic obstructive pulmonary disease, asthma, cystic fibrosis, emphysema, bronchiectasis, and age-related loss of pulmonary function. In another specific embodiment, the senescence-associated disease or disorder is an eye disease or disorder selected from macular degeneration, glaucoma, cataracts, and vision loss. In another specific embodiment, the senescence-associated disease or disorder is an age-related disorder selected from renal disease, renal failure, frailty, hearing loss, muscle fatigue, skin conditions, skin wound healing, liver fibrosis, pancreatic fibrosis, oral submucosa fibrosis, and sarcopenia. In another specific embodiment, the senescence-associated disease or disorder is a dermatological disease or disorder is selected from eczema, psoriasis, hyperpigmentation, nevi, rashes, atopic dermatitis, urticaria, diseases and disorders related to photosensitivity or photoaging, rhytides; pruritis; dysesthesia; eczematous eruptions; eosinophilic dermatosis; reactive neutrophilic dermatosis; pemphigus; pemphigoid; immunobullous dermatosis; fibrohistocytic proliferations of skin; cutaneous lymphomas; and cutaneous lupus. In another specific embodiment, the senescence-associated disease or disorder is atherosclerosis; osteoarthritis; idiopathic pulmonary fibrosis; or chronic obstructive pulmonary disease. In another specific embodiment, n the senescence-associated disease or disorder is osteoarthritis and the senolytic agent is administered directly to the osteoarthritic joint. In another specific embodiment, the senolytic agent is administered intra-articularly to the osteoarthritic joint. In another specific embodiment, the senolytic agent is administered topically, transdermally, or intradermally. In another specific embodiment, the senescence-associated disease or disorder is osteoarthritis and the senolytic agent induces production of Type II collagen in a joint. In another specific embodiment, the senescence-associated disease or disorder is osteoarthritis and the senolytic agent inhibits erosion of a proteoglycan layer in a joint. In another specific embodiment, the senescence-associated disease or disorder is osteoarthritis and the senolytic agent inhibits erosion of a bone of a joint. In another specific embodiment, the senescence-associated disease or disorder is idiopathic pulmonary fibrosis and the senolytic agent reduces the amount of fibrotic pulmonary tissue in the lung. In another specific embodiment, the senolytic agent is administered intranasally, by inhalation, intratracheally, or by intubation. In another specific embodiment, the senolytic agent is combined with at least one pharmaceutically acceptable excipient to formulate a pharmaceutically acceptable composition to provide timed-release of the senolytic agent. In another specific embodiment, the senolytic agent is administered as a bolus infusion. In another specific embodiment, the senescence-associated disease or disorder is atherosclerosis, and wherein the senolytic agent increases stability of atherosclerotic plaque. In another specific embodiment, the senescence-associated disease or disorder is atherosclerosis, and wherein the senolytic agent inhibits formation of atherosclerotic plaque in a blood vessel of the subject. In another specific embodiment, the senescence-associated disease or disorder is atherosclerosis, and wherein the senolytic agent reduces the lipid content of an atherosclerotic plaque in a blood vessel of the subject. In another specific embodiment, the senescence-associated disease or disorder is atherosclerosis, and wherein the senolytic agent increases the fibrous cap thickness of the plaque. In another specific embodiment, the senescence-associated disease or disorder is atherosclerosis, and wherein the likelihood of occurrence of myocardial infarction, angina, stroke, carotid thrombosis, or coronary thrombosis is reduced. In another specific embodiment, the senescent cells are senescent preadipocytes, senescent endothelial cells, senescent fibroblasts, senescent neurons, senescent epithelial cells, senescent mesenchymal cells, senescent smooth muscle cells, senescent macrophages, or senescent chondrocytes. In another specific embodiment, the senolytic agent kills at least 20% of the senescent cells and kills no more than 5% of non-senescent cells. In another specific embodiment, the senolytic agent kills at least 25% of the senescent cells.

In one embodiment, a method is provided herein for inhibiting metastasis in a subject who has a cancer, comprising administering to the subject a single small molecule senolytic agent that selectively kills senescent cells over non-senescent cells, wherein the senolytic agent is administered to the subject on one or more days beginning on at least the sixth day subsequent to an administration cycle of a chemotherapy and not concurrent with the chemotherapy, and wherein the senolytic agent is not a chemotherapeutic agent for treating the cancer and wherein the senolytic agent is selected from an MDM2 inhibitor; an inhibitor of one or more BCL-2 anti-apoptotic protein family members wherein the inhibitor inhibits at least BCL-XL selected from a BCL-2/BCL-xL inhibitor; a BCL-2/BCL-xL/BCL-w inhibitor; and a BCL-xL selective inhibitor; and an Akt specific inhibitor. In a specific embodiment, metastasis is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells. In another specific embodiment, the MDM2 inhibitor to the subject comprises three or more treatment cycles. In another specific embodiment, the MDM2 inhibitor is a cis-imidazoline compound, a spiro-oxindole compound, or a benzodiazepine compound. In another specific embodiment, the cis-imidazoline compound is a nutlin compound. In another specific embodiment, the nutlin compound is Nutlin-3a. In another specific embodiment, the cis-imidazoline compound is RG-7112, RG7388, or RO5503781, or a dihydroimidazothiazole compound. In another specific embodiment, the dihydroimidazothiazole compound is DS-3032b. In another specific embodiment, the MDM2 inhibitor is a spiro-oxindole compound selected from MI-63, MI-126; MI-122, MI-142, MI-147, MI-18, MI-219, MI-220, MI-221, MI-773, and 3-(4-chlorophenyl)-3-((1-(hydroxymethyl)cyclopropyl)methoxy)-2-(4-nitrobenzyl)isoindolin-1-one. In another specific embodiment, the MDM2 inhibitor is Serdemetan; a piperidinone compound; an MDM2 inhibitor that also inhibits MDMX and is selected from RO-2443 and RO-5963; or CGM097. In another specific embodiment, the piperidinone compound is AM-8553. In another specific embodiment, the inhibitor of one or more BCL-2 anti-apoptotic protein family members is a BCL-2/BCL-xL inhibitor; a BCL-2/BCL-xL/BCL-w inhibitor; or a BCL-xL selective inhibitor. In another specific embodiment, the inhibitor of the one or more BCL-2 anti-apoptotic protein family members is a benzothiazole-hydrazone compound, an aminopyridine compound, a benzimidazole compound, a tetrahydroquinolin compound, or a phenoxyl compound. In another specific embodiment, the benzothiazole-hydrazone compound is a WEHI-539. In another specific embodiment, the inhibitor of the one or more BCL-2 anti-apoptotic protein family members is A-1155463, ABT-263, or ABT-737. In another specific embodiment, senolytic agent is an AKT inhibitor. In still another particular embodiment, the AKT inhibitor is MK-2206.

In another embodiment, a method is provided for identifying a senolytic agent comprising (a) inducing cells to senesce to provide established senescent cells; (b) contacting a sample of the senescent cells with a candidate agent and contacting a sample of control non-senescent cells with the candidate agent; (c) determining the level of survival of the senescent cells and the level of survival of the non-senescent cells wherein when the level of survival of the senescent cells is less than the level of survival of the non-senescent cells, the candidate agent is a senolytic agent. In a specific embodiment, the method further comprises contacting the senolytic agent identified in step (c) and cells capable of producing collagen; and determining the level of collagen produced by the cells, thereby identifying a senolytic agent for treating osteoarthritis. In a specific embodiment, the cells capable of producing collagen are chondrocytes. In a specific embodiment, the collagen produced is Type 2 collagen. In a specific embodiment, the method further comprises administering the senolytic agent to a non-human animal with osteoarthritic lesions in a joint and determining one or more of (a) the level of senescent cells in the joint; (b) physical function of the animal; (c) the level of one or more markers of inflammation; (d) histology of the joint; and (e) the level of Type 2 collagen produced, thereby determining therapeutic efficacy of the senolytic agent wherein one or more of the following is observed in the treated animal compared with an animal not treated with the senolytic agent: (i) a decrease in the level of senescent cells in the joint of the treated animal; (ii) improved physical function of the treated animal; (iii) a decrease in the level of one or more markers of inflammation in the treated animal; (iv) increased histological normalcy in the joint of the treated animal; and (v) an increase in the level of Type 2 collagen produced in the treated animal. In a specific embodiment, the method further comprises administering the senolytic agent to a non-human animal of an atherosclerosis animal model, which animal has atherosclerotic plaques, and determining one or more of (a) the level of one or more markers of inflammation; and (b) the level of atherosclerotic plaque thereby determining therapeutic efficacy of the senolytic agent wherein one or more of the following is observed in the treated animal compared with an animal not treated with the senolytic agent: (i) a decrease in the level of one or more markers of inflammation in the treated animal; and (ii) a decrease in the level of atherosclerotic plaques in the treated animal; thereby identifying a senolytic agent for treating atherosclerosis. In a specific embodiment, the method further comprises administering the senolytic agent to non-human animal of pulmonary disease animal model, which animal has pulmonary fibrotic tissue, and determining one or more of (a) the level of one or more markers of inflammation; and (b) the level of pulmonary fibrotic tissue thereby determining therapeutic efficacy of the senolytic agent wherein one or more of the following is observed in the treated animal compared with an animal not treated with the senolytic agent: (i) a decrease in the level of one or more markers of inflammation in the treated animal; and (ii) a decrease in the level of pulmonary fibrotic tissue in the treated animal, thereby identifying a senolytic agent for treating a senescence-associated pulmonary disease.

In another embodiment, a method is provided for treating a senescence-associated disease or disorder in a subject comprising: (a) detecting the level of senescent cells in the subject; and (b) administering to the subject a senolytic agent that selectively kills senescent cells, wherein the senolytic agent is selected from a small molecule and is selected from an MDM2 inhibitor, an Akt specific inhibitor, an inhibitor of one or more BCL-2 anti-apoptotic protein family members wherein the inhibitor inhibits at least BCL-xL. In a specific embodiment, the method further comprises the inhibitor of one or more BCL-2 anti-apoptotic protein family members is a Bcl-2/Bcl-xL/Bcl-w inhibitor, a Bcl-2/Bcl-xL inhibitor, a Bcl-xL/Bcl-w inhibitor, or a Bcl-xL selective inhibitor.

In other particular embodiments, a method is provided for treating, reducing the likelihood of occurrence of, or delaying onset of a senescent cell-associated disease or disorder in a subject who has a senescent cell-associated disease or disorder or who has at least one predisposing factor for developing the senescent cell-associated disease or disorder, comprising administering to the subject a senolytic agent that alters either one or both of a cell survival signaling pathway and an inflammatory pathway in the senescent cell, thereby promoting death of the senescent cell, with the proviso that if the subject has a cancer, the senolytic agent is not a primary therapy for treating the cancer, wherein the senolytic agent is administered once every 0.5-12 months, and wherein the senescent cell-associated disease or disorder is a cardiovascular disease or disorder, inflammatory disease or disorder, a pulmonary disease or disorder, a neurological disease or disorder, a chemotherapeutic side effect, a radiotherapy side effect, or metastasis. In another specific embodiment, a method is provided for treating, reducing the likelihood of occurrence of, or delaying onset of a senescent cell-associated disease or disorder in a subject who has a senescent cell-associated disease or disorder or who has at least one predisposing factor for developing the senescent cell-associated disease or disorder, comprising administering to the subject a senolytic agent that alters either one or both of a cell survival signaling pathway and an inflammatory pathway in the senescent cell, thereby promoting death of the senescent cell, wherein the senolytic agent is administered once every 4-12 months.

Also provided herein are uses of the senolytic agents described herein. In one embodiment, a use is provided for a senolytic agent for treating a senescence-associated disease or disorder wherein a therapeutically-effective amount of a small molecule senolytic agent that selectively kills senescent cells over non-senescent cells is suitable for administration in at least two treatment cycles, wherein each treatment cycle independently comprises a treatment course of from 1 day to 3 months followed by a non-treatment interval of at least 2 weeks; provided that if the senolytic agent is an MDM2 inhibitor, the MDM2 inhibitor is administered as a monotherapy, and each treatment course is at least 5 days long during which the MDM2 inhibitor is administered on at least 5 days; wherein the senescence-associated disease or disorder is not a cancer. The senolytic agents described herein may be used for the manufacture of a medicament for treating a senescence-associated disease or disorder as described herein.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. For example, the use of "about X" shall encompass +/−1%, 2%, 3%, 4%, 5%, 6%, 7%, 8%, 9%, 10%, 11%, 12%, 13%, 14% and 15% of the value X. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIGS. 2A-D show the effect of Nutlin-3a on survival of fibroblasts induced to senesce by irradiation. FIG. 2A illustrates effect of Nutlin-3a at 0, 2.5 or 10 µM after 9 days of treatment (D9) on irradiated (IR) senescent foreskin fibroblasts (Sen(IR)HCA2). FIG. 2B shows percent survival of irradiated BJ cells (Sen(IR)BJ) treated with Nutlin 3a at the concentrations shown. FIG. 2C shows percent survival of irradiated lung fibroblasts (Sen(IR)IMR90)), and FIG. 2D shows percent survival of irradiated mouse embryonic fibroblasts (MEFs) treated with Nutlin-3a.

FIG. 3A shows the effect of Nutlin-3a on doxorubicin-treated (Doxo) senescent foreskin fibroblasts (HCA2). FIG. 3B illustrates the effect of Nutlin-3a on doxorubicin-treated (Doxo) senescent aortic endothelial cells (Endo Aort) (FIG. 3B).

FIG. 5A and FIG. 5B show that Nutlin-3a is non-toxic to non-senescent aortic endothelial (Non Sen Endo Aort) cells and to non-senescent pre-adipocytes (Non Sen Pread), respectively.

FIGS. 9A-E illustrate the level of mRNA of endogenous mmp-3, IL-6, p21, p16, and p53 in the skin and fat from animals after treatment with doxorubicin alone (DOXO) or doxorubicin plus Nutlin-3a (DOXO+NUT). The values represent the fold induction of the particular mRNA compared with untreated control animals. FIG. 9A: p21; FIG. 9B: $p16^{INK4a}$ (p16); FIG. 9C: p53; FIG. 9D: mmp-3; and FIG. 9E: IL-6. Data were obtained from doxorubicin-treated mice (Doxo N=3), and doxorubicin+Nutlin-3a-treated mice (Doxo+Nutlin N=6).

FIGS. 10A-B present data showing that Nutlin-3a reduced the number of cells with doxorubicin-induced DNA damage. FIG. 10A presents immunofluorescence microscopy of lung sections from doxorubicin treated animals (DOXO) (left panel) and doxorubicin and Nutlin-3a-treated mice (DOXO+NUTLIN) detected by binding to a primary rabbit polyclonal antibody specific for γH2AX followed by incubation with a secondary goat anti-rabbit antibody, and then counterstained with DAPI. FIG. 10B shows the percent positive cells from immunofluorescence microscopy calculated and represented as percentage of the total number of cells. Data were obtained from doxorubicin-treated mice (Doxo N=3), and doxorubicin+Nutlin-3a-treated mice (Doxo-Nutlin N=3).

FIG. 12C illustrates the relative level of IL-6 secretion in senescent cells treated with Nutlin-3a (Sen (IR) Nut3a 10 µM) or vehicle (Sen (IR) DMSO) at Days 9, 12 and 15 (D9, D12, D15, respectively). The fold increase compared to non-senescent cells (Fold NS, y-axis) is shown.

FIG. 15 depicts an exemplary timeline and treatment protocol in senescent (irradiated cells) and non-senescent cells (non-radiated cells) for a cell counting assay.

FIG. 29A presents a graph showing the effect of ABT-263 (Navi) treatment in combination with 10 nM MK-2206 in non-senescent and senescent IMR90 cells. FIG. 29B illustrates percent survival of non-senescent IMR90 cells (IMR90 NS) and senescent IMR90 cells (IMR90 Sen(IR)) when exposed to MK-2206 alone.

FIG. 35 depicts animal study designs for assessing the efficacy of removal of senescent cells by Nutlin-3A treatment in C57BL6/J mice or by GCV treatment in 3MR mice in inhibiting signs and progression of osteoarthritis. Group 1 animals (16×C57BL6/J mice; 1×3MR mouse) represent the anterior cruciate ligament (ACL) control group that undergo surgery to cut the ACL (ACL surgery or osteoarthritis surgery (OA)) of one hind limb to induce osteoarthritis. Group 1 animals receive intra-articular injections of vehicle (10 µl) qd for 5 days during week 2 post-surgery and an optional second treatment cycle at week 4 post-surgery, parallel to the GCV treatment in the test animals. Group 2 animals (3×3MR mice) represent one treatment group that receives ACL surgery and intra-articular injections of GCV (2.5 µg/joint) qd for 5 days during week 2 post-surgery and an optional second treatment cycle at week 4 post-surgery. Group 3 animals (12×C57BL6/J) represent a second treatment group that received ACL surgery and intra-articular injections of Nutlin-3A (5.8 µg/joint) qod for 2 weeks starting at week 3 post-surgery. Group 4 animals represent a second control group having a sham surgery that does not sever the ACL and receiving intra-articular injections of vehicle (10 µl) qd for 5 days during week 2 post-surgery and an optional second treatment cycle at week 4 post-surgery, parallel to the GCV treated 3MR mice. This study design can be adapted, such as the dosing amount and dosing schedule (e.g., number of days), for other senolytic agents.

Figure 42:
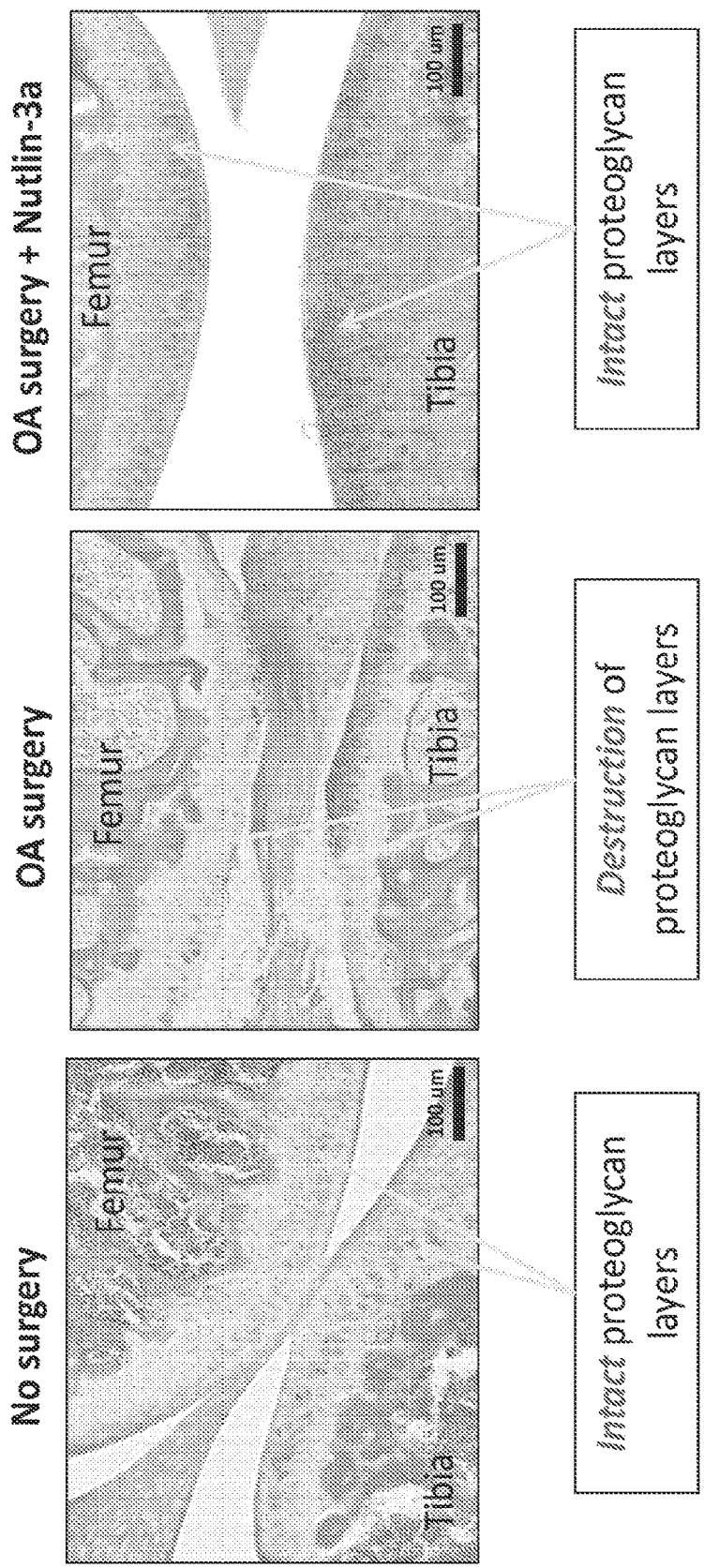

FIG. 42 presents histopathology results from animals not treated by surgery (No Surgery (C57B)); animals that received osteoarthritis surgery and received vehicle (OA surgery (3MR)); and animals that received OA surgery and were treated with Nulin-3a (OA surgery+Nutlin-3a). Arrows point to intact or destroyed proteoglycan layers in the joint.

Figure 43A:
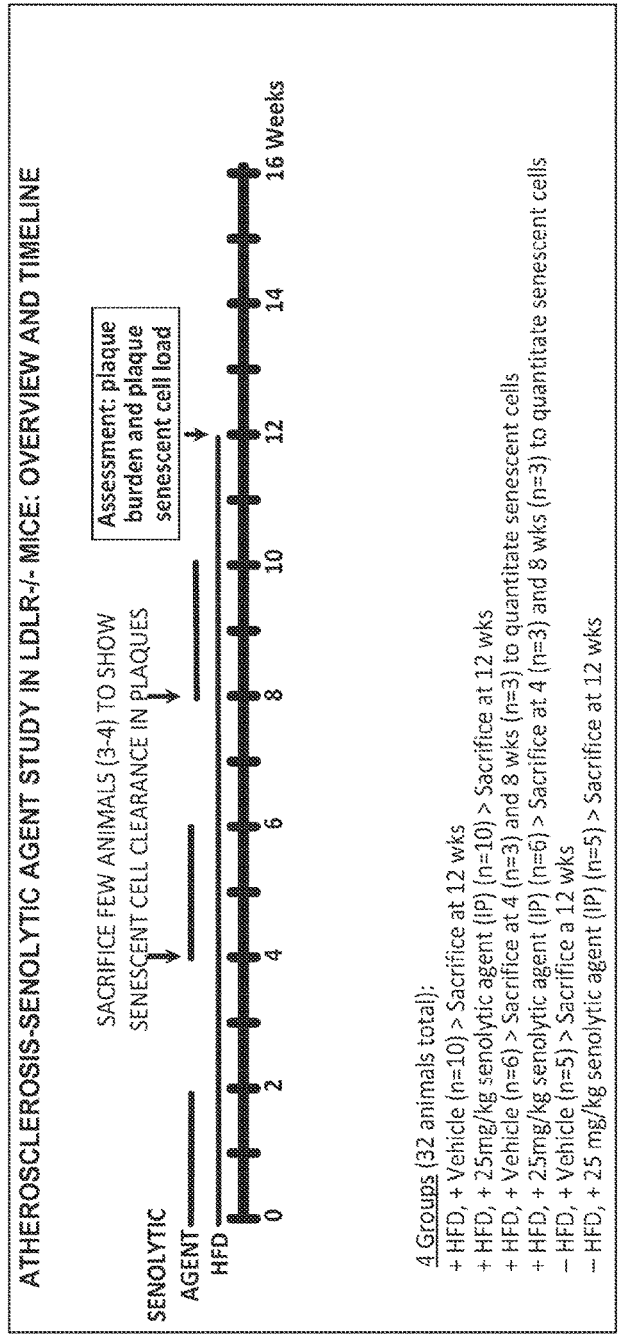
Figure 43B:
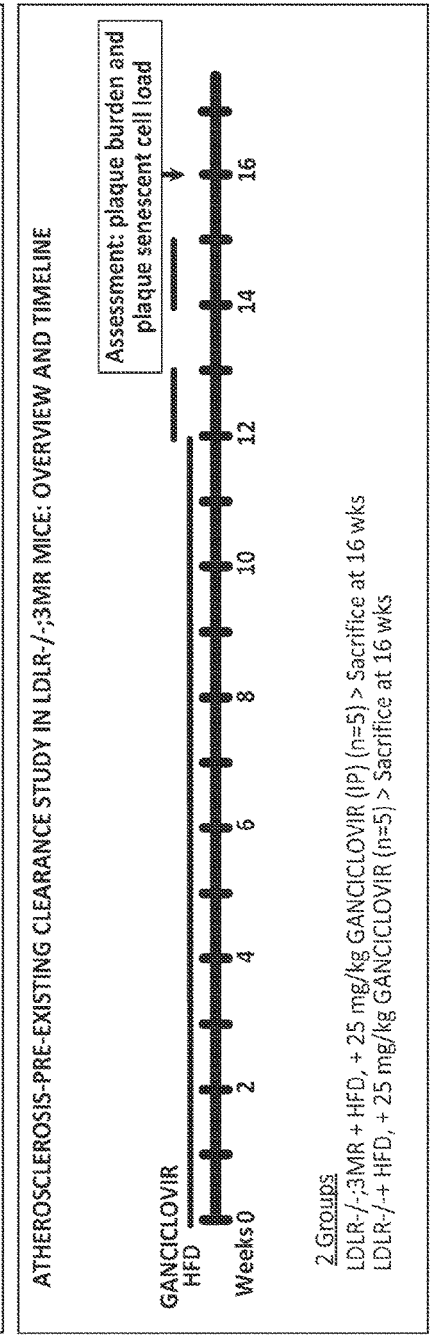

FIGS. 43A-B illustrate schematics of two atherosclerosis animal model studies in LDLR$^{-/-}$ transgenic mice fed a high fat diet (HFD). The study illustrated in FIG. 43A assesses the extent to which clearance of senescent cells from plaques in LDLR$^{-/-}$ mice with a senolytic agent (e.g., Nutlin-3A) reduces plaque load. The study illustrated in FIG. 43B assesses the extent to which ganciclovir-based clearance of senescent cells from LDLR$^{-/-}$/3MR double transgenic mice improves pre-existing atherogenic disease.

Figures 44A, 44B, 44C, 44D:
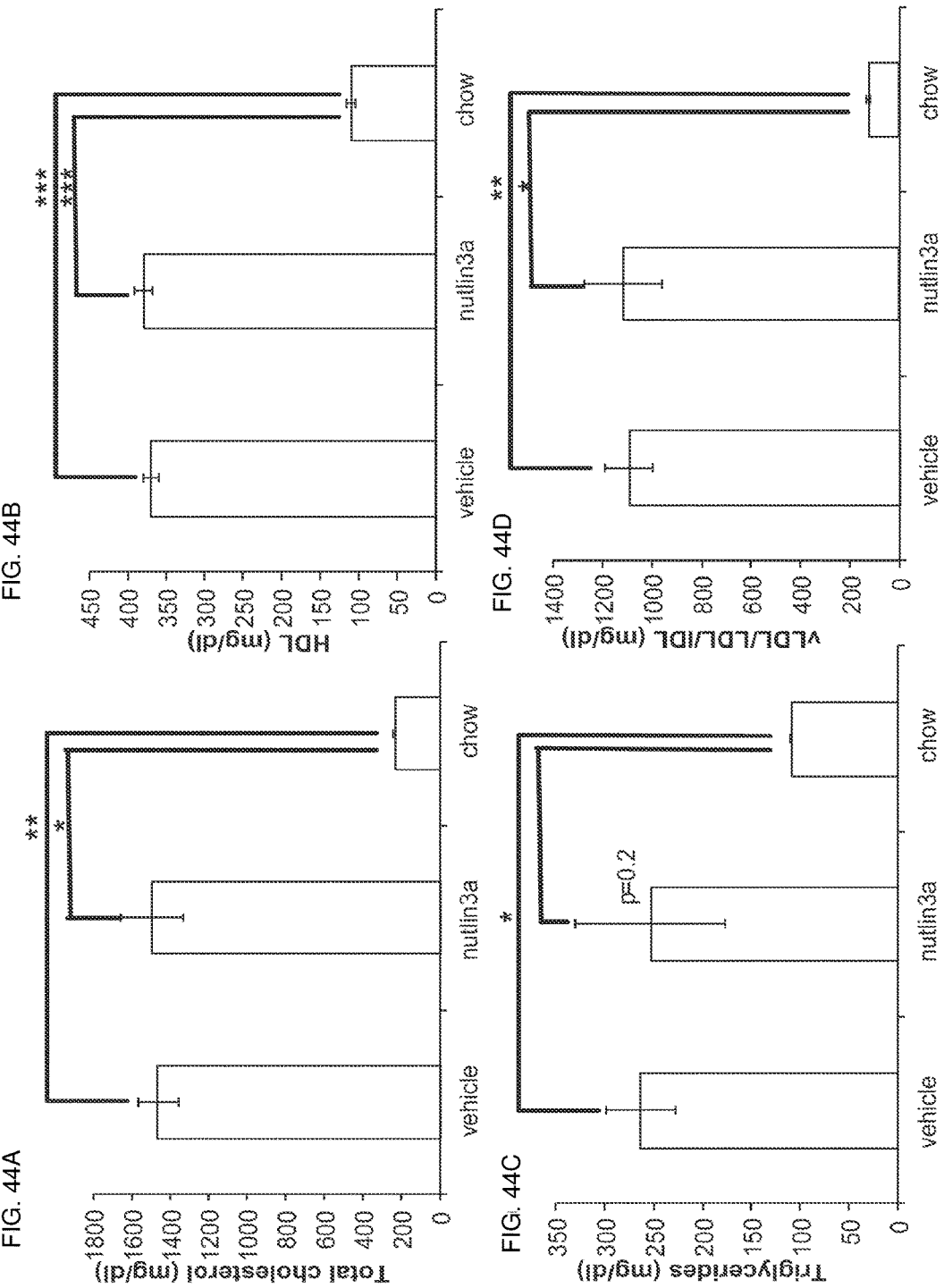

FIGS. 44A-D depict graphs of the plasma lipid levels in LDLR$^{-/-}$ mice fed a HFD after one treatment cycle of Nutlin-3A or vehicle. FIG. 44A shows total cholesterol levels in vehicle or Nutlin-3A treated LDLR$^{-/-}$ mice compared to LDLR$^{-/-}$ fed a non-HFD. FIG. 44B shows HDL levels in vehicle or Nutlin-3A treated LDLR$^{-/-}$ mice compared to LDLR$^{-/-}$ fed a non-HFD. FIG. 44C shows triglyceride levels in vehicle or Nutlin-3A treated LDLR$^{-/-}$ mice compared to LDLR$^{-/-}$ fed a non-HFD. FIG. 44D shows vLDL/LDL/IDL levels in vehicle or Nutlin-3A treated LDLR$^{-/-}$ mice compared to LDLR$^{-/-}$ fed a non-HFD.

FIGS. 45A-D illustrate RT-PCR analysis of SASP factors and senescence markers in aortic arches of LDLR$^{-/-}$ mice fed a HFD after one treatment cycle of Nutlin-3A or vehicle. FIG. 45A illustrates the aortic arch (boxed). FIG. 45B-45C show expression levels of SASP factors and senescence markers, normalized to GAPDH and expressed as fold change vs. non-HFD, vehicle-treated, age-matched LDLR$^{-/-}$ mice. FIG. 45D shows the data from FIGS. 45B-C in numerical form.

Figures 46A, 46B, 46C:
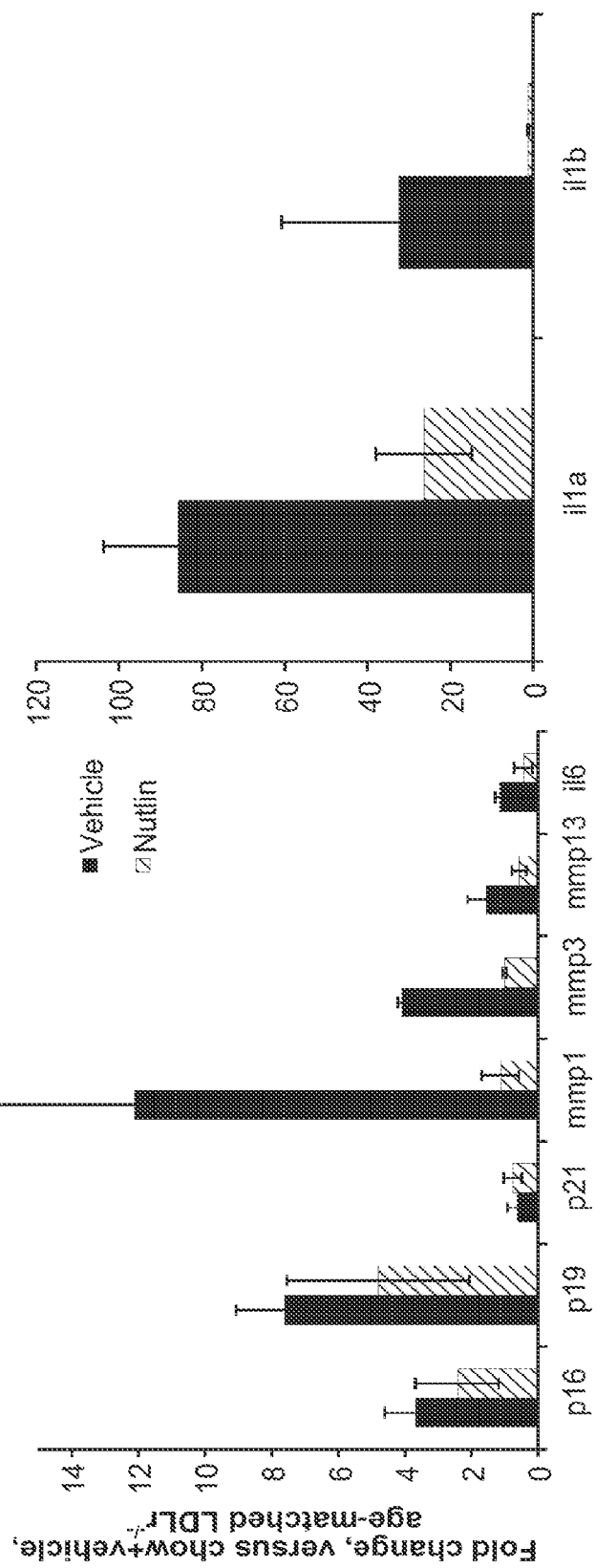

FIGS. 46A-C illustrate RT-PCR analysis of SASP factors and senescence markers in aortic arches of LDLR$^{-/-}$ mice fed a HFD after two treatment cycles of Nutlin-3A or vehicle. FIGS. 46A-B expression levels of SASP factors and senescence markers, normalized to GAPDH and expressed as fold change vs. non-HFD, vehicle-treated, age-matched LDLR$^{-/-}$ mice. FIG. 46C shows the data from FIGS. 46A-B in numerical form.

Figure 47C:
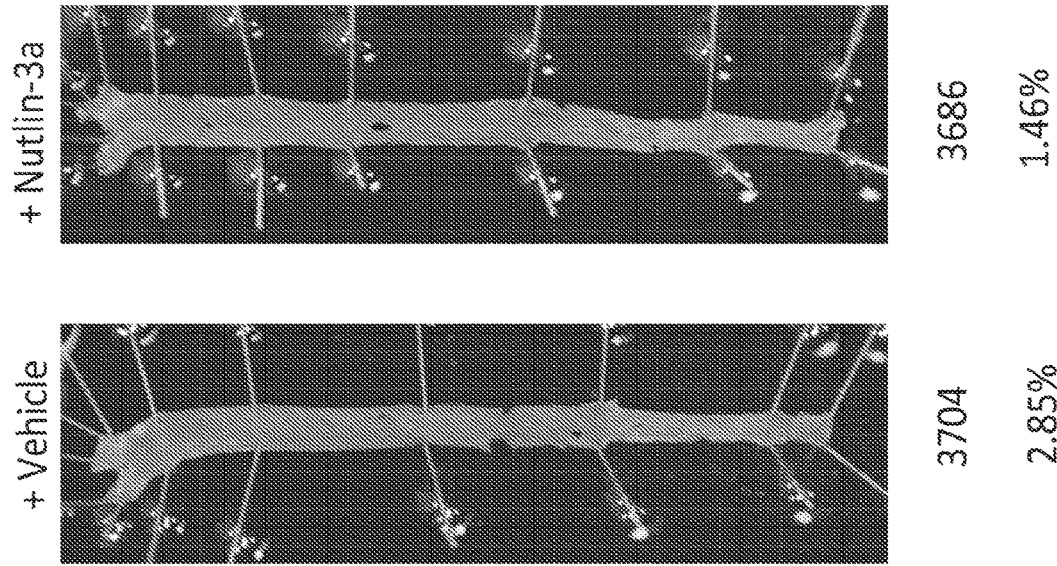
Figure 47B:
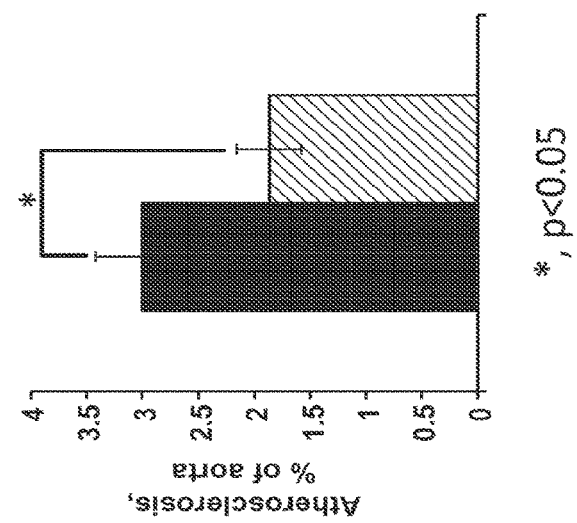
Figure 47A:
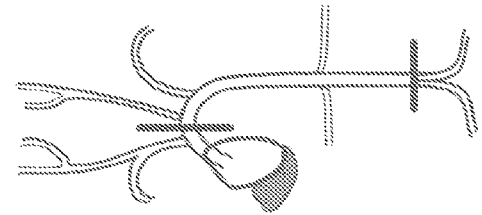

FIGS. 47A-C illustrate staining analysis for aortic plaques in LDLR$^{-/-}$ mice fed a HFD after three treatment cycles of Nutlin-3A or vehicle. FIG. 47A illustrates the aorta. FIG. 47B shows the % of the aorta covered in plaques. FIG. 47C shows Sudan IV staining of the aorta to visualize the plaques and the area covered by the lipid plaque was expressed as a percentage of the total surface area of the aorta in each sample.

FIGS. 48A-B depict plots of platelet (FIG. 48A) and lymphocyte counts (FIG. 48B) from LDLR$^{-/-}$ mice fed a HFD after three treatment cycles of Nutlin-3A or vehicle.

Figure 49A:
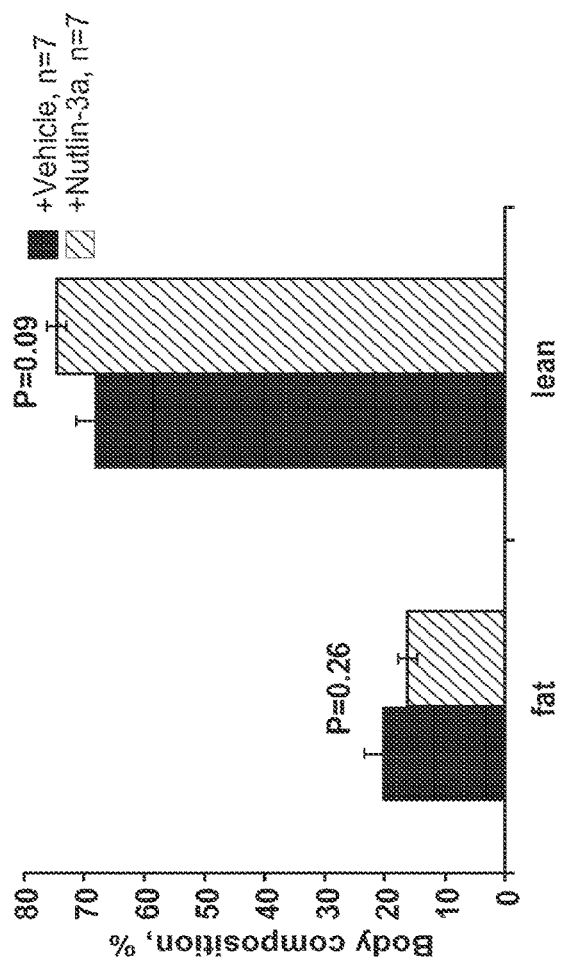
Figure 49B:
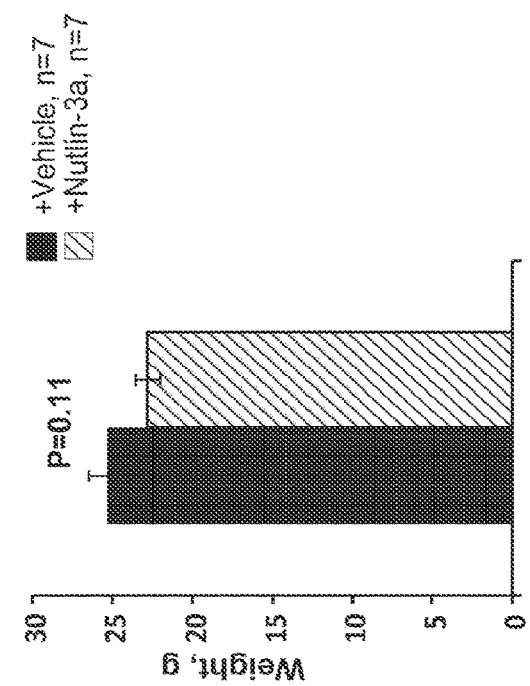

FIGS. 49A-49B depict plots of weight (FIG. 49A) and body fat/lean tissue composition (%) (FIG. 49B) of LDLR$^{-/-}$ mice fed a HFD after three treatment cycles of Nutlin-3A or vehicle.

Figure 50:
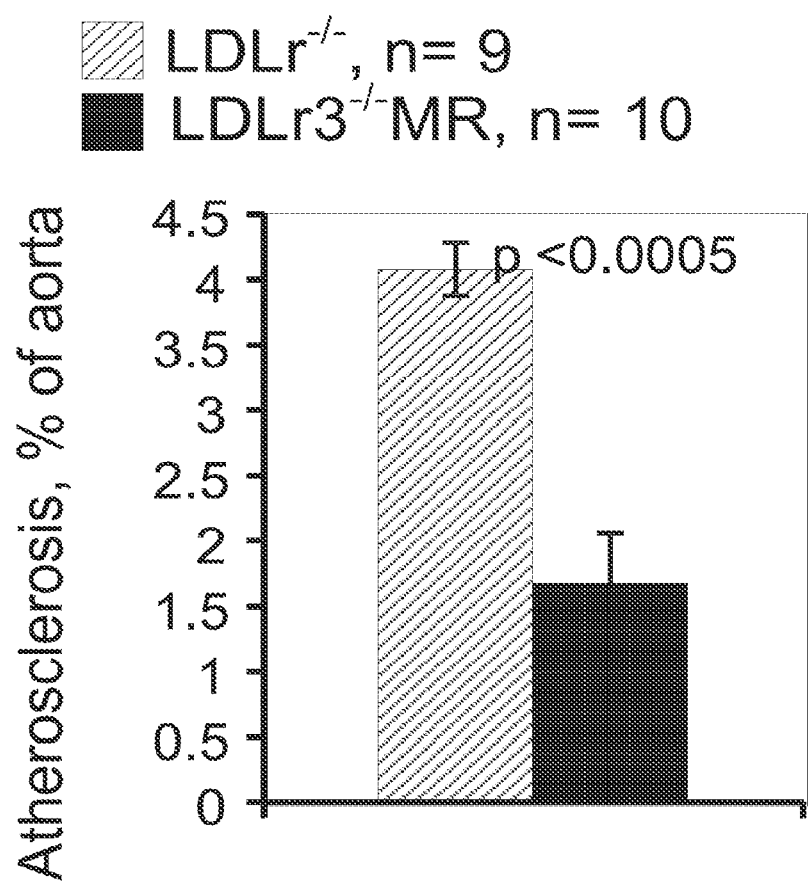

FIG. 50 depicts a graph of the effect of clearance of senescent cells with ganciclovir in LDLR$^{-/-}$ and LDLR$^{-/-}$/3MR mice fed a HFD, as measured by the % of the aorta covered in plaques.

Figure 51:
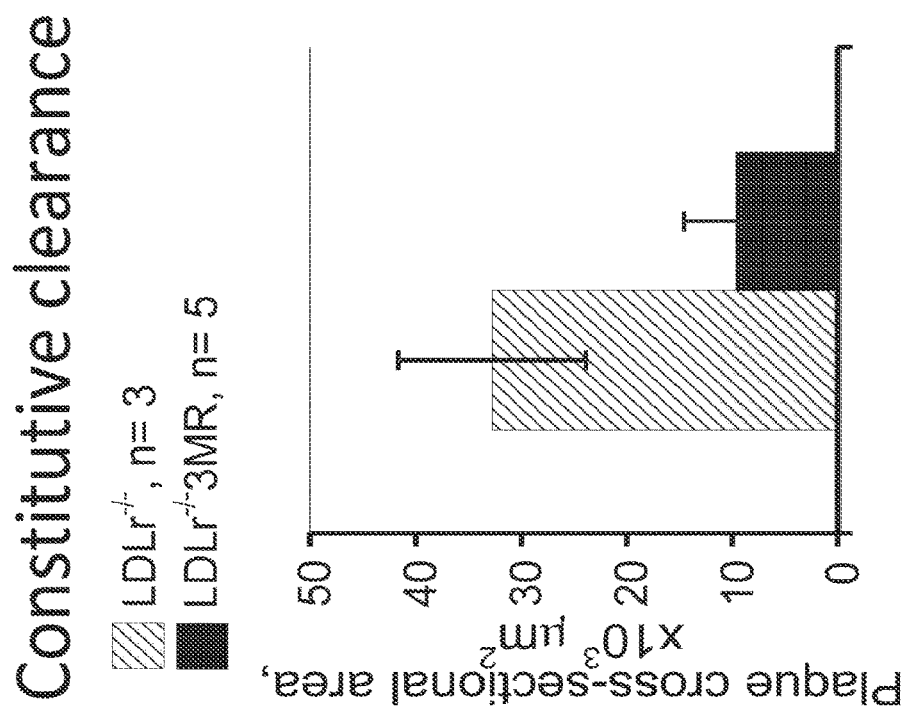

FIG. 51 depicts a graph of the effect of clearance of senescent cells with ganciclovir in LDLR$^{-/-}$ and LDLR$^{-/-}$/3MR mice fed a HFD, as measured by the plaque cross-sectional area of the aorta.

Figure 52:
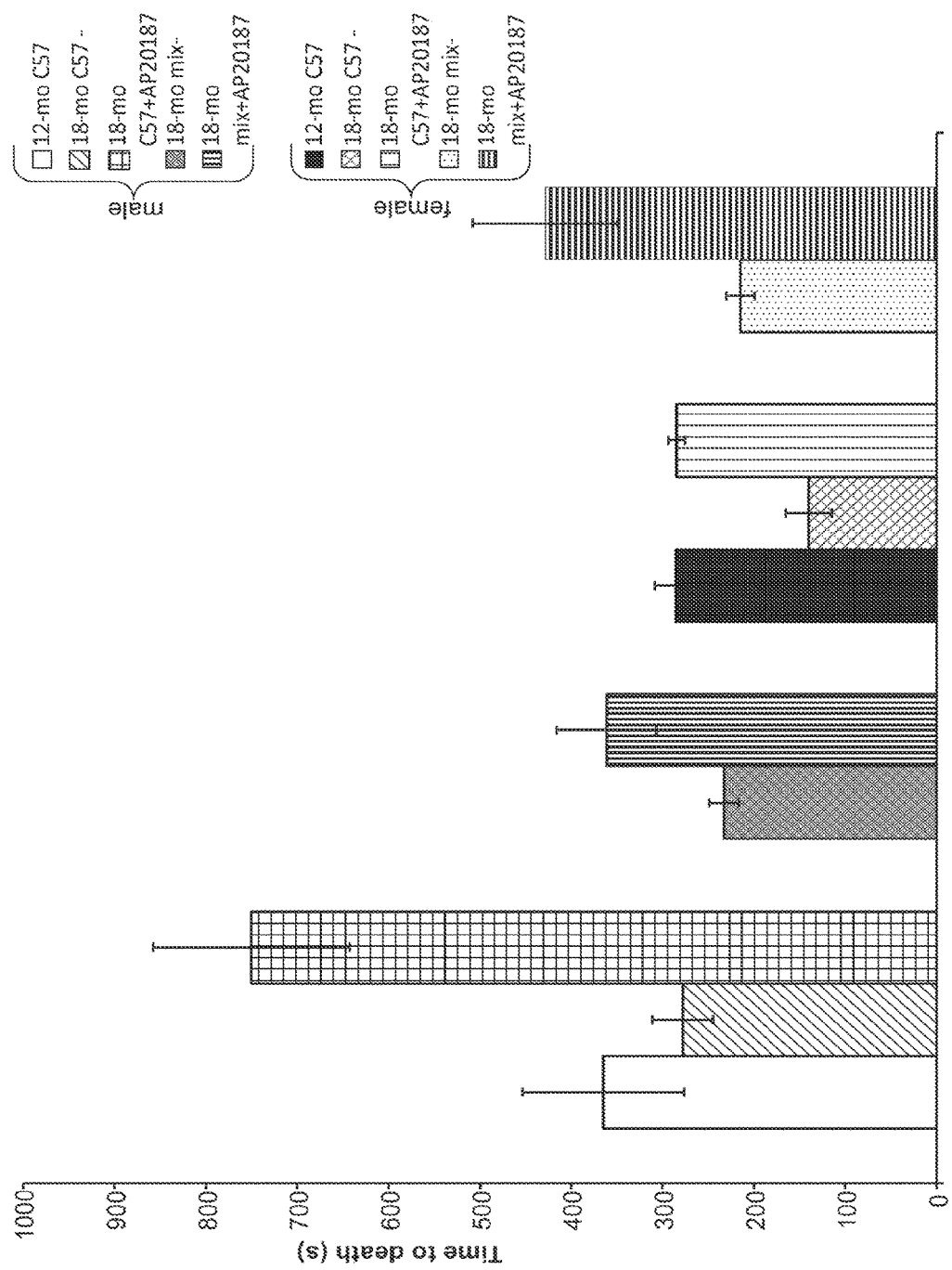

FIG. 52 shows the effect of senescent cell clearance on resistance to cardiac stress with aging. 12 month old INK-ATTAC transgenic mice on FVBx129Sv/ExC57BL/6 mixed of C57BL/6 pure genetic backgrounds were injected 3x/week with AP20187 (0.2 mg/kg for the mixed cohort and 2 mg/kg for the C57BL/6 cohort, respectively). At 18 months, subsets of male and female mice from each cohort were subjected to a cardiac stress test and time to cardiac arrest was recorded. Control cohort received injections of vehicle.

Figure 53:
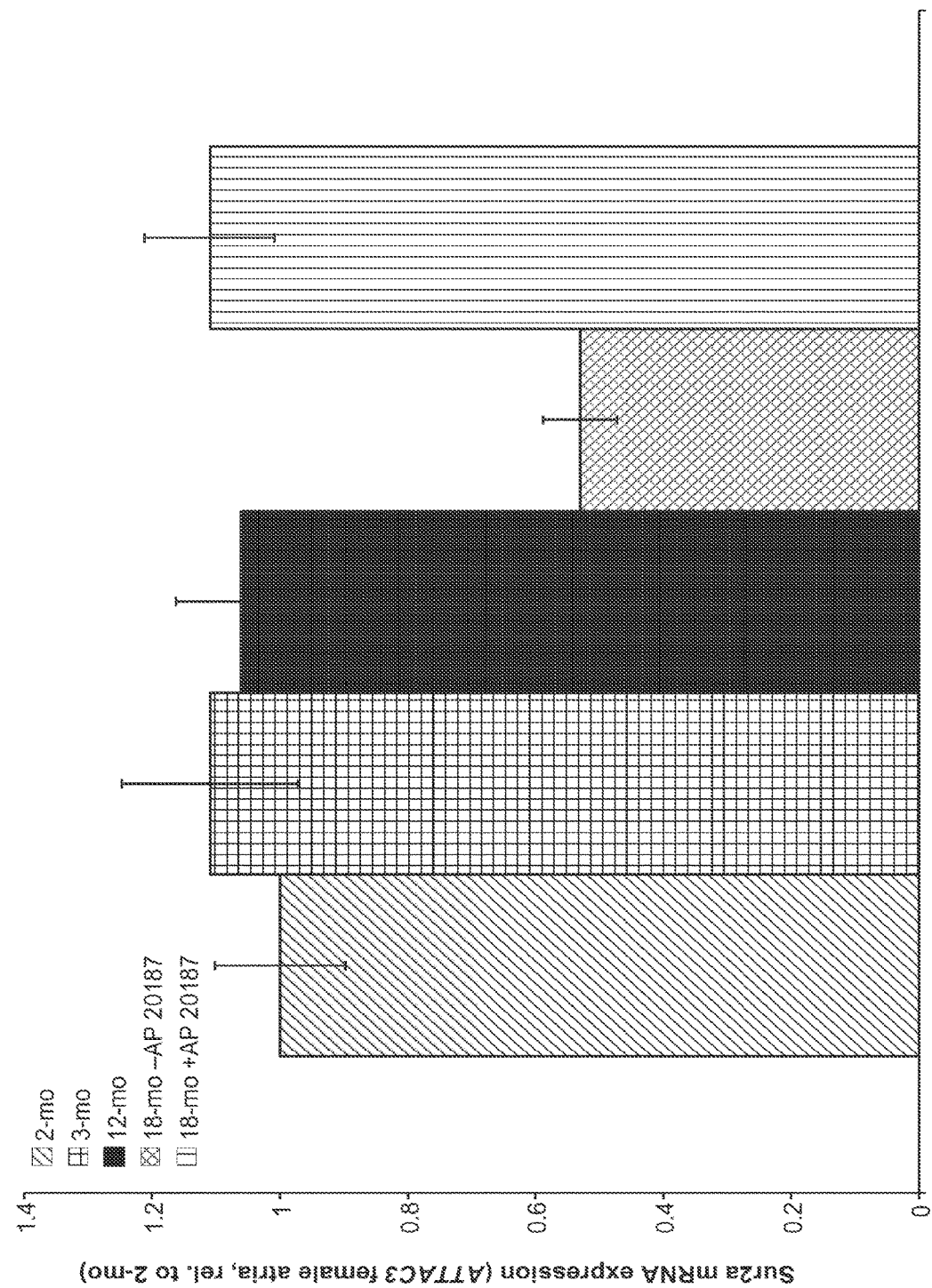

FIG. 53 shows the RT-PCR analysis of Sur2a expression in female INK-ATTAC transgenic mice described in FIG. 52.

Figure 54C:
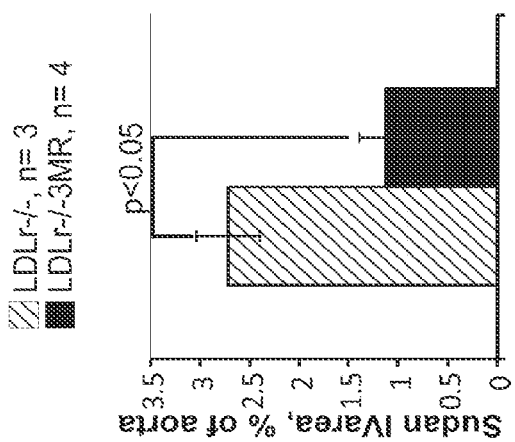
Figure 54B:
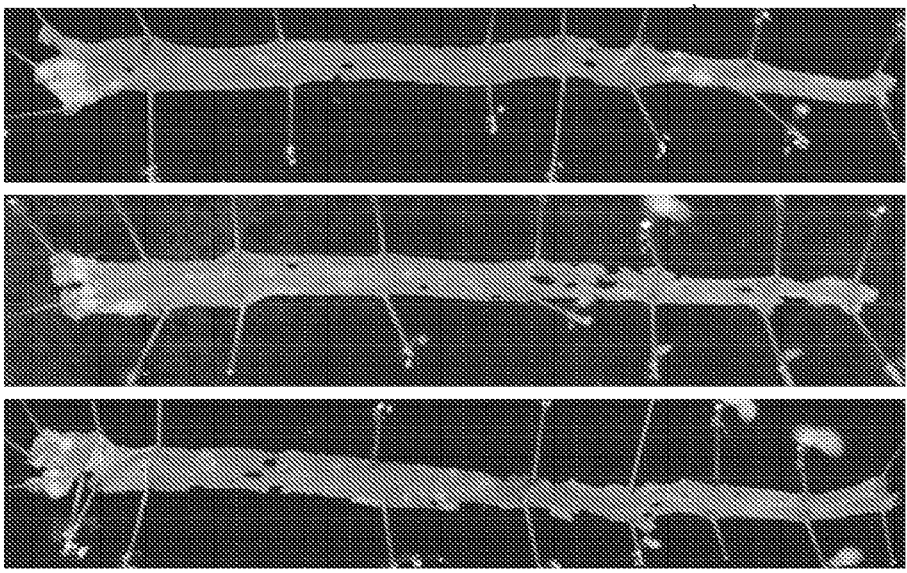
Figure 54A:
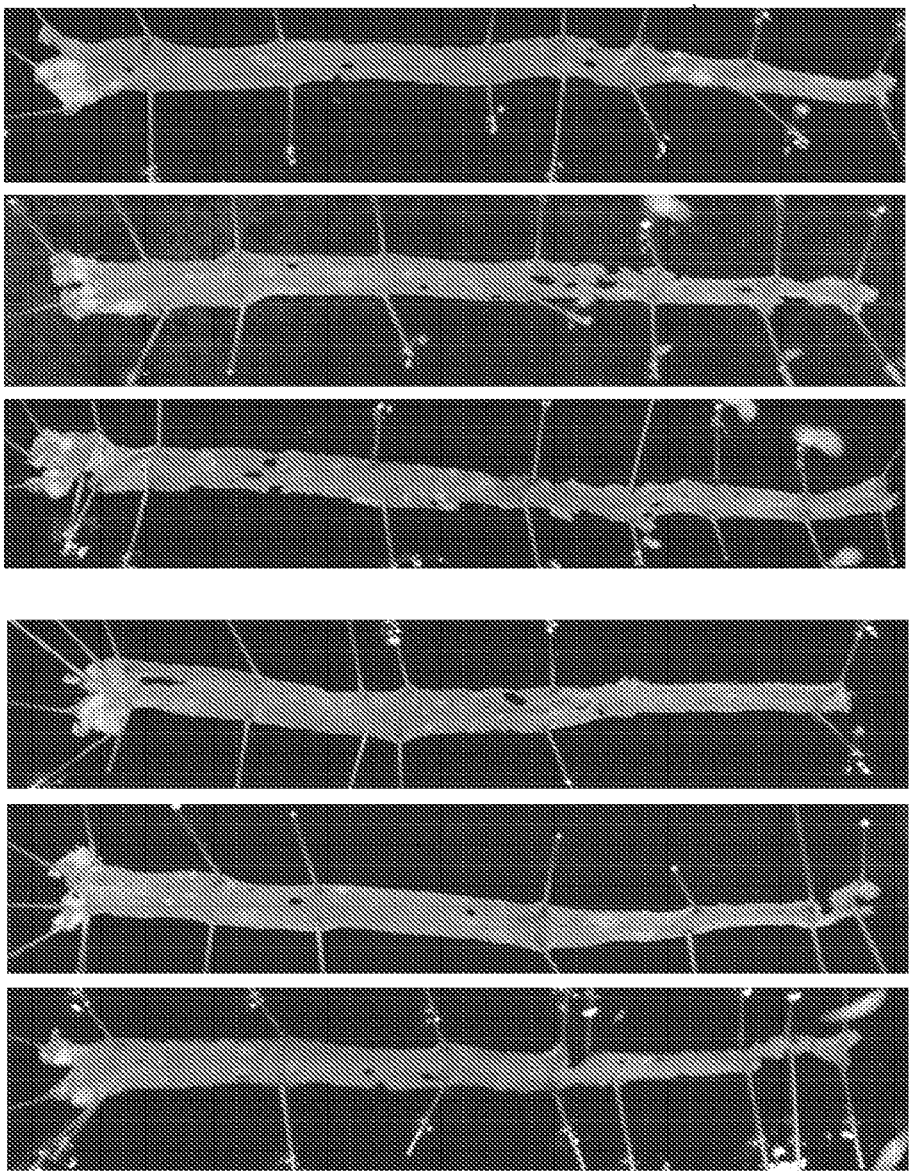

FIGS. 54A-C illustrate staining analysis for aortic plaques in LDLR$^{-/-}$/3MR double transgenic mice and LDLR$^{-/-}$ control mice fed a HFD after a 100 day treatment period with ganciclovir. FIGS. 54A-54B show Sudan IV staining of the aorta to visualize the plaques in LDLR$^{-/-}$ control mice and LDLR$^{-/-}$/3MR mice, respectively. FIG. 54C shows the % of the aorta covered in plaques as measured by area of Sudan IV staining.

Figure 55A:
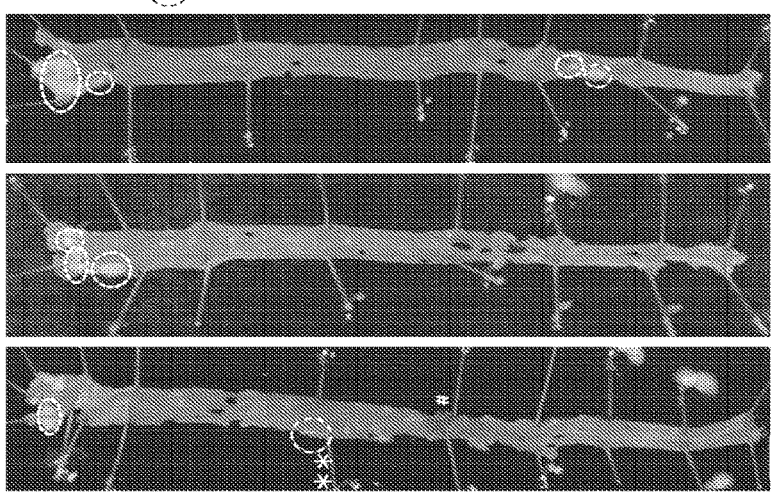
Figure 55C:
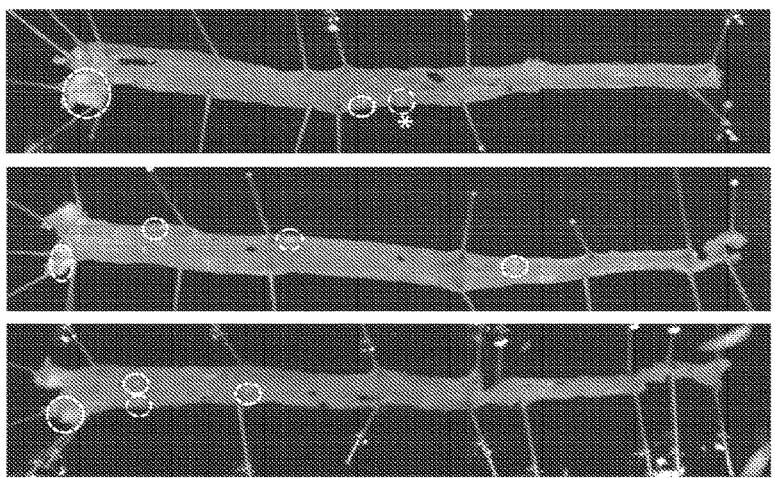
Figure 55B:
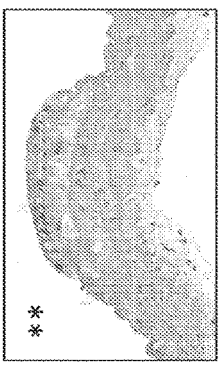
Figure 55D:
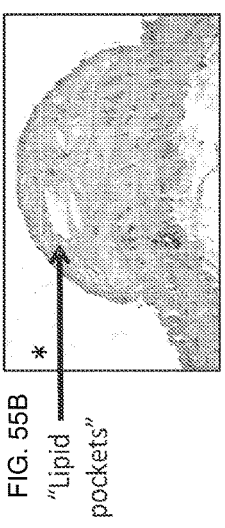

FIGS. 55A-D illustrate plaque morphology analysis in LDLR$^{-/-}$/3MR double transgenic mice and LDLR$^{-/-}$ control mice fed a HFD after a 100 day treatment period with ganciclovir. FIG. 55A and FIG. 55C show Sudan IV staining of the aorta to visualize the plaques in LDLR$^{-/-}$ control mice and LDLR$^{-/-}$/3MR mice, respectively. Plaques that are circled were harvested and cut into cross-sections and stained with to characterize the general architecture of the atherosclerotic plaques (FIG. 55B and FIG. 55D). "#" marks fat located on the outside of the aorta.

Figure 56:
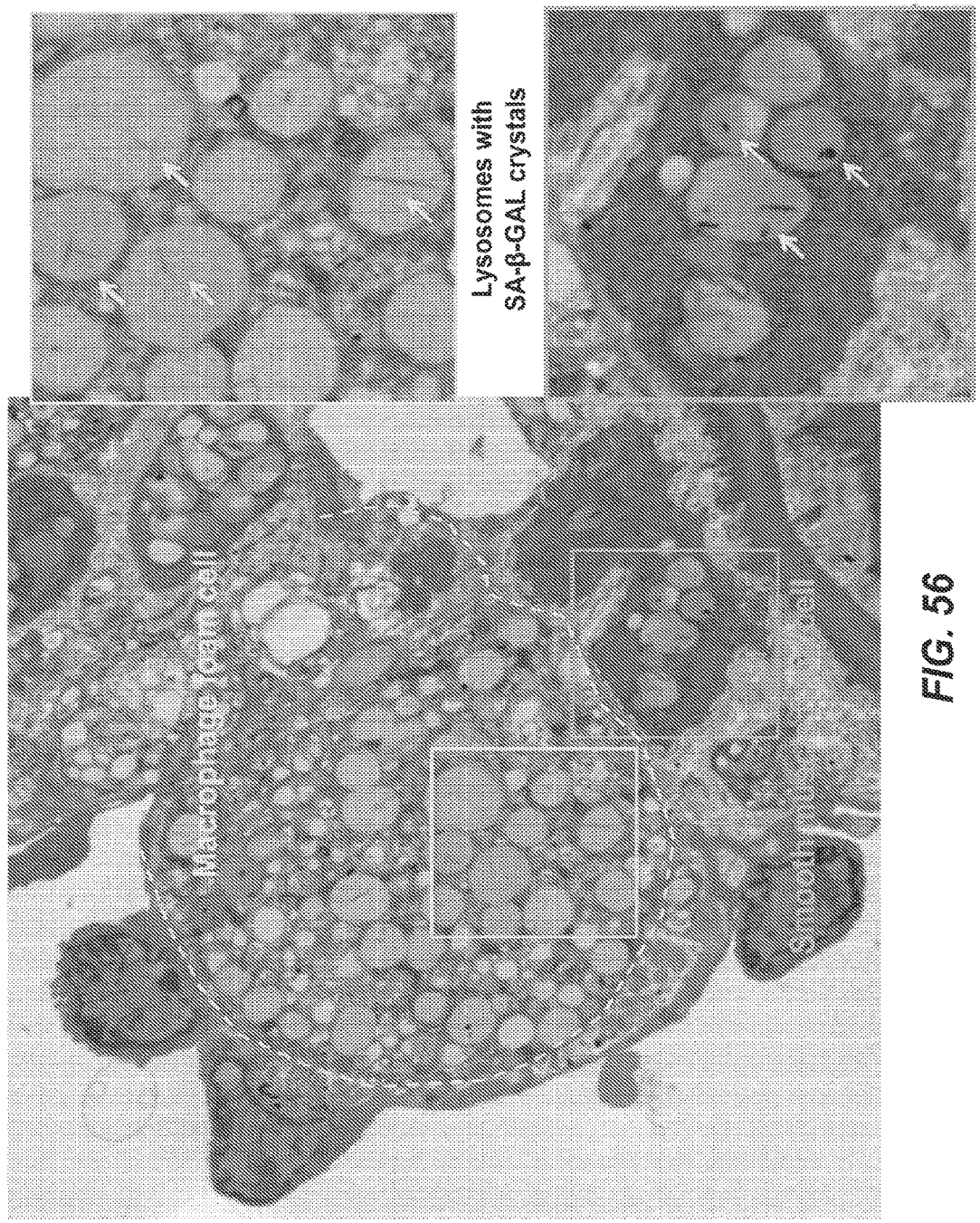

FIG. 56 shows that SA-β-GAL crystals localize to lipid-bearing foam cells from an atherosclerotic artery of a mouse fed a high-fat diet. The macrophage foam cell is shown by a white dotted outline and adjacent to the macrophage foam cell is a smooth muscle foam cell. The left boxed area in the macrophage foam cell is magnified and shown on the upper right to illustrate lysosomes with SA-β-GAL crystals. The boxed area within the smooth muscle foam cell is magnified and shown on the lower right side of the figure.

Figure 57:
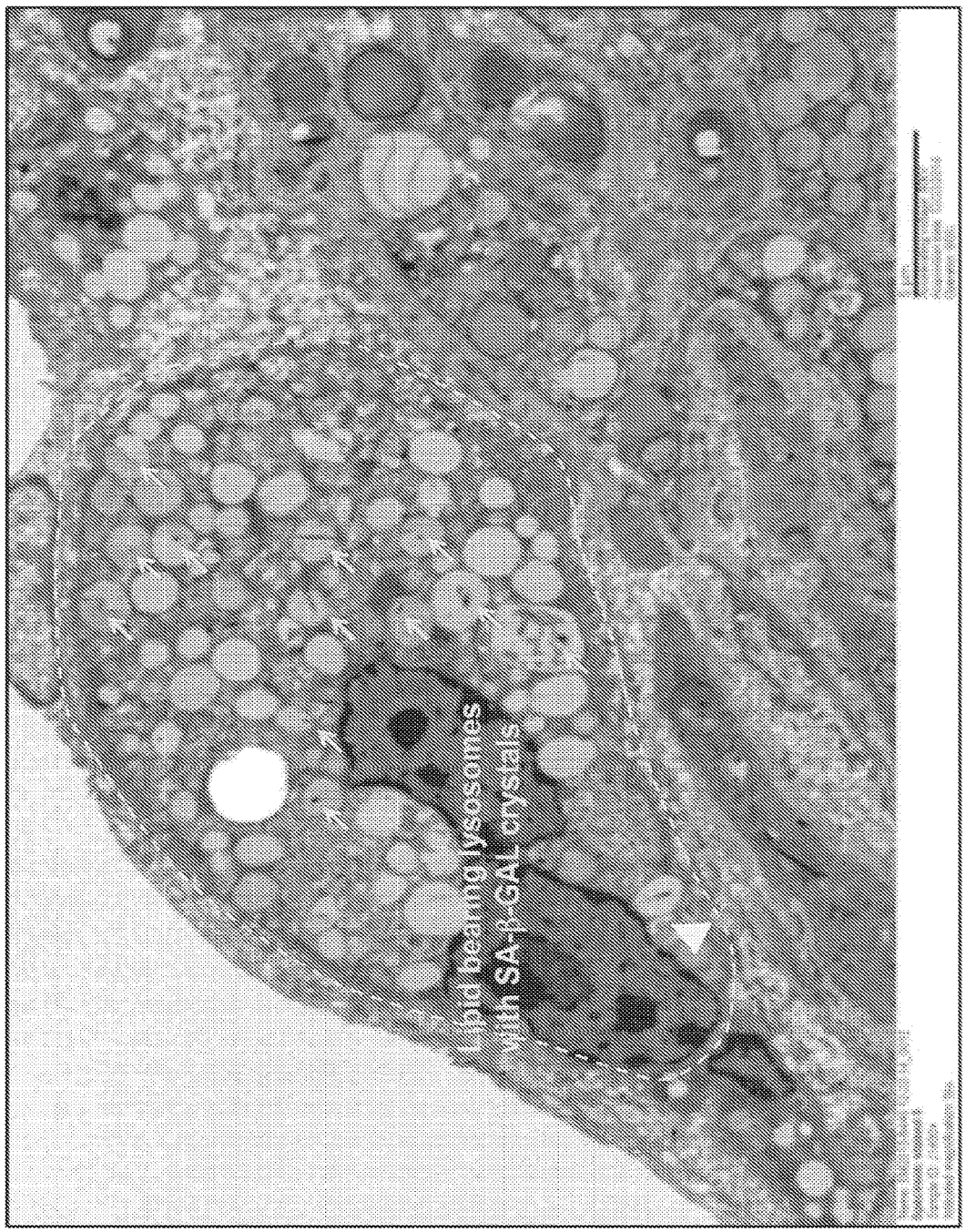
Figure 58:
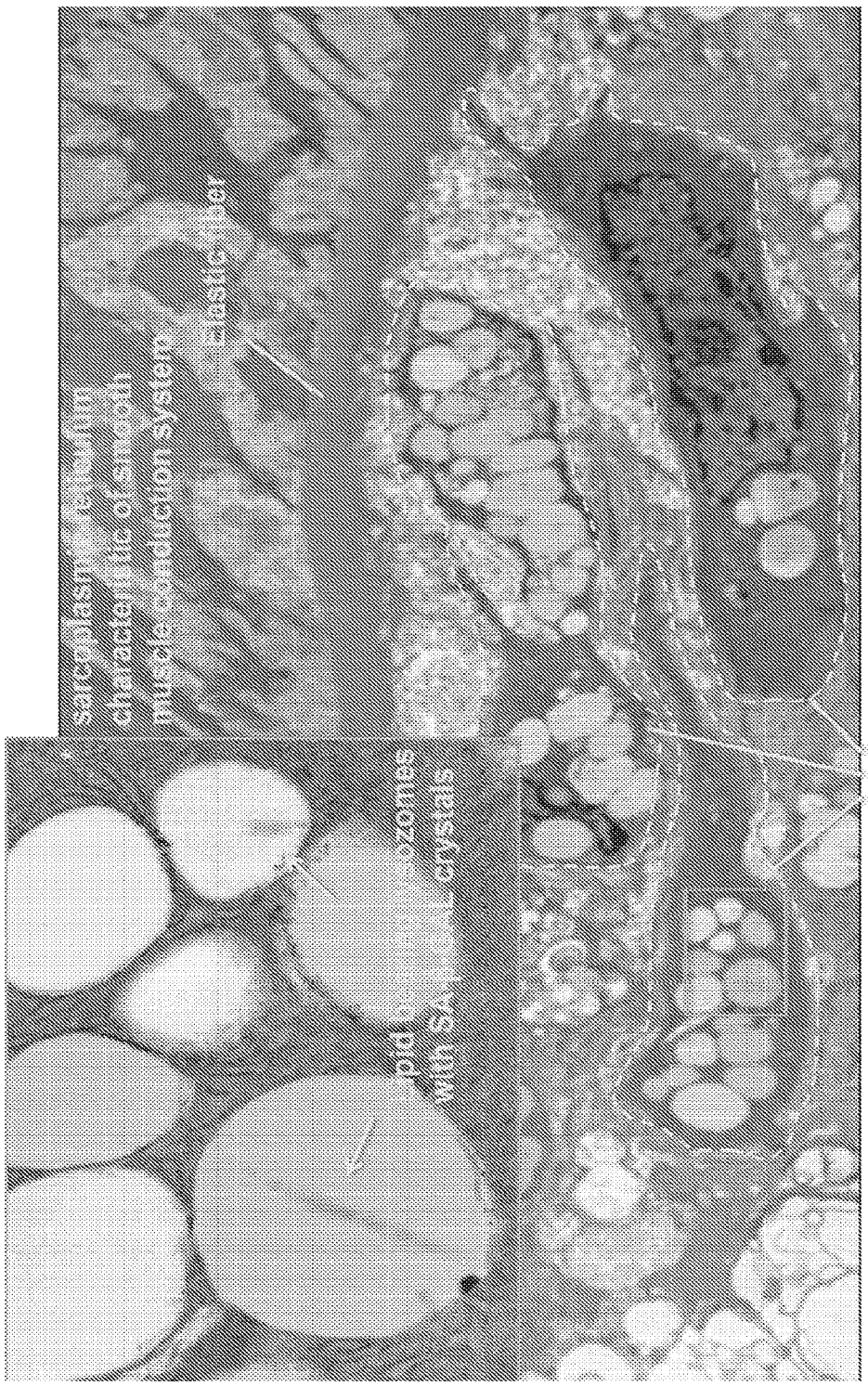

FIG. 57 presents a macrophage foam cell from an atherosclerotic artery of a mouse fed a high-fat diet. Lipid-bearing lysosomes containing SA-β-GAL crystals are noted by the arrows. FIG. 58 shows that SA-β-GAL crystals localize in the lysozomes of smooth muscle foam cells in an atherosclerotic artery of a mouse fed a high-fat diet. The boxed area in the lower left portion of the illustration is magnified and shown in the insert at the top left.

Figure 59:
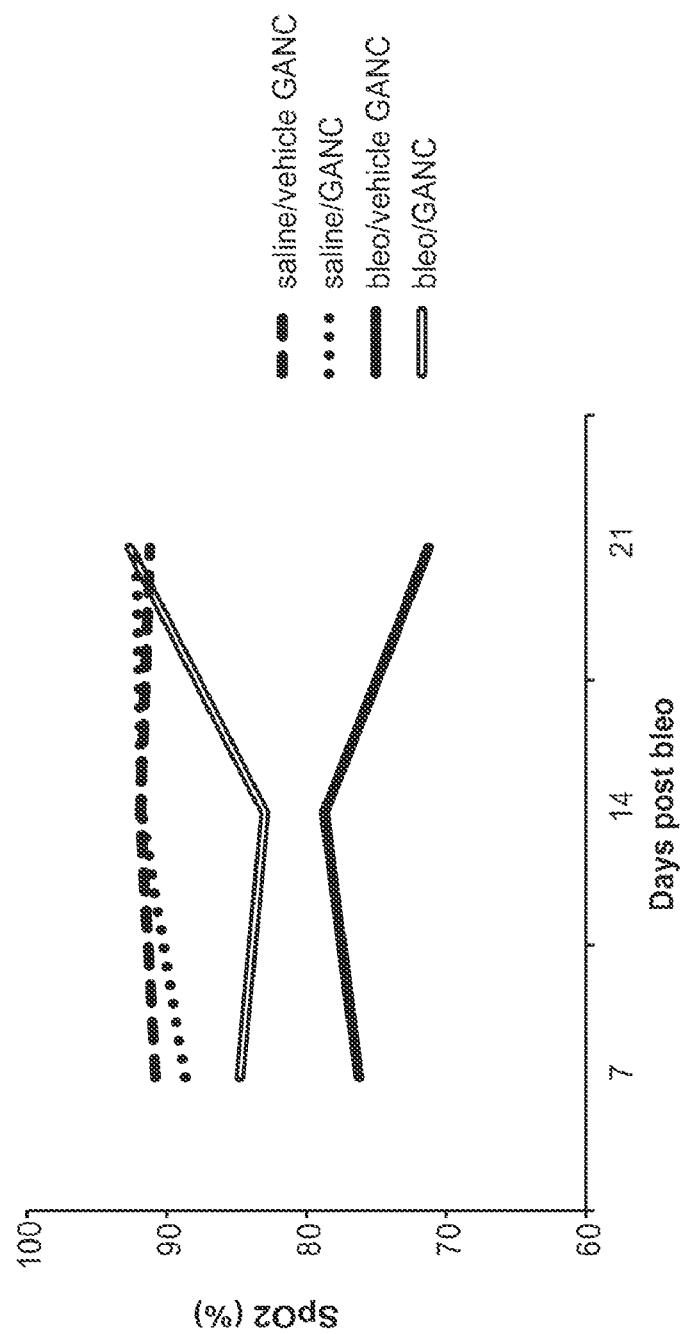

FIG. 59 shows the effect of senescent cell clearance on peripheral capillary oxygen saturation (SpO$_2$) in bleomycin exposed mice.

Figure 60A:
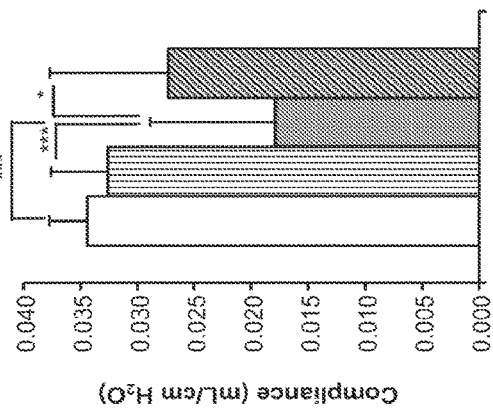
Figure 60C:
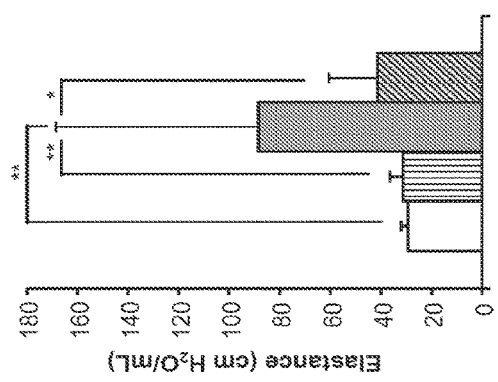
Figure 60B:
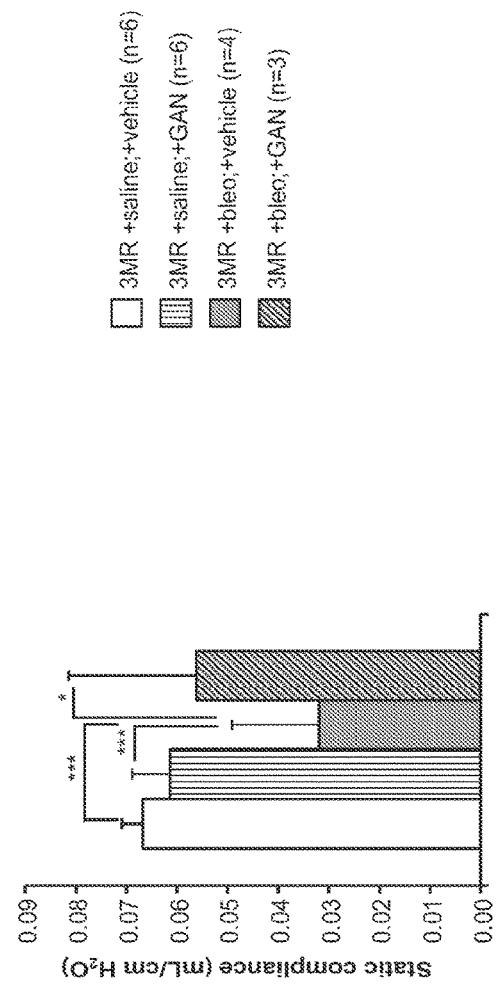

FIGS. 60A-C illustrate the effect of senescent cell clearance with ganciclovir on lung function in 3MR mice exposed to bleomycin. FIG. 60A shows the effect of ganciclovir treatment on lung elastance of 3MR mice exposed to bleomycin. FIG. 60B shows the effect of ganciclovir treatment on dynamic lung compliance of 3MR mice exposed to bleomycin. FIG. 60C shows the effect of ganciclovir treatment on static lung compliance of 3MR mice exposed to bleomycin.

Figure 61:
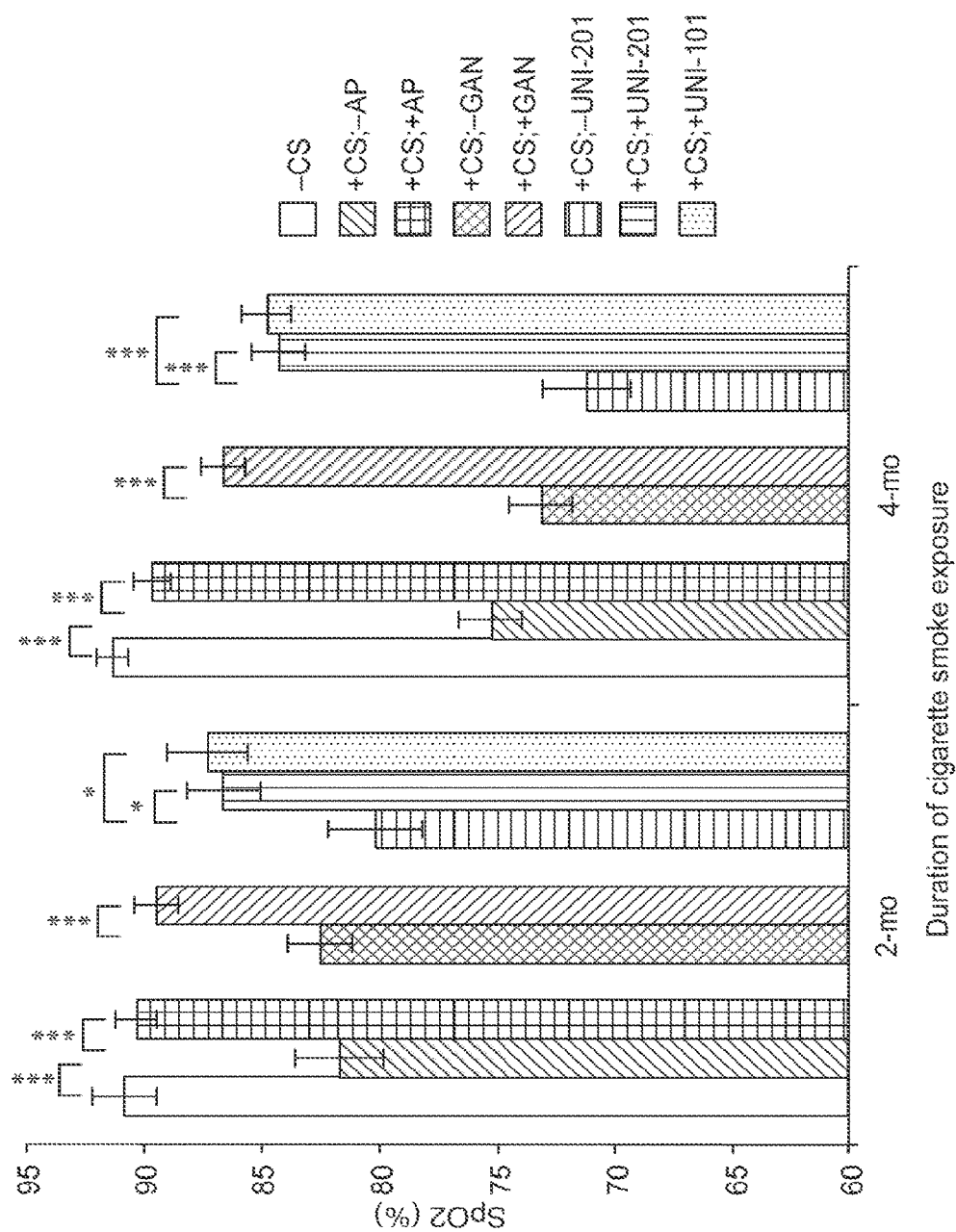

FIG. 61 shows the effect of senescent cell clearance on peripheral capillary oxygen saturation (SpO$_2$) in mice after 2 months and 4 months of cigarette smoke (CS) exposure. AP=AP20187; GAN=ganciclovir; Navi=Navitoclax (ABT-263); and Nutlin=Nutlin 3A.

Figure 62A:
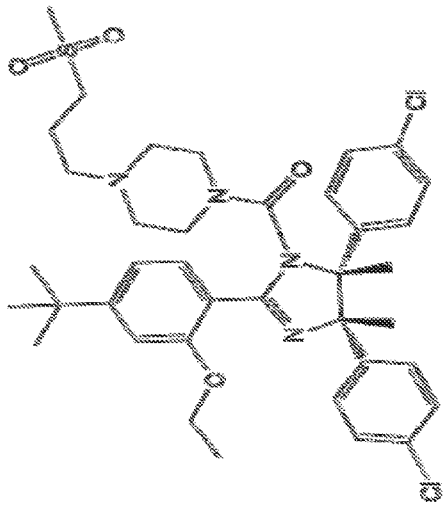
Figure 62C:
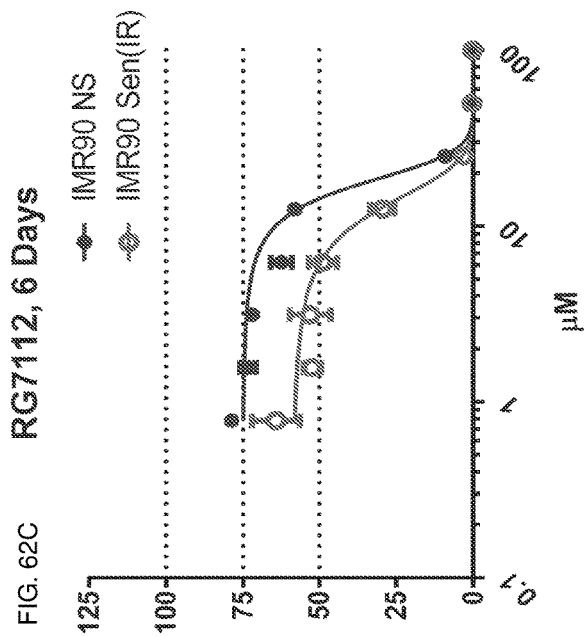
Figure 62B:
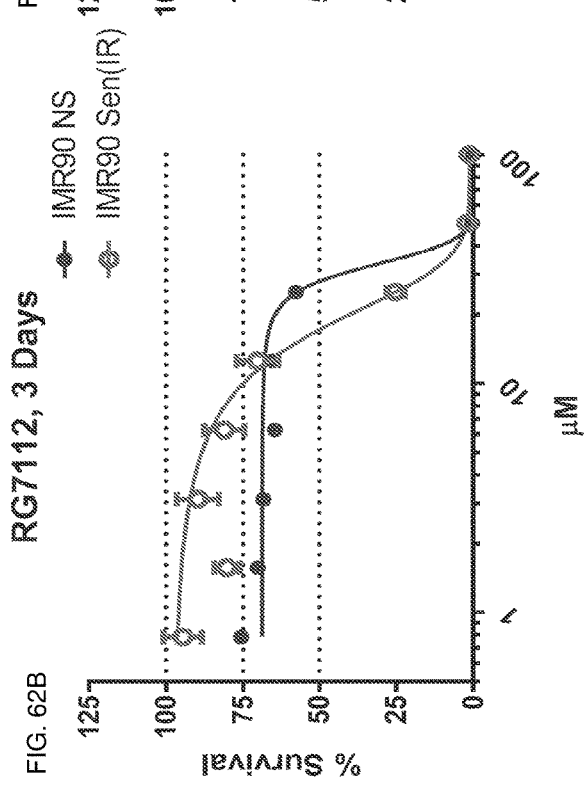

FIGS. 62A-C illustrate the effect of RG-7112 (structure shown in FIG. 62A) on percent survival of senescent irradiated lung fibroblasts IMR90 cells ((IMR90)Sen(IR)) and non-senescent IMR90 cells, which were not exposed to radiation (IMR90 NS) after 3 days of treatment (as shown in FIG. 62B) and after six days of treatment with RG-7112 (as shown in FIG. 62C).

Figure 63A:
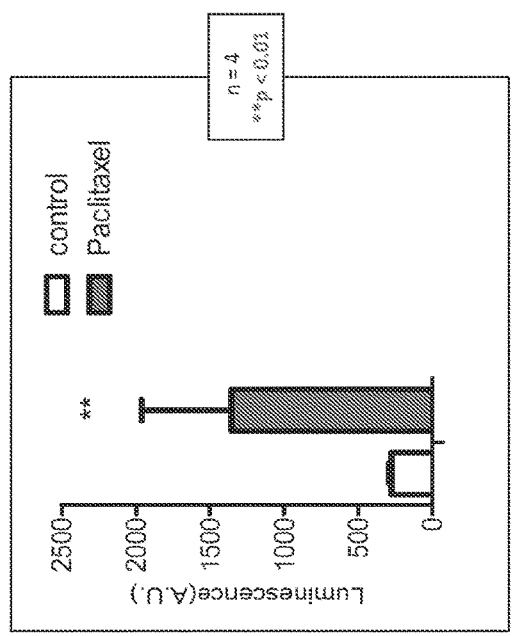
Figure 63B:
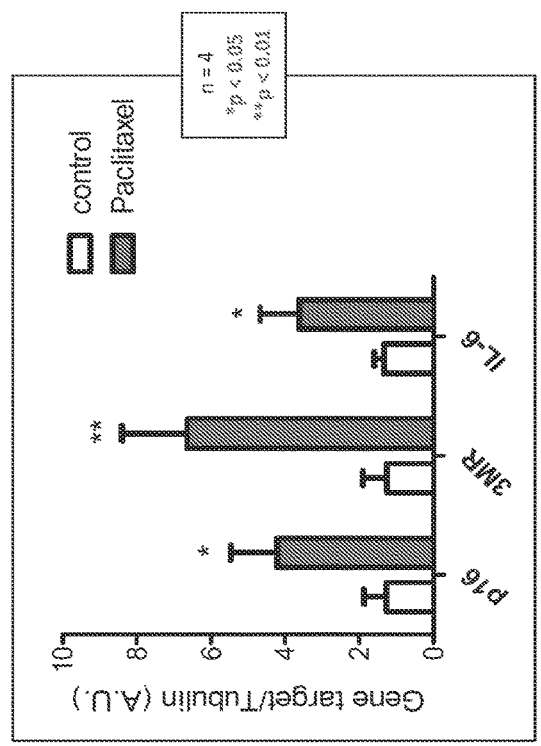

FIGS. 63A-B illustrates that paclitaxel induces senescence in p16-3MR mice. Groups of mice (n=4) were treated three times every two days with 20 mg/kg paclitaxel or vehicle. The level of luminescence in mice treated with paclitaxel is shown in FIG. 63A. The level of mRNA in skin was determined for each of the target genes: p16, 3MR transgene, and IL-6 in animals treated with paclitaxel as shown in FIG. 63B.

Figure 64:
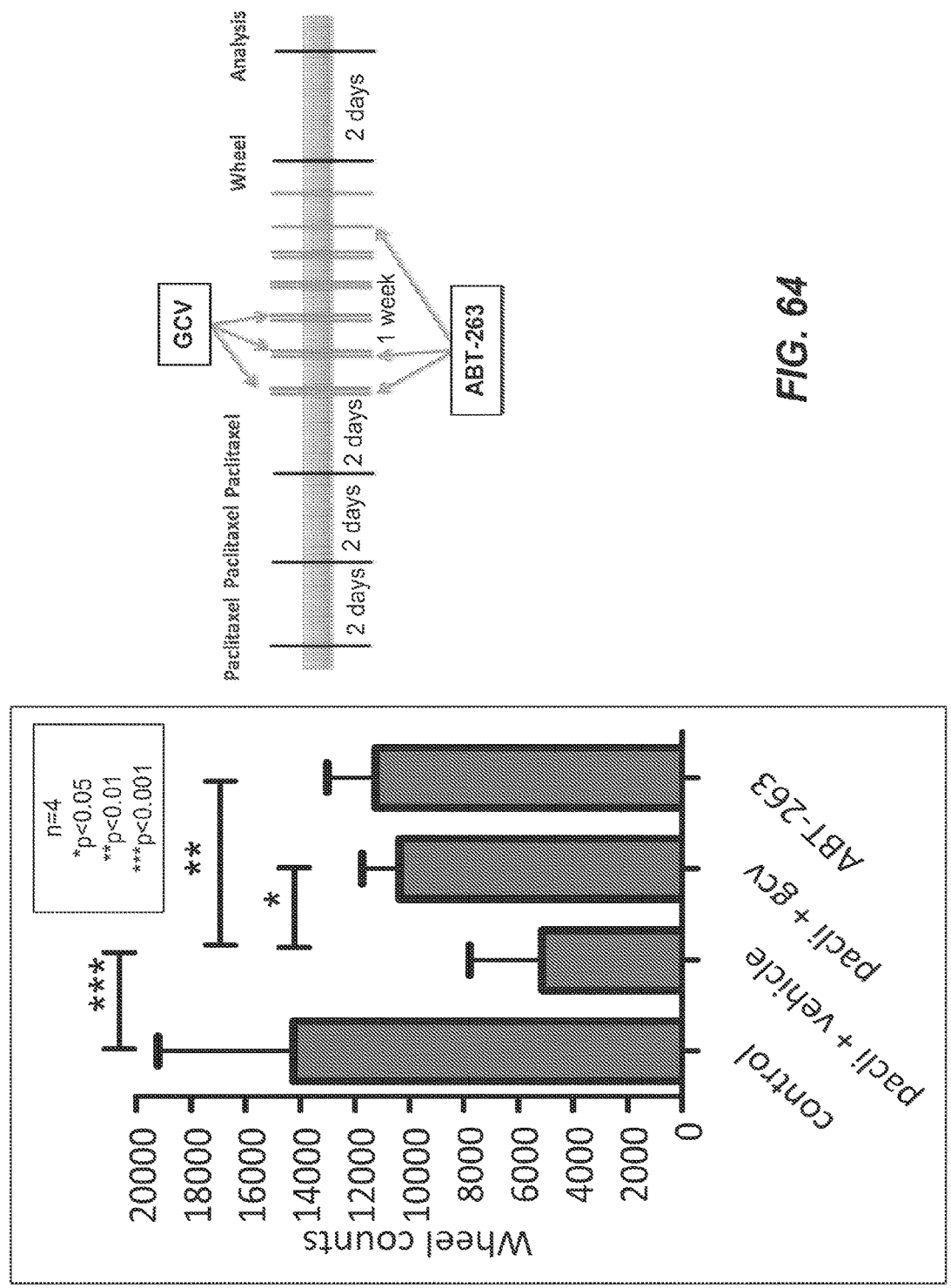

FIG. 64 shows the effect of ABT-263 on mice that were initially treated with paclitaxel. The schematic of the experiment performed in 3MR mice is shown at the right-hand side of the figure. Mice were first treated with paclitaxel, followed by treatment with either vehicle, ganciclovir (gcv) or ABT-263. Wheel counts were measured for each group of mice (n=4) treated with paclitaxel+vehicle (pacli+vehicle); paclitaxel+ganciclovir (pacli+gcv); paclitaxel+ABT-263 (pacli+ABT-263); and control animals that did not receive paclitaxel (see graph at left side of FIG. 64).

Figure 65:
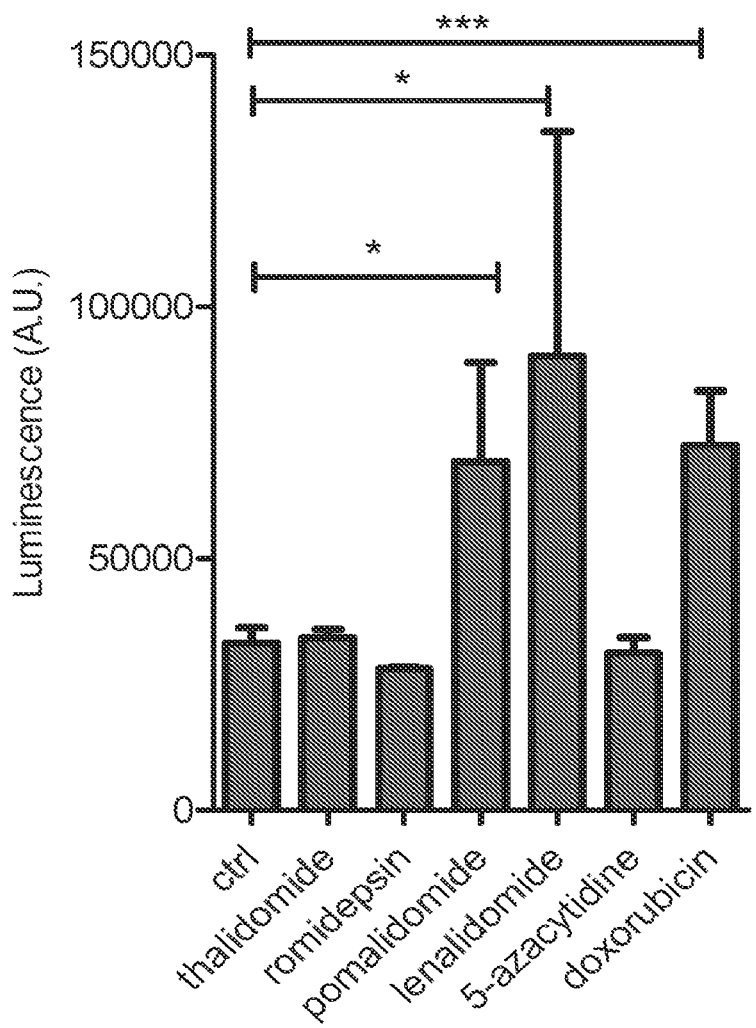

FIG. 65 shows the level of senescence induced in groups of p16-3MR animals (n=4) treated with chemotherapeutic drugs: thalidomide (100 mg/kg; 7 daily injections); romidepsin (1 mg/kg; 3 injections); pomalidomide (5 mg/kg; 7 daily injections); lenalidomide (50 mg/kg; 7 daily injections); 5-azacytidine (5 mg/kg; 3 injections) and doxorubicin (10 mg/kg; 2-4 injections during a week). The level of luminescence was measured in animals treated with the drugs.

Figure 66:
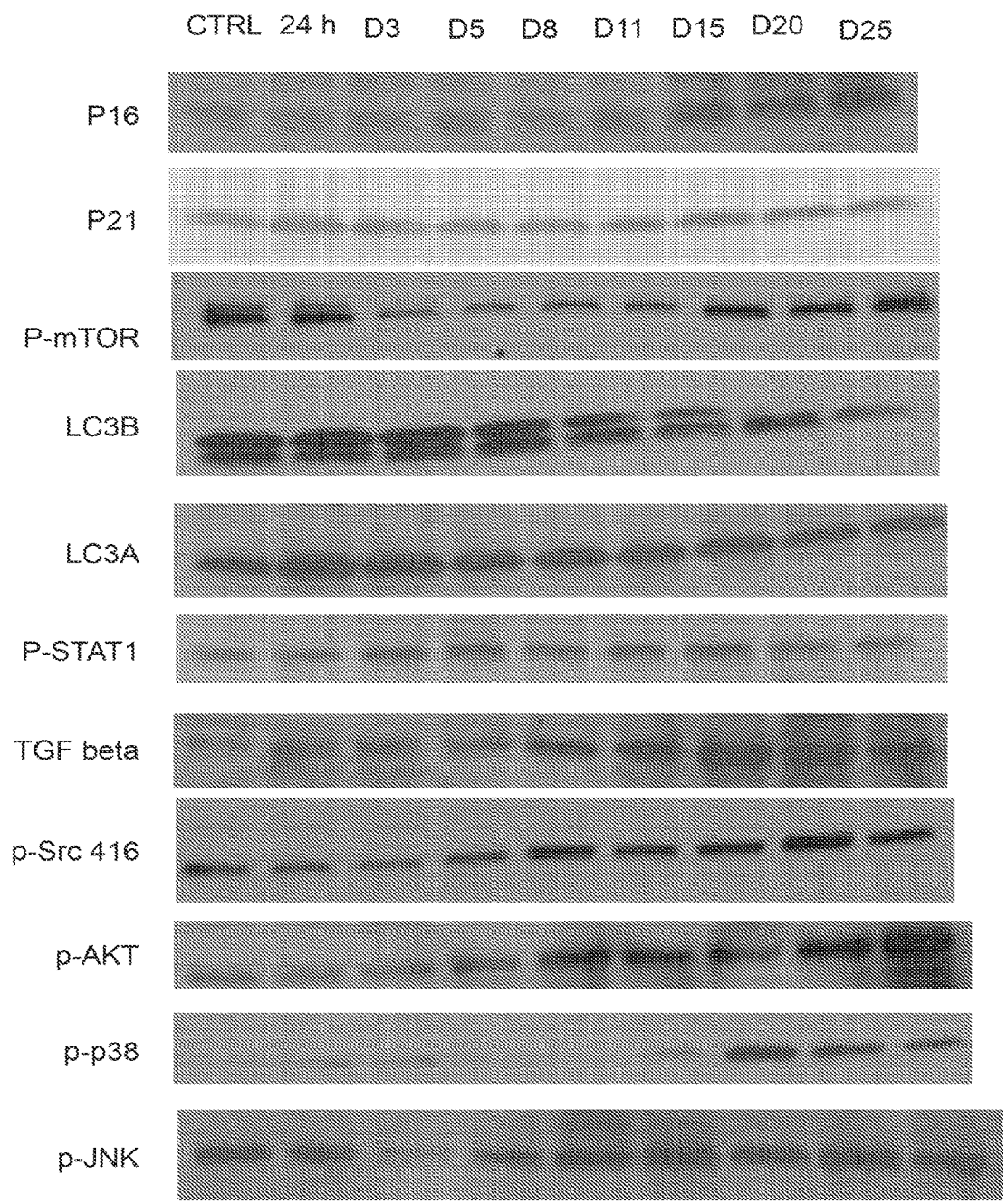

FIG. 66 shows an immunoblot showing the level of different cellular proteins in senescent and non-senescent human abdominal subcutaneous preadipocytes. Senescence was induced as described in Example 28. Lysates were prepared at several time points after induction of senescence, and the level of each protein in the lysates detected at 24 hours and at days 3, 5, 8, 11, 15, 20, and 25 (D3, D5, D8, D11, D15, D20, and D25).

Figure 67:
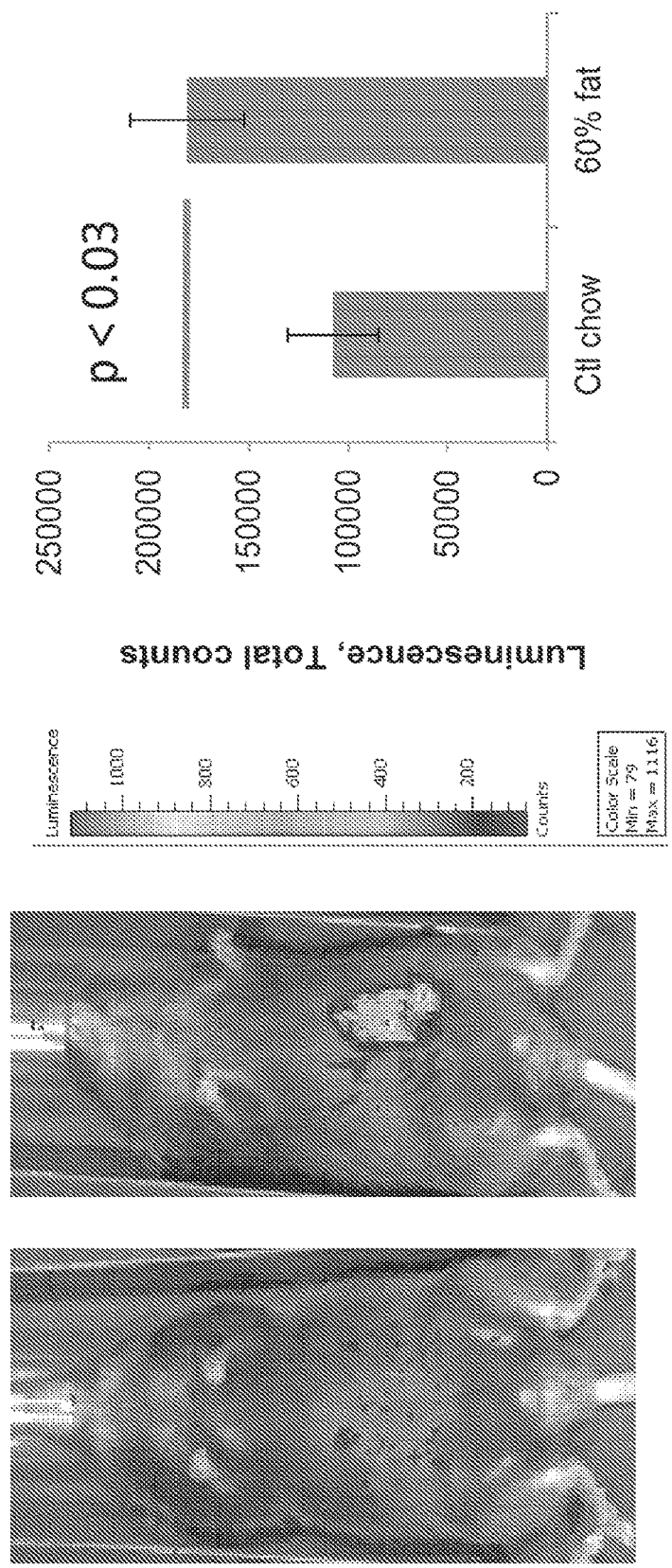

FIG. 67 shows that groups of p16-3MR mice (n=6) fed a high fat diet (high fat) for four months have increased numbers of senescence cells compared with mice fed a regular chow diet (chow fed) (n=6).

Figure 68:
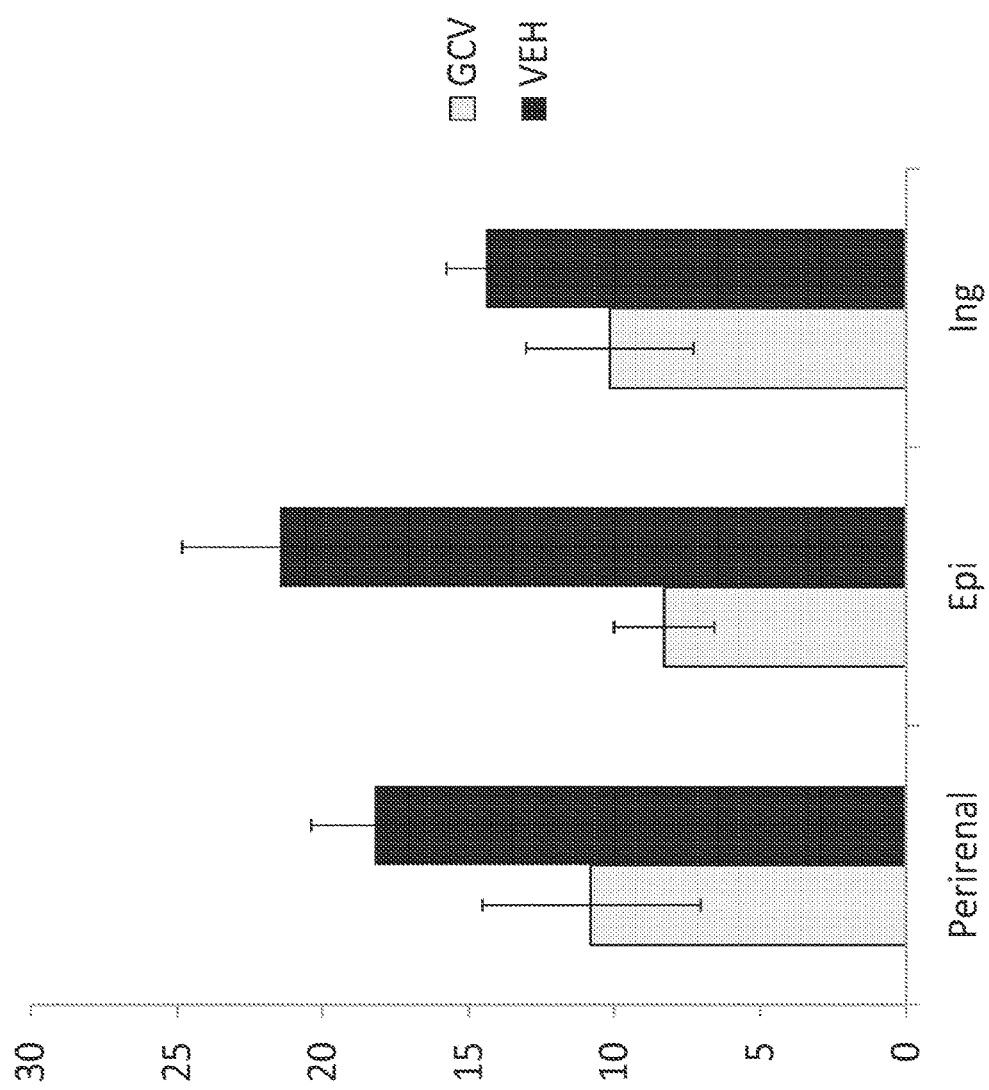

FIG. 68 illustrates decrease of senescent cells in adipose tissue of p16-3MR mice fed a high fat diet for four months and then treated with ganciclovir compared to mice treated with vehicle. The presence of senescent cells in perirenal, epididymal (Epi), or subcutaneous inguinal (Ing) adipose tissue was detected by SA-β-Gal staining.

Figure 69A:
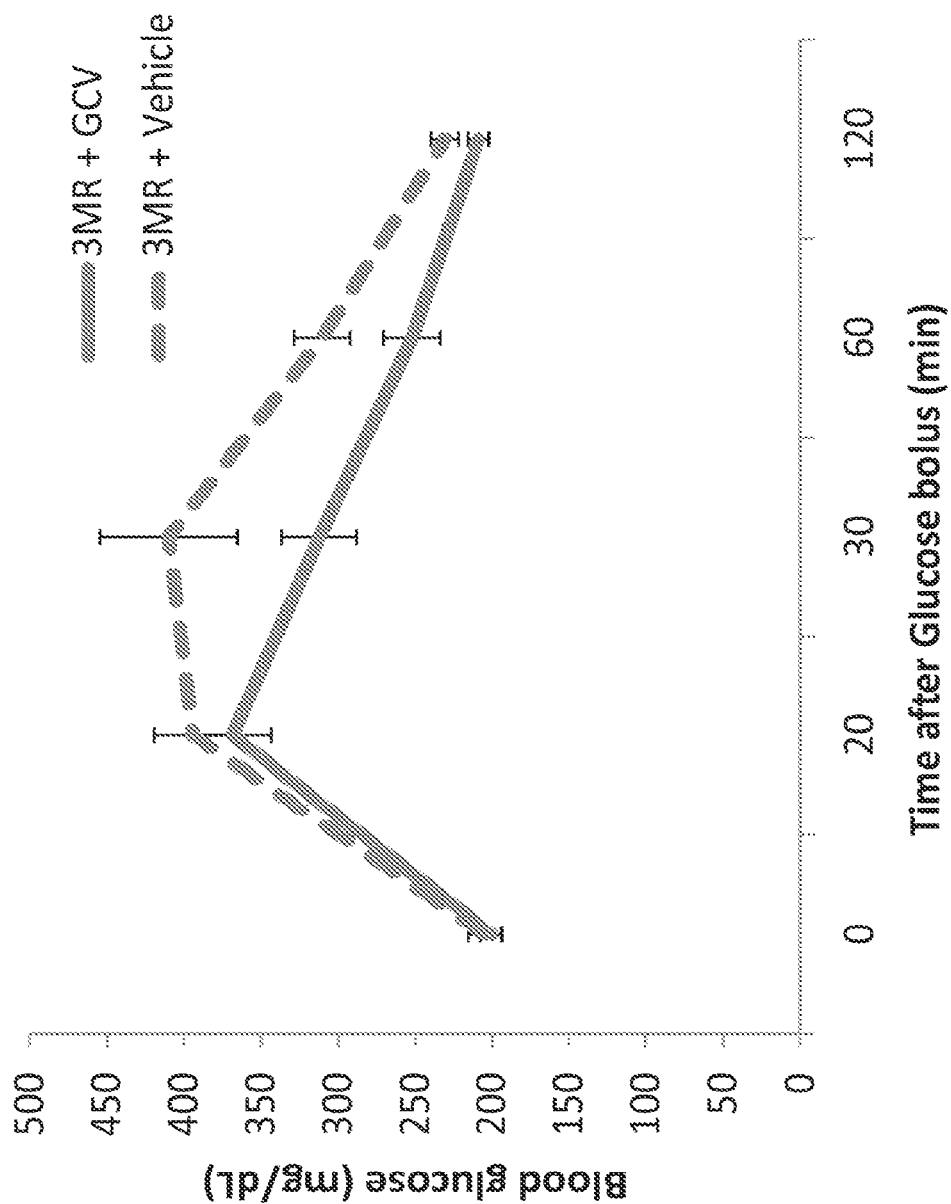
Figure 69B:
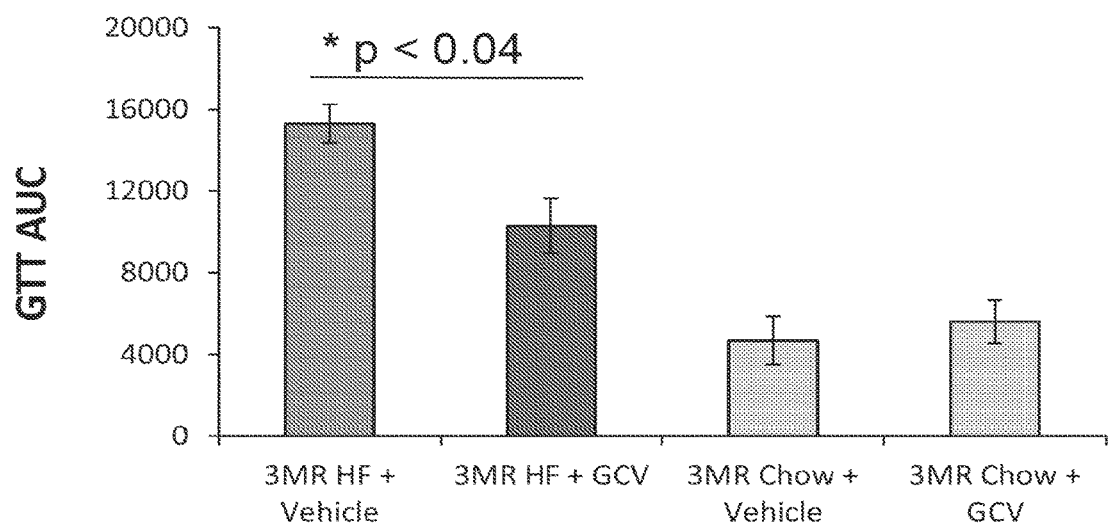
Figure 69C:
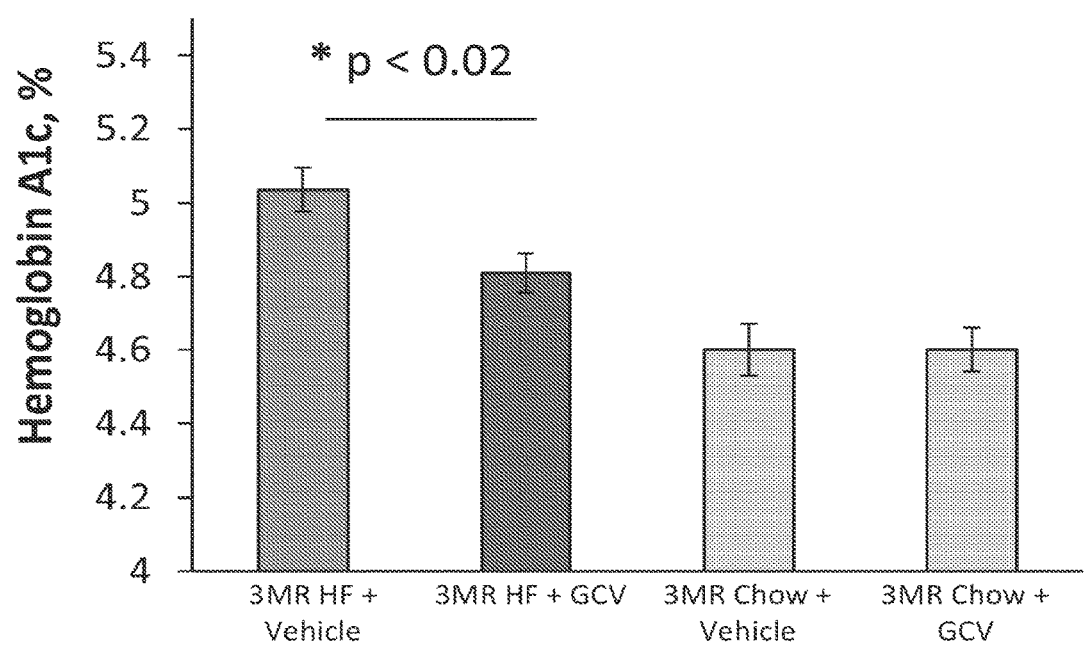

FIGS. 69A-C show the effect of ganciclovir treatment on glucose tolerance in p16-3MR mice fed a high fat diet. A bolus of glucose was given at time zero, and blood glucose was monitored for up to 2 hours to determine efficacy of glucose disposal (FIG. 69A). This is quantified as area under the curve (AUC), with a higher AUC indicating glucose intolerance. The glucose tolerance test (GTT) AUC's of mice treated with ganciclovir is shown in FIG. 69B. Hemoglobin A1c is shown in FIG. 69C. n=9; ANOVA.

Figure 70A:
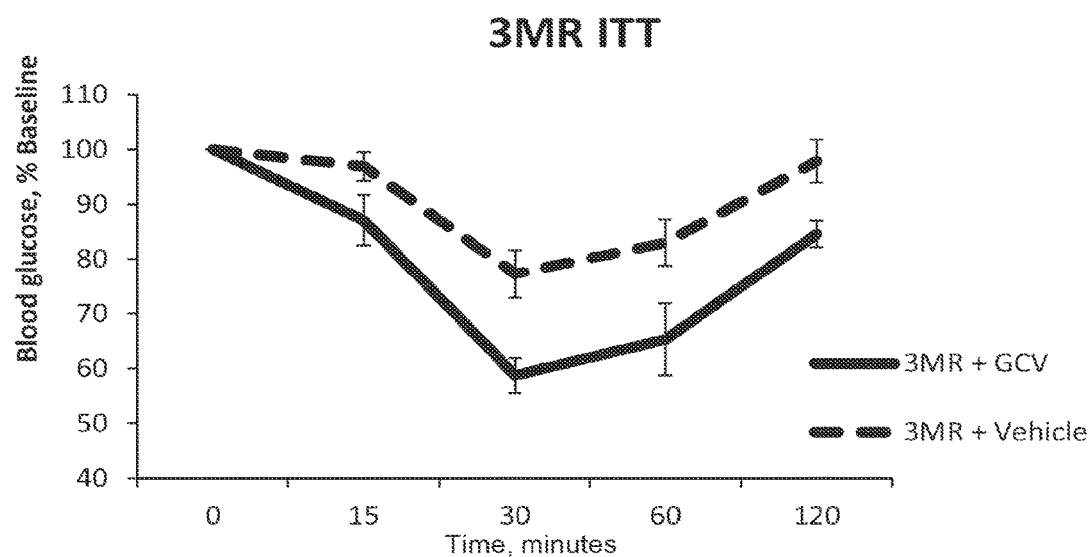
Figure 70B:
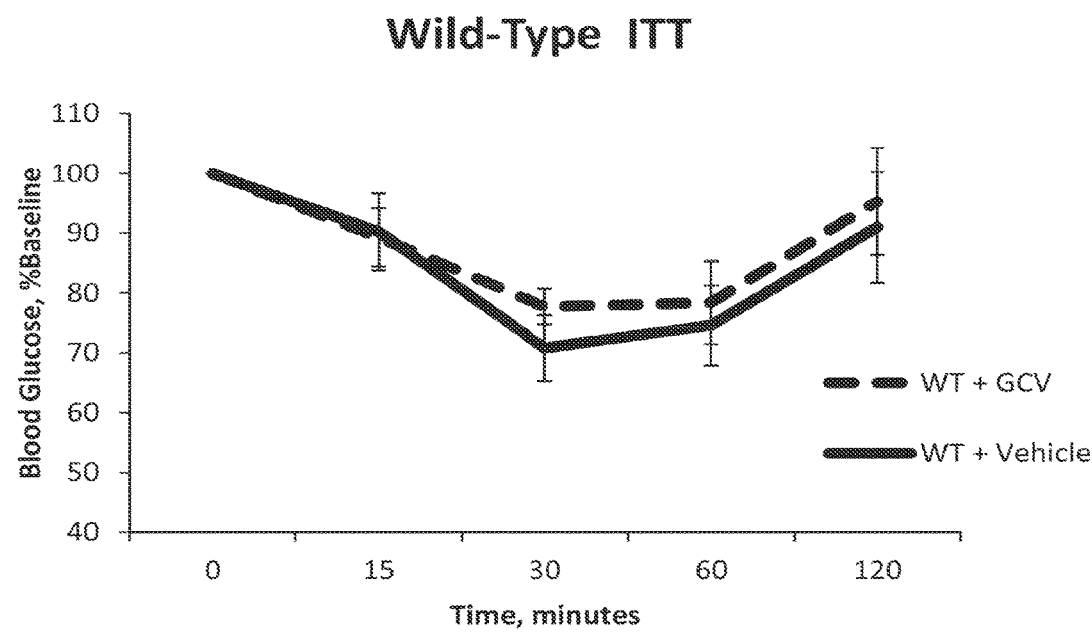

FIGS. 70A-70B show insulin sensitivity (Insulin Tolerance Testing (ITT)) of p16-3MR mice fed a high fat diet after ganciclovir administration. Blood glucose levels were measured at 0, 14, 30, 60, and 120 minutes after the administration of glucose bolus at time zero (see FIG. 70A). A change in insulin tolerance testing when ganciclovir was administered to wild-type mice was not observed (see FIG. 70B).

Figure 71:
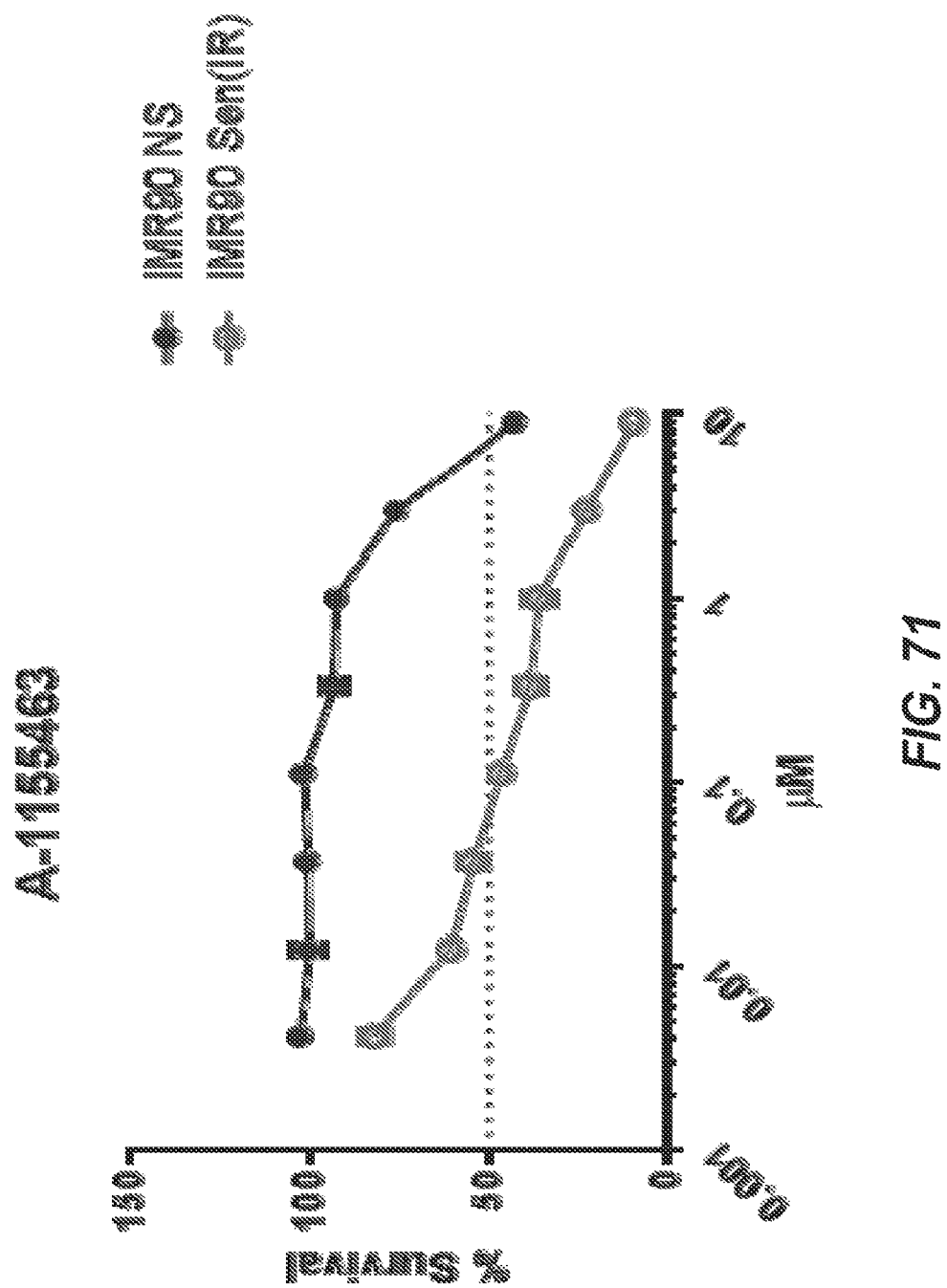

FIG. 71 illustrates the effect of A-1155463 on percent survival of senescent irradiated lung fibroblasts (Sen(IR) IMR90)) and percent survival of non-senescent IMR90 cells (Sen(IR)). NS=Non-senescent cells, which were not exposed to radiation.

DETAILED DESCRIPTION

Aging is a risk factor for most chronic diseases, disabilities, and declining health. Senescent cells, which are cells in replicative arrest, accumulate as an individual ages and may contribute partially or significantly to cell and tissue deterioration that underlies aging and age related diseases. Cells may also become senescent after exposure to an environmental, chemical, or biological insult or as a result of a disease. Provided herein are methods and agents for selective killing of senescent cells that are associated with numerous pathologies and diseases, including age-related pathologies and diseases. As disclosed herein, senescent cell associated diseases and disorders may be treated or prevented (i.e., likelihood of occurrence or development is reduced) by administering at least one senolytic agent. The senescent cell-associated disease or disorder treated or prevented by the agents and methods described herein include a cardiovascular disease or disorder, inflammatory or autoimmune disease or disorder, a pulmonary disease or disorder, a neurological disease or disorder, a dermatological disease or disorder, a chemotherapeutic side effect, a radiotherapy side effect, or metastasis, or a metabolic disease, all of which are described in greater detail herein. In certain specific embodiments, the senescent cell-associated diseases or disorders treated or prevented by the senolytic agents and methods described herein include, by way of example, idiopathic pulmonary fibrosis (IPF), chronic obstructive pulmonary disease (COPD), osteoarthritis, and cardiovascular diseases and disorders associated with arteriosclerosis, such as atherosclerosis. In certain embodiments, the senescence associated disease or disorder is not a cancer. As described in greater detail herein, senolytic agents include, for example, MDM2 inhibitors (e.g., nutlin 3a, RG-7112); inhibitors of one or more BCL-2 anti-apoptotic protein family members, which inhibitors inhibit a function of at least the anti-apoptotic protein, BCL-xL (e.g., ABT-263, ABT-737, WEHI-539, A-1155463); and Akt specific inhibitors (e.g., MK-2206).

Senolytic agents described herein are sufficient to kill significant numbers of senescent cells. Even though cells continue to become senescent in a treated subject, establishment of senescence, such as shown by the presence of a senescence-associated secretory phenotype (SASP), occurs over several days (see, e.g., Laberge et al., *Aging Cell* 11:569-78 (2012); Coppe et al., *PLoS Biol* 6: 2853-68 (2008); Coppe et al. *PLoS One* 5:39188 (2010); Rodier et al., *Nat. Cell Biol.* 11:973-979; Freund et al., *EMBO J.* 30:1536-1548 (2011)). Use of the senolytic agents described herein, therefore, offers the advantage that these agents can be administered less frequently, intermittently, and/or at a lower dose than many therapeutic agents commonly used for treating these diseases and disorders. The methods described herein describe use of such agents as senolytic agents that may be administered less frequently, intermittently, and/or at a lower dose than when the agents are used for treating cancer other diseases.

Senolytic Agents

A senolytic agent as used herein is an agent that "selectively" (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill (destroy, cause the death of) a non-senescent cell in a clinically significant or biologically significant manner. In certain embodiments, the senolytic agents described herein alter at least one signaling pathway in a manner that induces (initiates, stimulates, triggers, activates, promotes) and results in (i.e., causes, leads to) death of the senescent cell. The senolytic agent may alter, for example, either or both of a cell survival signaling pathway (e.g., Akt pathway) or an inflammatory pathway, for example, by antagonizing a protein within the cell survival and/or inflammatory pathway in a senescent cell.

Without wishing to be bound by a particular theory, the mechanism by which the inhibitors and antagonists described herein selectively kill senescent cells is by inducing (activating, stimulating, removing inhibition of) an apoptotic pathway that leads to cell death. Non-senescent cells may be proliferating cells or may be quiescent cells. In certain instances, exposure of non-senescent cells to the senolytic agent as used in the methods described herein may temporarily reduce the capability of non-senescent cell to proliferate; however, an apoptotic pathway is not induced and the non-senescent cell is not destroyed.

Certain senolytic agents that may be used in the methods described herein have been described as useful for treating a cancer; however, in the methods for treating a senescence associated disorder or disease, the senolytic agents are administered in a manner that would be considered different and likely ineffective for treating a cancer. The method used for treating a senescence associated disease or disorder with a senolytic agent described herein may comprise one or more of a decreased daily dose, decreased cumulative dose over a single treatment cycle, or decreased cumulative dose of the agent from multiple treatment cycles than the dose of an agent required for cancer therapy; therefore, the likelihood is decreased that one or more adverse effects (i.e., side effects) will occur, which adverse effects are associated with treating a subject according to a regimen optimized for treating a cancer. In contrast, as a senolytic agent, the compounds described herein may be administered at a lower dose than presently described in the art or in a manner that selectively kill senescent cells (e.g., intermittent dosing). In certain embodiments, the senolytic agents described herein may be administered at a lower cumulative dose per treatment course or treatment cycle that would likely be insufficiently cytotoxic to cancer cells to effectively treat the cancer. In other words, according to the methods described herein, the senolytic agent is not used in a manner that would be understood by a person skilled in the art as a primary therapy for treating a cancer, whether the agent is administered alone or together with one or more additional chemotherapeutic agents or radiotherapy to treat the cancer. Even though an agent as used in the methods described herein is not used in a manner that is sufficient to be considered as a primary cancer therapy, the methods and senolytic combinations described herein may be used in a manner (e.g., a short term course of therapy) that is useful for inhibiting metastases. A "primary therapy for cancer" as used herein means that when an agent, which may be used alone or together with one or more agents, is intended to be or is known to be an efficacious treatment for the cancer as determined by a person skilled in the medical and oncology arts, administration protocols for treatment of the cancer using the agent have been designed to achieve the relevant cancer-related endpoints. To further reduce toxicity, a senolytic agent may be administered at a site proximal to or in contact with senescent cells (not tumor cells). Localized delivery of senolytic agents is described in greater detail herein.

The senolytic agents described herein alter (i.e., interfere with, affect) one or more cellular pathways that are activated during the senescence process of a cell. Senolytic agents may alter either a cell survival signaling pathway (e.g., Akt pathway) or an inflammatory pathway or alter both a cell survival signaling pathway and an inflammatory pathway in a senescent cell. Activation of certain cellular pathways during senescence decreases or inhibits the cell's capability to induce, and ultimately undergo apoptosis. Without wishing to be bound by theory, the mechanism by which a senolytic agent selectively kills senescent cells is by inducing (activating, stimulating, removing inhibition of) an apoptotic pathway that leads to cell death. A senolytic agent may alter one or more signaling pathways in a senescent cell by interacting with one, two, or more target proteins in the one or more pathways, which results in removing or reducing suppression of a cell death pathway, such as an apoptotic pathway. Contacting or exposing a senescent cell to a senolytic agent to alter one, two, or more cellular pathways in the senescent cell, may restore the cell's mechanisms and pathways for initiating apoptosis. In certain embodiments, a senolytic agent is an agent that alters a signaling pathway in a senescent cell, which in turn inhibits secretion and/or expression of one or more gene products important for survival of a senescent cell. The senolytic agent may inhibit a biological activity of the gene product(s) important for survival of the senescent cell. Alternatively, the decrease or reduction of the level of the gene product(s) in the senescent cell may alter the biological activity of another cellular component, which triggers, initiates, activates, or stimulates an apoptotic pathway or removes or reduces suppression of the apoptotic pathway. As described herein, the senolytic agents are the biologically active agents and capable of selectively killing senescent cells in the absence of linkage or conjugation to a cytotoxic moiety (e.g., a toxin or cytotoxic peptide or cytotoxic nucleic acid). The senolytic agents are also active in selectively killing senescent cells in the absence of linkage or conjugation to a targeting moiety (e.g., an antibody or antigen-binding fragment thereof; cell binding peptide) that selectively binds senescent cells.

Two alternative modes of cell death can be distinguished, apoptosis and necrosis. The term apoptosis was initially used by Kerr and colleagues (*Br. J. Cancer* 26:239-57 (1972)) to describe the phenomenon as a mode of cell death morphologically distinct from coagulative necrosis. Apoptosis is typically characterized by the rounding of the cell, chromatin condensation (pyknosis), nuclear fragmentation (karyorhexis), and engulfment by neighboring cells (see, e.g., Kroemer et al., *Cell Death Differ.* 16:3-11 (2009)). Several molecular assays have been developed and are used in the art; however, the morphological changes, which are detected by light and electron microscopy, are viewed in the art as the optimal techniques to differentiate the two distinct modes of cell death (see, e.g., Kroemer et al., supra). Alternative cell death modes, such as caspase-independent apoptosis-like programmed cell death (PCD), autophagy, necrosis-like PCD, and mitotic catastrophe, have also been characterized (see, e.g., Golstein, *Biochem. Sci.* 32:37-43 (2007); Leist et al., *Nat. Rev. Mol. Cell Biol.* 2:589-98 (2001)). See, e.g., Caruso et al., *Rare Tumors* 5(2): 68-71 (2013); published online 2013 Jun. 7. doi: 10.3081/rt.2013.e18. Techniques and methods routinely practiced in the art and described herein (e.g., TUNEL) may be used to show that apoptotic cell death results from contact with the senolytic agents described herein.

In certain embodiments, a senolytic agent as used in the methods described herein is a small molecule compound. These senolytic agents that are small molecules may also be called herein senolytic compounds. In certain embodiments, the senolytic agents that are small molecules include those that are activated or that are pro-drugs which are converted to the active form by enzymes within the cell. In a more specific embodiment, the enzymes that convert a pro-drug to an active senolytic form are those expressed at a higher level in senescent cells than in non-senescent cells.

Senolytic agents described herein that may alter at least one signaling pathway include an agent that inhibits an activity of at least one of the target proteins within the pathway. The senolytic agent may be a specific inhibitor of one or more BCL-2 anti-apoptotic protein family members wherein the inhibitor inhibits at least BCL-xL (e.g., a Bcl-2/Bcl-xL/Bcl-w inhibitor; a selective Bcl-xL inhibitor; a Bcl-xL/Bcl-w inhibitor); an Akt kinase specific inhibitor; or an MDM2 inhibitor. In embodiments, molecules such as quercetin (and analogs thereof), enzastaurin, and dasatinib are excluded and are not compounds used in the methods and compositions described herein. In other particular embodiments, methods comprise use of at least two senolytic agents wherein at least one senolytic agent and a second senolytic agent are each different and independently alter either one or both of a survival signaling pathway and an inflammatory pathway in a senescent cell.

Small Molecules

Senolytic agents that may be used in the methods for treating or preventing a senescence-associated disease or disorder include small organic molecules. Small organic molecules (also called small molecules or small molecule compounds herein) typically have molecular weights less than $10^5$ daltons, less than $10^4$ daltons, or less than $10^3$ daltons. In certain embodiments, a small molecule senolytic agent does not violate the following criteria more than once: (1) no more than 5 hydrogen bond donors (the total number of nitrogen-hydrogen and oxygen-hydrogen bonds); (2) not more than 10 hydrogen bond acceptors (all nitrogen or oxygen atoms); (3) a molecular mass less than 500 daltons; (4) an octanol-water partition coefficient[5] log P not greater than 5.

MDM2 Inhibitors

In certain embodiments, the senolytic agent may be an MDM2 inhibitor. An MDM2 (murine double minute 2) inhibitor that may be used in the methods for selectively killing senescent cells and treating or preventing (i.e., reducing or decreasing the likelihood of occurrence or development of) a senescence-associated disease or disorder may be a small molecule compound that belongs to any one of the following classes of compounds, for example, a cis-imidazoline compound, a spiro-oxindole compound, a benzodiazepine compound, a piperidinone compound, a tryptamine compound, and CGM097, and related analogs. In certain embodiments, the MDM2 inhibitor is also capable of binding to and inhibiting an activity of MDMX (murine double minute X, which is also known as HDMX in humans). The human homolog of MDM2 is called HDM2 (human double minute 2) in the art. Therefore, when a subject treated by the methods described herein is a human subject, the compounds described herein as MDM2 inhibitors also inhibit binding of HDM2 to one or more of its ligands.

MDM2 is described in the art as an E3 ubiquitin ligase that can promote tumor formation by targeting tumor suppressor proteins, such as p53, for proteasomal degradation through the 26S proteasome (see, e.g., Haupt et al. *Nature* 387: 296-299 1997; Honda et al., *FEBS Lett* 420: 25-27 (1997); Kubbutat et al., *Nature* 387: 299-303 (1997)). MDM2 also affects p53 by directly binding to the N-terminal end of p53, which inhibits the transcriptional activation function of p53 (see, e.g., Momand et al., *Cell* 69: 1237-1245 (1992); Oliner et al., *Nature* 362: 857-860 (1993)). Mdm2 is in turn regulated by p53; p53 response elements are located in the promoter of the Mdm2 gene (see, e.g., Barak et al., *EMBO J* 12:461-68 (1993)); Juven et al., *Oncogene* 8:3411-16 (1993)); Perry et al., *Proc. Natl. Acad. Sci.* 90:11623-27 (1993)). The existence of this negative feedback loop between p53 and Mdm2 has been confirmed by single-cell studies (see, e.g., Lahav, *Exp. Med. Biol.* 641: 28-38 (2008)). See also Manfredi, *Genes & Development* 24:1580-89 (2010).

Reports have described several activities and biological functions of MDM2. These reported activities include the following: acts as a ubiquitin ligase E3 toward itself and ARRB1; permits nuclear export of p53; promotes proteasome-dependent ubiquitin-independent degradation of retinoblastoma RB1 protein; inhibits DAXX-mediated apoptosis by inducing its ubiquitination and degradation; component of TRIM28/KAP1-MDM2-p53 complex involved in stabilizing p53; component of TRIM28/KAP1-ERBB4-MDM2 complex that links growth factor and DNA damage response pathways; mediates ubiquitination and subsequent proteasome degradation of DYRK2 in the nucleus; ubiquitinates IGF1R and SNAI1 and promotes them to proteasomal degradation. MDM2 has also been reported to induce mono-ubiquitination of the transcription factor FOXO4 (see, e.g., Brenkman et al., *PLOS One* 3(7):e2819, doi:10.1371/journal.pone.0002819). The MDM2 inhibitors described herein may disrupt the interaction between MDM2 and any one or more of the aforementioned cellular components.

In one embodiment, a compound useful for the methods described herein is a cis-imidazoline small molecule inhibitor. Cis-imidazoline compounds include those called nutlins in the art. Similar to other MDM2 inhibitors described herein, nutlins are cis-imidazoline small molecule inhibitors of the interaction between MDM2 and p53 (see Vassilev et al., *Science* 303 (5659): 844-48 (2004)). Exemplary cis-imidazolines compounds that may be used in the methods for selectively killing senescent cells and treating or preventing (i.e., reducing or decreasing the likelihood of occurrence or development of) a senescence-associated disease or disorder are described in U.S. Pat. Nos. 6,734,302; 6,617, 346; 7,705,007 and in U.S. Patent Application Publication Nos. 2005/0282803; 2007/0129416; 2013/0225603. In certain embodiments, the methods described herein comprise use of a nutlin compound called Nutlin-1; or a nutlin compound called Nutlin-2; or a Nutlin compound called Nutlin-3 (see CAS Registry No. 675576-98-4 and No. 548472-68-0). The active enantiomer of Nutlin-3 (4-[[4S, 5R)-4,5-bis(4-chlorophenyl)-4,5-dihydro-2-[4-methoxy-2-(1-methylethoxy)phenyl]-1H-imidazol-1-yl]carbonyl]-2- piperazinone) is called Nutlin-3a in the art. In certain embodiments, the methods described herein comprise use of Nutlin-3a for selectively killing senescent cells.

Nutlin-3 is described in the art as a nongenotoxic activator of the p53 pathway, and the activation of p53 is controlled by the murine double minute 2 (MDM2) gene. The MDM2 protein is an E3 ubiquitin ligase and controls p53 half-life by way of ubiquitin-dependent degradation. Nutlin-3a has been investigated in pre-clinical studies (e.g., with respect to pediatric cancers) and clinical trials for treatment of certain cancers (e.g., retinoblastoma). To date in vitro and pre-clinical studies with Nutlin-3 have suggested that the compound has variable biological effects on the function of cells exposed to the compound. For example, Nutlin-3 reportedly increases the degree of apoptosis of cancer cells in hematological malignancies including B-cell malignancies (see, e.g., Zauli et al., Clin. Cancer Res. 17:762-70 (2011; online publication on Nov. 24, 2010) and references cited therein) and in combination with other chemotherapeutic drugs, such as dasatinib, the cytotoxic effect appears synergistic (see, e.g., Zauli et al., supra).

Another exemplary cis-imidazoline small molecule compound useful for selectively killing senescent cells is RG-7112 (Roche) (CAS No: 939981-39-2; IUPAC name: ((4S,5R)-2-(4-(tert-butyl)-2-ethoxyphenyl)-4,5-bis(4-chlorophenyl)-4,5-dimethyl-4,5-dihydro-1H-imidazol-1-yl)(4-(3-(methylsulfonyl)propyl)piperazin-1-yl)methanone. See U.S. Pat. No. 7,851,626; Tovar et al., Cancer Res. 72:2587-97 (2013).

In another particular embodiment, the MDM2 inhibitor is a cis-imidazoline compound called RG7338 (Roche) (IPUAC Name: 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid) (CAS 1229705-06-9); Ding et al., J. Med. Chem. 56(14):5979-83. Doi: 10.1021/jm400487c. Epub 2013 Jul. 16; Zhao et al., J. Med. Chem. 56(13):5553-61 (2013) doi: 10.1021/jm4005708. Epub 2013 Jun. 20). Yet another exemplary nutlin compound is RO5503781. Other potent cis-imidazoline small molecule compounds include dihydroimidazothiazole compounds (e.g., DS-3032b; Daiichi Sankyo) described by Miyazaki, (see, e.g., Miyazaki et al., Bioorg. Med. Chem. Lett. 23(3):728-32 (2013) doi: 10.1016/j.bmcl.2012.11.091. Epub 2012 Dec. 1; Miyazaki et al., Bioorg. Med. Chem. Lett. 22(20):6338-42 (2012) doi: 10.1016/j.bmcl.2012.08.086. Epub 2012 Aug. 30; Int'l Patent Appl. Publ. No. WO 2009/151069 (2009)).

In still other embodiments, a cis-imidazoline compound that may be used in the methods described herein is a dihydroimidazothiazole compound.

In other embodiments, the MDM2 small molecule inhibitor is a spiro-oxindole compound. See, for example, compounds described in Ding et al., J. Am. Chem. Soc. 2005; 127:10130-31; Shangary et al., Proc Natl Acad Sci USA 2008; 105:3933-38; Shangary et al., Mol Cancer Ther 2008; 7:1533-42; Shangary et al., Mol Cancer Ther 2008; 7:1533-42; Hardcastle et al., Bioorg. Med. Chem. Lett. 15:1515-20 (2005); Hardcastle et al., J. Med. Chem. 49(21):6209-21 (2006); Watson et al., Bioorg. Med. Chem. Lett. 21(19): 5916-9 (2011) doi: 10.1016/j.bmcl.2011.07.084. Epub 2011 Aug. 9. Other examples of spiro-oxindole compounds that are MDM2 inhibitors are called in the art MI-63, MI-126; MI-122, MI-142, MI-147, MI-18, MI-219, MI-220, MI-221, and MI-773. Another specific spiro-oxindole compound is 3-(4-chlorophenyl)-3-((1-(hydroxymethyl)cyclopropyl) methoxy)-2-(4-nitrobenzyl)isoindolin-1-one. Another compound is called MI888 (see, e.g., Zhao et al., J. Med. Chem. 56(13):5553-61 (2013); Int'l Patent Appl. Publ. No. WO 2012/065022).

In still other embodiments, the MDM2 small molecule inhibitor that may be used in the methods described herein is a benzodiazepinedione (see, e.g., Grasberger et al., J Med Chem 2005; 48:909-12; Parks et al., Bioorg Med Chem Lett 2005; 15:765-70; Raboisson et al., Bioorg. Med. Chem. Lett. 15:1857-61 (2005); Koblish et al., Mol. Cancer Ther. 5:160-69 (2006)). Benzodiazepinedione compounds that may be used in the methods described herein include 1,4-benzodiazepin-2,5-dione compounds. Examples of benzodiazepinedione compounds include 5-[(3S)-3-(4-chlorophenyl)-4-[(R)-1-(4-chlorophenyl)ethyl]-2,5-dioxo-7-phenyl-1,4-diazepin-1-yl]valeric acid and 5-[(3S)-7-(2-bromophenyl)-3-(4-chlorophenyl)-4-[(R)-1-(4-chlorophenyl)ethyl]-2,5-dioxo-1,4-diazepin-1-yl]valeric acid (see, e.g., Raboisson et al., supra). Other benzodiazepinedione compounds are called in the art TDP521252 (IUPAC Name: 5-[(3S)-3-(4-chlorophenyl)-4-[(1R)-1-(4-chlorophenyl)ethyl]-7-ethynyl-2,5-dioxo-3H-1,4-benzodiazepin-1-yl]pentanoic acid) and TDP665759 (IUPAC Name: (3S)-4-[(1R)-1-(2-amino-4-chlorophenyl)ethyl]-3-(4-chlorophenyl)-7-iodo-1-[3-(4-methylpiperazin-1-yl)propyl]-3H-1,4-benzodiazepine-2,5-dione) (see, e.g., Parks et al., supra; Koblish et al., supra) (Johnson & Johnson, New Brunswick, N.J.).

In yet another embodiment, the MDM2 small molecule inhibitor is a terphenyl (see, e.g., Yin et al., Angew Chem Int Ed Engl 2005; 44:2704-707; Chen et al., Mol Cancer Ther 2005; 4:1019-25). In yet another specific embodiment, the MDM2 inhibitor that may be used in the methods described herein is a quinilol (see, e.g., Lu et al., J Med Chem 2006; 49:3759-62). In yet another certain embodiment, the MDM2 inhibitor is a chalcone (see, e.g., Stoll et al., Biochemistry 2001; 40:336-44). In yet another particular embodiment, the MDM2 inhibitor is a sulfonamide (e.g., NSC279287) (see, e.g., Galatin et al., J Med Chem 2004; 47:4163-65).

In other embodiments, a compound that may be used in the methods described herein is a tryptamine, such as serdemetan (JNJ-26854165; chemical name: N1-(2-(1H-indol-3-yl)ethyl)-N4-(pyridine-4-yl)benzene-1,4-diamine; CAS No. 881202-45-5) (Johnson & Johnson, New Brunswick, N.J.). Serdemetan is a tryptamine derivative that activates p53 and acts as a HDM2 ubiquitin ligase antagonist (see, e.g., Chargari et al., Cancer Lett. 312(2):209-18 (2011) doi: 10.1016/j.canlet.2011.08.011. Epub 2011 Aug. 22; Kojima et al., Mol. Cancer Ther. 9:2545-57 (2010); Yuan et al., J. Hematol. Oncol. 4:16 (2011)).

In other particular embodiments, MDM2 small molecule inhibitors that may be used in the methods described herein include those described in Rew et al., J. Med. Chem. 55:4936-54 (2012); Gonzalez-Lopez de Turiso et al., J. Med. Chem. 56:4053-70 (2013); Sun et al., J. Med. Chem. 57:1454-72 (2014); Gonzalez et al., J. Med. Chem. 2014 Mar. 4 [Epub ahead of print]; Gonzalez et al., J. Med. Chem. 2014 Mar. 6 [Epub ahead of print].

In still other embodiments, the MDM2 inhibitor is a piperidinone compound. An example of a potent MDM2 piperidinone inhibitor is AM-8553 ({(3R,5R,6S)-5-(3-Chlorophenyl)-6-(4-chlorophenyl)-1-[(2S,3S)-2-hydroxy-3-pentanyl]-3-methyl-2-oxo-3-piperidinyl}acetic acid; CAS No. 1352064-70-0) (Amgen, Thousand Oaks, Calif.).

In other particular embodiments, an MDM2 inhibitor that may be used in the methods described herein is a piperidine (Merck, Whitehouse Station, N.J.) (see, e.g., Int'l Patent Appl. Publ. No. WO 2011/045771). In other embodiments, an MDM2 inhibitor that may be used in the methods is an imidazole-indole compound (Novartis) (see, e.g., Int'l Patent Appl. Publ. No. WO 2008/119741).

Examples of compounds that bind to MDM2 and to MDMX and that may be used in the methods described herein include RO-2443 and RO-5963 ((Z)-2-(4-((6-Chloro-7-methyl-1H-indol-3-yl)methylene)-2,5-dioxoimidazolidin-1-yl)-2-(3,4-difluorophenyl)-N-(1,3-dihydroxpropan-2-yl) acetamide) (see, e.g., Graves et al., *Proc. Natl. Acad. Sci. USA* 109:11788-93 (2012); see also, e.g., Zhao et al., 2013, *BioDiscovery*, supra).

In another specific embodiment, an MDM2 inhibitor referred to in the art as CGM097 may be used in the methods described herein for selectively killing senescent cells and for treating a senescence-associated disease or disorder.

Inhibitors of BCL-2 Anti-Apoptotic Family of Proteins

In certain embodiments, the senolytic agent may be an inhibitor of one or more proteins in the BCL-2 family. In certain embodiments, the at least one senolytic agent is selected from an inhibitor of one or more BCL-2 anti-apoptotic protein family members wherein the inhibitor inhibits at least BCL-xL. Inhibitors of BCL-2 anti-apoptotic family of proteins alter at least a cell survival pathway. Apoptosis activation may occur via an extrinsic pathway triggered by the activation of cell surface death receptors or an intrinsic pathway triggered by developmental cues and diverse intracellular stresses. This intrinsic pathway, also known as the stress pathway or mitochondrial pathway, is primarily regulated by the BCL-2 family, a class of key regulators of caspase activation consisting of anti-apoptotic (pro-survival) proteins having BH1-BH4 domains (BCL-2 (i.e., the BCL-2 protein member of the BCL-2 anti-apoptotic protein family), BCL-xL, BCL-w, A1, MCL-1, and BCL-B); pro-apoptotic proteins having BH1, BH2, and BH3 domains (BAX, BAK, and BOK); and pro-apoptotic BH3-only proteins (BIK, BAD, BID, BIM, BMF, HRK, NOXA, and PUMA) (see, e.g., Cory et al., *Nature Reviews Cancer* 2:647-56 (2002); Cory et al., *Cancer Cell* 8:5-6 (2005); Adams et al., *Oncogene* 26:1324-1337 (2007)). BCL-2 anti-apoptotic proteins block activation of pro-apoptotic multi-domain proteins BAX and BAK (see, e.g., Adams et al., *Oncogene* 26:1324-37 (2007)). While the exact mechanism of apoptosis regulation is unknown, it is hypothesized that BH3-only proteins unleashed by intracellular stress signals bind to anti-apoptotic BCL-2 like proteins via a BH3 "ligand" to a "receptor" BH3 binding groove formed by BH1-3 regions on anti-apoptotic proteins, thereby neutralizing the anti-apoptotic proteins (see, e.g., Letai et al., *Cancer Cell* 2:183-92 (2002); Adams et al., *Oncogene*, supra). BAX and BAK can then form oligomers in mitochondrial membranes, leading to membrane permeabilization, release of cytochrome C, caspase activation, and ultimately apoptosis (see, e.g., Adams et al., *Oncogene*, supra).

As used herein and unless otherwise stated, a BCL-2 family member that is inhibited by the agents described herein is a pro-survival (anti-apoptotic) family member. The senolytic agents used in the methods described herein inhibit one or more functions of the BCL-2 anti-apoptotic protein, BCL-xL (which may also be written herein and in the art as Bcl-xL, BCL-XL, Bcl-xl, or Bcl-XL). In certain embodiments, in addition to inhibiting BCL-xL function, the inhibitor may also interact with and/or inhibit one or more functions of BCL-2 (i.e., BCL-xL/BCL-2 inhibitors). In yet another certain embodiment, senolytic agents used in the methods described herein are classified as inhibitors of each of BCL-xL and BCL-w (i.e., BCL-xL/BCL-w inhibitors). In still another specific embodiment, senolytic agents used in the methods described herein that inhibit BCL-xL may also interact with and inhibit one or more functions of each of BCL-2 (i.e., the BCL-2 protein) and BCL-w (i.e., BCL-xL/BCL-2/BCL-w inhibitors), thereby causing selective killing of senescent cells. In certain embodiments, a BCL-2 anti-apoptotic protein inhibitor interferes with the interaction between the BCL-2 anti-apoptotic protein family member (which includes at least BCL-xL) and one or more ligands or receptors to which the BCL-2 anti-apoptotic protein family member would bind in the absence of the inhibitor. In other particular embodiments, an inhibitor of one or more BCL-2 anti-apoptotic protein family members wherein the inhibitor inhibits at least BCL-xL specifically binds only to one or more of BCL-xL, BCL-2, BCL-w and not to other Bcl-2 anti-apoptotic Bcl-2 family members, such as Mcl-1 and BCL2A1.

In still another embodiment, the senolytic agent used in the methods described herein is a BCL-xL selective inhibitor and inhibits one or more functions of BCL-xL. Such senolytic agents that are BCL-xL selective inhibitors do not inhibit the function of one or more other BCL-2 anti-apoptotic proteins in a biologically or statistically significant manner. BCL-xL may also be called BCL2L1, BCL2-like 1, BCLX, BCL2L, BCLxL, or BCL-xL herein and in the art. In one embodiment, BCL-xL selective inhibitors alter (e.g., reduce, inhibit, decrease, suppress) one or more functions of BCL-xL but do not significantly inhibit one or more functions of other proteins in the BCL-2 anti-apoptotic protein family (e.g., BCL-2 or BCL-w). In certain embodiments, a BCL-xL selective inhibitor interferes with the interaction between BCL-xL and one or more ligands or receptors to which BCL-xL would bind in the absence of the inhibitor. In certain particular embodiments, a senolytic agent that inhibits one or more of the functions of BCL-xL selectively binds to human BCL-xL but not to other proteins in the BCL-2 family, which effects selective killing of senescent cells.

BCL-xL is an anti-apoptotic member of the BCL-2 protein family. BCL-xL also plays an important role in the crosstalk between autophagy and apoptosis (see, e.g., Zhou et al., *FEBS J.* 278:403-13 (2011)). BCL-xL also appears to play a role in bioenergetic metabolism, including mitochondrial ATP production, $Ca^{2+}$ fluxes, and protein acetylation, as well as on several other cellular and organismal processes such as mitosis, platelet aggregation, and synaptic efficiency (see, e.g., Michels et al., *International Journal of Cell Biology*, vol. 2013, Article ID 705294, 10 pages, 2013. doi:10.1155/2013/705294). In certain embodiments, the BCL-xL inhibitors described herein may disrupt the interaction between BCL-xL and any one or more of the aforementioned BH3-only proteins to promote apoptosis in cells.

In certain embodiments, a BCL-xL inhibitor is a selective inhibitor, meaning, that it preferentially binds to BCL-xL over other anti-apoptotic BCL2 family members (e.g., BCL-2, MCL-1, BCL-w, BCL-b, and BFL-1/A1). In certain embodiments, a BCL-XL selective inhibitor exhibits at least a 5-fold, 10-fold, 50-fold, 100-fold, 1000-fold, 10000-fold, 20000-fold, or 30000-fold selectivity for binding a BCL-XL protein or nucleic add over a BCL-2 protein or nucleic acid. In certain embodiments, a BCL-xL selective inhibitor exhibits at least a 5-fold, 10-fold, 50-fold, 100-fold, 1000-fold, 10000-fold, 20000-fold, or 30000-fold selectivity for binding a BCL-xL protein or nucleic acid over a MCL-1 protein or nucleic acid. In certain embodiments, a BCL-xL selective inhibitor exhibits at least a 5-fold, 10-fold, 50-fold, 100-fold, 1000-fold, 10000-fold, 20000-fold, or 30000-fold selectivity for binding a BCL-xL protein or nucleic acid over a BCL-w protein or nucleic acid. In certain embodiments, a BCL-xL selective inhibitor exhibits at least a 5-fold, 10-fold, 50-fold, 100-fold, 1000-fold, 10000-fold, 20000-fold, or 30000-fold selectivity for binding a BCL-XL protein or nucleic acid over a BCL-B protein or nucleic add. In certain embodiments, a BCL-XL selective inhibitor exhibits at least a 5-fold, 10-fold, 50-fold, 100-fold, 1000-fold, 10000-fold, 20000-fold, or 30000-fold selectivity for binding a BCL-xL protein or nucleic acid over an A1 protein or nucleic acid. As described herein, in certain embodiments, an inhibitor of one or more BCL-2 anti-apoptotic protein family members wherein the inhibitor inhibits at least BCL-xL (e.g., a BCL-xL selective inhibitor) has no detectable binding to MCL-1 or to BCL2A1.

Methods for measuring binding affinity of a BCL-xL inhibitor for BCL-2 family proteins are known in the art. By way of example, binding affinity of a BCL-xL inhibitor may be determined using a competition fluorescence polarization assay in which a fluorescent BAK BH3 domain peptide is incubated with BCL-xL protein (or other BCL-2 family protein) in the presence or absence of increasing concentrations of the BCL-XL inhibitor as previously described (see, e.g., U.S. Patent Publication 20140005190; Park et al., Cancer Res. 73:5485-96 (2013); Wang et al., Proc. Natl. Acad. Sci USA 97:7124-9 (2000); Zhang et al., Anal. Biochem, 307:70-5 (2002); Bruncko et al., J. Med. Chem, 50:641-62 (2007)). Percent inhibition may be determined by the equation: 1-[(mP value of well–negative control)/range)]×100%. Inhibitory constant ($K_i$) value is determined by the formula: $K_i=[I]_{50}/([L]_{50}/K_d+[P]_0/K_d+1)$ as described in Bruncko et al., J. Med. Chem. 50:641-62 (2007) (see, also, Wang, FEBS Lett. 360:111-114 (1995)).

Agents (e.g., BCL-xL selective inhibitors, BCL-xL/BCL-2 inhibitors, BCL-xL/BCL-2/BCL-w inhibitors, BCL-xL/BCL-w inhibitors) used in the methods described herein that selectively kill senescent cells include, by way of example, a small molecule.

In particular embodiments, the BCL-xL inhibitor is a small molecule compound that belongs to any one of the following classes of compounds, for example, a benzothiazole-hydrazone compound, aminopyridine compound, benzimidazole compound, tetrahydroquinoline compound, and phenoxyl compound and related analogs.

In one embodiment, a BCL-xL selective inhibitor useful for the methods described herein is a benzothiazole-hydrazone small molecule inhibitor. Benzothiazole-hydrazone compounds include WEHI-539 (5-[3-[4-(aminomethyl)phenoxy]propyl]-2-[(8E)-8-(1,3-benzothiazol-2-ylhydrazinylidene)-6,7-dihydro-5H-naphthalen-2-yl]-1,3-thiazole-4-carboxylic acid), a BH3 peptide mimetic that selectively targets BCL-xL (see, e.g., Lessene et al., Nature Chemical Biology 9:390-397 (2013)). In certain embodiments, the methods described herein comprise use of WEHI-539 for selectively killing senescent cells.

In other embodiments, the BCL-xL selective inhibitor is an aminopyridine compound. An aminopyridine compound that may be used as a selective BCL-xL inhibitor is BXI-61 (3-[(9-amino-7-ethoxyacridin-3-yl)diazenyl]pyridine-2,6-diamine) (see, e.g., Park et al., Cancer Res. 73:5485-96 (2013); U.S. Patent Publ. No. 2009-0118135). In certain embodiments, the methods described herein comprise use of BXI-61 for selectively killing senescent cells.

In still other embodiments, the BCL-xL selective inhibitor that may be used in the methods described herein is a benzimidazole compound. An example of a benzimidazole compound that may be used as a selective BCL-XL inhibitor is BXI-72 (2'-(Hydroxyphenyl)-5-(4-methyl-1-piperazinyl)-2,5'-bi(1H-benzimidazole)trihydrochloride) (see, e.g., Park et al., supra). In certain embodiments, the methods described herein comprise use of BXI-72 for selectively killing senescent cells.

In yet another embodiment, the BCL-xL selective inhibitor is a tetrahydroquinoline compound (see, e.g., U.S. Patent Publ. No. 2014-0005190). Examples of tetrahydroquinoline compounds that may be used as selective BCL-xL inhibitors are shown in Table 1 of U.S. Patent Publ. No. 2014-0005190 and described therein. Other inhibitors described therein may inhibit other BCL-2 family members (e.g., BCL-2) in addition to BCL-xL.

In other embodiments, a BCL-xL selective inhibitor is a phenoxyl compound. An example of a phenoxyl compound that may be used as a selective BCL-xL inhibitor is 2[[3-(2,3-dichlorophenoxy) propyl]amino]ethanol (2,3-DCPE) (see, Wu et al., Cancer Res. 64:1110-1113 (2004)). In certain embodiments, the methods described herein comprise use of 2,3-DCPE for selectively killing senescent cells.

In still another embodiment, an inhibitor of a Bcl-2 anti-apoptotic family member that inhibits at least BCL-xL is described in U.S. Pat. No. 8,232,273. In a particular embodiment, the inhibitor is a BCL-xL selective inhibitor called A-1155463 (see, e.g., Tao et al., ACS Med. Chem. Lett., 2014, 5(10): 1088-1093).

In other embodiments, a senolytic agent of interest inhibits other BCL-2 anti-apoptotic family members in addition to BCL-xL. For example, methods described herein comprise use of BCL-xL/BCL-2 inhibitors, BCL-xL/BCL-2/BCL-w inhibitors, and BCL-xL/BCL-w inhibitors and analogs thereof. In certain embodiments, the inhibitors include compounds that inhibit BCL-2 and BCL-xL, which inhibitors may also inhibit BCL-w. Examples of these inhibitors include ABT-263 (4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide or IUPAC, (R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide) (see, e.g., Park et al., 2008, J. Med. Chem. 51:6902; Tse et al., Cancer Res., 2008, 68:3421; Int'l Patent Appl. Pub. No. WO 2009/155386; U.S. Pat. Nos. 7,390,799, 7,709,467, 7,906,505, 8,624,027) and ABT-737 (4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]benzamide, Benzamide, 4-[4-[(4'-chloro[1,1'-biphenyl]-2-yl)methyl]-1-piperazinyl]-N-[[4-[[(1R)-3-(dimethylamino)-1-[(p-henylthio)methyl]propyl]amino]-3-nitrophenyl]sulfonyl]- or 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (see, e.g., Oltersdorf et al., Nature, 2005, 435:677; U.S. Pat. Nos. 7,973, 161; 7,642,260). In other embodiments, the BCL-2 anti-apoptotic protein inhibitor is a quinazoline sulfonamide compound (see, e.g., Sleebs et al., 2011, J. Med. Chem. 54:1914). In still another embodiment, the BCL-2 anti-apoptotic protein inhibitor is a small molecule compound as described in Zhou et al., J. Med. Chem., 2012, 55:4664 (see, e.g., Compound 21 (R)-4-(4-chlorophenyl)-3-(3-(4-(4-(4-((4-(dimethylamino)-1-(phenylthio)butan-2-yl)amino)-3-nitrophenylsulfonamido)phenyl)piperazin-1-yl)phenyl)-5-ethyl-1-methyl-1H-pyrrole-2-carboxylic acid) and Zhou et al., J. Med. Chem., 2012, 55:6149 (see, e.g., Compound 14 (R)-5-(4-Chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-ethyl-2-methyl-1H- pyrrole-3-carboxylic acid; Compound 15 (R)-5-(4-Chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-isopropyl-2-methyl-1H-pyrrole-3-carboxylic acid). In other embodiments, the BCL-2 anti-apoptotic protein inhibitor is a BCL-2/BCL-xL inhibitor such as BM-1074 (see, e.g., Aguilar et al., 2013, *J. Med. Chem.* 56:3048); BM-957 (see, e.g., Chen et al., 2012, *J. Med. Chem.* 55:8502); BM-1197 (see, e.g., Bai et al., *PLoS One* 2014 Jun. 5; 9(6):e99404. Doi: 10.1371/journal.pone.009904); U.S. Patent Appl. No. 2014/0199234; N-acylsufonamide compounds (see, e.g., Int'l Patent Appl. Pub. No. WO 2002/024636, Int'l Patent Appl. Pub. No. WO 2005/049593, Int'l Patent Appl. Pub. No. WO 2005/049594, U.S. Pat. Nos. 7,767,684, 7,906,505). In still another embodiment, the BCL-2 anti-apoptotic protein inhibitor is a small molecule macrocyclic compound (see, e.g., Int'l Patent Appl. Pub. No. WO 2006/127364, U.S. Pat. No. 7,777,076). In yet another embodiment, the BCL-2 anti-apoptotic protein inhibitor is an isoxazolidine compound (see, e.g., Int'l Patent Appl. Pub. No. WO 2008/060569, U.S. Pat. Nos. 7,851,637, 7,842,815).

In certain embodiments, the senolytic agent is a compound that is an inhibitor of Bcl-2, Bcl-w, and Bcl-xL, such as ABT-263 or ABT-737. In certain specific embodiments, the senolytic agent is a compound or a pharmaceutically acceptable salt, stereoisomer, tautomer, or prodrug thereof as illustrated below, which depicts the structure of ABT-263. ABT-263 is also known as Navitoclax in the art.

PI3K inhibitors such as PX-866. This category also includes compounds such as Perifosine (KRX-0401) (Aeterna Zentaris/Keryx). The third class contains a group of compounds called pseudosubstrate inhibitors. These include compounds such as AKTide-2 T and FOXO3 hybrid. The fourth class consists of allosteric inhibitors of AKT kinase domain, and include compounds such as MK-2206 (8-[4-(1-aminocyclobutyl)phenyl]-9-phenyl-2H-[1,2,4]triazolo[3,4-f][1,6]naphthyridin-3-one; dihydrochloride) (Merck & Co.) (see, e.g., U.S. Pat. No. 7,576,209). The fifth class consists of antibodies and include molecules such as GST-anti-Akt1-MTS. The last class comprises compounds that interact with the PH domain of Akt, and includes Triciribine and PX-316. Other compounds described in the art that act as AKT inhibitors include, for example, GSK-2141795 (GlaxoSmithKline), VQD-002, miltefosine, AZD5363, GDC-0068, and API-1. Techniques for determining the activity of AKT inhibitors are routinely practiced by persons skilled in the art In a specific embodiment, the senolytic agent is a compound that is an Akt kinase inhibitor, which has the structure as shown below (also called MK-2206 herein and in the art), 8-[4-(1-aminocyclobutyl)phenyl]-9-phenyl-2H-[1,2,4]triazolo[3,4-f][1,6]naphthyridin-3-one;) or a pharmaceutically acceptable salt, stereoisomer, tautomer, or prodrug thereof. The dihydrochloride salt is shown.

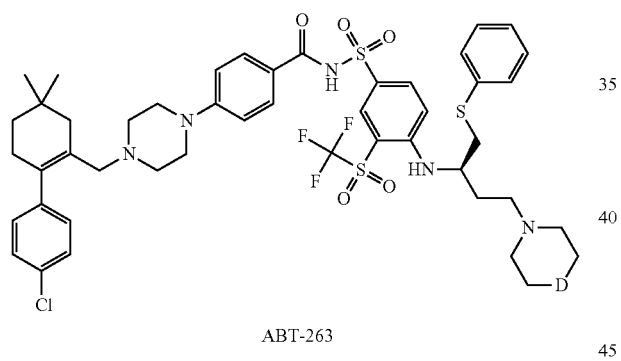

ABT-263

Akt Kinase Inhibitors

In certain embodiments the senolytic agent is an Akt Kinase inhibitor. For example, a senolytic agent can be a small molecule compound and analogs thereof that inhibits Akt. In some embodiments, the senolytic agent is a compound that selectively inhibits Akt1, Akt2, and Akt3, relative to other protein kinases.

Akt inhibitors (which may also be called Akt kinase inhibitors or AKT kinase inhibitors) can be divided into six major classes based on their mechanisms of action (see, e.g., Bhutani et al., *Infectious Agents and Cancer* 2013, 8:49 doi:10.1186/1750-9378-8-49). Akt is also called protein kinase B (PKB) in the art. The first class contains ATP competitive inhibitors of Akt and includes compounds such as CCT128930 and GDC-0068, which inhibit Akt2 and Akt1. This category also includes the pan-Akt kinase inhibitors such as GSK2110183 (afuresertib), GSK690693, and AT7867. The second class contains lipid-based Akt inhibitors that act by inhibiting the generation of PIP3 by PI3K. This mechanism is employed by phosphatidylinositol analogs such as Calbiochem Akt Inhibitors I, II and III or other

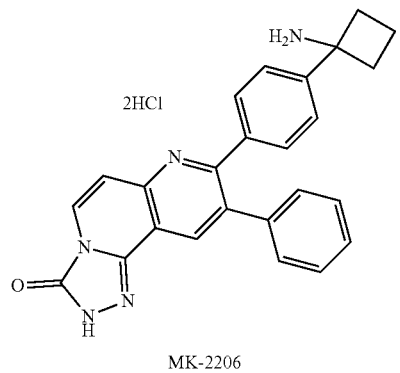 [SMILES: NC1(c2ccc(-c3nc4ccn5c(=O)[nH]nc5c4cc3-c3ccccc3)cc2)CCC1]

MK-2206

In certain embodiments, at least one senolytic agent may be administered with at least one other senolytic agent, which two or more senolytic agents act additively or synergistically to selectively kill senescent cells. In particular embodiments, methods are provided for using a senolytic agent wherein the senolytic agent alters either a cell survival signaling pathway or an inflammatory pathway or alters both the cell survival signaling pathway and the inflammatory pathway in a senescent cell. In other particular embodiments, methods comprise use of at least two senolytic agents wherein at least one senolytic agent and a second senolytic agent are each different and independently alter either one or both of a survival signaling pathway and an inflammatory pathway in a senescent cell. For convenience, when two or more senolytic agents are described herein as being used in combination, one senolytic agent will be called a first senolytic agent, another senolytic agent will be called the second senolytic agent, etc. In other certain embodiments, the methods described herein comprise administering at least three senolytic agents (a first senolytic agent, second senolytic agent, and third senolytic agent). The adjectives, first, second, third, and such, in this context are used for convenience only and are not to be construed as describing order or administration, preference, or level of senolytic activity or other parameter unless expressly described otherwise. In particular embodiments, when two or more senolytic agents are used in the methods described herein, each senolytic agent is a small molecule. In other certain embodiments, the methods described herein comprise administering at least three senolytic agents (a first senolytic agent, second senolytic agent, and third senolytic agent). In certain embodiments, use of at least two senolytic agents results in significantly increased killing of senescent cells compared with use of each senolytic agent alone. In other particular embodiments, use of at least two senolytic agents results in significant killing of senescent cells compared with use of each senolytic agent alone and which effect may be additive or synergistic. In certain embodiments, the at least two senolytic agents are each different and selected from (1) an inhibitor of one or more BCL-2 anti-apoptotic protein family members wherein the inhibitor inhibits at least BCL-xL; (for example, a Bcl-2/Bcl-xL/Bcl-w inhibitor, a Bcl-2/Bcl-xL inhibitor, a selective Bcl-xL inhibitor, or a Bcl-xL/Bcl-w inhibitor); an Akt kinase specific inhibitor; a MDM2 inhibitor. In one particular embodiment, when at least one senolytic agent administered to a subject in need thereof is an inhibitor of one or more BCL-2 anti-apoptotic protein family members wherein the inhibitor inhibits at least BCL-XL (e.g., a Bcl-2/Bcl-xL/Bcl-w inhibitor, a Bcl-2/Bcl-xL inhibitor, a selective Bcl-xL inhibitor, or a Bcl-xL/Bcl-w inhibitor), a second senolytic agent is administered. In other certain embodiments, one of the two senolytic agents is the inhibitor of one or more BCL-2 anti-apoptotic protein family members wherein the inhibitor inhibits at least BCL-xL and the second senolytic agent is an MDM2 inhibitor. In yet still more particular embodiments, when at least one senolytic agent administered to a subject in need thereof is a selective Bcl-xL inhibitor, a second senolytic agent is administered. In still more particular embodiments, when at least one senolytic agent administered to a subject in need thereof is an MDM2 inhibitor, a second senolytic agent is administered. In still more particular embodiments, when at least one senolytic agent administered to a subject in need thereof is an Akt kinase inhibitor, a second senolytic agent is administered. In even more particular embodiments, the inhibitor of one or more BCL-2 anti-apoptotic protein family members wherein the inhibitor inhibits at least BCL-xL is used alone or in combination with another senolytic agent that is also an inhibitor of one or more BCL-2 anti-apoptotic protein family members wherein the inhibitor inhibits at least BCL-xL or is a different senolytic agent as described herein. In particular embodiments, an inhibitor of one or more BCL-2 anti-apoptotic protein family members wherein the inhibitor inhibits at least BCL-xL is combined with an inhibitor of Akt kinase. By way of non-limiting example, the Bcl-2/Bcl-xL/Bcl-w inhibitor ABT-263 may be used in combination with an Akt kinase inhibitor (e.g., MK-2206).

In still other particular embodiments, an MDM2 inhibitor that is a senolytic agent is used in combination with at least one additional senolytic agent in the methods for treating a senescence-associated disease or disorder; the additional senolytic agent (which may be referred to for convenience as a second senolytic agent) may be another MDM2 inhibitor or may be a senolytic agent that is not a MDM2 inhibitor. In one embodiment, an inhibitor of a Bcl-2 anti-apoptotic family member that inhibits at least Bcl-xL is used in combination with an AKT inhibitor. In a more specific embodiment, the inhibitor of a Bcl-2 anti-apoptotic family member is ABT-263, ABT-737, or WEHI-539 and the AKT inhibitor is MK-2206.

In other certain embodiments, the methods described herein comprise administering at least three senolytic agents (a first senolytic agent, second senolytic agent, and third senolytic agent).

mTOR, NFκB, and PI3-k Pathway Inhibitors:

A small molecule compound that may be used together with a senolytic agent described herein in the methods for selectively killing senescent cells and treating a senescence-associated disease or disorder may be a small molecule compound that inhibits one or more of mTOR, NFκB, and PI3-k pathways. As described herein, methods are also provided for selectively killing senescent cells and for treating a senescence-associated disease or disorder, wherein the methods comprise administering to a subject in need thereof at least one senolytic agent, which methods may further comprise administering an inhibitor of one or more of mTOR, NFκB, and PI3-k pathways. Inhibitors of these pathways are known in the art.

Examples of mTOR inhibitors include sirolimus, temsirolimus, everolimus, ridaforolimus, 32-deoxorapamycin, zotarolimus, PP242, INK128, PP30, Torin1, Ku-0063794, WAY-600, WYE-687 and WYE-354. Inhibitors of an NFκB pathway include, for example, NFκB activity abrogation through TPCA-1 (an IKK2 inhibitor); BAY 11-7082 (an IKK inhibitor poorly selective for IKK1 and IKK2); and MLN4924 (an NEDD8 activating enzyme (NAE)-inhibitor); and MG132.

Examples of inhibitors of PI3-k that may also inhibit mTOR or AKT pathways include perifosine (KRX-0401), idelalisib, PX-866, IPI-145, BAY 80-6946, BEZ235, RP6530, TGR 1201, SF1126, INK1117, GDC-0941, BKM120, XL147 (SAR245408), XL765 (SAR245409), Palomid 529, GSK1059615, GSK690693, ZSTK474, PWT33597, IC87114, TG100-115, CAL263, RP6503, PI-103, GNE-477, CUDC-907, AEZS-136, BYL719, BKM120, GDC-0980, GDC-0032, and MK2206.

Small Molecule Compounds—Salts and General Synthesis Procedures.

The small molecule compounds described herein as senolytic agents include physiologically acceptable salts (i.e., pharmaceutically acceptable salts), hydrates, solvates, polymorphs, metabolites, and prodrugs of the senolytic agents. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, malonic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Additional salts include those in which the counterion is a cation. Suitable inorganic bases included (but are not limited to) the hydroxide or other salt of sodium, potassium, lithium, ammonium, calcium, barium, magnesium, iron, zinc, copper, manganese, aluminum, and the like, and organic bases such as substituted ammonium salts (for example, dibenzylammonium, benzylammonium, 2-hydroxyethylammonium). Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Thus, the term "pharmaceutically acceptable salt" of compounds described herein is intended to encompass any and all pharmaceutically suitable salt forms.

Compounds may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt. In other specific embodiments, the compounds described herein exist as the potassium salt.

Furthermore, some of the crystalline forms of any compound described herein may exist as polymorphs, which are also included and contemplated by the present disclosure. In addition, some of the compounds may form solvates with water or other organic solvents. Often crystallizations produce a solvate of the disclosed compounds. As used herein, the term "solvate" refers to an aggregate that comprises one or more molecules of any of the disclosed compounds with one or more molecules of solvent. The solvent may be water, in which case the solvate may be a hydrate. Alternatively, the solvent may be an organic solvent. Thus, the presently disclosed compounds may exist as a hydrate, including a monohydrate, dihydrate, hemihydrate, sesquihydrate, trihydrate, tetrahydrate and the like, as well as the corresponding solvated forms. Certain embodiments of the compounds may be true solvates, while in other instances, some embodiments of the compounds may merely retain adventitious water or be a mixture of water plus some adventitious solvent.

In general, the compounds used in the methods described herein may be made according to organic synthesis techniques known to those skilled in this art, starting from commercially available chemicals and/or from compounds described in the chemical literature. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002. Methods known to one of ordinary skill in the art may be identified through various reference books and databases. Suitable reference books and treatises detail the synthesis of reactants useful in the preparation of compounds described herein, or provide references to articles that describe the preparation.

Assays and techniques for identifying senolytic agents are described in greater detail herein. In addition, identifying and selecting small compounds as senolytic agents, a person skilled in the medicinal chemistry art may also consider other properties of the small molecule, such as solubility, bioavailability, pharmacokinetics, Lipinski Rule of 5, and the like.

Polypeptides, Antibodies, and Nucleic Acids

In other certain embodiments, a senolytic agent may be a polypeptide, peptide, antibody, antigen-binding fragment (i.e., peptides and polypeptides comprising at least one complementary determining region (CDR)), peptibody, recombinant viral vector, or a nucleic acid. In certain embodiments, a senolytic agent is an antisense oligonucleotide, siRNA, shRNA, or a peptide. For example, senolytic agents such as polypeptides, antibodies, nucleic acids, and the like, include, for example, MDM2 inhibitors, BCL-2 family inhibitors, or Akt kinase inhibitors. In other embodiments, polypeptides, peptides, antibodies (including antigen-binding fragments thereof) that specifically bind to a ligand or target protein of a small molecule senolytic agent described herein, may be used in assays and methods for characterizing or monitoring the use of the small molecule senolytic agent.

A polynucleotide or oligonucleotide that specifically hybridizes to a portion of mRNA that encodes a target protein (e.g., Bcl-xL, Bcl-2, Bcl-w, MDM2, Akt) of a cell that is a senescent cell or that is a cell in a disease microenvironment may induce the cell to senescence by aging, a biologically damaging (i.e., cell damaging) medical therapy, or an environmental insult. In other embodiments, the target protein may be a ligand, or protein either downstream or upstream in a cell survival pathway or inflammatory pathway or apoptotic pathway. Polynucleotides and oligonucleotides may be complementary to at least a portion of a nucleotide sequence encoding a target polypeptide (e.g., a short interfering nucleic acid, an antisense polynucleotide, a ribozyme, or a peptide nucleic acid) and that may be used to alter gene and/or protein expression. These polynucleotides that specifically bind to or hybridize to nucleic acid molecules that encode a target polypeptide may be prepared using the nucleotide sequences available in the art. In another embodiment, nucleic acid molecules such as aptamers that are not sequence-specific may also be used to alter gene and/or protein expression.

Antisense polynucleotides bind in a sequence-specific manner to nucleic acids such as mRNA or DNA. Identification of oligonucleotides and ribozymes for use as antisense agents and identification of DNA encoding the target gene for targeted delivery involve methods well known in the art. For example, the desirable properties, lengths, and other characteristics of such oligonucleotides are well known. Antisense technology can be used to control gene expression through interference with binding of polymerases, transcription factors, or other regulatory molecules (see, e.g., Gee et al., In Huber and Carr, *Molecular and Immunologic Approaches*, Futura Publishing Co. (Mt. Kisco, N.Y.; 1994)).

Short interfering RNAs may be used for modulating (decreasing or inhibiting) the expression of a gene encoding a target polypeptide of interest (see, e.g., Examples herein). Small nucleic acid molecules, such as short interfering RNA (siRNA), micro-RNA (miRNA), and short hairpin RNA (shRNA) molecules may be used according to the methods described herein to modulate the expression of a target protein. A siRNA polynucleotide preferably comprises a double-stranded RNA (dsRNA) but may comprise a single-stranded RNA (see, e.g., Martinez et al., *Cell* 110:563-74 (2002)). A siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein and known and used by persons skilled in the art.

The term "siRNA" refers to a double-stranded interfering RNA unless otherwise noted. Typically, an siRNA is a double-stranded nucleic acid molecule comprising two nucleotide strands, each strand having about 19 to about 28 nucleotides (i.e., about 19, 20, 21, 22, 23, 24, 25, 26, 27, or 28 nucleotides). In certain embodiments, each strand is 19, 20, 21, 22, or 23 nucleotides. In other particular embodiments, the siRNA comprises two nucleotide strands, each strand having about 15, 16, 17, or 18 nucleotides. In other certain embodiments, one strand of the double stranded siRNA is at least two nucleotides longer, for example, one strand may have a two-base overhang (such as TT) at one end, usually the 3' terminal end.

Short hairpin interfering RNA molecules comprise both the sense and antisense strands of an interfering RNA in a stem-loop or hairpin structure (e.g., a shRNA). An shRNA may be expressed from a DNA vector in which the DNA oligonucleotides encoding a sense interfering RNA strand are linked to the DNA oligonucleotides encoding the reverse complementary antisense interfering RNA strand by a short spacer. If needed, 3' terminal T's and nucleotides forming restriction sites may be added. The resulting RNA transcript folds back onto itself to form a stem-loop structure.

In addition to siRNA molecules, other interfering RNA and RNA-like molecules can interact with RISC and silence gene expression, such as short hairpin RNAs (shRNAs), single-stranded siRNAs, microRNAs (miRNAs), and dicer-substrate 27-mer duplexes. Such RNA-like molecules may contain one or more chemically modified nucleotides, one or more non-nucleotides, one or more deoxyribonucleotides, and/or one or more non-phosphodiester linkages. RNA or RNA-like molecules that can interact with RISC and participate in RISC-related changes in gene expression may be referred to herein as "interfering RNAs" or "interfering RNA molecules." Single-stranded interfering RNA in certain instances effects mRNA silencing, but less efficiently than double-stranded RNA.

A person skilled in the art will also recognize that RNA molecules, such as siRNA, miRNA, shRNA, may be chemically modified to confer increased stability against nuclease degradation while retaining the capability to bind to the target nucleic acids that may be present in cells. The RNA may be modified at any position of the molecule so long as the modified RNA binds to the target sequence of interest and resists enzymatic degradation. Modifications in the siRNA may be in the nucleotide base, the ribose, or the phosphate. By way of example, the 2' position of ribose can be modified, which modification can be accomplished using any one of a number of different methods routinely practiced in the art. An RNA may be chemically modified by the addition of a halide such as fluoro. Other chemical moieties that have been used to modify RNA molecules include methyl, methoxyethyl, and propyl groups (see, e.g., U.S. Pat. No. 8,675,704).

In a particular embodiment, the polynucleotide or oligonucleotide (e.g., including a shRNA) may be delivered by a recombinant vector in which the polynucleotide or oligonucleotide of interest has been incorporated. In other embodiments, the recombinant viral vector may be a recombinant expression vector into which a polynucleotide sequence that encodes an antibody, an antigen-binding fragment, polypeptide or peptide that inhibits a protein in a cell survival pathway or an inflammatory pathway, including the proteins described herein such as Bcl-xL, Bcl-2, Bcl-w, MDM2, and Akt is inserted such that the encoding sequence is operatively linked with one or more regulatory control sequences to drive expression of the polypeptide, antibody, an antigen-binding fragment, or peptide. The recombinant vector or the recombinant expression vector may be a viral recombinant vector or a viral recombinant expression vector. Exemplary viral vectors include, without limitation, a lentiviral vector genome, poxvirus vector genome, vaccinia virus vector genome, adenovirus vector genome, adenovirus-associated virus vector genome, herpes virus vector genome, and alpha virus vector genome. Viral vectors may be live, attenuated, replication conditional or replication deficient, and typically is a non-pathogenic (defective), replication competent viral vector. Procedures and techniques for designing and producing such viral vectors are well known to and routinely practiced by persons skilled in the art.

In certain specific embodiments a senolytic agent that may be used in the methods described herein is an antisense oligonucleotide. By way of non-limiting example, BCL-xL specific antisense oligonucleotides that have been previously described may be used in the methods described herein (see, e.g., PCT Publ. No. WO 00/66724; Xu et al., *Intl. J. Cancer* 94:268-74 (2001); Olie et al., *J. Invest. Dermatol.* 118:505-512 (2002); and Wacheck et al., *Br. J. Cancer* 89:1352-1357 (2003)).

In certain embodiments, a senolytic agent that may be used in the methods described herein is a peptide. By way of example and in certain embodiments, a BCL-xL selective peptide inhibitor is a BH3 peptide mimetic. Examples of BCL-xL selective BH3 peptide mimetics include those previously described (see, e.g., Kutzki et al., *J. Am. Chem. Soc.* 124:11838-39 (2002); Yin et al., *Bioorg. Med. Chem. Lett.* 22:1375-79 (2004); Matsumura et al., *FASEB J.* 7:2201 (2010)).

In certain embodiments, a senolytic agent useful for the methods described herein does not include a polynucleotide, or a fragment thereof, that encodes the exonuclease, EXO1, or a vector (including a viral vector) that comprises a polynucleotide that encodes the EXO1 enzyme (i.e., a polynucleotide encoding an EXO1 enzyme, a fragment of the polynucleotide, or a vector containing such a polynucleotide is excluded). A senolytic agent useful for the methods described herein also does not include the EXO1 enzyme polypeptide (i.e., the EXO1 enzyme is excluded) or biologically active peptide or polypeptide fragment thereof. In addition, such molecules are not inhibitors of one or both of a cell signaling pathway, such as an inflammatory pathway or a cell survival pathway; instead EXO1 encodes a 5'-3' exonuclease that degrades capping defective telomeres (see, e.g., Int'l Patent Application No. WO 2006/018632).

A senolytic agent described herein may be a polypeptide that is an antibody, or antigen-binding fragment. An antigen-binding fragment may be an F(ab')$_2$, Fab, Fab', Fv, and Fd and also includes a peptide or polypeptide that comprises at least one complementary determining region (CDR). The antibody may be an internalizing antibody or antigen-binding fragment that is internalized by the senescent cell via interaction with a target protein.

Binding properties of an antibody to its cognate antigen, may generally be determined and assessed using methods that may be readily performed by those having ordinary skill in the art (see, e.g., Harlow et al., *Antibodies: A Laboratory Manual*, Cold Spring Harbor Laboratory (1988)). As used herein, an antibody is said to be "immunospecific," "specific for" or to "specifically bind" to an antigen if it reacts at a detectable level with the polypeptide. Affinities of antibodies and antigen binding fragments thereof can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.).

The antibodies may be polyclonal or monoclonal. A variable region or one or more complementarity determining regions (CDRs) may be identified and isolated from antigen-binding fragment or peptide libraries. An antibody, or antigen-binding fragment, may be recombinantly engineered and/or recombinantly produced. An antibody may belong to any immunoglobulin class, for example IgG, IgE, IgM, IgD, or IgA and may be obtained from or derived from an animal, for example, fowl (e.g., chicken) and mammals, which include but are not limited to a mouse, rat, hamster, rabbit, or other rodent, a cow, horse, sheep, goat, camel, human, or other primate. For use in human subjects, antibodies and antigen-binding fragments are typically human, humanized, or chimeric to reduce an immunogenic response by the subject to non-human peptides and polypeptide sequences.

The antibody may be a monoclonal antibody that is a human antibody, humanized antibody, chimeric antibody, bispecific antibody, or an antigen-binding fragment (e.g., F(ab')$_2$, Fab, Fab', Fv, and Fd) prepared or derived therefrom. An antigen-binding fragment may also be any synthetic or genetically engineered protein (see, e.g., Hayden et al., *Curr. Opin. Immunol.* 9:201-12 (1997); Coloma et al., *Nat. Biotechnol.* 15:159-63 (1997); U.S. Pat. No. 5,910,573); Holliger et al., *Cancer Immunol. Immunother.* 45:128-30 (1997); Drakeman et al., *Expert Opin. Investig. Drugs* 6:1169-78 (1997); Koelemij et al., *J. Immunother.* 22:514-24 (1999); Marvin et al., *Acta Pharmacol. Sin.* 26:649-58 (2005); Das et al., *Methods Mol. Med.* 109:329-46 (2005); International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. Nos. 5,223,409; 5,733,731; 5,498,530; 5,432,018; 5,338,665; 1994; U.S. Pat. No. 5,922,545; International Application Publication Nos. WO 96/40987 and WO 98/15833). A peptide that is a minimal recognition unit or a CDR (i.e., any one or more of the three CDRs present in a heavy chain variable region and/or one or more of the three CDRs present in a light chain variable region) may be identified by computer modeling techniques, which can be used for comparing and predicting a peptide sequence that will specifically bind to a target protein of interest (see, e.g., Bradley et al., *Science* 309:1868 (2005); Schueler-Furman et al., *Science* 310:638 (2005)). Useful strategies for designing humanized antibodies are described in the art (see, e.g., Jones et al., *Nature* 321:522-25 (1986); Riechmann et al., *Nature* 332:323-27 (1988; Padlan et al., *FASEB* 9:133-39 (1995); Chothia et al., *Nature,* 342:377-83 (1989)).

Senescent Cells

The senolytic agents described herein may be used to selectively kill or destroy a senescent cell in a clinically significant or biologically significant manner. As discussed in detail herein, the one or more senolytic agents is used in an amount and for a time sufficient that selectively kills established senescent cells but is insufficient to kill (destroy, cause the death of) a non-senescent cell in a clinically significant or biologically significant manner. The senolytic agents may selectively kill one or more types of senescent cells (e.g., senescent preadipocytes, senescent endothelial cells, senescent fibroblasts, senescent neurons, senescent epithelial cells, senescent mesenchymal cells, senescent smooth muscle cells, senescent macrophages, or senescent chondrocytes).

A senescent cell may exhibit any one or more of the following seven characteristics. (1) Senescence growth arrest is essentially permanent and cannot be reversed by known physiological stimuli. (2) Senescent cells increase in size, sometimes enlarging more than twofold relative to the size of non-senescent counterparts. (3) Senescent cells express a senescence-associated β-galactosidase (SA-β-gal), which partly reflects the increase in lysosomal mass. (4) Most senescent cells express p16INK4a, which is not commonly expressed by quiescent or terminally differentiated cells. (5) Cells that senesce with persistent DDR signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules associated with senescence, which in certain instances may be observed in the presence of persistent DDR signaling, which in certain instances may be dependent on persistent DDR signaling for their expression. (7) The nuclei of senescent cells lose structural proteins such as Lamin B1 or chromatin-associated proteins such as histones and HMGB1. See, e.g., Freund et al., *Mol. Biol. Cell* 23:2066-75 (2012); Davalos et al., *J. Cell Biol.* 201: 613-29 (2013); Ivanov et al., *J. Cell Biol.* DOI: 10.1083/jcb.201212110, page 1-15; published online Jul. 1, 2013; Funayama et al., *J. Cell Biol.* 175:869-80 (2006)).

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta galactosidase (SA-βgal) (see, e.g., Dimri et al., *Proc. Natl. Acad. Sci. USA* 92: 9363-9367 (1995)). The presence of the senescent cell-associated polypeptide p16 can be determined by any one of numerous immunochemistry methods practiced in the art, such as immunoblotting analysis. Expression of p16 mRNA in a cell can be measured by a variety of techniques practiced in the art including quantitative PCR. The presence and level of senescent cell associated polypeptides (e.g., polypeptides of the SASP) can be determined by using automated and high throughput assays, such as an automated Luminex array assay described in the art (see, e.g., Coppe et al., *PLoS Biol* 6: 2853-68 (2008)).

The presence of senescent cells can also be determined by detection of senescent cell-associated molecules, which include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities (see, e.g., Coppe et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005). ECM associated factors include inflammatory proteins and mediators of ECM remodeling and which are strongly induced in senescent cells (see, e.g., Kuilman et al., *Nature Reviews* 9:81-94 (2009)). Other senescent cell-associated molecules include extracellular polypeptides (proteins) described collectively as the DNA damage secretory program (DDSP) (see, e.g., Sun et al., *Nature Medicine* 18:1359-1368 (2012)). Senescent cell-associated proteins also include cell surface proteins (or receptors) that are expressed on senescent cells, which include proteins that are present at a detectably lower amount or are not present on the cell surface of a non-senescent cell.

Senescence cell-associated molecules include secreted factors which may make up the pro-inflammatory phenotype of a senescent cell (e.g., SASP). These factors include, without limitation, GM-CSF, GROα, GROα,β,γ, IGFBP-7, IL-1α, IL-6, IL-7, IL-8, MCP-1, MCP-2, MIP-1α, MMP-1, MMP-10, MMP-3, Amphiregulin, ENA-78, Eotaxin-3, GCP-2, GITR, HGF, ICAM-1, IGFBP-2, IGFBP-4, IGFBP-5, IGFBP-6, IL-13, IL-1β, MCP-4, MIF, MIP-3α, MMP-12, MMP-13, MMP-14, NAP2, Oncostatin M, osteoprotegerin, PIGF, RANTES, sgp130, TIMP-2, TRAIL-R3, Acrp30, angiogenin, Axl, bFGF, BLC, BTC, CTACK, EGF-R, Fas, FGF-7, G-CSF, GDNF, HCC-4, I-309, IFN-γ, IGFBP-1, IGFBP-3, IL-1 R1, IL-11, IL-15, IL-2R-α, IL-6 R, I-TAC, Leptin, LIF, MMP-2, MSP-a, PAI-1, PAI-2, PDGF-BB, SCF, SDF-1, sTNF RI, sTNF RII, Thrombopoietin, TIMP-1, tPA, uPA, uPAR, VEGF, MCP-3, IGF-1, TGF-β3, MIP-1-delta, IL-4, FGF-7, PDGF-BB, IL-16, BMP-4, MDC, MCP-4, IL-10, TIMP-1, Flt-3 Ligand, ICAM-1, Axl, CNTF, INF-γ, EGF, BMP-6. Additional identified factors, which include those sometimes referred to in the art as senescence messaging secretome (SMS) factors, some of which are included in the listing of SASP polypeptides, include without limitation, IGF1, IGF2, and IGF2R, IGFBP3, IDFBP5, IGFBP7, PAI1, TGF-β, WNT2, IL-1α, IL-6, IL-8, and CXCR2-binding chemokines. Cell-associated molecules also include without limitation the factors described in Sun et al., *Nature Medicine*, supra, and include, including, for example, products of the genes, MMP1, WNT16B, SFRP2, MMP12, SPINK1, MMP10, ENPP5, EREG, BMP6, ANGPTL4, CSGALNACT, CCL26, AREG, ANGPT1, CCK, THBD, CXCL14, NOV, GAL, NPPC, FAM150B, CST1, GDNF, MUCL1, NPTX2, TMEM155, EDN1, PSG9, ADAMTS3, CD24, PPBP, CXCL3, MMP3, CST2, PSG8, PCOLCE2, PSG7, TNFSF15, C17orf67, CALCA, FGF18, IL8, BMP2, MATN3, TFP1, SERPINI 1, TNFRSF25, and IL23A. Senescent cell-associated proteins also include cell surface proteins (or receptors) that are expressed on senescent cells, which include proteins that are present at a detectably lower amount or are not present on the cell surface of a non-senescent cell.

In certain embodiments, senolytic agents that selectively kill at least senescent preadipocytes may be useful for treatment of diabetes (particularly type 2 diabetes), metabolic syndrome, or obesity. In other embodiments, senolytic agents are capable of selectively killing at least senescent endothelial cells, senescent smooth muscle cells, and/or senescent macrophages. Such senolytic agents may be useful for treatment of a cardiovascular disease (e.g., atherosclerosis). In other particular embodiments, the senolytic agents are capable of selectively killing at least senescent fibroblasts. In still another embodiment, the senolytic agents may selectively kill at least senescent neurons, including dopamine-producing neurons. In still another embodiment, the senolytic agents may kill at least senescent retinal pigmented epithelial cells or other senescent epithelial cells (e.g., pulmonary senescent epithelial cells or senescent kidney (renal) epithelial cells). Selective killing of at least senescent pulmonary epithelial cells may be useful for treating pulmonary diseases, such as chronic obstructive pulmonary disease or idiopathic pulmonary fibrosis. In yet other embodiments, the senolytic agents may selectively kill at least senescent immune cells (such as senescent macrophages). In still another embodiment, the senolytic agents may kill at least senescent chondrocytes, which may be useful for treatment of an inflammatory disorder, such as osteoarthritis.

Methods for Selective Killing of Senescent Cells

Provided herein are methods for selectively killing senescent cells and thereby treating or preventing (reducing the likelihood of occurrence of) a senescence-associated disease or disorder and comprises use of a senolytic agent as described herein. As described herein, these senolytic agents are administered in a manner that would be considered ineffective for treating a cancer. Because the method used for treating a senescence associated disease with a senolytic agent described herein comprises one or more of a decreased daily dose, decreased cumulative dose over a single therapeutic cycle, or decreased cumulative dose of the senolytic agent (e.g., an MDM2 inhibitor; an inhibitor of at least one Bcl-2 anti-apoptotic family member that inhibits at least Bcl-xL; an Akt inhibitor) over multiple therapeutic cycles compared with the amount required for cancer therapy, the likelihood is decreased that one or more adverse effects (i.e., side effects) will occur, which adverse effects are associated with treating a subject according to a regimen optimized for treating a cancer.

The treatment regimen of the methods for treating a senescence associated disease or disorder, comprises administering a senolytic agent for a time sufficient and in an amount sufficient that selectively kills senescent cells. In certain embodiments, the senolytic agent is administered within a treatment cycle, which treatment cycle comprises a treatment course followed by a non-treatment interval. A treatment course of administration refers herein to a finite time frame over which one or more doses of the senolytic agent on one or more days are administered. The finite time frame may be also called herein a treatment window.

In one embodiment, a method is provided herein for treating a senescence-associated disease or disorder, which is not a cancer, and which method comprises administering to a subject in need thereof a small molecule senolytic agent that selectively kills senescent cells and is administered within a treatment cycle. In a particular embodiment, the methods comprise administering the senolytic agent in at least two treatment cycles. In a specific embodiment, the non-treatment interval may be at least about 2 weeks or between at least about 0.5-12 months, such as at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months (i.e., 1 year). In other certain particular embodiments, the non-treatment interval is between 1-2 years or between 1-3 years, or longer. In certain embodiments, each treatment course is no longer than about 1 month, no longer than about 2 months, or no longer than about 3 months; or is no longer than 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days.

In certain embodiments, the treatment window (i.e., treatment course) is only one day. In other certain embodiments, a single treatment course occurs over no longer than 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days. During such treatment windows, the senolytic agent may be administered at least on two days (i.e., two days or more) with a variable number of days on which the agent is not administered between the at least two days of administration. Stated another way, within a treatment course when the senolytic agent is administered on two or more days, the treatment course may have one or more intervals of one or more days when the senolytic agent, is not administered. By way of non-limiting example, when the senolytic agent is administered on 2 or more days during a treatment course not to exceed 21 days, the agent may be administered on any total number of days between from 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days. In certain embodiments, the senolytic agent is administered to a subject during a treatment course of 3 days or more, and the agent may be administered every $2^{nd}$ day (i.e., every other day). In other certain embodiments when the senolytic agent is administered to a subject for a treatment window of 4 days or more, the senolytic agent may be administered every $3^{rd}$ day (i.e., every other third day). In one embodiment, the senolytic agent is administered on at least two days (i.e., 2 or more) during a treatment course that is at least 2 days and no more than about 21 days (i.e., from about 2-21 days); at least 2 days and no longer than about 14 days (i.e., from about 2-14 days); at least 2 days and no longer than about 10 days (i.e., from about 2-10 days); or at least 2 days and no longer than about 9 days (i.e., from about 2-9 days); or at least 2 days and no longer than about 8 days (i.e., from about 2-8 days). In other specific embodiments, the senolytic agent is administered on at least two days (i.e., 2 or more) during a treatment window is at least 2 days and no longer than about 7 days (i.e., from about 2-7 days); at least 2 days and no longer than about 6 days (i.e., from about 2-6 days) or at least 2 days and no more than about 5 days (i.e., from about 2-5 days) or at least 2 days and no longer than about 4 days (i.e., from about 2-4 days). In yet another embodiment, the treatment window is at least 2 days and no longer than 3 days (i.e., 2-3 days), or 2 days. In certain particular embodiments, the treatment course is no longer than 3 days. In other embodiments, the treatment course is no longer than 5 days. In still other specific embodiments, the treatment course is no longer than 7 days, 10 days, or 14 days or 21 days. In certain embodiments, the senolytic agent is administered on at least two days (i.e., 2 or more days) during a treatment window that is at least 2 days and no longer than about 11 days (i.e., 2-11 days); or the senolytic agent is administered on at least two days (i.e., 2 or more days) during a treatment window that is at least 2 days and no longer than about 12 days (i.e., 2-12 days); or the senolytic agent is administered on at least two days (i.e., 2 or more days) during a treatment window that is at least 2 days and no more than about 13 days (i.e., 2-13 days); or the senolytic agent is administered on at least two days (i.e., 2 or more days) during a treatment course that is at least 2 days and no more than about 15 days (i.e., 2-15 days); or the senolytic agent is administered on at least two days (i.e., 2 or more days) during a treatment course that is at least 2 days and no longer than about 16 days, 17 days, 18 days, 19 days, or 20 days (i.e., 2-16, 2-17, 2-18, 2-19, 2-20 days, respectively). In other embodiments, the senolytic agent may be administered on at least 3 days over a treatment course of at least 3 days and no longer than any number of days between 3 and 21 days; or is administered on at least 4 days over a treatment course of at least 4 days and no longer than any number of days between 4 and 21 days; or is administered on at least 5 days over a treatment course of at least 5 days and no longer than any number of days between 5 and 21 days; or is administered on at least 6 days over a treatment course of at least 6 days and no longer than any number of days between 6 and 21 days; or is administered at least 7 days over a treatment course of at least 7 days and no longer than any number of days between 7 and 21 days; or is administered at least 8 or 9 days over a treatment course of at least 8 or 9 days, respectively, and no longer than any number of days between 8 or 9 days, respectively, and 21 days; or is administered at least 10 days over a treatment course of at least 10 days and no longer than any number of days between 10 and 21 days; or is administered at least 14 days over a treatment course of at least 14 days and no longer than any number of days between 14 and 21 days; or is administered at least 11 or 12 days over a treatment course of at least 11 or 12 days, respectively, and no longer than any number of days between 11 or 12 days, respectively, and 21 days; or is administered at least 15 or 16 days over a treatment course of at least 15 or 16 days, respectively, and no longer than any number of days between 15 or 16 days, respectively, and 21 days. By way of additional example, when the treatment course is no longer than 14 days, a senolytic agent may be administered on at least 2, 3, 4, 5, 6, 7, 8, 9, 10, 11, 12, 13, and 14 days over a treatment of window of at least 2, 3, 4, 5, 6, 7, 8, 9, 10, 11, 12, 13, and 14 days, respectively, and no longer than 14 days. When the treatment course is no longer than 10 days, a senolytic agent may be administered on at least 2, 3, 4, 5, 6, 7, 8, 9, or 10 days over a treatment of window of at least 2, 3, 4, 5, 6, 7, 8, 9, or 10 days, respectively, and no longer than 10 days. Similarly, when the treatment course is no longer than 7 days, a senolytic agent may be administered on at least 2, 3, 4, 5, 6, or 7 days over a treatment window of at least 2, 3, 4, 5, 6, or 7 days, respectively, and no longer than 7 days. In still another example, when the treatment course is no longer than 5 days, a senolytic agent may be administered on at least 2, 3, 4, or 5 days over a treatment of window of at least 2, 3, 4, or 5 days, respectively, and no longer than 5 days.

With respect to a treatment course of three or more days, doses of the senolytic agent may be administered for a lesser number of days than the total number of days within the particular treatment window. By way of non-limiting example, when a course of treatment has a treatment course of no more than 7, 10, 14, or 21 days, the number of days on which the senolytic agent may be administered is any number of days between 2 days and 7, 10, 14, or 21 days, respectively, and at any interval appropriate for the particular disease being treated, the senolytic agent being administered, the health status of the patient and other relevant factors, which are discussed in greater detail herein. A person skilled in the art will readily appreciate that when the senolytic agent is administered on two or more days over a treatment window, the agent may be delivered on the minimum number days of the window, the maximum number of days of the window, or on any number of days between the minimum and the maximum.

In certain specific embodiments, a treatment course is one day or the treatment course is of a length not to exceed 2, 3, 4, 5, 6, 7, 8, 9, 10, 11, 12, 13, or 14 days, which are examples of a course wherein the senolytic agent is administered on two or more days over a treatment course not to exceed (i.e., no longer than) 2, 3, 4, 5, 6, 7, 8, 9, 10, 11, 12, 13, or 14 days, respectively. In other certain embodiments, the treatment course is about 2 weeks (about 14 days or 0.5 months), about 3 weeks (about 21 days), about 4 weeks (about one month), about 5 weeks, about 6 weeks (about 1.5 months), about 2 months (or about 60 days), or about 3 months (or about 90 days). In a particular embodiment, a treatment course is a single daily dosing of the senolytic agent. In other embodiments, with respect to any treatment course a daily dose of the senolytic agent may be as a single administration or the dose may be divided into 2, 3, 4, or 5 separate administrations to provide the total daily dose of the agent.

As described herein, in certain specific embodiments, within a treatment window when the senolytic agent is administered on two are more days, the treatment course may have one or more intervals of one or more days when the senolytic agent, is not administered. Solely as a non-limiting example, when a treatment window is between two and seven days, a first dose may be administered on the first day of the treatment window and a second dose may be administered on the third day of the course, and a third dose may be administered on the seventh day of the treatment window. A person skilled in the art will appreciate that varying dosing schedules may be used during a particular treatment window. In other specific embodiments, the senolytic agent is administered daily on each consecutive day for the duration of the treatment course. A daily dose may be administered as a single dose or the daily dose may be divided into 2, 3, or 4, or 5 separate administrations to provide the total daily dose of the senolytic agent.

In certain embodiments, the treatment course comprises a length of time during which the senolytic agent is administered daily. In one specific embodiment, the senolytic agent is administered daily for 2 days. In another specific embodiment, the senolytic agent is administered daily for 3 days. In yet another particular embodiment, the senolytic agent is administered daily for 4 days. In one specific embodiment, the senolytic agent is administered daily for 5 days. In yet another particular embodiment, the senolytic agent is administered daily for 6 days. In another specific embodiment, the senolytic agent is administered daily for 7 days. In yet another particular embodiment, the senolytic agent is administered daily for 8 days. In still another specific embodiment, the senolytic agent is administered daily for 9 days. In yet another particular embodiment, the senolytic agent is administered daily for 10 days. In yet another particular embodiment, the senolytic agent is administered daily for 11 days. In yet another particular embodiment, the senolytic agent is administered daily for 12 days. In yet another particular embodiment, the senolytic agent is administered daily for 13 days. In yet another particular embodiment, the senolytic agent is administered daily for 14 days. The treatment window (i.e., course) for each of the above examples is no longer than 2, 3, 4, 5, 6, 7, 8, 9, 10, 11, 12, 13, 14 days, respectively.

In other specific embodiments, the senolytic agent is administered every $2^{nd}$ day (i.e., every other day) for 3, 4, 5, 6, 7, 8, 9, 10, 11, 12, 13, or 14 days. In still other specific embodiments, the senolytic agent is administered every $3^{nd}$ day (i.e., one day receiving the agent followed by two days without receiving the agent) for 4, 5, 6, 7, 8, 9, 10, 11, 12, 13, or 14 days. In still other specific embodiments, the senolytic agent may be administered on every $2^{nd}$-$3^{rd}$ day during a treatment window of 3, 4, 5, 6, 7, 8, 9, 10, 11, 12, 13, or 14 days. In yet other embodiments, the senolytic agent may be administered every $4^{th}$ day during a treatment course of 5, 6, 7, 8, 9, 10, 11, 12, 13, or 14 days; or every $5^{th}$ day during a treatment course of 6, 7, 8, 9, 10, 11, 12, 13, or 14 days. A person skilled in the art can readily appreciate the minimum numbers of days in a treatment window when the senolytic agent is administered every $6^{th}$, $7^{th}$, etc. day over a treatment window of a finite number of days as described herein.

In certain particular embodiments, a senolytic agent may be administered daily for a longer duration than 14 days and may be administered at least 15, 16, 17, 18, 19, 20, or at least 21 days. In other specific embodiments, the senolytic agent may be administered daily on each of the 15, 16, 17, 18, 19, 20, or 21 days. In another specific embodiment, the senolytic agent may be administered every second day during a treatment window of 15, 16, 17, 18, 19, 20, or 21 days. In another specific embodiment, the senolytic agent may be administered every third day during a treatment window of 15, 16, 17, 18, 19, 20, or 21 days. In still other specific embodiments, the senolytic agent may be administered on every $2^{nd}$-$3^{rd}$ day during a treatment window of 15, 16, 17, 18, 19, 20, or 21 days. In yet other embodiments, the senolytic agent may be administered every $4^{th}$ day during a treatment course of 15, 16, 17, 18, 19, 20, or 21 days; or every $5^{th}$ day during a treatment course of 15, 16, 17, 18, 19, 20, or 21 days. A person skilled in the art can readily appreciate the minimum numbers of days in a treatment window when the senolytic agent is administered every $6^{th}$, $7^{th}$, etc. day over a treatment window of a finite number of days as described herein.

In another certain particular embodiment, a senolytic agent may be administered daily for a longer duration than 14 days and may be administered at least 15, 16, 17, 18, 19, 20, or at least 21 days. In other specific embodiments, the senolytic agent may be administered daily on each of the 15, 16, 17, 18, 19, 20, or 21 days. In another specific embodiment, the senolytic agent may be administered every second day during a treatment window of 15, 16, 17, 18, 19, 20, or 21 days. In another specific embodiment, the senolytic agent may be administered every third day during a treatment window of 15, 16, 17, 18, 19, 20, or 21 days. In still other specific embodiments, the senolytic agent may be administered on every $2^{nd}$-$3^{rd}$ day during a treatment window of 15, 16, 17, 18, 19, 20, or 21 days. In yet other embodiments, the senolytic agent may be administered every $4^{th}$ day during a treatment course of 15, 16, 17, 18, 19, 20, or 21 days; or everyday during a $5^{th}$ treatment course of 15, 16, 17, 18, 19, 20, or 21 days. A person skilled in the art can readily appreciate the minimum numbers of days in a treatment window when the senolytic agent is administered every $6^{th}$, $7^{th}$, etc. day over a treatment window of a finite number of days as described herein.

In another certain particular embodiment, a senolytic agent may be administered in a treatment course daily for a longer duration than 14 days or 21 days and may be administered in a treatment course of about one month, about two months, or about three months. In other specific embodiments, the senolytic agent may be administered daily on each of a one month, two month, or three month treatment course. In another specific embodiment, the senolytic agent may be administered every second day during a treatment course of about one month, about two months, or about three months. In another specific embodiment, the senolytic agent may be administered every third day during a treatment course of about one month, about two months, or about three months. In still other specific embodiments, the senolytic agent may be administered on every $2^{nd}$-$3^{rd}$ day during a treatment course of about one month, about two months, or about three months. In yet other embodiments, the senolytic agent may be administered every $4^{th}$ day during a treatment course of about one month, about two months, or about three months; or every $5^{th}$ day during a treatment course of about one month, about two months, or about three months s. A person skilled in the art can readily appreciate the minimum numbers of days in a treatment course when the senolytic agent is administered every $6^{th}$, $7^{th}$, etc. day over a treatment window of a finite number of days as described herein.

By way of non-limiting example, a longer treatment window with a decreased dose per day may be a treatment option for a subject. In other particular embodiments and by way of example, the stage or severity of the senescence associated disease or disorder or other clinical factor may indicate that a longer term course may provide clinical benefit. In certain embodiments, the senolytic agent is administered daily, or optionally, every other day (every $2^{nd}$ day) or every $3^{rd}$ day, or greater interval (i.e., every $4^{th}$ day, $5^{th}$ day, $6^{th}$ day) during a treatment course of about 1-2 weeks (e.g., about 5-14 days), about 1-3 weeks (e.g., about 5-21 days), about 1-4 weeks (e.g., about 5-28 days, about 5-36 days, or about 5-42 days, 7-14 days, 7-21 days, 7-28 days, 7-36 days, or 7-42 days; or 9-14 days, 9-21 days, 9-28 days, 9-36 days, or 9-42 days. In other certain embodiments, the treatment course is between about 1-3 months. In a specific embodiment, the senolytic agent is administered daily for at least five days, and in another particular embodiment, the senolytic agent is administered daily for 5-14 days. In other particular embodiments, the senolytic agent is administered for at least seven days, for example, for 7-14, 7-21, 7-28 days, 7-36 days, or 7-42 days. In other particular embodiments, the senolytic agent is administered for at least nine days, for example, for 9-14 days, 9-21 days, 9-28 days, 9-36 days, or 9-42 days.

Even though as discussed herein and above, a treatment course comprising administering a senolytic agent provides clinical benefit, in other certain embodiments, a treatment course is repeated with a time interval between each treatment course when the senolytic agent is not administered (i.e., non-treatment interval, off-drug treatment). A treatment cycle as described herein and in the art comprises a treatment course followed by a non-treatment interval. A treatment cycle may be repeated as often as needed. For example, a treatment cycle may be repeated at least once, at least twice, at least three times, at least four times, at least five times, or more often as needed. In certain specific embodiments, a treatment cycle is repeated once (i.e., administration of the senolytic agent comprises 2 treatment cycles). In other certain embodiments, the treatment cycle is repeated twice or repeated 3 or more times. Accordingly, in certain embodiments, one, two, three, four, five, six, seven, eight, nine, ten, or more treatment cycles of treatment with a senolytic agent are performed. In particular embodiments, a treatment course or a treatment cycle may be repeated, such as when the senescence associated disease or disorder recurs, or when symptoms or sequelae of the disease or disorder that were significantly diminished by one treatment course as described above have increased or are detectable, or when the symptoms or sequelae of the disease or disorder are exacerbated, a treatment course may be repeated. In other embodiments when the senolytic agent is administered to a subject to prevent (i.e., reduce likelihood of occurrence or development) or to delay onset, progression, or severity of senescence associated disease or disorder, a subject may receive the senolytic agent over two or more treatment cycles. Accordingly, in certain embodiments, one cycle of treatment is followed by a subsequent cycle of treatment. Each treatment course of a treatment cycle or each treatment course of two or more treatment cycles are typically the same in duration and dosing of the senolytic agent. In other embodiments, the duration and dosing of the senolytic agent during each treatment course of a treatment cycle may be adjusted as determined by a person skilled in the medical art depending, for example, on the particular disease or disorder being treated, the senolytic agent being administered, the health status of the patient and other relevant factors, which are discussed in greater detail herein. Accordingly, a treatment course of a second or any subsequent treatment cycle may be shortened or lengthened as deemed medically necessary or prudent. In other words, as would be appreciated by a person skilled in the art, each treatment course of two or more treatment cycles are independent and the same or different; and each non-treatment interval of each treatment cycle is independent and the same or different.

As described herein, each course of treatment in a treatment cycle is separated by a time interval of days, weeks, or months without treatment with a senolytic agent (i.e., non-treatment time interval or off-drug interval; called non-treatment interval herein). The non-treatment interval (such as days, weeks, months) between one treatment course and a subsequent treatment course is typically greater than the longest time interval (i.e., number of days) between any two days of administration in the treatment course. By way of example, if a treatment course is no longer than 14 days and the agent is administered every other day during this treatment course, the non-treatment interval between two treatment courses is greater than 2 days, such as 3, 4, 5, 6, 7, 8, 9, 10, 11, 12, 13, or 14 days or about 3 weeks, about 4 weeks, about 6 weeks, or about 2 months or longer as described herein. In particular embodiments, the non-treatment interval between two treatment courses is about 5 days, about 1 week, about 2 weeks, about 3 weeks, about 1 month, about 6 weeks, about 2 months (8 weeks), about 3 months, about 4 months, about 5 months, about 6 months, about 7 months, about 8 months, about 9 months, about 10 months, about 11 months, about 12 months (about 1 year), about 18 months (about 1.5 years), or longer. In certain specific embodiments, the non-treatment interval is about 2 years or about 3 years. In certain specific embodiments, the non-treatment time interval is at least about 14 days, at least about 21 days, at least about 1 month, at least about 2 months, at least about 3 months, at least about 4 months, at least about 5 months, at least about 6 months, or at least about 1 year. In certain embodiments, a course of treatment (whether daily, every other day, every $3^{rd}$ day, or other interval between administrations within the treatment course as described above (e.g., 1-14 days, 2-14 days, 2-21 days, or 1-21 days)) is administered about every 14 days (i.e., about every 2 weeks) (i.e., 14 days without senolytic agent treatment), about every 21 days (i.e., about every 3 weeks), about every 28 days (i.e., about every 4 weeks), about every one month, about every 36 days, about every 42 days, about every 54 days, about every 60 days, or about every month (about every 30 days), about every two months (about every 60 days), about every quarter (about every 90 days), or about semi-annually (about every 180 days). In other certain embodiments, a course of treatments (e.g., by way of non-limiting example, administration on at least one day or on at least two days during a course for about 2-21 days, about 2-14, days, about 5-14 days, about 7-14 days, about 9-14 days, about 5-21 days, about 7-21 days, about 9-21 days) is administered every 28 days, every 36 days, every 42 days, every 54 days, every 60 days, or every month (about every 30 days), every two months (about every 60 days), every quarter (about every 90 days), or semi-annually (about every 180 days), or about every year (about 12 months). In other embodiments, a course of treatment (such as by way of non-limiting examples, e.g., for about 5-28 days, about 7-28 days, or about 9-28 days whether daily, every other day, every $3^{rd}$ day, or other interval between administrations within the treatment course) is administered every 36 days, 42 days, 54 days, 60 days, or every month (about every 30 days), every two months (about every 60 days), every quarter (about every 90 days), or semi-annually (about every 180 days). In other particular embodiments, a course of treatment (e.g., for about 5-36 days, 7-36 days, or 9-36 days whether daily, every other day, every $3^{rd}$ day, or other interval between administrations within the treatment course) is administered every 42 days, 54 days, 60 days, or every month (about every 30 days), every two months (about every 60 days), every quarter (about every 90 days), or semi-annually (about every 180 days), or about every year (about 12 months).

In a particular embodiment, the treatment course is one day and the non-treatment interval is at least about 14 days, about 21 days, about 1 month, about 2 months (8 weeks), about 3 months, about 4 months, about 5 months, about 6 months, about 7 months, about 8 months, about 9 months, about 10 months, about 11 months, about 12 months (about 1 year), about 18 months (about 1.5 years), or longer. In other certain embodiments, the treatment course is at least two days or is at least 3 days and no longer than 10 days, and the non-treatment interval is at least about 14 days, about 21 days, about 1 month, about 2 months (8 weeks), about 3 months, about 4 months, about 5 months, about 6 months, about 7 months, about 8 months, about 9 months, about 10 months, about 11 months, about 12 months (about 1 year), about 18 months (about 1.5 years), or longer. In still another embodiment, the treatment course is at least three days and no longer than 10 days, no longer than 14 days, or no longer than 21 days, and the non-treatment interval is at least about 14 days, about 21 days, about 1 month, about 2 months (8 weeks), about 3 months, about 4 months, about 5 months, about 6 months, about 7 months, about 8 months, about 9 months, about 10 months, about 11 months, about 12 months (about 1 year), about 18 months (about 1.5 years), or longer. In still another embodiment, a treatment course (e.g., for about 5-42, 7-42, or 9-42 days whether daily, every other day, every $3^{rd}$ day, or other interval between administrations within the treatment course) is administered every 42 days, 60 days, or every month (about every 30 days), every two months (about every 60 days), every quarter (about every 90 days), or semi-annually (about every 180 days), or about every year (about 12 months). In a particular embodiment, the senolytic agent is administered daily for 5-14 days every 14 days (about every 2 weeks), or every 21-42 days. In another particular embodiment, the senolytic agent is administered daily for 5-14 days quarterly. In another particular embodiment, the senolytic agent is administered daily for 7-14 days every 21-42 days. In another particular embodiment, the senolytic agent is administered daily for 7-14 days quarterly. In still other particular embodiments, the senolytic agent is administered daily for 9-14 days every 21-42 days or every 9-14 days quarterly. In still other embodiments, the non-treatment interval may vary between treatment courses. By way of non-limiting example, the non-treatment interval may be 14 days after the first course of treatment and may be 21 days or longer after the second, third, or fourth (or more) course of treatment. In other particular embodiments, the senolytic agent is administered to the subject in need thereof once every 0.5-12 months. In other certain embodiments, the senolytic agent is administered to the subject in need once every 4-12 months.

In certain embodiments, a senolytic agent is administered to a subject to reduce the likelihood or the risk that the subject will develop a particular disorder or to delay onset of one or more symptoms of a senescence-associated disease or disorder. In certain embodiments, the senolytic agent is administered for one or more days (e.g., any number of consecutives days between and including 2-3, -4, -5, -6, -7, -8, -9, -10, -11, -12, -13, -14, -15, -16, -17, -18, -19, -20, and 2-21 days) every 3, 4, 5, 6, 7, 8, 9, 10, 11, or 12 months. In a particular embodiment, the senolytic agent is administered for one or more days (e.g., any number of consecutives days between and including 1-9 days) every 5 or 6 months.

Without wishing to be bound by any particular theory, periodic administration of the senolytic agent kills newly formed senescent cells and thereby reduces (decreases, diminishes) the total number of senescent cells accumulating in the subject. In another embodiment, the total number of senescent cells accumulating in the subject is decreased or inhibited by administering the senolytic agent once or twice weekly or according to any of the other treatment courses described above. The total daily dose of a senolytic agent may be delivered as a single dose or as multiple doses on each day of administration. In other certain particular embodiments, when multiple cycles of the senolytic agent are administered, the dose of a senolytic agent administered on a single day may be less than the daily dose administered if only a single treatment course is intended to be administered.

In certain embodiments, method for treating a senescence-associated disease or disorder comprising administering to a subject in need thereof a small molecule senolytic agent that selectively kills senescent cells; wherein the senescence-associated disease or disorder is not a cancer, and wherein the senolytic agent is administered within one or two treatment cycles, typically two treatment cycles. In certain specific embodiments, the non-treatment interval is at least 2 weeks and each treatment course is no longer than 3 months.

Also provided herein are methods for selectively killing a senescent cell comprising contacting the senescent cell with a senolytic agent described herein (i.e., facilitating interaction or in some manner allowing the senescent cell and senolytic agent to interact) under conditions and for a time sufficient to kill the senescent cell. In such embodiments, the agent selectively kills senescent cells over non-senescent cells (i.e., the agent selectively kills senescent cells compared with killing of non-senescent cells). In certain embodiments, the senescent cell to be killed is present in a subject (e.g., a human or non-human animal). The senolytic agent(s) may be administered to the subject according to the treatment cycles, treatment courses, and non-treatment intervals described above and herein.

In particular embodiments, a single (i.e., only, sole) senolytic agent is administered to the subject for treating a senescence-associated disease or disorder. In certain embodiments, administration of a single senolytic agent may be sufficient and clinically beneficial to treat a senescence-associated disease or disorder. Accordingly, in certain particular embodiments, a senolytic agent is administered as a monotherapy and is the single (i.e., only, sole) active agent administered to the subject for treating the condition or disease. Medications that are not necessarily excluded from administration to the subject when a senolytic agent is administered as a monotherapy include, by way of non-limiting examples, medications for other purposes such as palliative care or comfort (e.g., aspirin, acetominophen, ibuprofen, or prescription pain-killers; anti-itching topical medications) or for treating a different disease or condition, especially if the other medications are not senolytic agents, such as drugs for lowering cholesterol, statins, eye wetting agents, and other such medications familiar to a person skilled in the medical art.

In specific embodiments, if the senolytic agent is an MDM2 inhibitor, the MDM2 inhibitor is administered as a monotherapy (i.e., the only active therapeutic agent), and each treatment course is at least 5 days long during which course the MDM2 inhibitor is administered on at least 5 days. In certain other embodiments, the MDM2 inhibitor is administered on at least 9 days. In still more specific embodiments, the MDM2 inhibitor is Nutlin-3a.

The dosing regimens, treatment courses, and treatment cycles (can be reviewed and modified or adjusted, continued or discontinued, as determined by a person skilled in the art, depending on the responsiveness of the subject to the senolytic agent, the stage of the disease, the general health of the subject, and other factors that are described herein and in the art.

As described herein, certain senolytic agents that may be used in the methods have been described as useful or potentially useful for treating a cancer; however, in embodiments of the methods for treating a senescence associated disorder or disease, the senolytic agents are administered in a manner that would be considered different and likely ineffective for treating a cancer. Accordingly, the methods described herein are useful for treating a senescence-associated disorder or disease but are not described as also useful as a primary therapy (alone or with another chemotherapy agent or radiotherapy) for treating a cancer. In one embodiment, the method used for treating a senescence associated disease or disorder with a senolytic agent may comprise a decreased daily dose compared with the daily dose of the agent as required for cancer therapy. In another embodiment, the method used for treating a senescence associated disease or disorder with a senolytic agent described herein may comprise decreased cumulative dose over a single treatment cycle compared with the cumulative dose of the agent as required for cancer therapy. In still another embodiment, the method used for treating a senescence associated disease or disorder with a senolytic agent described herein may comprise or decreased cumulative dose of the agent administered over multiple treatment cycles compared with the dose of the agent as required for multiple cancer therapy cycles.

By way of example, in certain embodiments, when the senolytic agent is an agent that can be cytotoxic to cancer cells and may be used in the oncology art in a manner for treating a cancer (for example, an MDM2 inhibitor (e.g., Nutlin-3a; RG-7112) or an inhibitor of one or more BCL-2 anti-apoptotic protein family members and which inhibits at least Bcl-xL (e.g., ABT-263, ABT-737, WEHI-539, A-1155463)), the methods for treating a senescence associated disease or disorder comprise administering the senolytic agent in one or two or more treatment cycles, and the total dose of the senolytic agent administered during each treatment course, each treatment cycle, and/or cumulatively over two or more treatment cycles is an amount less than the amount effective for a cancer treatment. The amount of such a senolytic agent administered to a subject over a given time period (such as one week, two weeks, one month, six months, one year) for treating a senescence associated disease or disorder, for example, may be about from a 20-fold decrease to about a 5000-fold decrease in total amount compared with the total amount of the same agent administered to a subject who is receiving the agent for treatment of a cancer. The fold decrease in the amount (i.e., lesser amount) of the senolytic agent administered over a given time period (i.e., number of days, months, years) for treating a senescence associated disease or disorder may be about a 20-fold decrease, about a 25-fold decrease, about a 30-fold decrease, about a 40-fold decrease, about a 50-fold decrease, about a 60-fold decrease, about a 75-fold decrease, about a 100-fold decrease, about a 125-fold decrease, about a 150-fold decrease, about a 175-fold decrease, about a 200-fold decrease, about a 300-fold decrease, about a 400-fold decrease, about a 500-fold decrease, about a 750-fold decrease, about a 1000-fold decrease, about a 1250-fold decrease, about a 1500-fold decrease, about a 1750-fold decrease, about a 2000-fold decrease, about a 2250-fold decrease, about a 2500-fold decrease, about a 2750-fold decrease, about a 3000-fold decrease, about a 3250-fold decrease, about a 3500-fold decrease, about a 3750-fold decrease, about a 3000-fold decrease, about a 3500-fold decrease, about a 4000-fold decrease, about a 4500-fold decrease, or about a 5000-fold decrease compared with the amount of the agent administered to a subject for treating a cancer over the same length of time. A lower dose required for treating a senescence associated disease may also be attributable to the route of administration. For example, when a senolytic agent is used for treating a senescence-associated pulmonary disease or disorder (e.g., COPD, IPF), the senolytic agent may be delivered directly to the lungs (e.g., by inhalation, by intubation, intranasally, or intratracheally), and a lower dose per day and/or per treatment course is required than if the agent were administered orally. Also, by way of another example, when a senolytic agent is used for treating osteoarthritis or a senescence-associated dermatological disease or disorder, the senolytic agent may be delivered directly to the osteoarthritic joint (e.g., intra-articularly, intradermally, topically, transdermally) or to the skin (e.g., topically, subcutaneously, intradermally, transdermally), respectively, at a lower does per day and/or per treatment course than if the senolytic agent were administered orally. When a senolytic agent is delivered orally, for example, the dose of the senolytic agent per day may be the same amount as administered to a patient for treating a cancer; however, the amount of the agent that is delivered over a treatment course or treatment cycle is significantly less than the amount administered to a subject who receives the appropriate amount of the agent for treating a cancer.

In certain embodiments, the methods described herein comprise using the senolytic agent in an amount that is a reduced amount compared with the amount that may be delivered systemically, for example, orally or intravenously to a subject who receives the senolytic agent when the agent is used for treating a cancer. In certain specific embodiments, methods of treating a senescence-associated disease or disorder by selectively killing senescent cells comprises administering the senolytic agent at a dose that is at least 10% (i.e., one-tenth), at least 20% (one-fifth), 25% (one-fourth), 30%-33% (about one-third), 40% (two-fifths), or at least 50% (half) of the dose that is administered to a subject who has cancer for killing cancer cells during a treatment course, a treatment cycle, or two or more treatment cycles that form the cancer therapy protocol (i.e., regimen). In other particular embodiments, the dose of the senolytic agent(s) used in the methods described herein is at least 60%, 70%, 80%, 85%, 90%, or 95% of the dose that is administered to a subject who has cancer. The therapeutic regimen, comprising the dose of senolytic agent and schedule and manner of administration that may be used for treating a senescence-associated disorder or disease is also a regimen insufficient to be significantly cytotoxic to non-senescent cells.

In certain embodiments, a method for treating a senescence-associated disease or disorder that is not a cancer comprises administering to a subject in need thereof a therapeutically effective amount of a small molecule senolytic agent that selectively kills senescent cells (i.e., selectively kills senescent cells over non-senescent cells or compared with non-senescent cells) and which agent is cytotoxic to cancer cells, wherein the senolytic agent is administered within at least one treatment cycle, which treatment cycle comprises a treatment course followed by a non-treatment interval. The total dose of the senolytic agent administered during the treatment course, and/or the total dose of the senolytic agent administered during the treatment cycle, and/or the total dose of the senolytic agent administered during two or more treatment cycles is an amount less than the amount effective for a cancer treatment. In certain embodiments, the senolytic agent is an inhibitor of a Bcl-2 anti-apoptotic protein family member that inhibits at least Bcl-xL; an MDM2 inhibitor; or an Akt specific inhibitor. Examples of these inhibitors are described herein. In other certain embodiments, the senolytic agent is administered as a monotherapy, and is the single active senolytic agent administered to the subject for treating the disease or disorder. The number of days in the treatment course and the treatment interval are described in detail herein.

In one embodiment, a method is provided herein for treating a senescence-associated disease or disorder, wherein the senescence-associated disease is not cancer and the method comprises administering to a subject in need thereof a senolytic agent or small molecule senolytic compound that selectively kills senescent cells, and the administration is for a short duration (e.g., shorter than may be used for a particular agent for treating a cancer), such as a single day, 2 days, 3 days, 4 days, 5 days, 6 days, 7 days, 8 days, 9 days, 10 days, 11 days, 12 days, 13 days, 14 days, or 15 days. In these particular embodiments, this treatment course on any number of days between 1-15 days is a single treatment course and is not repeated. In another particular embodiment, a senolytic agent is administered for 16 days, 17 days, 18 days, 19 days, 20 days, 21 days, 22 days, 23 days, 24 days, 25 days, 26 days, 27 days, 28 days, 29 days, 30 days, or 31 days as a single treatment course that is not repeated.

In certain specific embodiments, the senolytic agent is ABT-263 (navitoclax). In some embodiments, navitoclax is administered in a treatment window comprising 21 days. In some embodiments, navitoclax is administered daily for 14 days followed by 7 days off. In some embodiments, navitoclax is administered daily for 13 days followed by 8 days off. In some embodiments, navitoclax is administered daily for 12 days followed by 9 days off. In some embodiments, navitoclax is administered daily for 11 days followed by 10 days off. In some embodiments, navitoclax is administered daily for 10 days followed by 11 days off. In some embodiments, navitoclax is administered daily for 9 days followed by 12 days off. In some embodiments, navitoclax is administered daily for 8 days followed by 13 days off. In some embodiments, navitoclax is administered daily for 7 days followed by 14 days off. In some embodiments, navitoclax is administered daily for 6 days followed by 15 days off. In some embodiments, navitoclax is administered daily for 5 days followed by 16 days off. In some embodiments, navitoclax is administered daily for 4 days followed by 17 days off. In some embodiments, navitoclax is administered daily for 3 days followed by 18 days off. In some embodiments, navitoclax is administered daily for 2 days followed by 19 days off. In some embodiments, navitoclax is administered for 1 day followed by 20 days off.

In some embodiments, navitoclax is administered daily for 21 days in a dose of about 150 mg to 325 mg. In some embodiments, navitoclax is administered daily for 21 days in a dose of about 150 mg to 300 mg. In some embodiments, navitoclax is administered daily for 21 days in a dose of about 150 mg to 275 mg. In some embodiments, navitoclax is administered daily for 21 days in a dose of about 150 mg to 250 mg. In some embodiments, navitoclax is administered daily for 21 days in a dose of about 150 mg to 225 mg. In some embodiments, navitoclax is administered daily for 21 days in a dose of about 150 mg to 200 mg. In some embodiments, navitoclax is administered daily for 21 days in a dose of about 150 mg to 175 mg. In some embodiments, navitoclax is administered daily for 21 days in a dose of about 150 mg. In some embodiments, navitoclax is administered daily for 21 days in a dose of about 125 mg. In some embodiments, navitoclax is administered daily for 21 days in a dose of about 100 mg. In some embodiments, navitoclax is administered daily for 21 days in a dose of about 75 mg. In some embodiments, navitoclax is administered daily for 21 days in a dose of about 50 mg. In some embodiments, navitoclax is administered daily for 21 days in a dose of about 25 mg.

In some embodiments, navitoclax is administered daily for 14 days in a dose of about 150 mg to 325 mg. In some embodiments, navitoclax is administered daily for 14 days in a dose of about 150 mg to 300 mg. In some embodiments, navitoclax is administered daily for 14 days in a dose of about 150 mg to 275 mg. In some embodiments, navitoclax is administered daily for 14 days in a dose of about 150 mg to 250 mg. In some embodiments, navitoclax is administered daily for 14 days in a dose of about 150 mg to 225 mg. In some embodiments, navitoclax is administered daily for 14 days in a dose of about 150 mg to 200 mg. In some embodiments, navitoclax is administered daily for 14 days in a dose of about 150 mg to 175 mg. In some embodiments, navitoclax is administered daily for 14 days in a dose of about 150 mg. In some embodiments, navitoclax is administered daily for 14 days in a dose of about 125 mg. In some embodiments, navitoclax is administered daily for 14 days in a dose of about 100 mg. In some embodiments, navitoclax is administered daily for 14 days in a dose of about 75 mg. In some embodiments, navitoclax is administered daily for 14 days in a dose of about 50 mg. In some embodiments, navitoclax is administered daily for 14 days in a dose of about 25 mg.

In some embodiments, navitoclax is administered daily for 7 days in a dose of about 150 mg to 325 mg. In some embodiments, navitoclax is administered daily for 7 days in a dose of about 150 mg to 300 mg. In some embodiments, navitoclax is administered daily for 7 days in a dose of about 150 mg to 275 mg. In some embodiments, navitoclax is administered daily for 7 days in a dose of about 150 mg to 250 mg. In some embodiments, navitoclax is administered daily for 7 days in a dose of about 150 mg to 225 mg. In some embodiments, navitoclax is administered daily for 7 days in a dose of about 150 mg to 200 mg. In some embodiments, navitoclax is administered daily for 7 days in a dose of about 150 mg to 175 mg. In some embodiments, navitoclax is administered daily for 7 days in a dose of about 150 mg. In some embodiments, navitoclax is administered daily for 7 days in a dose of about 125 mg. In some embodiments, navitoclax is administered daily for 7 days in a dose of about 100 mg. In some embodiments, navitoclax is administered daily for 7 days in a dose of about 75 mg. In some embodiments, navitoclax is administered daily for 7 days in a dose of about 50 mg. In some embodiments, navitoclax is administered daily for 7 days in a dose of about 25 mg. In other particular embodiments, the above doses are administered daily for 1, 2, 3, 4, 5, or 6 days, 8, 9, 10, 11, 12, 13, 15, 16, 17, 18, 19, or 20 days.

In some embodiments, the senolytic agent is nutlin-3a. In some embodiments, nutlin-3a is administered in a treatment window comprising 28 days. In some embodiments, nutlin-3a is administered daily for 10 days, followed by 18 days off. In some embodiments, nutlin-3a is administered daily for 9 days, followed by 19 days off. In some embodiments, nutlin-3a is administered daily for 8 days, followed by 20 days off. In some embodiments, nutlin-3a is administered daily for 7 days, followed by 21 days off. In some embodiments, nutlin-3a is administered daily for 6 days, followed by 22 days off. In some embodiments, nutlin-3a is administered daily for 5 days, followed by 23 days off. In some embodiments, nutlin-3a is administered daily for 4 days, followed by 24 days off. In some embodiments, nutlin-3a is administered daily for 3 days, followed by 25 days off. In some embodiments, nutlin-3a is administered daily for 2 days, followed by 26 days off. In some embodiments, nutlin-3a is administered for 1 day, followed by 27 days off.

In some specific embodiments, nutlin-3a is administered daily for 10 days in a dose of about 20 mg/m$^2$. In some embodiments, nutlin-3a is administered daily for 10 days in a dose of about 19 mg/m$^2$. In some embodiments, nutlin-3a is administered daily for 10 days in a dose of about 18 mg/m$^2$. In some embodiments, nutlin-3a is administered daily for 10 days in a dose of about 17 mg/m$^2$. In some embodiments, nutlin-3a is administered daily for 10 days in a dose of about 16 mg/m$^2$. In some embodiments, nutlin-3a is administered daily for 10 days in a dose of about 15 mg/m$^2$. In some embodiments, nutlin-3a is administered daily for 10 days in a dose of about 14 mg/m$^2$. In some embodiments, nutlin-3a is administered daily for 10 days in a dose of about 13 mg/m$^2$. In some embodiments, nutlin-3a is administered daily for 10 days in a dose of about 12 mg/m$^2$. In some embodiments, nutlin-3a is administered daily for 10 days in a dose of about 11 mg/m$^2$. In some embodiments, nutlin-3a is administered daily for 10 days in a dose of about 10 mg/m$^2$. In some embodiments, nutlin-3a is administered daily for 10 days in a dose of about 9 mg/m$^2$. In some embodiments, nutlin-3a is administered daily for 10 days in a dose of about 8 mg/m$^2$. In some embodiments, nutlin-3a is administered daily for 10 days in a dose of about 7 mg/m$^2$. In some embodiments, nutlin-3a is administered daily for 10 days in a dose of about 6 mg/m$^2$. In some embodiments, nutlin-3a is administered daily for 10 days in a dose of about 5 mg/m$^2$. In some embodiments, nutlin-3a is administered daily for 10 days in a dose of about 4 mg/m$^2$. In some embodiments, nutlin-3a is administered daily for 10 days in a dose of about 3 mg/m$^2$. In some embodiments, nutlin-3a is administered daily for 10 days in a dose of about 2 mg/m$^2$. In some embodiments, nutlin-3a is administered daily for 10 days in a dose of about 1 mg/m$^2$. In some embodiments, nutlin-3a is administered daily for 10 days in a dose of about 0.75 mg/m$^2$. In some embodiments, nutlin-3a is administered daily for 10 days in a dose of about 0.5 mg/m$^2$. In some embodiments, nutlin-3a is administered daily for 10 days in a dose of about 0.25 mg/m$^2$. In some embodiments, nutlin-3a is administered daily for 10 days in a dose of about 0.1 mg/m$^2$. In some embodiments, nutlin-3a is administered daily for 10 days in a dose of about 0.01 mg/m$^2$. In certain embodiments, nutlin-3a is administered for 5, 6, 7, 8, 9, 11, 12, 13, or for 14 days at the doses described above.

Senescence-Associated Diseases and Disorders

Methods are provided herein for treating conditions, diseases, or disorders related to, associated with, or caused by cellular senescence, including age-related diseases and disorders in a subject in need thereof. A senescence-associated disease or disorder may also be called herein a senescent cell-associated disease or disorder. Senescence-associated diseases and disorders include, for example, cardiovascular diseases and disorders, inflammatory diseases and disorders, autoimmune diseases and disorders, pulmonary diseases and disorders, eye diseases and disorders, metabolic diseases and disorders, neurological diseases and disorders (e.g., neurodegenerative diseases and disorders); age-related diseases and disorders induced by senescence; skin conditions; age-related diseases; dermatological diseases and disorders; and transplant related diseases and disorders. A prominent feature of aging is a gradual loss of function, or degeneration that occurs at the molecular, cellular, tissue, and organismal levels. Age-related degeneration gives rise to well-recognized pathologies, such as sarcopenia, atherosclerosis and heart failure, osteoporosis, pulmonary insufficiency, renal failure, neurodegeneration (including macular degeneration, Alzheimer's disease, and Parkinson's disease), and many others. Although different mammalian species vary in their susceptibilities to specific age-related pathologies, collectively, age-related pathologies generally rise with approximately exponential kinetics beginning at about the mid-point of the species-specific life span (e.g., 50-60 years of age for humans) (see, e.g., Campisi, *Annu. Rev. Physiol.* 75:685-705 (2013); Naylor et al., *Clin. Pharmacol. Ther.* 93:105-16 (2013)).

Examples of senescence-associated conditions, disorders, or diseases that may be treated by administering any one of the senolytic agents described herein according to the methods described herein include, cognitive diseases (e.g., mild cognitive impairment (MCI), Alzheimer's disease and other dementias; Huntington's disease); cardiovascular disease (e.g., atherosclerosis, cardiac diastolic dysfunction, aortic aneurysm, angina, arrhythmia, cardiomyopathy, congestive heart failure, coronary artery disease, myocardial infarction, endocarditis, hypertension, carotid artery disease, peripheral vascular diseases, cardiac stress resistance, cardiac fibrosis); metabolic diseases and disorders (e.g., obesity, diabetes, metabolic syndrome); motor function diseases and disorders (e.g., Parkinson's disease, motor neuron dysfunction (MND); Huntington's disease); cerebrovascular disease; emphysema; osteoarthritis; benign prostatic hypertrophy; pulmonary diseases (e.g., idiopathic pulmonary fibrosis, chronic obstructive pulmonary disease (COPD), emphysema, obstructive bronchiolitis, asthma); inflammatory/autoimmune diseases and disorders (e.g., osteoarthritis, eczema, psoriasis, osteoporosis, mucositis, transplantation related diseases and disorders); ophthalmic diseases or disorders (e.g., age-related macular degeneration, cataracts, glaucoma, vision loss, presbyopia); diabetic ulcer; metastasis; a chemotherapeutic side effect, a radiotherapy side effect; aging-related diseases and disorders (e.g., kyphosis, renal dysfunction, frailty, hair loss, hearing loss, muscle fatigue, skin conditions, sarcopenia, and herniated intervertebral disc) and other age-related diseases that are induced by senescence (e.g., diseases/disorders resulting from irradiation, chemotherapy, smoking tobacco, eating a high fat/high sugar diet, and environmental factors); wound healing; skin nevi; fibrotic diseases and disorders (e.g., cystic fibrosis, renal fibrosis, liver fibrosis, pulmonary fibrosis, oral submucous fibrosis, cardiac fibrosis, and pancreatic fibrosis) . In certain embodiments, any one or more of the diseases or disorders described above or herein may be excluded.

In a more specific embodiment, methods are provided for treating a senescence-associated disease or disorder by killing senescent cells (i.e., established senescent cells) associated with the disease or disorder in a subject who has the disease or disorder by administering a senolytic agent, wherein the disease or disorder is osteoarthritis; idiopathic pulmonary fibrosis; chronic obstructive pulmonary disease (COPD); or atherosclerosis.

Subjects (i.e., patients, individuals (human or non-human animals)) who may benefit from use of the methods described herein that comprise administering a senolytic agent include those who may also have a cancer. The subject treated by these methods may be considered to be in partial or complete remission (also called cancer remission). As discussed in detail herein, the senolytic agents for use in methods for selective killing of senescent cells are not intended to be used as a treatment for cancer, that is, in a manner that kills or destroys the cancer cells in a statistically significant manner. Therefore, the methods disclosed herein do not encompass use of the senolytic agents in a manner that would be considered a primary therapy for the treatment of a cancer. Even though a senolytic agent, alone or with other chemotherapeutic or radiotherapy agents, are not used in a manner that is sufficient to be considered as a primary cancer therapy, the methods and senolytic agents described herein may be used in a manner (e.g., a short term course of therapy) that is useful for inhibiting metastases. In other certain embodiments, the subject to be treated with the senolytic agent does not have a cancer (i.e., the subject has not been diagnosed as having a cancer by a person skilled in the medical art).

Cardiovascular Diseases and Disorders.

In another embodiment, the senescence-associated disease or disorder treated by the methods described herein is a cardiovascular disease. The cardiovascular disease may be any one or more of angina, arrhythmia, atherosclerosis, cardiomyopathy, congestive heart failure, coronary artery disease (CAD), carotid artery disease, endocarditis, heart attack (coronary thrombosis, myocardial infarction [MI]), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease (e.g., peripheral artery disease (PAD)), cardiac stress resistance, and stroke.

In certain embodiments, methods are provided for treating senescence-associated cardiovascular disease that is associated with or caused by arteriosclerosis (i.e., hardening of the arteries). The cardiovascular disease may be any one or more of atherosclerosis (e.g., coronary artery disease (CAD) and carotid artery disease); angina, congestive heart failure, and peripheral vascular disease (e.g., peripheral artery disease (PAD)). The methods for treating a cardiovascular disease that is associated with or caused by arteriosclerosis may reduce the likelihood of occurrence of high blood pressure/hypertension, angina, stroke, and heart attack (i.e., coronary thrombosis, myocardial infarction (MI)). In certain embodiments, methods are provided for stabilizing atherosclerotic plaque(s) in a blood vessel (e.g., artery) of a subject, thereby reducing the likelihood of occurrence or delaying the occurrence of a thrombotic event, such as stroke or MI. In certain embodiments, these methods comprising administration of a senolytic agent reduce (i.e., cause decrease of) the lipid content of an atherosclerotic plaque in a blood vessel (e.g., artery) of the subject and/or increase the fibrous cap thickness (i.e., cause an increase, enhance or promote thickening of the fibrous cap).

Atherosclerosis is characterized by patchy intimal plaques (atheromas) that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and its branches, and major arteries of the extremities. Atherosclerosis is characterized by patchy intimal plaques (atheromas) that encroach on the lumen of medium-sized and large arteries; the plaques contain lipids, inflammatory cells, smooth muscle cells, and connective tissue.

In one embodiment, methods are provided for inhibiting the formation of atherosclerotic plaques (or reducing, diminishing, causing decrease in formation of atherosclerotic plaques) by administering a senolytic agent. In other embodiments, methods are provided for reducing (decreasing, diminishing) the amount (i.e., level) of plaque. Reduction in the amount of plaque in a blood vessel (e.g., artery) may be determined, for example, by a decrease in surface area of the plaque, or by a decrease in the extent or degree (e.g., percent) of occlusion of a blood vessel (e.g., artery), which can be determined by angiography or other visualizing methods used in the cardiovascular art. Also provided herein are methods for increasing the stability (or improving, promoting, enhancing stability) of atherosclerotic plaques that are present in one or more blood vessels (e.g., one or more arteries) of a subject, which methods comprise administering to the subject any one of the senolytic agents described herein.

Atherosclerosis is often referred to as a "hardening" or furring of the arteries and is caused by the formation of multiple atheromatous plaques within the arteries. Atherosclerosis (also called arteriosclerotic vascular disease or ASVD herein and in the art) is a form of arteriosclerosis in which an artery wall thickens. Symptoms develop when growth or rupture of the plaque reduces or obstructs blood flow; and the symptoms may vary depending on which artery is affected. Atherosclerotic plaques may be stable or unstable. Stable plaques regress, remain static, or grow slowly, sometimes over several decades, until they may cause stenosis or occlusion. Unstable plaques are vulnerable to spontaneous erosion, fissure, or rupture, causing acute thrombosis, occlusion, and infarction long before they cause hemodynamically significant stenosis. Most clinical events result from unstable plaques, which do not appear severe on angiography; thus, plaque stabilization may be a way to reduce morbidity and mortality. Plaque rupture or erosion can lead to major cardiovascular events such as acute coronary syndrome and stroke (see, e.g., Du et al., *BMC*

*Cardiovascular Disorders* 14:83 (2014); Grimm et al., *Journal of Cardiovascular Magnetic Resonance* 14:80 (2012)). Disrupted plaques were found to have a greater content of lipid, macrophages, and had a thinner fibrous cap than intact plaques (see, e.g., Felton et al., *Arteriosclerosis, Thrombosis, and Vascular Biology* 17:1337-45 (1997)).

Atherosclerosis is a syndrome affecting arterial blood vessels due in significant part to a chronic inflammatory response of white blood cells in the walls of arteries. This is promoted by low-density lipoproteins (LDL, plasma proteins that carry cholesterol and triglycerides) in the absence of adequate removal of fats and cholesterol from macrophages by functional high-density lipoproteins (HDL). The earliest visible lesion of atherosclerosis is the "fatty streak," which is an accumulation of lipid-laden foam cells in the intimal layer of the artery. The hallmark of atherosclerosis is atherosclerotic plaque, which is an evolution of the fatty streak and has three major components: lipids (e.g., cholesterol and triglycerides); inflammatory cells and smooth muscle cells; and a connective tissue matrix that may contain thrombi in various stages of organization and calcium deposits. Within the outer-most and oldest plaque, calcium and other crystallized components (e.g., microcalcification) from dead cells can be found. Microcalcification and properties related thereto are also thought to contribute to plaque instability by increasing plaque stress (see, e.g., Bluestein et al., *J. Biomech.* 41(5):1111-18 (2008); Cilla et al., *Journal of Engineering in Medicine* 227:588-99 (2013)). Fatty streaks reduce the elasticity of the artery walls, but may not affect blood flow for years because the artery muscular wall accommodates by enlarging at the locations of plaque. Lipid-rich atheromas are at increased risk for plaque rupture and thrombosis (see, e.g., Felton et al., supra; Fuster et al., *J. Am. Coll. Cardiol.* 46:1209-18 (2005)). Reports have found that of all plaque components, the lipid core exhibits the highest thrombogenic activity (see, e.g., Fernandez-Ortiz et al., *J. Am. Coll. Cardiol.* 23:1562-69 (1994)). Within major arteries in advanced disease, the wall stiffening may also eventually increase pulse pressure.

A vulnerable plaque that may lead to a thrombotic event (stroke or MI) and is sometimes described as a large, soft lipid pool covered by a thin fibrous cap (see, e.g., Li et al., *Stroke* 37:1195-99 (2006); Trivedi et al., *Neuroradiology* 46:738-43 (2004)). An advanced characteristic feature of advance atherosclerotic plaque is irregular thickening of the arterial intima by inflammatory cells, extracellular lipid (atheroma) and fibrous tissue (sclerosis) (see, e.g., Newby et al., *Cardiovasc. Res.* 345-60 (1999)). Fibrous cap formation is believe to occur from the migration and proliferation of vascular smooth muscle cells and from matrix deposition (see, e.g., Ross, *Nature* 362:801-809 (1993); Sullivan et al., *J. Angiology* at dx.doi.org/10.1155/2013/592815 (2013)). A thin fibrous cap contributes instability of the plaque and to increased risk for rupture (see, e.g., Li et al., supra).

Both proinflammatory macrophages (M1) and anti-inflammatory macrophages (M2) can be found in arteriosclerotic plaque. The contribution of both types to plaque instability is a subject of active investigation, with results suggesting that an increased level of the M1 type versus the M2 type correlates with increased instability of plaque (see, e.g., Medbury et al., *Int. Angiol.* 32:74-84 (2013); Lee et al., *Am. J. Clin. Pathol.* 139:317-22 (2013); Martinet et al., *Cir. Res.* 751-53 (2007)).

Subjects suffering from cardiovascular disease can be identified using standard diagnostic methods known in the art for cardiovascular disease. Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Diagnosis may be confirmed by angiography, ultrasonography, or other imaging tests. Subjects at risk of developing cardiovascular disease include those having any one or more of predisposing factors, such as a family history of cardiovascular disease and those having other risk factors (i.e., predisposing factors) such as high blood pressure, dyslipidemia, high cholesterol, diabetes, obesity and cigarette smoking, sedentary lifestyle, and hypertension. In a certain embodiment, the cardiovascular disease that is a senescence cell associated disease/disorder is atherosclerosis.

The effectiveness of one or more senolytic agents for treating or preventing (i.e., reducing or decreasing the likelihood of developing or occurrence of) a cardiovascular disease (e.g., atherosclerosis) can readily be determined by a person skilled in the medical and clinical arts. One or any combination of diagnostic methods, including physical examination, assessment and monitoring of clinical symptoms, and performance of analytical tests and methods described herein and practiced in the art (e.g., angiography, electrocardiography, stress test, non-stress test), may be used for monitoring the health status of the subject. The effects of the treatment of a senolytic agent or pharmaceutical composition comprising same can be analyzed using techniques known in the art, such as comparing symptoms of patients suffering from or at risk of cardiovascular disease that have received the treatment with those of patients without such a treatment or with placebo treatment.

Inflammatory and Autoimmune Diseases and Disorders.

In certain embodiments, a senescence-associated disease or disorder is an inflammatory disease or disorder, such as by way of non-limiting example, osteoarthritis, that may be treated or prevented (i.e., likelihood of occurrence is reduced) according to the methods described herein that comprise administration of a senolytic agent. Other inflammatory or autoimmune diseases or disorders that may be treated by administering a senolytic agent such as the inhibitors and antagonists described herein include osteoporosis, psoriasis, oral mucositis, rheumatoid arthritis, inflammatory bowel disease, eczema, kyphosis, herniated intervertebral disc, and the pulmonary diseases, COPD and idiopathic pulmonary fibrosis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. It is a common cause of chronic disability in the elderly. Symptoms of osteoarthritis include sore or stiff joints, particularly the hips, knees, and lower back, after inactivity or overuse; stiffness after resting that goes away after movement; and pain that is worse after activity or toward the end of the day.

Osteoarthritis may also affect the neck, small finger joints, the base of the thumb, ankle, and big toe.

Chronic inflammation is thought to be the main age-related factor that contributes to osteoarthritis. In combination with aging, joint overuse and obesity appear to promote osteoarthritis.

Unexpectedly, by selectively killing senescent cells a senolytic agent prevents (i.e., reduces the likelihood of occurrence), reduces or inhibits loss or erosion of proteoglycan layers in a joint, reduces inflammation in the affected joint, and promotes (i.e., stimulates, enhances, induces) production of collagen (e.g., type 2 collagen). Removal of senescent cells causes a reduction in the amount (i.e., level) of inflammatory cytokines, such as IL-6, produced in a joint and inflammation is reduced. Methods are provided herein for treating osteoarthritis, for selectively killing senescent cells in an osteoarthritic joint of a subject, and/or inducing collagen (such as Type 2 collagen) production in the joint of a subject in need thereof by administering at least one senolytic agent (which may be combined with at least one pharmaceutically acceptable excipient to form a pharmaceutical composition) to the subject. A senolytic agent also may be used for decreasing (inhibiting, reducing) production of metalloproteinase 13 (MMP-13), which degrades collagen in a joint, and for restoring proteoglycan layer or inhibiting loss and/or degradation of the proteoglycan layer. Treatment with the senolytic agent thereby also prevents (i.e., reduces likelihood of occurrence of), inhibits, or decreases erosion, or slows (i.e., decreases rate) erosion of the bone. As described in detail herein, in certain embodiments, the senolytic agent is administered directly to an osteoarthritic joint (e.g., by intra-articularly, topical, transdermal, intradermal, or subcutaneous delivery). Treatment with a senolytic agent can also restore, improve, or inhibit deterioration of strength of a joint. In addition, the methods comprising administering a senolytic agent can reduce joint pain and are therefore useful for pain management of osteoarthritic joints.

The effectiveness of one or more senolytic agents for treatment or prophylaxis of osteoarthritis in a subject and monitoring of a subject who receives one or more senolytic agents can readily be determined by a person skilled in the medical and clinical arts. One or any combination of diagnostic methods, including physical examination (such as determining tenderness, swelling or redness of the affected joint), assessment and monitoring of clinical symptoms (such as pain, stiffness, mobility), and performance of analytical tests and methods described herein and practiced in the art (e.g., determining the level of inflammatory cytokines or chemokines; X-ray images to determine loss of cartilage as shown by a narrowing of space between the bones in a joint; magnetic resonance imaging (MRI), providing detailed images of bone and soft tissues, including cartilage), may be used for monitoring the health status of the subject. The effects of the treatment of one or more senolytic agents can be analyzed by comparing symptoms of patients suffering from or at risk of an inflammatory disease or disorder, such as osteoarthritis, who have received the treatment with those of patients who have not received such a treatment or who have received a placebo treatment.

In certain embodiments, senolytic agents may be used for treating and/or preventing (i.e., decreasing or reducing the likelihood of occurrence) rheumatoid arthritis (RA). Dysregulation of innate and adaptive immune responses characterize rheumatoid arthritis (RA), which is an autoimmune disease the incidence of which increases with age. Rheumatoid arthritis is a chronic inflammatory disorder that typically affects the small joints in hands and feet. Whereas osteoarthritis results from, at least in part, wear and tear of a joint, rheumatoid arthritis affects the lining of joints, resulting in a painful swelling that can lead to bone erosion and joint deformity. RA can sometimes also affect other organs of the body, such as the skin, eyes, lungs and blood vessels. RA can occur in a subject at any age; however, RA usually begins to develop after age 40. The disorder is much more common in women. In certain embodiments of the methods described herein, RA is excluded.

Chronic inflammation may also contribute to other age-related or aging related diseases and disorders, such as kyphosis and osteoporosis. Kyphosis is a severe curvature in the spinal column, and it is frequently seen with normal and premature aging (see, e.g., Katzman et al. (2010) *J. Orthop. Sports Phys. Ther.* 40: 352-360). Age-related kyphosis often occurs after osteoporosis weakens spinal bones to the point that they crack and compress. A few types of kyphosis target infants or teens. Severe kyphosis can affect lungs, nerves, and other tissues and organs, causing pain and other problems. Kyphosis has been associated with cellular senescence. Characterizing the capability of a senolytic agent for treating kyphosis may be determined in pre-clinical animal models used in the art. By way of example, TTD mice develop kyphosis (see, e.g., de Boer et al. (2002) *Science* 296: 1276-1279); other mice that may be used include BubR1$^{H/H}$ mice, which are also known to develop kyphosis (see, e.g., Baker et al. (2011) *Nature* 479: 232-36). Kyphosis formation is visually measured over time. The level of senescent cells decreased by treatment with the senolytic agent can be determined by detecting the presence of one or more senescent cell associated markers such as by SA-β-Gal staining.

Osteoporosis is a progressive bone disease that is characterized by a decrease in bone mass and density that may lead to an increased risk of fracture. Bone mineral density (BMD) is reduced, bone microarchitecture deteriorates, and the amount and variety of proteins in bone are altered. Osteoporosis is typically diagnosed and monitored by a bone mineral density test. Post-menopausal women or women who have reduced estrogen are most at risk. While both men and women over 75 are at risk, women are twice as likely to develop osteoporosis than men. The level of senescent cells decreased by treatment with the senolytic agent can be determined by detecting the presence of one or more senescent cell associated markers such as by SA-β-Gal staining.

In still other embodiments, an inflammatory/autoimmune disorder that may be treated or prevented (i.e., likelihood of occurrence is reduced) with the senolytic agents described herein includes irritable bowel syndrome (IBS) and inflammatory bowel diseases, such as ulcerative colitis and Crohn's disease. Inflammatory bowel disease (IBD) involves chronic inflammation of all or part of the digestive tract. In addition to life-threatening complications arising from IBD, the disease can be painful and debilitating. Ulcerative colitis is an inflammatory bowel disease that causes long-lasting inflammation in part of the digestive tract. Symptoms usually develop over time, rather than suddenly. Ulcerative colitis usually affects only the innermost lining of the large intestine (colon) and rectum. Crohn's disease is an inflammatory bowel disease that causes inflammation anywhere along the lining of your digestive tract, and often extends deep into affected tissues. This can lead to abdominal pain, severe diarrhea, and malnutrition. The inflammation caused by Crohn's disease can involve different areas of the digestive tract. Diagnosis and monitoring of the diseases is performed according to methods and diagnostic tests routinely practiced in the art, including blood tests, colonoscopy, flexible sigmoidoscopy, barium enema, CT scan, MRI, endoscopy, and small intestine imaging.

In other embodiments, the methods described herein may be useful for treating a subject who has herniated intervertebral discs. Subjects with these herniated discs exhibit elevated presence of cell senescence in the blood and in vessel walls (see e.g., Roberts et al. (2006) *Eur. Spine J.* 15 Suppl 3: S312-316). Symptoms of a herniated intervertebral disc may include pain, numbness or tingling, or weakness in an arm or leg. Increased levels of proinflammatory molecules and matrix metalloproteases are also found in aging and degenerating discs tissues, suggesting a role for senescence cells (see e.g., Chang-Qing et al. (2007) *Ageing Res. Rev.* 6: 247-61). Animal models may be used to characterize the effectiveness of a senolytic agent in treating herniated intervertebral discs; degeneration of the intervertebral disc is induced in mice by compression and disc strength evaluated (see e.g., Lotz et al. (1998) *Spine* (Philadelphia Pa. 1976). 23:2493-506).

Other inflammatory or autoimmune diseases that may be treated or prevented (i.e., likelihood of occurrence is reduced) by using a senolytic agent include eczema, psoriasis, osteoporosis, and pulmonary diseases (e.g., chronic obstructive pulmonary disease (COPD), idiopathic pulmonary fibrosis (IPF), asthma), inflammatory bowel disease, and mucositis (including oral mucositis, which in some instances is induced by radiation). Certain fibrosis or fibrotic conditions of organs such as renal fibrosis, liver fibrosis, pancreatic fibrosis, cardiac fibrosis, skin wound healing, and oral submucous fibrosis may be treated with using the senolytic agent.

In certain embodiments, the senescent cell associated disorder is an inflammatory disorder of the skin, such as by way of a non-limiting examples, psoriasis and eczema that may be treated or prevented (i.e., likelihood of occurrence is reduced) according to the methods described herein that comprise administration of a senolytic agent. Psoriasis is characterized by abnormally excessive and rapid growth of the epidermal layer of the skin. A diagnosis of psoriasis is usually based on the appearance of the skin. Skin characteristics typical for psoriasis are scaly red plaques, papules, or patches of skin that may be painful and itch. In psoriasis, cutaneous and systemic overexpression of various proinflammatory cytokines is observed such as IL-6, a key component of the SASP. Eczema is an inflammation of the skin that is characterized by redness, skin swelling, itching and dryness, crusting, flaking, blistering, cracking, oozing, or bleeding. The effectiveness of senolytic agents for treatment of psoriasis and eczema and monitoring of a subject who receives such a senolytic agent can be readily determined by a person skilled in the medical or clinical arts. One or any combination of diagnostic methods, including physical examination (such as skin appearance), assessment of monitoring of clinical symptoms (such as itching, swelling, and pain), and performance of analytical tests and methods described herein and practiced in the art (i.e., determining the level of pro-inflammatory cytokines).

Other immune disorders or conditions that may be treated or prevented (i.e., likelihood of occurrence is reduced) with a senolytic agent include conditions resulting from a host immune response to an organ transplant (e.g., kidney, bone marrow, liver, lung, or heart transplant), such as rejection of the transplanted organ. The senolytic agent may be used for treating or reducing the likelihood of occurrence of graft-vs-host disease.

Pulmonary Diseases and Disorders.

In one embodiment, methods are provided for treating ore preventing (i.e., reducing the likelihood of occurrence of) a senescence-associated disease or disorder that is a pulmonary disease or disorder by killing senescent cells (i.e., established senescent cells) associated with the disease or disorder in a subject who has the disease or disorder by administering a senolytic agent. Senescence associated pulmonary diseases and disorders include, for example, idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue (emphysema) and the dysfunction of the small airways (obstructive bronchiolitis). Primary symptoms of COPD include shortness of breath, wheezing, chest tightness, chronic cough, and excess sputum production. Elastase from cigarette smoke-activated neutrophils and macrophages disintegrates the extracellular matrix of alveolar structures, resulting in enlarged air spaces and loss of respiratory capacity (see, e.g., Shapiro et al., *Am. J. Respir. Cell Mol. Biol.* 32, 367-372 (2005)). COPD is most commonly caused by tobacco smoke (including cigarette smoke, cigar smoke, secondhand smoke, pipe smoke), occupational exposure (e.g., exposure to dust, smoke or fumes), and pollution, occurring over decades thereby implicating aging as a risk factor for developing COPD.

The processes involved in causing lung damage include, for example, oxidative stress produced by the high concentrations of free radicals in tobacco smoke; cytokine release due to inflammatory response to irritants in the airway; and impairment of anti-protease enzymes by tobacco smoke and free radicals, allowing proteases to damage the lungs. Genetic susceptibility can also contribute to the disease. In about 1% percent of people with COPD, the disease results from a genetic disorder that causes low level production of alpha-1-antitrypsin in the liver. The enzyme is normally secreted into the bloodstream to help protect the lungs.

Pulmonary fibrosis is a chronic and progressive lung disease characterized by stiffening and scarring of the lung, which may lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis. As the name connotes, the etiology of IPF is unknown. The involvement of cellular senescence in IPF is suggested by the observations that the incidence of the disease increases with age and that lung tissue in IPF patients is enriched for SA-β-Gal-positive cells and contains elevated levels of the senescence marker p21 (see, e.g., Minagawa et al., *Am. J. Physiol. Lung Cell. Mol. Physiol.* 300:L391-L401 (2011); see also, e.g., Naylor et al., supra). Short telomeres are a risk factor common to both IPF and cellular senescence (see, e.g., Alder et al., *Proc. Natl. Acad. Sci. USA* 105:13051-56 (2008)). Without wishing to be bound by theory, the contribution of cellular senescence to IPF is suggested by the report that SASP components of senescent cells, such as IL-6, IL-8, and IL-1β, promote fibroblast-to-myofibroblast differentiation and epithelial-mesenchymal transition, resulting in extensive remodeling of the extracellular matrix of the alveolar and interstitial spaces (see, e.g., Minagawa et al., supra).

Subjects at risk of developing pulmonary fibrosis include those exposed to environmental or occupational pollutants, such as asbestosis and silicosis; who smoke cigarettes; having some typical connective tissue diseases such as rheumatoid arthritis, SLE and scleroderma; having other diseases that involve connective tissue, such as sarcoidosis and Wegener's granulomatosis; having infections; taking certain medications (e.g., amiodarone, bleomycin, busufan, methotrexate, and nitrofurantoin); those subject to radiation therapy to the chest; and those whose family member has pulmonary fibrosis.

Symptoms of COPD may include any one of shortness of breath, especially during physical activities; wheezing; chest tightness; having to clear your throat first thing in the morning because of excess mucus in the lungs; a chronic cough that produces sputum that may be clear, white, yellow or greenish; blueness of the lips or fingernail beds (cyanosis); frequent respiratory infections; lack of energy; unintended weight loss (observed in later stages of disease). Subjects with COPD may also experience exacerbations, during which symptoms worsen and persist for days or longer. Symptoms of pulmonary fibrosis are known in the art and include shortness of breath, particularly during exercise; dry, hacking cough; fast, shallow breathing; gradual unintended weight loss; tiredness; aching joints and muscles; and clubbing (widening and rounding of the tips of the fingers or toes).

Subjects suffering from COPD or pulmonary fibrosis can be identified using standard diagnostic methods routinely practiced in the art. Monitoring the effect of one or more senolytic agents administered to a subject who has or who is at risk of developing a pulmonary disease may be performed using the methods typically used for diagnosis. Generally, one or more of the following exams or tests may be performed: physical exam, patient's medical history, patient's family's medical history, chest X-ray, lung function tests (such as spirometry), blood test (e.g., arterial blood gas analysis), bronchoalveolar lavage, lung biopsy, CT scan, and exercise testing.

Other pulmonary diseases or disorders that may be treated by using a senolytic agent include, for example, emphysema, asthma, bronchiectasis, and cystic fibrosis (see, e.g., Fischer et al., *Am J Physiol Lung Cell Mol Physiol*. 304(6): L394-400 (2013)). These diseases may also be exacerbated by tobacco smoke (including cigarette smoke, cigar smoke, secondhand smoke, pipe smoke), occupational exposure (e.g., exposure to dust, smoke or fumes), infection, and/or pollutants that induce cells into senescence and thereby contribute to inflammation. Emphysema is sometimes considered as a subgroup of COPD.

Bronchiectasis is results from damage to the airways that causes them to widen and become flabby and scarred. Bronchiectasis usually is caused by a medical condition that injures the airway walls or inhibits the airways from clearing mucus. Examples of such conditions include cystic fibrosis and primary ciliary dyskinesia (PCD). When only one part of the lung is affected, the disorder may be caused by a blockage rather than a medical condition.

The methods described herein for treating or preventing (i.e., reducing the likelihood of occurrence of) a senescence associate pulmonary disease or disorder may also be used for treating a subject who is aging and has loss (or degeneration) of pulmonary function (i.e., declining or impaired pulmonary function compared with a younger subject) and/or degeneration of pulmonary tissue. The respiratory system undergoes various anatomical, physiological and immunological changes with age. The structural changes include chest wall and thoracic spine deformities that can impair the total respiratory system compliance resulting in increased effort to breathe. The respiratory system undergoes structural, physiological, and immunological changes with age. An increased proportion of neutrophils and lower percentage of macrophages can be found in bronchoalveolar lavage (BAL) of older adults compared with younger adults. Persistent low grade inflammation in the lower respiratory tract can cause proteolytic and oxidant-mediated injury to the lung matrix resulting in loss of alveolar unit and impaired gas exchange across the alveolar membrane seen with aging. Sustained inflammation of the lower respiratory tract may predispose older adults to increased susceptibility to toxic environmental exposure and accelerated lung function decline. (See, for example, Sharma et al., *Clinical Interventions in Aging* 1:253-60 (2006)). Oxidative stress exacerbates inflammation during aging (see, e.g., Brod, *Inflamm Res* 2000; 49:561-570; Hendel et al., *Cell Death and Differentiation* (2010) 17:596-606). Alterations in redox balance and increased oxidative stress during aging precipitate the expression of cytokines, chemokines, and adhesion molecules, and enzymes (see, e.g., Chung et al., *Ageing Res Rev* 2009; 8:18-30). Constitutive activation and recruitment of macrophages, T cells, and mast cells foster release of proteases leading to extracellular matrix degradation, cell death, remodeling, and other events that can cause tissue and organ damage during chronic inflammation (see, e.g., Demedts et al., *Respir Res* 2006; 7: 53-63). By administering a senolytic agent to an aging subject (which includes a middle-aged adult who is asymptomatic), the decline in pulmonary function may be decelerated or inhibited by killing and removing senescent cells from the respiratory tract.

The effectiveness of a senolytic agent can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of the treatment of a senolytic agent or pharmaceutical composition comprising the agent can be analyzed using techniques known in the art, such as comparing symptoms of patients suffering from or at risk of the pulmonary disease that have received the treatment with those of patients without such a treatment or with placebo treatment. In addition, methods and techniques that evaluate mechanical functioning of the lung, for example, techniques that measure lung capacitance, elastance, and airway hypersensitivity may be performed. To determine lung function and to monitor lung function throughout treatment, any one of numerous measurements may be obtained, expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MVV), peak expiratory flow (PEF), slow vital capacity (SVC). Total lung volumes include total lung capacity (TLC), vital capacity (VC), residual volume (RV), and functional residual capacity (FRC). Gas exchange across alveolar capillary membrane can be measured using diffusion capacity for carbon monoxide (DLCO). Peripheral capillary oxygen saturation (SpO$_2$) can also be measured; normal oxygen levels are typically between 95% and 100%. An SpO$_2$ level below 90% suggests the subject has hypoxemia. Values below 80% are considered critical and requiring intervention to maintain brain and cardiac function and avoid cardiac or respiratory arrest.

Neurological Diseases and Disorders.

Senescence-associated diseases or disorders treatable by administering a senolytic agent described herein include neurological diseases or disorders. Such senescence-associated diseases and disorders include Parkinson's disease, Alzheimer's disease (and other dementias), motor neuron dysfunction (MND), mild cognitive impairment (MCI), Huntington's disease, and diseases and disorders of the eyes, such as age-related macular degeneration. Other diseases of the eye that are associated with increasing age are glaucoma, vision loss, presbyopia, and cataracts.

Parkinson's disease (PD) is the second most common neurodegenerative disease. It is a disabling condition of the brain characterized by slowness of movement (bradykinesia), shaking, stiffness, and in the later stages, loss of balance. Many of these symptoms are due to the loss of certain nerves in the brain, which results in the lack of dopamine. This disease is characterized by neurodegeneration, such as the loss of about 50% to 70% of the dopaminergic neurons in the substantia nigra pars compacta, a profound loss of dopamine in the striatum, and/or the presence of intracytoplasmic inclusions (Lewy bodies), which are composed mainly of alpha-synuclein and ubiquitin. Parkinson's disease also features locomotor deficits, such as tremor, rigidity, bradykinesia, and/or postural instability. Subjects at risk of developing Parkinson's disease include those having a family history of Parkinson's disease and those exposed to pesticides (e.g., rotenone or paraquat), herbicides (e.g., agent orange), or heavy metals. Senescence of dopamine-producing neurons is thought to contribute to the observed cell death in PD through the production of reactive oxygen species (see, e.g., Cohen et al., *J. Neural Transm. Suppl.* 19:89-103 (1983)); therefore, the methods and senolytic agents described herein are useful for treatment and prophylaxis of Parkinson's disease.

Methods for detecting, monitoring or quantifying neurodegenerative deficiencies and/or locomotor deficits associated with Parkinson's diseases are known in the art, such as histological studies, biochemical studies, and behavioral assessment (see, e.g., U.S. Application Publication No. 2012/0005765). Symptoms of Parkinson's disease are known in the art and include, but are not limited to, difficulty starting or finishing voluntary movements, jerky, stiff movements, muscle atrophy, shaking (tremors), and changes in heart rate, but normal reflexes, bradykinesia, and postural instability. There is a growing recognition that people diagnosed with Parkinson's disease may have cognitive impairment, including mild cognitive impairment, in addition to their physical symptoms.

Alzheimer's disease (AD) is a neurodegenerative disease that shows a slowly progressive mental deterioration with failure of memory, disorientation, and confusion, leading to profound dementia. Age is the single greatest predisposing risk factor for developing AD, which is the leading cause of dementia in the elderly (see, e.g., Hebert, et al., *Arch. Neurol.* 60:1119-1122 (2003)). Early clinical symptoms show remarkable similarity to mild cognitive impairment (see below). As the disease progresses, impaired judgment, confusion, behavioral changes, disorientation, and difficulty in walking and swallowing occur.

Alzheimer's disease is characterized by the presence of neurofibrillary tangles and amyloid (senile) plaques in histological specimens. The disease predominantly involves the limbic and cortical regions of the brain. The argyrophilic plaques containing the amyloidogenic Aβ fragment of amyloid precursor protein (APP) are scattered throughout the cerebral cortex and hippocampus. Neurofibrillary tangles are found in pyramidal neurons predominantly located in the neocortex, hippocampus, and nucleus basalis of Meynert. Other changes, such as granulovacuolar degeneration in the pyramidal cells of the hippocampus, and neuron loss and gliosis in the cortex and hippocampus, are observed. Subjects at risk of developing Alzheimer's disease include those of advanced age, those with a family history of Alzheimer's disease, those with genetic risk genes (e.g., ApoE4) or deterministic gene mutations (e.g., APP, PS1, or PS2), and those with history of head trauma or heart/vascular conditions (e.g., high blood pressure, heart disease, stroke, diabetes, high cholesterol).

A number of behavioral and histopathological assays are known in the art for evaluating Alzheimer's disease phenotype, for characterizing therapeutic agents, and assessing treatment. Histological analyses are typically performed postmortem. Histological analysis of Aβ levels may be performed using Thioflavin-S. Congo red, or anti-Aβ staining (e.g., 4G8, 10D5, or 6E10 antibodies) to visualize Aβ deposition on sectioned brain tissues (see, e.g., Holcomb et al., 1998, *Nat. Med.* 4:97-100; Borchelt et al., 1997, *Neuron* 19:939-945; Dickson et al., 1988, *Am. J. Path.* 132:86-101). In vivo methods of visualizing Aβ deposition in transgenic mice have been also described. BSB ((trans, trans)-1-bromo-2,5-bis-(3-hydroxycarbonyl-4-hydroxy)styrylbenzene) and PET tracer $^{11}$C-labelled Pittsburgh Compound-B (PIB) bind to Aβ plaques (see, e.g., Skovronsky et al., 2000, *Proc. Natl. Acad. Sci. USA* 97:7609-7614; Klunk et al., 2004, *Ann. Neurol.* 55:306-319). $^{19}$F-containing amyloidophilic Congo red-type compound FSB ((E,E)-1-fluoro-2,5-bis-(3-hydroxycarbonyl-4-hydroxy)styrylbenzene) allows visualization of Aβ plaques by MRI (see, e.g., Higuchi et al., 2005, *Nature Neurosci.* 8:527-533). Radiolabeled, putrescine-modified amyloid-beta peptide labels amyloid deposits in vivo in a mouse model of Alzheimer's disease (see, e.g., Wengenack et al., 2000, *Nat. Biotechnol.* 18:868-872).

Increased glial fibrillary acidic protein (GFAP) by astrocytes is a marker for astroglial activation and gliosis during neurodegeneration. Aβ plaques are associated with GFAP-positive activated astrocytes, and may be visualized via GFAP staining (see, e.g., Nagele et al. 2004, *Neurobiol. Aging* 25:663-674; Mandybur et al., 1990, *Neurology* 40:635-639; Liang et al., 2010, *J. Biol. Chem.* 285:27737-27744). Neurofibrillary tangles may be identified by immunohistochemistry using thioflavin-S fluorescent microscopy and Gallyas silver stains (see, e.g., Gotz et al., 2001, *J. Biol. Chem.* 276:529-534; U.S. Pat. No. 6,664,443). Axon staining with electron microscopy and axonal transport studies may be used to neuronal degeneration (see, e.g., Ishihara et al., 1999, *Neuron* 24:751-762).

Subjects suffering from Alzheimer's disease can be identified using standard diagnostic methods known in the art for Alzheimer's disease. Generally, diagnosis of Alzheimer's disease is based on symptoms (e.g., progressive decline in memory function, gradual retreat from and frustration with normal activities, apathy, agitation or irritability, aggression, anxiety, sleep disturbance, dysphoria, aberrant motor behavior, disinhibition, social withdrawal, decreased appetite, hallucinations, dementia), medical history, neuropsychological tests, neurological and/or physical examination of a patient. Cerebrospinal fluid may also be for tested for various proteins that have been associated with Alzheimer pathology, including tau, amyloid beta peptide, and AD7C-NTP. Genetic testing is also available for early-onset familial Alzheimer disease (eFAD), an autosomal-dominant genetic disease. Clinical genetic testing is available for individuals with AD symptoms or at-risk family members of patients with early-onset disease. In the U.S., mutations for PS2, and APP may be tested in a clinical or federally approved laboratory under the Clinical Laboratory Improvement Amendments. A commercial test for PS1 mutations is also available (Elan Pharmaceuticals).

The effectiveness of one or more senolytic agents described herein and monitoring of a subject who receives one or more senolytic agents can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of administering one or more senolytic agents can be analyzed using techniques known in the art, such as comparing symptoms of patients suffering from or at risk of Alzheimer's disease that have received the treatment with those of patients without such a treatment or with placebo treatment.

Mild Cognitive Impairment (MCI).

MCI is a brain-function syndrome involving the onset and evolution of cognitive impairments beyond those expected based on age and education of the individual, but which are not significant enough to interfere with this individual's daily activities. MCI is an aspect of cognitive aging that is considered to be a transitional state between normal aging and the dementia into which it may convert (see, Pepeu, *Dialogues in Clinical Neuroscience* 6:369-377, 2004). MCI that primarily affects memory is known as "amnestic MCI." A person with amnestic MCI may start to forget important information that he or she would previously have recalled easily, such as recent events. Amnestic MCI is frequently seen as prodromal stage of Alzheimer's disease. MCI that affects thinking skills other than memory is known as "non-amnestic MCI." This type of MCI affect thinking skills such as the ability to make sound decisions, judge the time or sequence of steps needed to complete a complex task, or visual perception. Individuals with non-amnestic MCI are believed to be more likely to convert to other types of dementias (e.g., dementia with Lewy bodies).

Persons in the medical art have a growing recognition that people diagnosed with Parkinson's disease may have MCI in addition to their physical symptoms. Recent studies show 20-30% of people with Parkinson's disease have MCI, and that their MCI tends to be non-amnestic. Parkinson's disease patients with MCI sometimes go on to develop full blown dementia (Parkinson's disease with dementia).

Methods for detecting, monitoring, quantifying or assessing neuropathological deficiencies associated with MCI are known in the art, including astrocyte morphological analyses, release of acetylcholine, silver staining for assessing neurodegeneration, and PiB PET imaging to detect beta amyloid deposits (see, e.g., U.S. Application Publication No. 2012/0071468; Pepeu, 2004, supra). Methods for detecting, monitoring, quantifying or assessing behavioral deficiencies associated with MCI are also known in the art, including eight-arm radial maze paradigm, non-matching-to-sample task, allocentric place determination task in a water maze, Morris maze test, visuospatial tasks, and delayed response spatial memory task, olfactory novelty test (see, id.).

Motor Neuron Dysfunction (MND).

MND is a group of progressive neurological disorders that destroy motor neurons, the cells that control essential voluntary muscle activity such as speaking, walking, breathing and swallowing. It is classified according to whether degeneration affects upper motor neurons, lower motor neurons, or both. Examples of MNDs include, but are not limited to Amyotrophic Lateral Sclerosis (ALS), also known as Lou Gehrig's Disease, progressive bulbar palsy, pseudobulbar palsy, primary lateral sclerosis, progressive muscular atrophy, lower motor neuron disease, and spinal muscular atrophy (SMA) (e.g., SMA1 also called Werdnig-Hoffmann Disease, SMA2, SMA3 also called Kugelberg-Welander Disease, and Kennedy's disease), post-polio syndrome, and hereditary spastic paraplegia. In adults, the most common MND is amyotrophic lateral sclerosis (ALS), which affects both upper and lower motor neurons. It can affect the arms, legs, or facial muscles. Primary lateral sclerosis is a disease of the upper motor neurons, while progressive muscular atrophy affects only lower motor neurons in the spinal cord. In progressive bulbar palsy, the lowest motor neurons of the brain stem are most affected, causing slurred speech and difficulty chewing and swallowing. There are almost always mildly abnormal signs in the arms and legs. Patients with MND exhibit a phenotype of Parkinson's disease (e.g., having tremor, rigidity, bradykinesia, and/or postural instability). Methods for detecting, monitoring or quantifying locomotor and/or other deficits associated with Parkinson's diseases, such as MND, are known in the art (see, e.g., U.S. Application Publication No. 20120005765).

Methods for detecting, monitoring, quantifying or assessing motor deficits and histopathological deficiencies associated with MND are known in the art, including histopathological, biochemical, and electrophysiological studies and motor activity analysis (see, e.g., Rich et al., *J Neurophysiol* 88:3293-3304, 2002; Appel et al., *Proc. Natl. Acad. Sci. USA* 88:647-51, 1991). Histopathologically, MNDs are characterized by death of motor neurons, progressive accumulation of detergent-resistant aggregates containing SOD1 and ubiquitin and aberrant neurofilament accumulations in degenerating motor neurons. In addition, reactive astroglia and microglia are often detected in diseased tissue. Patients with an MND show one or more motor deficits, including muscle weakness and wasting, uncontrollable twitching, spasticity, slow and effortful movements, and overactive tendon reflexes.

Ophthalmic Diseases and Disorders:

In certain embodiments, a senescence-associated disease or disorder is an ocular disease, disorder, or condition, for example, presbyopia, macular degeneration, or cataracts. In other certain embodiments, the senescence-associated disease or disorder is glaucoma. Macular degeneration is a neurodegenerative disease that causes the loss of photoreceptor cells in the central part of retina, called the macula. Macular degeneration generally is classified into two types: dry type and wet type. The dry form is more common than the wet, with about 90% of age-related macular degeneration (ARMD or AMD) patients diagnosed with the dry form. The wet form of the disease usually leads to more serious vision loss. While the exact causes of age-related macular degeneration are still unknown, the number of senescent retinal pigmented epithelial (RPE) cells increases with age. Age and certain genetic factors and environmental factors are risk factors for developing ARMD (see, e.g., Lyengar et al., *Am. J. Hum. Genet.* 74:20-39 (2004) (Epub 2003 Dec. 19); Kenealy et al., *Mol. Vis.* 10:57-61 (2004); Gorin et al., *Mol. Vis.* 5:29 (1999)). Environment predisposing factors include omega-3 fatty acids intake (see, e.g., Christen et al., *Arch Ophthalmol.* 129:921-29 (2011)); estrogen exposure (see, e.g., Feshanich et al., *Arch Ophthalmol* 126(4):519-24 (2008)); and increased serum levels of vitamin D (see, e.g., Millen, et al., *Arch Ophthalmol.* 129(4):481-89 (2011)). Genetic predisposing risk factors include reduced levels Dicer1 (enzyme involved in maturation of micro RNA) in eyes of patients with dry AMD, and decreased micro RNAs contributes to a senescent cell profile; and DICER1 ablation induces premature senescence (see, e.g., Mudhasani *J. Cell. Biol.* (2008)).

Dry ARMD is associated with atrophy of RPE layer, which causes loss of photoreceptor cells. The dry form of ARMD may result from aging and thinning of macular tissues and from deposition of pigment in the macula. Senescence appears to inhibit both replication and migration of RPE, resulting in permanent RPE depletion in the macula of dry AMD patients (see, e.g., Iriyama et al., *J. Biol. Chem.* 283:11947-953 (2008)). With wet ARMD, new blood vessels grow beneath the retina and leak blood and fluid. This abnormal leaky choroidal neovascularization causes the retinal cells to die, creating blind spots in central vision. Different forms of macular degeneration may also occur in younger patients. Non-age related etiology may be linked to heredity, diabetes, nutritional deficits, head injury, infection, or other factors.

Declining vision noticed by the patient or by an ophthalmologist during a routine eye exam may be the first indicator of macular degeneration. The formation of exudates, or "drusen," underneath the Bruch's membrane of the macula is often the first physical sign that macular degeneration may develop. Symptoms include perceived distortion of straight lines and, in some cases, the center of vision appears more distorted than the rest of a scene; a dark, blurry area or "white-out" appears in the center of vision; and/or color perception changes or diminishes. Diagnosing and monitoring of a subject with macular degeneration may be accomplished by a person skilled in the ophthalmic art according to art-accepted periodic eye examination procedures and report of symptoms by the subject.

Presbyopia is an age-related condition where the eye exhibits a progressively diminished ability to focus on near objects as the speed and amplitude of accommodation of a normal eye decreases with advancing age. Loss of elasticity of the crystalline lens and loss of contractility of the ciliary muscles have been postulated as its cause (see, e.g., Heys et al., 2004, *Mol. Vis.* 10:956-63; Petrash, 2013, *Invest. Ophthalmol. Vis. Sci.* 54:ORSF54-ORSF59). Age-related changes in the mechanical properties of the anterior lens capsule and posterior lens capsule suggest that the mechanical strength of the posterior lens capsule decreases significantly with age (see, e.g., Krag et al., *Invest. Ophthalmol. Vis. Sci.* 44:691-96 (2003); Krag et al., *Invest. Ophthalmol. Vis. Sci.* 38:357-63 (1997)).

The laminated structure of the capsule also changes and may result, at least in part, from a change in the composition of the tissue (see, e.g., Krag et al., 1997, supra, and references cited therein). The major structural component of the lens capsule is basement membrane type IV collagen that is organized into a three-dimensional molecular network (see, e.g., Cummings et al., *Connect. Tissue Res.* 55:8-12 (2014); Veis et al., *Coll. Relat. Res.* 1981; 1:269-86). Type IV collagen is composed of six homologous α chains (α1-6) that associate into heterotrimeric collagen IV protomers with each comprising a specific chain combination of α112, α345, or α556 (see, e.g., Khoshnoodi et al., *Microsc. Res. Tech.* 2008; 71:357-70). Protomers share structural similarities of a triple-helical collagenous domain with the triplet peptide sequence of Gly-X-Y (Timpl et al., *Eur. J. Biochem.* 1979; 95:255-263), ending in a globular C-terminal region termed the non-collagenous 1 (NC1) domain. The N-termini are composed of a helical domain termed the 7S domain (see, e.g., Risteli et al., *Eur. J. Biochem.* 1980; 108:239-250), which is also involved in protomer-protomer interactions.

Research has suggested that collagen IV influences cellular function which is inferred from the positioning of basement membranes underneath epithelial layers, and data support the role of collagen IV in tissue stabilization (see, e.g., Cummings et al., supra). Posterior capsule opacification (PCO) develops as a complication in approximately 20-40% of patients in subsequent years after cataract surgery (see, e.g., Awasthi et al., *Arch Ophthalmol.* 2009; 127:555-62). PCO results from proliferation and activity of residual lens epithelial cells along the posterior capsule in a response akin to wound healing (see, e.g., Awasthi et al., *Arch Ophthalmol.* 2009; 127:555-62). Growth factors, such as fibroblast growth factor, transforming growth factor β, epidermal growth factor, hepatocyte growth factor, insulin-like growth factor, and interleukins IL-1 and IL-6 may also promote epithelial cell migration, (see, e.g., Awasthi et al., supra; Raj et al., supra). As discussed herein, production of these factors and cytokines by senescent cells contribute to the SASP. In contrast, in vitro studies show that collagen IV promotes adherence of lens epithelial cells (see, e.g., Olivero et al., *Invest. Ophthalmol. Vis. Sci.* 1993; 34:2825-34). Adhesion of the collagen IV, fibronectin, and laminin to the intraocular lens inhibits cell migration and may reduce the risk of PCO (see, e.g., Raj et al., *Int. J. Biomed. Sci.* 2007; 3:237-50).

Without wishing to be bound by any particular theory, selective killing of senescent cells by the senolytic agents described herein may slow or impede (delay, inhibit, retard) the disorganization of the type IV collagen network. Removal of senescence cells and thereby removing the inflammatory effects of SASP may decrease or inhibit epithelial cell migration and may also delay (suppress) the onset of presbyopia or decrease or slow the progressive severity of the condition (such as slow the advancement from mild to moderate or moderate to severe). The senolytic agents described herein may also be useful for post-cataract surgery to reduce the likelihood of occurrence of PCO.

While no direct evidence for the involvement of cellular senescence with the development of cataracts has been obtained from human studies, BubR1 hypomorphic mice develop posterior subcapsular cataracts bilaterally early in life, suggesting that senescence may play a role (see, e.g., Baker et al., *Nat. Cell Biol.* 10:825-36 (2008)). Cataracts are a clouding of the lens of an eye, causing blurred vision, and if left untreated can result in blindness. Surgery is effective and routinely performed to remove cataracts. Administration of one or more of the senolytic agents described herein may result in decreasing the likelihood of occurrence of a cataract or may slow or inhibit progression of a cataract. The presence and severity of a cataract can be monitored by eye exams using methods routinely performed by a person skilled in the ophthalmology art.

In certain embodiments, at least one senolytic agent that selectively kills senescent cells may be administered to a subject who is at risk of developing presbyopia, cataracts, or macular degeneration. Treatment with a senolytic agent may be initiated when a human subject is at least 40 years of age to delay or inhibit onset or development of cataracts, presbyopia, and macular degeneration. Because almost all humans develop presbyopia, in certain embodiments, the senolytic agent may be administered in a manner as described herein to a human subject after the subject reaches the age of 40 to delay or inhibit onset or development of presbyopia.

In certain embodiments, the senescence associated disease or disorder is glaucoma. Glaucoma is a broad term used to describe a group of diseases that causes visual field loss, often without any other prevailing symptoms. The lack of symptoms often leads to a delayed diagnosis of glaucoma until the terminal stages of the disease. Even if subjects afflicted with glaucoma do not become blind, their vision is often severely impaired. Normally, clear fluid flows into and out of the front part of the eye, known as the anterior chamber. In individuals who have open/wide-angle glaucoma, this fluid drains too slowly, leading to increased pressure within the eye. If left untreated, this high pressure subsequently damages the optic nerve and can lead to complete blindness. The loss of peripheral vision is caused by the death of ganglion cells in the retina. Ganglion cells are a specific type of projection neuron that connects the eye to the brain. When the cellular network required for the outflow of fluid was subjected to SA-β-Gal staining, a fourfold increase in senescence has been observed in glaucoma patients (see, e.g., Liton et al., *Exp. Gerontol.* 40:745-748 (2005)).

For monitoring the effect of a therapy on inhibiting progression of glaucoma, standard automated perimetry (visual field test) is the most widely used technique. In addition, several algorithms for progression detection have been developed (see, e.g., Wesselink et al., *Arch Ophthalmol.* 127(3):270-274 (2009), and references therein). Additional methods include gonioscopy (examines the trabecular meshwork and the angle where fluid drains out of the eye); imaging technology, for example scanning laser tomography (e.g., HRT3), laser polarimetry (e.g., GDX), and ocular coherence tomography); ophthalmoscopy; and pachymeter measurements that determine central corneal thickness.

Metabolic Disease or Disorder.

Senescence-associated diseases or disorders treatable by administering a senolytic agent include metabolic diseases or disorders. Such senescent cell associated diseases and disorders include diabetes, metabolic syndrome, diabetic ulcers, and obesity.

Diabetes is characterized by high levels of blood glucose caused by defects in insulin production, insulin action, or both. The great majority (90 to 95%) of all diagnosed cases of diabetes in adults are type 2 diabetes, characterized by the gradual loss of insulin production by the pancreas. Diabetes is the leading cause of kidney failure, nontraumatic lower-limb amputations, and new cases of blindness among adults in the U.S. Diabetes is a major cause of heart disease and stroke and is the seventh leading cause of death in the U.S. (see, e.g., Centers for Disease Control and Prevention, National diabetes fact sheet: national estimates and general information on diabetes and pre-diabetes in the United States, 2011 ("Diabetes fact sheet")). Senolytic agents described herein may be used for treating type 2 diabetes, particularly age-, diet- and obesity-associated type 2 diabetes.

Involvement of senescent cells in metabolic disease, such as obesity and type 2 diabetes, has been suggested as a response to injury or metabolic dysfunction (see, e.g., Tchkonia et al., *Aging Cell* 9:667-684 (2010)). Fat tissue from obese mice showed induction of the senescence markers SA-β-Gal, p53, and p21 (see, e.g., Tchkonia et al., supra; Minamino et al., *Nat. Med.* 15:1082-1087 (2009)). A concomitant up-regulation of pro-inflammatory cytokines, such as tumor necrosis factor-α and Ccl2/MCP1, was observed in the same fat tissue (see, e.g., Minamino et al., supra). Induction of senescent cells in obesity potentially has clinical implications because pro-inflammatory SASP components are also suggested to contribute to type 2 diabetes (see, e.g., Tchkonia et al., supra). A similar pattern of up-regulation of senescence markers and SASP components are associated with diabetes, both in mice and in humans (see, e.g., Minamino et al., supra). Accordingly, the methods described herein that comprise administering a senolytic agent may be useful for treatment or prophylaxis of type 2 diabetes, as well as obesity and metabolic syndrome. Without wishing to be bound by theory, contact of senescent pre-adipocytes with a senolytic agent thereby killing the senescent pre-adipocytes may provide clinical and health benefit to a person who has any one of diabetes, obesity, or metabolic syndrome.

Subjects suffering from type 2 diabetes can be identified using standard diagnostic methods known in the art for type 2 diabetes. Generally, diagnosis of type 2 diabetes is based on symptoms (e.g., increased thirst and frequent urination, increased hunger, weight loss, fatigue, blurred vision, slow-healing sores or frequent infections, and/or areas of darkened skin), medical history, and/or physical examination of a patient. Subjects at risk of developing type 2 diabetes include those who have a family history of type 2 diabetes and those who have other risk factors such as excess weight, fat distribution, inactivity, race, age, prediabetes, and/or gestational diabetes.

The effectiveness of a senolytic agent can readily be determined by a person skilled in the medical and clinical arts. One or any combination of diagnostic methods, including physical examination, assessment and monitoring of clinical symptoms, and performance of analytical tests and methods, such as those described herein, may be used for monitoring the health status of the subject. A subject who is receiving one or more senolytic agents described herein for treatment or prophylaxis of diabetes can be monitored, for example, by assaying glucose and insulin tolerance, energy expenditure, body composition, fat tissue, skeletal muscle, and liver inflammation, and/or lipotoxicity (muscle and liver lipid by imaging in vivo and muscle, liver, bone marrow, and pancreatic β-cell lipid accumulation and inflammation by histology). Other characteristic features or phenotypes of type 2 diabetes are known and can be assayed as described herein and by using other methods and techniques known and routinely practiced in the art.

Obesity and obesity-related disorders are used to refer to conditions of subjects who have a body mass that is measurably greater than ideal for their height and frame. Body Mass Index (BMI) is a measurement tool used to determine excess body weight, and is calculated from the height and weight of a subject. A human is considered overweight when the person has a BMI of 25-29; a person is considered obese when the person has a BMI of 30-39, and a person is considered severely obese when the person has a BMI of ≥40. Accordingly, the terms obesity and obesity-related refer to human subjects with body mass index values of greater than 30, greater than 35, or greater than 40. A category of obesity not captured by BMI is called "abdominal obesity" in the art, which relates to the extra fat found around a subject's middle, which is an important factor in health, even independent of BMI. The simplest and most often used measure of abdominal obesity is waist size. Generally abdominal obesity in women is defined as a waist size 35 inches or higher, and in men as a waist size of 40 inches or higher. More complex methods for determining obesity require specialized equipment, such as magnetic resonance imaging or dual energy X-ray absorptiometry machines.

A condition or disorder associated with diabetes and senescence is a diabetic ulcer (i.e., diabetic wound). An ulcer is a breakdown in the skin, which may extend to involve the subcutaneous tissue or even muscle or bone. These lesions occur, particularly, on the lower extremities. Patients with diabetic venous ulcer exhibit elevated presence of cellular senescence at sites of chronic wounds (see, e.g., Stanley et al. (2001) *J. Vas. Surg.* 33: 1206-1211). Chronic inflammation is also observed at sites of chronic wounds, such as diabetic ulcers (see, e.g., Goren et al. (2006) *Am. J. Pathol.* 7 168: 65-77; Seitz et al. (2010) *Exp. Diabetes Res.* 2010: 476969), suggesting that the proinflammatory cytokine phenotype of senescent cells has a role in the pathology.

Subjects who have type 2 diabetes or who are at risk of developing type 2 diabetes may have metabolic syndrome. Metabolic syndrome in humans is typically associated with obesity and characterized by one or more of cardiovascular disease, liver steatosis, hyperlipidemia, diabetes, and insulin resistance. A subject with metabolic syndrome may present with a cluster of metabolic disorders or abnormalities which may include, for example, one or more of hypertension, type-2 diabetes, hyperlipidemia, dyslipidemia (e.g., hypertriglyceridemia, hypercholesterolemia), insulin resistance, liver steatosis (steatohepatitis), hypertension, atherosclerosis, and other metabolic disorders.

Renal Dysfunction:

Nephrological pathologies, such as glomerular disease, arise in the elderly. Glomerulonephritis is characterized by inflammation of the kidney and by the expression of two proteins, IL1α and IL1β (see, e.g., Niemir et al. (1997) *Kidney Int.* 52:393-403). IL1α and IL1β are considered master regulators of SASP (see, e.g., Coppe et al. (2008) *PLoS. Biol.* 6: 2853-68). Glomerular disease is associated with elevated presence of senescent cells, especially in fibrotic kidneys (see, e.g., Sis et al. (2007) *Kidney Int.* 71:218-226).

Dermatological Disease or Disorder.

Senescence-associated diseases or disorders treatable by administering a senolytic agent described herein include dermatological diseases or disorders. Such senescent cell associated diseases and disorders include psoriasis and eczema, which are also inflammatory diseases and are discussed in greater detail above. Other dermatological diseases and disorders that are associated with senescence include rhytides (wrinkles due to aging); pruritis (linked to diabetes and aging); dysesthesia (chemotherapy side effect that is linked to diabetes and multiple sclerosis); psoriasis (as noted) and other papulosquamous disorders, for example, erythroderma, lichen planus, and lichenoid dermatosis; atopic dermatitis (a form of eczema and associated with inflammation); eczematous eruptions (often observed in aging patients and linked to side effects of certain drugs). Other dermatological diseases and disorders associated with senescence include eosinophilic dermatosis (linked to certain kinds of hemotologic cancers); reactive neutrophilic dermatosis (associated with underlying diseases such as inflammatory bowel syndrome); pemphigus (an autoimmune disease in which autoantibodies form against desmoglein); pemphigoid and other immunobullous dermatosis (autoimmune blistering of skin); fibrohistocytic proliferations of skin, which is linked to aging; and cutaneous lymphomas that are more common in older populations. Another dermatological disease that may be treatable according to the methods described herein includes cutaneous lupus, which is a symptom of lupus erythematosus. Late onset lupus may be linked to decreased (i.e., reduced) function of T-cell and B-cells and cytokines (immunosenescence) associated with aging.

Metastasis.

In a particular embodiment, methods are provided for treating or preventing (i.e., reducing the likelihood of occurrence or development of) a senescence cell associated disease (or disorder or condition), which is metastasis. The senolytic agents described herein may also be used according to the methods described herein for treating or preventing (i.e., reducing the likelihood of occurrence of) metastasis (i.e., the spreading and dissemination of cancer or tumor cells) from one organ or tissue to another organ or tissue in the body.

A senescent cell-associated disease or disorder includes metastasis, and a subject who has a cancer may benefit from administration of a senolytic agent as described herein for inhibiting metastasis. Such a senolytic agent when administered to a subject who has a cancer according to the methods described herein may inhibit tumor proliferation. Metastasis of a cancer occurs when the cancer cells (i.e., tumor cells) spread beyond the anatomical site of origin and initial colonization to other areas throughout the body of the subject. Tumor proliferation may be determined by tumor size, which can be measured in various ways familiar to a person skilled in the art, such as by PET scanning, MRI, CAT scan, biopsy, for example. The effect of the therapeutic agent on tumor proliferation may also be evaluated by examining differentiation of the tumor cells.

As used herein and in the art, the terms cancer or tumor are clinically descriptive terms that encompass diseases typically characterized by cells exhibiting abnormal cellular proliferation. The term cancer is generally used to describe a malignant tumor or the disease state arising from the tumor. Alternatively, an abnormal growth may be referred to in the art as a neoplasm. The term tumor, such as in reference to a tissue, generally refers to any abnormal tissue growth that is characterized, at least in part, by excessive and abnormal cellular proliferation. A tumor may be metastatic and capable of spreading beyond its anatomical site of origin and initial colonization to other areas throughout the body of the subject. A cancer may comprise a solid tumor or may comprise a "liquid" tumor (e.g., leukemia and other blood cancers).

Cells are induced to senesce by cancer therapies, such as radiation and certain chemotherapy drugs. The presence of senescent cells increases secretion of inflammatory molecules (see description herein of senescent cells), promotes tumor progression, which may include promoting tumor growth and increasing tumor size, promoting metastasis, and altering differentiation. When senescent cells are destroyed, tumor progression is significantly inhibited, resulting in tumors of small size and with little or no observed metastatic growth (see, e.g., Int'l Appl. Publication No. WO 2013/090645).

In one embodiment, methods are provided for preventing (i.e., reducing the likelihood of occurrence of), inhibiting, or retarding metastasis in a subject who has a cancer by administering a senolytic agent as described herein. In a particular embodiment, the senolytic agent is administered on one or more days within a treatment window (i.e., treatment course) of no longer than 7 days or 14 days. In other embodiments, the treatment course is no longer than 2, 3, 4, 5, 6, 7, 8, 9, 10, 11, 12, 13, 14, 15, 16, 17, 18, 19, 20, or no longer than 21 days. In other embodiments, the treatment course is a single day. In certain embodiments, the senolytic agent is administered on two or more days within a treatment window of no longer than 7 days or 14 days, on 3 or more days within a treatment window of no longer than 7 days or 14 days; on 4 or more days within a treatment window of no longer than 7 days or 14 days; on 5 or more days within a treatment window of no longer than 7 days or 14 days; on 6, 7, 8, 9, 10, 11, 12, 13, or 14 days within treatment window of no longer than 7 days or 14 days. In certain embodiments, when the at least one senolytic agent is administered to a subject for a treatment window of 3 days or more, the agent may be administered every $2^{nd}$ day (i.e., every other day). In other certain embodiments when the at least one senolytic agent is administered to a subject for a treatment window of 4 days or more, the agent may be administered every $3^{rd}$ day (i.e., every other third day).

Because cells may be induced to senesce by cancer therapies, such as radiation and certain chemotherapy drugs (e.g., doxorubicin; paclitaxel; gemcitabine; pomalidomide; lenalidomide), a senolytic agent described herein may be administered after the chemotherapy or radiotherapy to kill (or facilitate killing) of these senescent cells. As discussed herein and understood in the art, establishment of senescence, such as shown by the presence of a senescence-associated secretory phenotype (SASP), occurs over several days; therefore, administering a senolytic agent to kill senescent cells, and thereby reduce the likelihood of occurrence or reduce the extent of metastasis, is initiated when senescence has been established. As discussed herein, the following treatment courses for administration of the senolytic agent may be used in methods described herein for treating or preventing (i.e., reducing the likelihood of occurrence, or reducing the severity) a chemotherapy or radiotherapy side effect.

In certain embodiments, when chemotherapy or radiotherapy is administered in a treatment cycle of at least one day on-therapy (i.e., chemotherapy or radiotherapy)) followed by at least 3, 4, 5, 6, 7, 8, 9, 10, 11, 12, 13, 14 (or about 2 weeks), 15, 16, 17, 18, 19, 20, 21 (or about 3 weeks) days, or about 4 weeks (about one month) off-therapy (i.e., off chemo- or radio-therapy), the senolytic agent is administered on one or more days during the off-therapy time interval (time period) beginning on or after the second day of the off-therapy time interval and ending on or before the last day of the off-therapy time interval. By way of illustrative example, if n is the number of days off-therapy, then the senolytic agent is administered on at least one day and no more than n−1 days of the off-therapy time interval. In a certain particular embodiment when chemotherapy or radiotherapy is administered in a treatment cycle of at least one day on-therapy (i.e., chemotherapy or radiotherapy)) followed by at least one week off-therapy, the senolytic agent is administered on one or more days during the off-therapy time interval beginning on or after the second day of the off-therapy time interval and ending on or before the last day of the off-therapy time interval. In a more specific embodiment, when chemotherapy or radiotherapy is administered in a treatment cycle of at least one day on-therapy (i.e., chemotherapy or radiotherapy)) followed by at least one week off-therapy, the senolytic agent is administered on one day that is the sixth day of the off-therapy time interval. In other specific embodiments, when chemotherapy or radiotherapy is administered in a treatment cycle of at least one day on-therapy (i.e., chemotherapy or radiotherapy)) followed by at least two weeks off-therapy, the senolytic agent is administered beginning on the sixth day of the off-chemo- or radio-therapy time interval and ending at least one day or at least two days prior to the first day of a subsequent chemotherapy or radiation therapy treatment course. By way of example, if the off-chemo- or radio-therapy time interval is two weeks, a senolytic agent may be administered on at least one and on no more than 7 days (i.e., 1, 2, 3, 4, 5, 6, or 7 days) of the off-therapy time interval beginning on the sixth day after the chemotherapy or radiotherapy course ends (i.e., the sixth day of the off chemo-radio-therapy interval). When the off-chemo- or radio-therapy time interval is at least three weeks, a senolytic agent may be administered on at least one day and on no more than 14 days (i.e., 1-14 days: 1, 2, 3, 4, 5, 6, 7, 8, 9, 10, 11, 12, 13, or 14 days) of the off-therapy time interval beginning on the sixth day after the chemotherapy or radiotherapy course ends. In other embodiments, depending on the off-chemo-radio-therapy interval, the senolytic agent treatment course is at least one day and no longer than 2, 3, 4, 5, 6, 7, 8, 9, 10, 11, 12, 13, 14, 15, 16, 17, 18, 19, 20, or no more than 21 days (i.e., 1-21 days), provided that administration of the senolytic agent is not concurrent with the chemotherapy or radiotherapy. In certain embodiments, the senolytic agent treatment course is a single day. In certain embodiments, the senolytic agent is administered on two or more days within a treatment window of no longer than 14 days, on 3 or more days within a treatment window of no longer than 14 days; on 4 or more days within a treatment window of no longer than 14 days; on 5 or more days within a treatment window of no longer than 14 days; on 6, 7, 8, 9, 10, 11, 12, 13, or 14 days within treatment window of no longer than 14 days. In certain embodiments, when the at least one senolytic agent is administered to a subject during a treatment course of 3 days or more, the agent may be administered every $2^{nd}$ day (i.e., every other day). In other certain embodiments when the at least one senolytic agent is administered to a subject during a treatment course of 4 days or more, the agent may be administered every $3^{rd}$ day (i.e., every other third day).

Many chemotherapy and radiotherapy treatment regimens comprise a finite number of cycles of on-drug therapy followed by off-drug therapy or comprise a finite timeframe in which the chemotherapy or radiotherapy is administered. Such cancer treatment regimens may also be called treatment protocols. The protocols are determined by clinical trials, drug labels, and clinical staff in conjunction with the subject to be treated. The number of cycles of a chemotherapy or radiotherapy or the total length of time of a chemotherapy or radiotherapy regimen can vary depending on the patient's response to the cancer therapy. The timeframe for such treatment regimens is readily determined by a person skilled in the oncology art. In another embodiment for treating metastasis, a senolytic agent may be administered after the treatment regimen of chemotherapy or radiotherapy has been completed. In a particular embodiment, the senolytic agent is administered after the chemotherapy or radiotherapy has been completed on one or more days within treatment window (i.e., senolytic agent treatment course) of no longer than 14 days. In other embodiments, the senolytic agent treatment course is no longer than 2, 3, 4, 5, 6, 7, 8, 9, 10, 11, 12, 13, 14, 15, 16, 17, 18, 19, 20, or no more than 21 days. In other embodiments, the treatment course is a single day. In certain embodiments, the senolytic agent is administered on two or more days within a treatment window of no longer than 14 days, on 3 or more days within a treatment window of no longer than 14 days; on 4 or more days within a treatment window of no longer than 14 days; on 5 or more days within a treatment window of no longer than 14 days; on 6, 7, 8, 9, 10, 11, 12, 13, or 14 days within treatment window of no longer than 14 days. In certain embodiments, when the at least one senolytic agent is administered to a subject after chemotherapy or radiotherapy for a treatment window of 3 days or more, the agent may be administered every $2^{nd}$ day (i.e., every other day). In other certain embodiments when the at least one senolytic agent is administered to a subject for a treatment window of 4 days or more, the agent may be administered every $3^{rd}$ day (i.e., every other third day). In one embodiment, the treatment with the senolytic agent may be initiated at least 1, 2, 3, 4, 5, 6, 7, 8, 9, 10, 11, 12, 13, or 14 days or later after the cancer treatment regimen has been completed. In a more particular embodiment, the treatment with the senolytic agent may be initiated at least 6, 7, 8, 9, 10, 11, 12, 13, or 14 days or later after the cancer treatment regimen has been completed. Any of the additional treatment courses and treatment cycles for administration of a senolytic agent described herein may be followed for inhibiting metastasis in a subject after a chemotherapy or radiotherapy protocol has been completed.

A chemotherapy may be referred to as a chemotherapy, chemotherapeutic, or chemotherapeutic drug. Many chemotherapeutics are compounds referred to as small organic molecules. Chemotherapy is a term that is also used to describe a combination chemotherapeutic drugs that are administered to treat a particular cancer. As understood by a person skilled in the art, a chemotherapy may also refer to a combination of two or more chemotherapeutic molecules that are administered coordinately and which may be referred to as combination chemotherapy. Numerous chemotherapeutic drugs are used in the oncology art and include, without limitation, alkylating agents; antimetabolites; anthracyclines, plant alkaloids; and topoisomerase inhibitors.

A cancer that may metastasize may be a solid tumor or may be a liquid tumor (e.g., a blood cancer, for example, a leukemia). Cancers that are liquid tumors are classified in the art as those that occur in blood, bone marrow, and lymph nodes and include generally, leukemias (myeloid and lymphocytic), lymphomas (e.g., Hodgkin lymphoma), and melanoma (including multiple myeloma). Leukemias include for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors and occur in greater frequency in humans include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer. In certain specific embodiments, the senescent cell-associated disease or disorder treated or prevented (i.e., likelihood of occurrence or development is reduced) by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein are also useful for inhibiting, retarding or slowing progression of metastatic cancer of any one of the types of tumors described in the medical art. Types of cancers (tumors) include the following: adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac (heart) tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (DCIS), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric (stomach) cancer, gastrointestinal stromal tumors (GIST), childhood gastrointestinal stromal tumors (GIST), childhood extracranial germ cell tumor, extragonadal germ cell tumor, gestational trophoblastic tumor, glioma, head and neck cancer, childhood head and neck cancer, hepatocellular (liver) cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (ALL), acute myeloid leukemia (AML), chronic lymphocytic leukemia (CLL), chronic myelogenous leukemia (cml), hairy cell leukemia, lip cancer, liver cancer (primary), childhood liver cancer (primary), lobular carcinoma in situ (LCIS), lung cancer, non-small cell lung cancer, small cell lung cancer, lymphoma, aids-related lymphoma, burkitt lymphoma, cutaneous t-cell lymphoma, Hodgkin lymphoma, non-Hodgkin lymphoma, primary central nervous system lymphoma (CNS), melanoma, childhood melanoma, intraocular (eye) melanoma, Merkel cell carcinoma, malignant mesothelioma, childhood malignant mesothelioma, metastatic squamous neck cancer with occult primary, midline tract carcinoma involving NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, Ewing sarcoma family of tumors, Kaposi Sarcoma, osteosarcoma, rhabdomyosarcoma, childhood rhabdomyosarcoma, soft tissue sarcoma, uterine sarcoma, Sézary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, Waldenström macroglobulinemia.

Chemotherapy and Radiotherapy Side Effects.

In another embodiment, the senescence cell associated disorder or condition is a chemotherapeutic side effect or a radiotherapy side effect. Examples of chemotherapeutic agents that include non-cancer cells to senesce include anthracyclines (such as doxorubicin, daunorubicin); taxols (e.g., paclitaxel); gemcitabine; pomalidomide; and lenalidomide. One or more of the senolytic agents administered as described herein may be used for treating and/or preventing (i.e., reducing the likelihood of occurrence of) a chemotherapeutic side effect or a radiotherapy side effect. Removal or destruction of senescent cells may ameliorate acute toxicity, including acute toxicity comprising energy imbalance, of a chemotherapy or radiotherapy. Acute toxic side effects include but are not limited to gastrointestinal toxicity (e.g., nausea, vomiting, constipation, anorexia, diarrhea), peripheral neuropathy, fatigue, malaise, low physical activity, hematological toxicity (e.g., anemia), hepatotoxicity, alopecia (hair loss), pain, infection, mucositis, fluid retention, dermatological toxicity (e.g., rashes, dermatitis, hyperpigmentation, urticaria, photosensitivity, nail changes), mouth (e.g., oral mucositis), gum or throat problems, or any toxic side effect caused by a chemotherapy or radiotherapy. For example, toxic side effects caused by radiotherapy or chemotherapy (see, e.g., National Cancer Institute web site) may be ameliorated by the methods described herein. Accordingly, in certain embodiments, methods are provided herein for ameliorating (reducing, inhibiting, or preventing occurrence (i.e., reducing the likelihood of occurrence)) acute toxicity or reducing severity of a toxic side effect (i.e., deleterious side effect) of a chemotherapy or radiotherapy or both in a subject who receives the therapy, wherein the method comprises administering to the subject an agent that selectively kills, removes, or destroys or facilitates selective destruction of senescent cells. Administration of a senolytic agent for treating or reducing the likelihood of occurrence, or reducing the severity of a chemotherapy or radiotherapy side effect may be accomplished by the same treatment courses described above for treatment/prevention of metastasis. As described for treating or preventing (i.e., reducing the likelihood of occurrence of) metastasis, the senolytic agent is administered during the off-chemotherapy or off-radiotherapy time interval or after the chemotherapy or radiotherapy treatment regimen has been completed.

In a more specific embodiment, the acute toxicity is an acute toxicity comprising energy imbalance and may comprise one or more of weight loss, endocrine change(s) (e.g., hormone imbalance, change in hormone signaling), and change(s) in body composition. In certain embodiments, an acute toxicity comprising energy imbalance relates to decreased or reduced ability of the subject to be physically active, as indicated by decreased or diminished expenditure of energy than would be observed in a subject who did not receive the medical therapy. By way of non-limiting example, such an acute toxic effect that comprises energy imbalance includes low physical activity. In other particular embodiments, energy imbalance comprises fatigue or malaise.

In one embodiment, a chemotherapy side effect to be treated or prevented (i.e., likelihood of occurrence is reduced) by a senolytic agent is cardiotoxicity. A subject who has a cancer that is being treated with an anthracycline (such as doxorubicin, daunorubicin) may be treated with one or more senolytic agents described herein that reduce, ameliorate, or decrease the cardiotoxicity of the anthracycline. As is well understood in the medical art, because of the cardiotoxicity associated with anthracyclines, the maximum lifetime dose that a subject can receive is limited even if the cancer is responsive to the drug. Administration of one or more of the senolytic agents may reduce the cardiotoxicity such that additional amounts of the anthracycline can be administered to the subject, resulting in an improved prognosis related to cancer disease. In one embodiment, the cardiotoxicity results from administration of an anthracyline, such as doxorubicin. Doxorubicin is an anthracycline topoisomerase that is approved for treating patients who have ovarian cancer after failure of a platinum based therapy; Kaposi's sarcoma after failure of primary systemic chemotherapy or intolerance to the therapy; or multiple myeloma in combination with bortezomib in patients who have not previously received bortezomib or who have received at least one prior therapy. Doxorubicin may cause myocardial damage that could lead to congestive heart failure if the total lifetime dose to a patient exceeds 550 mg/m$^2$. Cardiotoxicity may occur at even lower doses if the patient also receives mediastinal irradiation or another cardiotoxic drug. See drug product inserts (e.g., DOXIL, ADRIAMYCIN).

In other embodiments, a senolytic agent described herein may be used in the methods as provided herein for ameliorating chronic or long term side effects. Chronic toxic side effects typically result from multiple exposures to or administrations of a chemotherapy or radiotherapy over a longer period of time. Certain toxic effects appear long after treatment (also called late toxic effects) and result from damage to an organ or system by the therapy. Organ dysfunction (e.g., neurological, pulmonary, cardiovascular, and endocrine dysfunction) has been observed in patients who were treated for cancers during childhood (see, e.g., Hudson et al., *JAMA* 309:2371-81 (2013)). Without wishing to be bound by any particular theory, by destroying senescent cells, particular normal cells that have been induced to senescence by chemotherapy or radiotherapy, the likelihood of occurrence of a chronic side effect may be reduced, or the severity of a chronic side effect may be reduced or diminished, or the time of onset of a chronic side effect may be delayed. Chronic and/or late toxic side effects that occur in subjects who received chemotherapy or radiation therapy include by way of non-limiting example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

In addition, by killing or removing senescent cells in a subject who has a cancer by administering a senolytic agent, the sensitivity to the chemotherapy or the radiotherapy may be enhanced in a clinically or statistically significant manner than if the senolytic agent was not administered. In other words, development of chemotherapy or radiotherapy resistance may be inhibited when a senolytic agent is administered to a subject treated with the respective chemotherapy or radiotherapy.

Age-Related Diseases and Disorders.

A senolytic agent may also be useful for treating or preventing (i.e., reducing the likelihood of occurrence) of an age-related disease or disorder that occurs as part of the natural aging process or that occurs when the subject is exposed to a senescence inducing agent or factor (e.g., irradiation, chemotherapy, smoking tobacco, high-fat/high sugar diet, other environmental factors). An age-related disorder or disease or an age-sensitive trait may be associated with a senescence-inducing stimulus. The efficacy of a method of treatment described herein may be manifested by reducing the number of symptoms of an age-related disorder or age-sensitive trait associated with a senescence-inducing stimulus, decreasing the severity of one or more symptoms, or delaying the progression of an age-related disorder or age-sensitive trait associated with a senescence-inducing stimulus. In other particular embodiments, preventing an age-related disorder or age-sensitive trait associated with a senescence-inducing stimulus refers to preventing (i.e., reducing the likelihood of occurrence) or delaying onset of an age-related disorder or age-sensitive trait associated with a senescence-inducing stimulus, or reoccurrence of one or more age-related disorder or age-sensitive trait associated with a senescence-inducing stimulus. Age related diseases or conditions include, for example, renal dysfunction, kyphosis, herniated intervertebral disc, frailty, hair loss, hearing loss, vision loss (blindness or impaired vision), muscle fatigue, skin conditions, skin nevi, diabetes, metabolic syndrome, and sarcopenia. Vision loss refers to the absence of vision when a subject previously had vision. Various scales have been developed to describe the extent of vision and vision loss based on visual acuity. Age-related diseases and conditions also include dermatological conditions, for example without limitation, treating one or more of the following conditions: wrinkles, including superficial fine wrinkles; hyperpigmentation; scars; keloid; dermatitis; psoriasis; eczema (including seborrheic eczema); rosacea; vitiligo; ichthyosis vulgaris; dermatomyositis; and actinic keratosis.

Frailty has been defined as a clinically recognizable state of increased vulnerability resulting from aging-associated decline in reserve and function across multiple physiologic systems that compromise a subject's ability to cope with every day or acute stressors. Frailty has been may be characterized by compromised energetics characteristics such as low grip strength, low energy, slowed waking speed, low physical activity, and/or unintentional weight loss. Studies have suggested that a patient may be diagnosed with frailty when three of five of the foregoing characteristics are observed (see, e.g., Fried et al., *J. Gerontol. A Biol. Sci. Med. Sci.* 2001; 56(3):M146-M156; Xue, *Clin. Geriatr. Med.* 2011; 27(1):1-15). In certain embodiments, aging and diseases and disorders related to aging may be treated or prevented (i.e., the likelihood of occurrence of is reduced) by administering a senolytic agent. The senolytic agent may inhibit senescence of adult stem cells or inhibit accumulation, kill, or facilitate removal of adult stem cells that have become senescent. See, e.g., Park et al., *J. Clin. Invest.* 113:175-79 (2004) and Sousa-Victor, *Nature* 506:316-21 (2014) describing importance of preventing senescence in stem cells to maintain regenerative capacity of tissues.

The effectiveness of a senolytic agent with respect to treating a senescence-associated disease or disorder described herein can readily be determined by a person skilled in the medical and clinical arts. One or any combination of diagnostic methods appropriate for the particular disease or disorder, which methods are well known to a person skilled in the art, including physical examination, patient self-assessment, assessment and monitoring of clinical symptoms, performance of analytical tests and methods, including clinical laboratory tests, physical tests, and exploratory surgery, for example, may be used for monitoring the health status of the subject and the effectiveness of the senolytic agent. The effects of the methods of treatment described herein can be analyzed using techniques known in the art, such as comparing symptoms of patients suffering from or at risk of a particular disease or disorder that have received the pharmaceutical composition comprising a senolytic agent with those of patients who were not treated with the senolytic agent or who received a placebo treatment.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the senolytic agent in an amount sufficient to provide therapeutic and/or prophylactic benefit. Therapeutic benefit for subjects to whom the senolytic agents described herein are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of the one or more senolytic agents may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. The effectiveness of the senolytic agents described herein may also mean prolonging survival when compared to expected survival if a subject were not receiving the senolytic agent that selectively kills senescent cells.

Administration of a senolytic agent described herein can prolong prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be treated prophylactically. A subject may have a genetic predisposition for developing a disease or disorder that would benefit from clearance of senescent cells or may be of a certain age wherein receiving a senolytic agent would provide clinical benefit to delay development or reduce severity of a disease, including an age-related disease or disorder.

In another embodiment, a method is provided for treating a senescence-associated disease or disorder that further comprises identifying a subject who would benefit from treatment with a senolytic agent described herein (i.e., phenotyping; individualized treatment). This method comprises first detecting the level of senescent cells in the subject, such as in a particular organ or tissue of the subject. A biological sample may be obtained from the subject, for example, a blood sample, serum or plasma sample, biopsy specimen, body fluids (e.g., lung lavage, ascites, mucosal washings, synovial fluid, vitreous fluid, spinal fluid), bone marrow, lymph nodes, tissue explant, organ culture, or any other tissue or cell preparation from a subject. The level of senescent cells may be determined according to any of the in vitro assays or techniques described herein. For example, senescence cells may be detected by morphology (as viewed by microscopy, for example); production of senescence associated markers such as, senescence-associated β-galactosidase (SA-β-gal), p16INK4a, p21, PAI-1, or any one or more SASP factors (e.g., IL-6, MMP3). The senescent cells and non-senescent cells of the biological sample may also be used in an in vitro cell assay in which the cells are exposed to any one of the senolytic agents described herein to determine the capability of the senolytic agent to kill the subject's senescent cells without undesired toxicity to non-senescent cells. As positive controls in these assays, the assay may incorporate any one of the senolytic agents (e.g., Nutlin-3a, RG-7112, ABT-263, ABT-737, WEHI-539, A-1155463, MK-2206) described herein. The subject then may be treated with an appropriate senolytic agent, which may be a MDM2 inhibitor; an inhibitor of one or more Bcl-2 anti-apoptotic protein family members wherein the inhibitor inhibits at least Bcl-xL (e.g., a Bcl-xL selective inhibitor, Bcl-2/Bcl-xL/Bcl-w inhibitor, a Bcl-2/Bcl-xL or a Bcl-xL/Bcl-w inhibitor); or an Akt specific inhibitor. In addition, these methods may be used to monitor the level of senescent cells in the subject before, during, and after treatment with a senolytic agent. In certain embodiments, the presence of senescence cells, may be detected (e.g., by determining the level of a senescent cell marker expression of mRNA, for example), and the treatment course and/or non-treatment interval can be adjusted accordingly.

A subject, patient, or individual in need of treatment with a senolytic agent as described herein may be a human or may be a non-human primate or other animal (i.e., veterinary use) who has developed symptoms of a senescence cell-associated disease or disorder or who is at risk for developing a senescence cell-associated disease or disorder. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, elephants, bears and other domestic, farm, and zoo animals.

Methods for Characterizing and Identifying Senolytic Agents

Characterizing a senolytic agent can be determined using one or more cell-based assays and one or more animal models described herein or in the art and with which a person skilled in the art will be familiar. A senolytic agent is an agent that selectively kills or destroys a senescent cell in a statistically significant, clinically significant, or biologically significant manner. A senolytic agent may selectively kill one or more types of senescent cells (e.g., senescent preadipocytes, senescent endothelial cells, senescent fibroblasts, senescent neurons, senescent epithelial cells, senescent mesenchymal cells, senescent smooth muscle cells, senescent macrophages, or senescent chondrocytes). In certain particular embodiments, a senolytic agent is capable of selectively killing at least senescent fibroblasts.

Characterizing an agent as a senolytic agent can be accomplished using one or more cell-based assays and one or more animal models described herein or in the art. A person skilled in the art will readily appreciate that characterizing an agent as a senolytic agent and determining the level of killing by an agent can be accomplished by comparing the activity of a test agent with appropriate negative controls (e.g., vehicle or diluent only and/or a composition or compound known in the art not to kill senescent cells) and appropriate positive controls. In vitro cell-based assays for characterizing senolytic agents also include controls for determining the effect of the agent on non-senescent cells (e.g., quiescent cells or proliferating cells). A senolytic agent reduces (i.e., decreases) percent survival of a plurality of senescent cells (i.e., in some manner reduces the quantity of viable senescent cells in the animal or in the cell-based assay) compared with one or more negative controls. Conditions for a particular in vitro assay include temperature, buffers (including salts, cations, media), and other components, which maintain the integrity of the test agent and reagents used in the assay, and which are familiar to a person skilled in the art and/or which can be readily determined.

The source of senescent cells for use in assays may be a primary cell culture, or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. In a particular embodiment, the senescent cell is isolated from biological sample obtained from a host or subject who has a senescent cell associated disease or disorder. In other embodiments, non-senescent cells, which may be obtained from a subject or may be a culture adapted line may be used and senescence induced by methods described herein and in the art, such as by exposure to irradiation or a chemotherapeutic agent (e.g., doxorubicin). The biological sample may be a blood sample, biopsy specimen, body fluids (e.g., lung lavage, ascites, mucosal washings, synovial fluid), bone marrow, lymph nodes, tissue explant, organ culture, or any other tissue or cell preparation from a subject. The sample may be a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject may be a human or non-human animal.

Transgenic animal models as described herein and in the art may be used to determine killing or removal of senescent cells (see, e.g., Baker et al., supra; *Nature*, 479:232-36 (2011); Int'l Patent Application Publication No. WO/2012/177927; Int'l Patent Application Publication No. WO 2013/090645). Exemplary transgenic animal models contain a transgene that includes a nucleic acid that allows for controlled clearance of senescence cells (e.g., p16$^{ink4a}$ positive senescent cells) as a positive control. The presence and level of senescent cells in the transgenic animals can be determined by measuring the level of a detectable label or labels that are expressed in senescent cells of the animal. The transgene nucleotide sequence includes a detectable label, for example, one or more of a red fluorescent protein; a green fluorescent protein; and one or more luciferases to detect clearance of senescent cells.

Animal models that are described herein or in the art includes art-accepted models for determining the effectiveness of a senolytic agent to treat or prevent (i.e., reduce the likelihood of occurrence of) a particular senescence associated disease or disorder, such as atherosclerosis models, osteoarthritis models, COPD models, and IPF models. As described herein, pulmonary disease murine models, such as a bleomycin pulmonary fibrosis model, and a chronic cigarette smoking model are applicable for diseases such as COPD and may be routinely practiced by a person skilled in the art. Animal models for determining the effectiveness of a senolytic agent to treat and/or prevent (i.e., reduce the likelihood of occurrence of) chemotherapy and radiotherapy side effect models or to treat or prevent (i.e., reduce the likelihood of occurrence of) metastasis are described in International Patent Application Publication Nos. WO 2013/

090645 and WO 2014/205244, which are incorporated herein by reference in their entirety. Animal models for determining the effectiveness of agents for treating eye diseases, particularly age-related macular degeneration are also routinely used in the art (see, e.g., Pennesi et al., *Mol. Aspects Med.* 33:487-509 (2012); Zeiss et al., *Vet. Pathol.* 47:396-413 (2010); Chavala et al., *J. Clin. Invest.* 123:4170-81 (2013)).

By way of non-limiting example and as described herein, osteoarthritis animal models have been developed. Osteoarthritis may be induced in the animal, for example, by inducing damage to a joint, for example, in the knee by surgical severing, incomplete or total, of the anterior cruciate ligament. Osteoarthritis animal models may be used for assessing the effectiveness of a senolytic agent to treat or prevent (i.e., reducing the likelihood of occurrence of) osteoarthritis and cause a decrease in proteoglycan erosion and to induce (i.e., stimulate, enhance) collagen (such as collagen type 2) production, and to reduce pain in an animal that has ACL surgery. Immunohistology may be performed to examine the integrity and composition of tissues and cells in a joint. Immunochemistry and/or molecular biology techniques may also be performed, such as assays for determining the level of inflammatory molecules (e.g., IL-6) and assays for determining the level of senescence markers as noted above, using methods and techniques described herein and that may be routinely practiced by a person skilled in the art.

By way of another non-limiting example and as described herein, atherosclerosis animal models have been developed. Atherosclerosis may be induced in the animal, for example, by feeding animals a high fat diet or by using transgenic animals highly susceptible to developing atherosclerosis. Animal models may be used for determining the effectiveness of a senolytic agent to reduce the amount of plaque or to inhibit formation of plaque in an atherosclerotic artery, to reduce the lipid content of an atherosclerotic plaque (i.e., reduce, decrease the amount of lipid in a plaque), and to cause an increase or to enhance fibrous cap thickness of a plaque. Sudan staining may be used to detect the level of lipid in an atherosclerotic vessel. Immunohistology and immunochemistry and molecular biology assays (e.g., for determining the level of inflammatory molecules (e.g., IL-6), and for determining the level of senescence markers as noted above), may all be performed according to methods described herein and that are routinely practiced in the art.

In still another example, and as described herein, mouse models in which animals are treated with bleomycin has been described (see, e.g., Peng et al., *PLoS One* 2013; 8(4):e59348. doi: 10.1371/journal.pone.0059348. Epub 2013 Apr. 2; Mouratis et al., *Curr. Opin. Pulm. Med.* 17:355-61 (2011)) for determining the effectiveness of an agent for treating IPF. In pulmonary disease animals models (e.g., a bleomycin animal model, smoke-exposure animal model, or the like), respiratory measurements may be taken to determine elastance, compliance, static compliance, and peripheral capillary oxygen saturation ($SpO_2$). Immunohistology and immunochemistry and molecular biology assays (e.g., for determining the level of inflammatory molecules (e.g., IL-6), and for determining the level of senescence markers as noted above), may all be performed according to methods described herein and that are routinely practiced in the art.

Determining the effectiveness of a senolytic agent to selectively kill senescent cells as described herein in an animal model may be performed using one or more statistical analyses with which a skilled person will be familiar. By way of example, statistical analyses such as two-way analysis of variance (ANOVA) may be used for determining the statistical significance of differences between animal groups treated with an agent and those that are not treated with the agent (i.e., negative control group, which may include vehicle only and/or a non-senolytic agent). Statistical packages such as SPSS, MINITAB, SAS, Statistika, Graphpad, GLIM, Genstat, and BMDP are readily available and routinely used by a person skilled in the animal model art.

A person skilled in the art will readily appreciate that characterizing a senolytic agent and determining the level of killing by the senolytic agent can be accomplished by comparing the activity of a test agent with appropriate negative controls (e.g., vehicle only and/or a composition, agent, or compound known in the art not to kill senescent cells) and appropriate positive controls. In vitro cell-based assays for characterizing the agent also include controls for determining the effect of the agent on non-senescent cells (e.g., quiescent cells or proliferating cells). A senolytic agent that is useful reduces (i.e., decreases) percent survival of senescent cells (i.e., in some manner reduces the quantity of viable senescent cells in the animal or in the cell-based assay) compared with one or more negative controls. Accordingly, a senolytic agent selectively kills senescent cells compared with killing of non-senescent cells (which may be referred to herein as selectively killing senescent cells over non-senescent cells). In certain embodiments (either in an in vitro assay or in vivo (in a human or non-human animal)), the at least one senolytic agent kills at least 20% of the senescent cells and kills no more than 5% of non-senescent cells. In other particular embodiments (either in an in vitro assay or in vivo (in a human or non-human animal)), the at least one senolytic agent kills at least about 25%, 30%, 35%, 40%, 45%, 50%, 55%, 60%, or 65% of the senescent cells and kills no more than about 5% or 10% of non-senescent cells. In other particular embodiments (either in an in vitro assay or in vivo (in a human or non-human animal)), the at least one senolytic agent kills at least about 30%, 35%, 40%, 45%, 50%, 55%, 60%, or 65% of the senescent cells and kills no more than about 5%, 10%, or 15% of non-senescent cells. In other particular embodiments (either in an in vitro assay or in vivo (in a human or non-human animal)), the at least one senolytic agent kills at least about 40%, 45%, 50%, 55%, 60%, or 65% of the senescent cells and kills no more than about 5%, 10%, 15%, 20%, or 25% of non-senescent cells. In other particular embodiments (either in an in vitro assay or in vivo (in a human or non-human animal)), the at least one senolytic agent kills at least about 50%, 55%, 60%, or 65% of the senescent cells and kills no more than about 5%, 10%, 15%, 20%, 25%, or 30% of non-senescent cells. Stated another way, a senolytic agent has at least 5-25, 10-50 or 10-100 times (5×-25×, 10×-50× or 10×-100×) greater selectively for killing senescent cells than for non-senescent cells (e.g., at least 5×, 10×, 20×, 25×, 30×, 40×, 50×, 60×, 75×, 80×, 90×, or 100×). With respect to specific embodiments of the methods described herein for treating a senescence-associated disease or disorder, the percent senescent cells killed may refer to the percent senescent cells killed in a tissue or organ that comprises senescent cells that contribute to onset, progression, and/or exacerbation of the disease or disorder. By way of non-limiting example, tissues of the brain, tissues and parts of the eye, pulmonary tissue, cardiac tissue, arteries, joints, skin, and muscles may comprise senescent cells that may be reduced in percent as described above by the senolytic agents described herein and thereby provide a therapeutic effect. Moreover, selectively removing at least 20% or at least 25% of senescent cells from an affected tissue or organ can have a clinically significant therapeutic effect. With respect to specific embodiments of the methods described herein, such as for treating a cardiovascular disease or disorder associated with arteriosclerosis, such as atherosclerosis, by administering a senolytic agent (i.e., in reference to vivo methods above), the percent senescent cells killed may refer to the percent senescent cells killed in an affected artery containing plaque versus non-senescent cells killed in the arterial plaque. In certain particular embodiments, in the methods for treating the cardiovascular disease, such as atherosclerosis, as described herein, the at least one senolytic agent kills at least 20% of the senescent cells and kills no more than 5% of non-senescent cells in the artery. In other particular embodiments, the senolytic agent selectively kills at least 25% of the senescent cells in the arteriosclerotic artery. In another embodiment, with respect to the methods described herein for treating osteoarthritis by administering a senolytic agent, the percent senescent cells killed may refer to the percent senescent cells killed in an osteoarthritic joint versus non-senescent cells killed in the osteoarthritic joint. In certain particular embodiments, in the methods for treating osteoarthritis as described herein, the at least one senolytic agent kills at least 20% of the senescent cells and kills no more than 5% of non-senescent cells in the osteoarthritic joint. In other particular embodiments, the senolytic agent selectively kills at least 25% of the senescent cells in the osteoarthritic joint. In still another embodiment, with respect to the methods described herein for treating senescence associated pulmonary disease or disorder (e.g., COPD, IPF) by administering at least one senolytic agent, the percent senescent cells killed may refer to the percent senescent cells killed in affected pulmonary tissue versus non-senescent cells killed in the affected pulmonary tissue of the lung. In certain particular embodiments, in the methods for treating senescence associated pulmonary diseases and disorders as described herein, a senolytic agent kills at least 20% of the senescent cells and kills no more than 5% of non-senescent cells in the affected pulmonary tissue. In other particular embodiments, the senolytic agent selectively kills at least 25% of the senescent cells in the affected pulmonary tissue.

In certain embodiments, methods are provided for identifying (i.e., screening for) agents that are useful senolytic agents for treating or preventing (i.e., reducing the likelihood of occurrence of) a senescence associated disease or disorder. In one embodiment, a method for identifying a senolytic agent for treating such diseases and disorders, comprises inducing cells to senesce to provide established senescent cells. Methods for inducing cells to senesce are described herein and in the art and include, for example, exposure to radiation (e.g., 10 Gy is typically sufficient) or a chemotherapeutic agent (e.g., doxorubicin or other anthracycline). After exposure to the agent, the cells are cultured for an appropriate time and under appropriate conditions (e.g., media, temperature, $CO_2/O_2$ level appropriate for a given cell type or cell line) to allow senescence to be established. As discussed herein, senescence of cells may be determined by determining any number of characteristics, such as changes in morphology (as viewed by microscopy, for example); production of, for example, senescence-associated β-galactosidase (SA-β-gal), p16INK4a, p21, or any one or more SASP factors (e.g., IL-6, MMP3). A sample of the senescent cells is then contacted with a candidate agent (i.e., mixed with, combined, or in some manner permitting the cells and the agent to interact). Persons skilled in the art will appreciate that the assay will include the appropriate controls, negative and positive, either historical or performed concurrently. For example, a sample of control non-senescent cells that have been cultured similarly as the senescent cells but not exposed to a senescence inducing agent are contacted with the candidate agent. The level of survival of the senescent cells is determined and compared with the level of survival of the non-senescent cells. A senolytic agent is identified when the level of survival of the senescent cells is less than the level of survival of the non-senescent cells.

In a particular embodiment, the above described method to identify a senolytic agent may further comprise steps for identifying whether the senolytic agent is useful for treating osteoarthritis. The method may further comprise contacting the identified senolytic agent with cells capable of producing collagen; and determining the level of collagen produced by the cells. In particular embodiments, the cells are chondrocytes and the collagen is Type 2 collagen. The method may further comprise administering a candidate senolytic agent to a non-human animal with arthritic lesions in a joint and determining one or more of (a) the level of senescent cells in the joint; (b) physical function of the animal; (c) the level of one or more markers of inflammation; (d) histology of the joint; and (e) the level of Type 2 collagen produced, thereby determining therapeutic efficacy of the senolytic agent wherein one or more of the following is observed in the treated animal compared with an animal not treated with the senolytic agent: (i) a decrease in the level of senescent cells in the joint of the treated animal; (ii) improved physical function of the treated animal; (iii) a decrease in the level of one or more markers of inflammation in the treated animal; (iv) increased histological normalcy in the joint of the treated animal; and (v) an increase in the level of Type 2 collagen produced in the treated animal. As described herein and in the art, the physical function of the animal may be determined by techniques that determine the sensitivity of a leg to an induced or natural osteoarthritic condition, for example, by the animal's tolerance to bear weight on an affected limb or the ability of the animal to move away from an unpleasant stimulus, such as heat or cold. Determining the effectiveness of an agent to kill senescent cells as described herein in an animal model may be performed using one or more statistical analyses with which a skilled person will be familiar. Statistical analyses as described herein and routinely practiced in the art may be applied to analyze data.

In another particular embodiment, the above described method to identify a senolytic agent may further comprise steps for identifying whether the senolytic agent is useful for treating a cardiovascular disease caused by or associated with arteriosclerosis. Accordingly, the method may further comprise administering the senolytic candidate agent in non-human animals of in animal models for determining the effectiveness of an agent to reduce the amount of plaque, to inhibit formation of plaque in an atherosclerotic artery, to reduce the lipid content of an atherosclerotic plaque (i.e., reduce, decrease the amount of lipid in a plaque), and/or to cause an increase or to enhance fibrous cap thickness of a plaque. Sudan staining may be used to detect the level of lipid in an atherosclerotic vessel. Immunohistology, assays for determining the level of inflammatory molecules (e.g., IL-6), and/or assays for determining the level of senescence markers as noted above, may all be performed according to methods described herein and routinely practiced in the art. In a specific embodiment, methods described herein for identifying a senolytic agent may further comprise administering a candidate senolytic agent to a non-human animal with atherosclerotic plaque and determining one or more of (a) the level of senescent cells in the artery; (b) physical function of the animal; (c) the level of one or more markers of inflammation; (d) histology of the affected blood vessel(s) (e.g., artery); and thereby determining therapeutic efficacy of the senolytic agent wherein one or more of the following is observed in the treated animal compared with an animal not treated with the senolytic agent: (i) a decrease in the level of senescent cells in the artery of the treated animal; (ii) improved physical function of the treated animal; (iii) a decrease in the level of one or more markers of inflammation in the treated animal; (iv) increased histological normalcy in the artery of the treated animal. As described herein and in the art, the physical function of the animal may be determined by measuring physical activity. Statistical analyses as described herein and routinely practiced in the art may be applied to analyze data.

In one embodiment, methods described herein for identifying a senolytic agent may comprise administering a candidate senolytic agent to a non-human animal pulmonary disease model such as a bleomycin model or a smoke-exposure animal model and determining one or more of (a) the level of senescent cells in a lung; (b) lung function of the animal; (c) the level of one or more markers of inflammation; (d) histology of pulmonary tissue, thereby determining therapeutic efficacy of the senolytic agent wherein one or more of the following is observed in the treated animal compared with an animal not treated with the senolytic agent: (i) a decrease in the level of senescent cells in the lungs and pulmonary tissue of the treated animal; (ii) improved lung function of the treated animal; (iii) a decrease in the level of one or more markers of inflammation in the treated animal; and (iv) increased histological normalcy in the pulmonary tissue of the treated animal. Respiratory measurements may be taken to determine elastance, compliance, static compliance, and peripheral capillary oxygen saturation ($SpO_2$). Lung function may be evaluated by determining any one of numerous measurements, such as expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MVVpeak expiratory flow (PEF), slow vital capacity (SVC). Total lung volumes include total lung capacity (TLC), vital capacity (VC),), residual volume (RV), and functional residual capacity (FRC). Gas exchange across alveolar capillary membrane can be measured using diffusion capacity for carbon monoxide (DLCO). Peripheral capillary oxygen saturation ($SpO_2$) can also be measured. Statistical analyses as described herein and routinely practiced in the art may be applied to analyze data.

The in vitro assays and in vivo assays (e.g., animal models) described herein for identifying and characterizing senolytic agents may include any one of the senolytic agents (e.g., Nutlin-3a, RG-7112, ABT-263, ABT-737, WEHI-539, A-1155463, MK-2206) described herein as positive controls. Conditions for a particular in vitro assay include temperature, buffers (including salts, cations, media), and other components (e.g., cells), which maintain the integrity of the test agent and reagents used in the assay, and which are familiar to a person skilled in the art and/or which can be readily determined. The assays and techniques described herein may also be used for toxicology analytical methods, quality control assays, and the like that are routinely performed during drug development and for quality assurance. Animal models for these methods and purposes may include non-human primate models, dog models, rodent models, or other animal models appropriate for determining the safety and efficacy of a senolytic agent.

Pharmaceutical Compositions

Also provided herein are pharmaceutical compositions that comprise a senolytic agent (e.g., a MDM2 inhibitor; an inhibitor of one or more Bcl-2 anti-apoptotic protein family members wherein the inhibitor inhibits at least Bcl-xL (e.g., a Bcl-xL selective inhibitor, Bcl-2/Bcl-xL/Bcl-w inhibitor, a Bcl-2/Bcl-xL or a Bcl-xL/Bcl-w inhibitor); or an Akt specific inhibitor), as described herein and at least one pharmaceutically acceptable excipient, which may also be called a pharmaceutically suitable excipient or carrier (i.e., a nontoxic material that does not interfere with the activity of the active ingredient). A pharmaceutical composition may be a sterile aqueous or non-aqueous solution, suspension or emulsion (e.g., a microemulsion). The excipients described herein are examples and are in no way limiting. An effective amount or therapeutically effective amount refers to an amount of the one or more senolytic agents administered to a subject, either as a single dose or as part of a series of doses, which is effective to produce a desired therapeutic effect.

When two or more senolytic agents are administered to a subject for treatment of a disease or disorder described herein, each of the senolytic agents may be formulated into separate pharmaceutical compositions. A pharmaceutical preparation may be prepared that comprises each of the separate pharmaceutical compositions (which may be referred to for convenience, for example, as a first pharmaceutical composition and a second pharmaceutical composition comprising each of the first and second senolytic agents, respectively). Each of the pharmaceutical compositions in the preparation may be administered at the same time (i.e., concurrently) and via the same route of administration or may be administered at different times by the same or different administration routes. Alternatively, two or more senolytic agents may be formulated together in a single pharmaceutical composition.

In other embodiments, a combination of at least one senolytic agent and at least one inhibitor of an mTOR, NFκB, or PI3-k pathway may be administered to a subject in need thereof. When at least one senolytic agent and an inhibitor of one or more of mTOR, NFκB, or PI3-k pathways are both used together in the methods described herein for selectively killing senescent cells, each of the agents may be formulated into the same pharmaceutical composition or formulated in separate pharmaceutical compositions. A pharmaceutical preparation may be prepared that comprises each of the separate pharmaceutical compositions, which may be referred to for convenience, for example, as a first pharmaceutical composition and a second pharmaceutical composition comprising each of the senolytic agent and the inhibitor of one or more of mTOR, NFκB, or PI3-k pathways, respectively. Each of the pharmaceutical compositions in the preparation may be administered at the same time and via the same route of administration or may be administered at different times by the same or different administration routes.

In particular embodiments, a single senolytic agent is administered to the subject and is the single (i.e., only, sole) active senolytic agent (i.e., monotherapy) used for treating the condition or disease. When a senolytic agent is the single senolytic agent, use of medications for other purposes such as palliative medications or medications that are used for comfort; or medications for treating a particular disease or condition but that are not senolytic agents, such as drugs for lowering cholesterol or an eye wetting agent, and other such medications familiar to a person skilled in the medical art, are not necessarily excluded. Examples of other agents and medications that can be administered to subjects with pulmonary diseases (e.g., COPD) include, by way of non-limiting example, bronchodilators (e.g., anti-cholinergics; beta-2 agonists); pain relief medication; Agents and medications that can be administered to subjects with osteoarthritis include hyaluronan, pain relievers (including topical medications), and steroids. Other agents and medications that can be administered to subjects with a cardiovascular disease include statins, beta blockers, nitroglyercin, aspirin.

Subjects may generally be monitored for therapeutic effectiveness using assays and methods suitable for the condition being treated, which assays will be familiar to those having ordinary skill in the art and are described herein. Pharmacokinetics of a senolytic agent (or one or more metabolites thereof) that is administered to a subject may be monitored by determining the level of the senolytic agent in a biological fluid, for example, in the blood, blood fraction (e.g., serum), and/or in the urine, and/or other biological sample or biological tissue from the subject. Any method practiced in the art and described herein to detect the agent may be used to measure the level of the senolytic agent during a treatment course.

The dose of a senolytic agent described herein for treating a senescence cell associated disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of the senolytic agent for treating a senescence-associated disease or disorder, suitable duration and frequency of administration of the senolytic agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a senolytic agent (including when administered for prophylactic benefit) described herein are well within the skill of a person skilled in the relevant art. When two or more senolytic agents are administered to treat a senescence-associated disease or disorder, the optimal dose of each senolytic agent may be different, such as less, than when either agent is administered alone as a single agent therapy. In certain particular embodiments, two senolytic agents in combination make act synergistically or additively, and either agent may be used in a lesser amount than if administered alone. An amount of a senolytic agent that may be administered per day may be, for example, between about 0.01 mg/kg and 100 mg/kg (e.g., between about 0.1 to 1 mg/kg, between about 1 to 10 mg/kg, between about 10-50 mg/kg, between about 50-100 mg/kg body weight. In other embodiments, the amount of a senolytic agent that may be administered per day is between about 0.01 mg/kg and 1000 mg/kg, between about 100-500 mg/kg, or between about 500-1000 mg/kg body weight. In particular embodiments, the total amount of an MDM2 inhibitor (e.g., Nutlin-3a), the total amount of the senolytic agent administered per course of treatment each treatment cycle does not exceed 2100 mg/kg; in other embodiments, the total amount administered per course of treatment does not exceed 1400 mg/kg. The optimal dose (per day or per course of treatment) may be different for the senescence-associated disease or disorder to be treated and may also vary with the administrative route and therapeutic regimen.

Pharmaceutical compositions comprising a senolytic agent can be formulated in a manner appropriate for the delivery method by using techniques routinely practiced in the art. The composition may be in the form of a solid (e.g., tablet, capsule), semi-solid (e.g., gel), liquid, or gas (aerosol). In other certain specific embodiments, the senolytic agent (or pharmaceutical composition comprising same) is administered as a bolus infusion. In certain embodiments when the senolytic agent is delivered by infusion, the senolytic agent is delivered to an organ or tissue comprising senescent cells to be killed via a blood vessel in accordance with techniques routinely performed by a person skilled in the medical art.

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the agent(s) of the composition upon administration. In other embodiments, the agent may be encapsulated within liposomes using technology known and practiced in the art. In certain particular embodiments, a senolytic agent (e.g., ABT-263) is not formulated within liposomes for application to a stent that is used for treating highly, though not totally, occluded arteries. Pharmaceutical compositions may be formulated for any appropriate manner of administration described herein and in the art.

A pharmaceutical composition may be delivered to a subject in need thereof by any one of several routes known to a person skilled in the art. By way of non-limiting example, the composition may be delivered orally, intravenously, intraperitoneally, by infusion (e.g., a bolus infusion), subcutaneously, enteral, rectal, intranasal, by inhalation, buccal, sublingual, intramuscular, transdermal, intradermal, topically, intraocular, vaginal, rectal, or by intracranial injection, or any combination thereof. In certain particular embodiments, administration of a dose, as described above, is via intravenous, intraperitoneal, directly into the target tissue or organ, or subcutaneous route. In certain embodiments, a delivery method includes drug-coated or permeated stents for which the drug is the senolytic agent. Formulations suitable for such delivery methods are described in greater detail herein.

In certain particular embodiments, a senolytic agent (which may be combined with at least one pharmaceutically acceptable excipient to form a pharmaceutical composition) is administered directly to the target tissue or organ comprising senescent cells that contribute to manifestation of the disease or disorder. In specific embodiments when treating osteoarthritis, the at least one senolytic agent is administered directly to an osteoarthritic joint (i.e., intra-articularly) of a subject in need thereof. In other specific embodiments, a senolytic agent(s) may be administered to the joint via topical, transdermal, intradermal, or subcutaneous route. In other certain embodiments, methods are provided herein for treating a cardiovascular disease or disorder associated with arteriosclerosis, such as atherosclerosis by administering directly into an artery. In another particular embodiment, a senolytic agent (which may be combined with at least one pharmaceutically acceptable excipient to form a pharmaceutical composition) for treating a senescent-associated pulmonary disease or disorder may be administered by inhalation, intranasally, by intubation, or intracheally, for example, to provide the senolytic agent more directly to the affected pulmonary tissue. By way of another non-limiting example, the senolytic agent (or pharmaceutical composition comprising the senolytic agent) may be delivered directly to the eye either by injection (e.g., intraocular or intravitreal) or by conjunctival application underneath an eyelid of a cream, ointment, gel, or eye drops. In more particular embodiments, the senolytic agent or pharmaceutical composition comprising the senolytic agent may be formulated as a timed release (also called sustained release, controlled release) composition or may be administered as a bolus infusion.

A pharmaceutical composition (e.g., for oral administration or for injection, infusion, subcutaneous delivery, intramuscular delivery, intraperitoneal delivery or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the senolytic agents described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A senolytic agent included in a pharmaceutical composition may be formulated for oral delivery with a flavoring agent, e.g., in a liquid, solid or semi-solid formulation and/or with an enteric coating.

A pharmaceutical composition comprising any one of the senolytic agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active agent contained within a sustained release formulation depends upon the site of implantation, the rate and expected duration of release, and the nature of the condition, disease or disorder to be treated or prevented.

In certain embodiments, the pharmaceutical compositions comprising a senolytic agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated (intradermally or subcutaneously). The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a senolytic agent can be formulated as emulsions for topical application. An emulsion contains one liquid distributed the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the senolytic agent(s) can be formulated with oleaginous bases or ointments to form a semisolid composition with a desired shape. In addition to the senolytic agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobellipophobe balance) emulsifiers, and assorted ionic and nonionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the active agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the senolytic agent. The matrices can be formed by solvent evaporation, spray drying, solvent extraction and other methods known to those skilled in the art.

In certain embodiments of a method described herein for treating a cardiovascular disease associated with or caused by arteriosclerosis, one or more senolytic agents may be delivered directly into a blood vessel (e.g., an artery) via a stent. In a particular embodiment, a stent is used for delivering a senolytic agent to an atherosclerotic blood vessel (an artery). A stent is typically a tubular metallic device, which has thin-metal screen-like scaffold, and which is inserted in a compressed form and then expanded at the target site. Stents are intended to provide long-term support for the expanded vessel. Several methods are described in the art for preparing drug-coated and drug-embedded stents. For example, a senolytic agent may be incorporated into polymeric layers applied to a stent. A single type of polymer may be used, and one or more layers of the senolytic agent permeated polymer may be applied to a bare metal stent to form the senolytic agent-coated stent. The senolytic agent may also be incorporated into pores in the metal stent itself, which may also be referred to herein as a senolytic agent-permeated stent or senolytic agent-embedded stent. In certain particular embodiments, a senolytic agent may be formulated within liposomes and applied to a stent; in other particular embodiments, for example, when the senolytic agent is ABT-263, the ABT-263 is not formulated in liposome. Placement of stents in an atherosclerotic artery is performed by a person skilled in the medical art. A senolytic agent-coated or -embedded stent not only expands the affected blood vessel (e.g., an artery) but also may be effective for one or more of (1) reducing the amount of plaque, (2) inhibiting formation of plaque, and (3) increasing stability of plaque (e.g., by decreasing lipid content of the plaque; and/or causing an increase in fibrous cap thickness), particularly with respect to plaque proximal to the agent coated or agent embedded stent.

In one particular embodiment, the senolytic agent administered to a subject who has an ophthalmic senescence associated or disease or disorder may be delivered intraocularly or intravitreally. In other specific embodiments, a senolytic agent(s) may be administered to the eye by a conjunctival route, applying the senolytic agent to the mucous membrane and tissues of the eye lid, either upper, lower, or both. Any of these administrations may be bolus infusions. In other particular embodiments, a pharmaceutical composition comprising any one of the senolytic agents described herein may be formulated for sustained or slow release (which may also be called timed release or controlled release), which formulations are described in greater detail herein. In certain embodiments, methods are provided herein for treating or preventing (i.e., reducing the likelihood of occurrence of; delaying the onset or development of, or inhibiting, retarding, slowing, or impeding progression or severity of) an ocular disease, disorder, or condition (e.g., presbyopia, cataracts, macular degeneration); for selectively killing senescent cells in an eye of a subject, and/or inducing collagen (such as Type IV collagen) production in the eye of a subject in need thereof by administering at least one senolytic agent (which may be combined with at least one pharmaceutically acceptable excipient to form a pharmaceutical composition) directly to an eye.

For pharmaceutical compositions comprising a nucleic acid molecule, the nucleic acid molecule may be present within any of a variety of delivery systems known to those of ordinary skill in the art, including nucleic acid, and bacterial, viral and mammalian expression systems such as, for example, recombinant expression constructs as provided herein. Techniques for incorporating DNA into such expression systems are well known to those of ordinary skill in the art. The DNA may also be "naked," as described, for example, in Ulmer et al., *Science* 259:1745-49, 1993 and reviewed by Cohen, *Science* 259:1691-92, 1993. The uptake of naked DNA may be increased by coating the DNA onto biodegradable beads, which are efficiently transported into the cells. Nucleic acid molecules may be delivered into a cell according to any one of several methods described in the art (see, e.g., Akhtar et al., *Trends Cell Bio.* 2:139 (1992); *Delivery Strategies for Antisense Oligonucleotide Therapeutics*, ed. Akhtar, 1995, Maurer et al., *Mol. Membr. Biol.* 16:129-40 (1999); Hofland et al., *Handb. Exp. Pharmacol.* 137:165-92 (1999); Lee et al., *ACS Symp. Ser.* 752:184-92 (2000); U.S. Pat. No. 6,395,713; Int'l Patent Appl. Publ. No. WO 94/02595); Selbo et al., *Int. J. Cancer* 87:853-59 (2000); Selbo et al., *Tumour Biol.* 23:103-12 (2002); U.S. Patent Appl. Publ. Nos. 2001/0007666, and 2003/077829).

Kits with unit doses of one or more of the agents described herein, usually in oral or injectable doses, are provided. Such kits may include a container containing the unit dose, an informational package insert describing the use and attendant benefits of the drugs in treating the senescent cell associated disease, and optionally an appliance or device for delivery of the composition.

EXAMPLES

Example 1

In Vitro Cell Assays for Determining Senolytic Activity of Nutlin-3A

Figure 1:
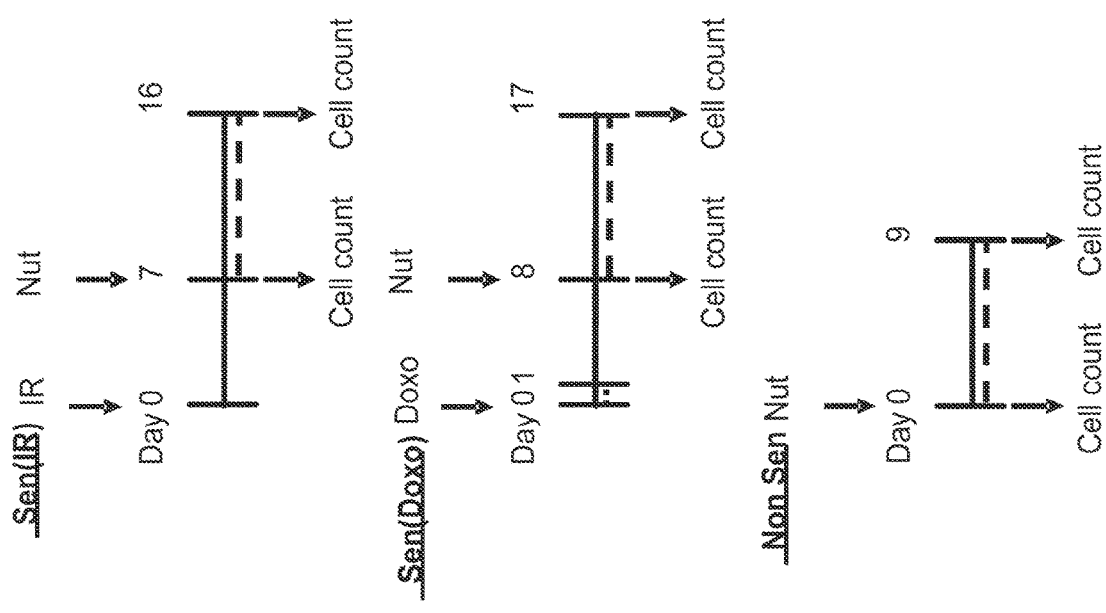
FIG. 1 provides a schematic of general timelines and procedures for treatment with Nutlin-3a (Nut) of (1) cells induced to senesce by irradiation (Sen(IR)); (2) cells induced to senesce by treatment with doxorubicin (Sen (Doxo)); and (3) non-senescent cells (Non Sen).

Foreskin fibroblast cell lines HCA2 and BJ, lung fibroblast cell line IMR90, and mouse embryonic fibroblasts were seeded in six-well plates and induced to senesce with 10 Gy of ionizing radiation (IR) or a 24 hr treatment with doxorubicin (Doxo). Senescent phenotype was allowed to develop for at least 7 days, at which point a cell count was made to determine the baseline number of cells. Nutlin-3a treatment was then initiated for a period of at least 9 days. Media alone or media with drug as appropriate was refreshed at least every three days. At the end of the assay time period, cells are counted. Each condition was seeded in three plate wells and counted independently. Initial cell count serves as a control to determine the induction of senescence, as compared to the last day count without nutlin treatment. Initial non-senescent cell count serves as a proxy to determine Nutlin-3a toxicity. FIG. 1 shows a schematic of the experiment design.

Foreskin fibroblast cell lines HCA2 and BJ, lung fibroblast cell line IMR90, and mouse embryonic fibroblasts were exposed to 10 Gy of ionizing radiation (IR) to induce senescence. Seven days following irradiation, the cell were treated with varying concentrations of Nutlin-3a (0, 2.5 µM, and 10 µM) for a period of 9 days, with the drug refreshed at least every 3 days. Percent survival was calculated as [cell count on day 9 of Nutlin-3a treatment/initial cell count on first day of Nutlin-3a treatment]. The results are shown in FIGS. 2A-D, which show that Nutlin-3a reduced cell survival of senescent foreskin fibroblasts (HCA2 and BJ), lung fibroblasts (IMR90), and mouse embryonic fibroblasts (MEF), indicating Nutlin-3a is a senolytic agent.

Figure 3B:
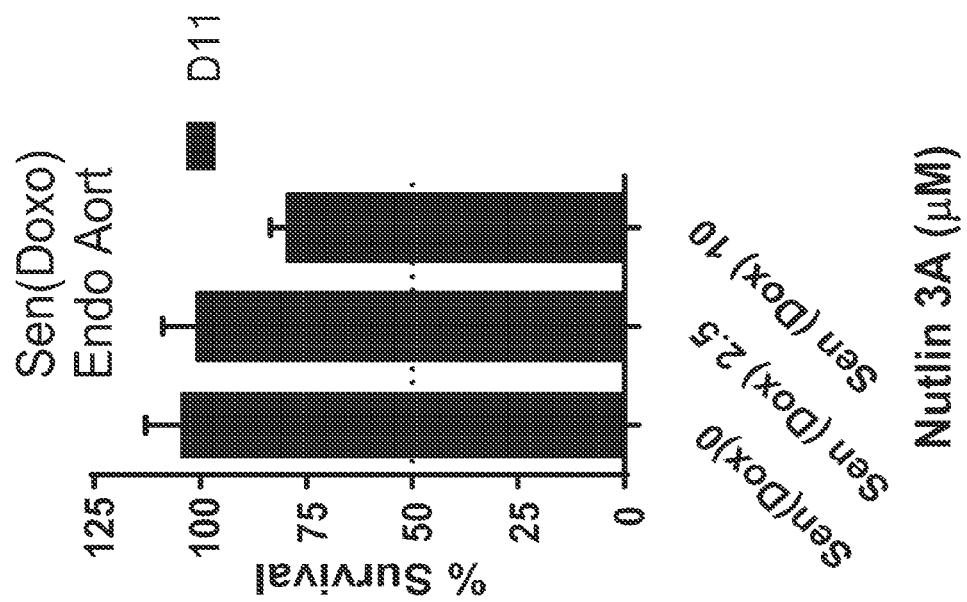
FIGS. 3A-B illustrate the effect of Nutlin-3a on survival of cells induced to senesce by treatment with doxorubicin. HCA2 cells were treated with Nutlin-3a for 9 days (D9), and aortic endothelial cells were treated with Nutlin-3a for 11 days (D11), and then percent survival was determined.
Figure 3A:
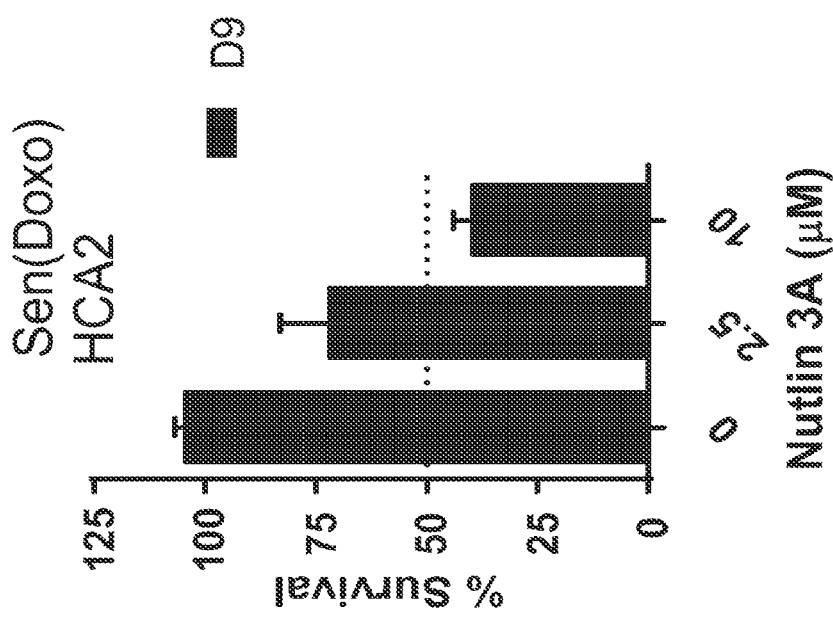

Foreskin fibroblasts (HCA2) and aortic endothelial cells (Endo Aort) were treated with doxorubicin (250 nM) for one day (24 hours) to induce senescence (see FIG. 1). Eight days following doxorubicin treatment, Nutlin-3a treatment was initiated. HCA2 cells were exposed to Nutlin-3a for 9 days, and aortic endothelial cells were exposed to Nutlin-3a for 11 days. Media containing the compound or control media was refreshed at least every 3 days. Percent survival was calculated as [cell count on the last day of Nutlin-3a treatment/initial cell count on first day of Nutlin-3a treatment]. The results are shown in FIGS. 3A-B, which show that doxorubicin-induced senescent cells are sensitive to Nutlin-3a.

Figure 4C:
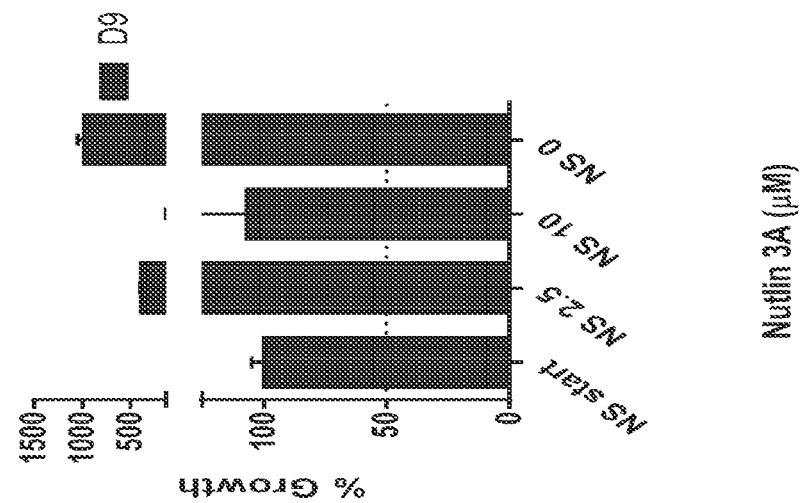
FIGS. 4A-C show percent growth of non-senescent fibroblasts treated with Nutlin-3a. Cells were treated with Nutlin-3a for 9 days and percent growth determined (D9). Nutlin-3a was non-toxic to non-senescent foreskin fibroblasts (Non Sen HCA2) as shown in FIG. 4A, non-toxic to non-senescent lung fibroblasts (Non Sen IMR90) as shown in FIG. 4B, and non-toxic to non-senescent lung mouse embryonic fibroblasts (Non Sen MEFs) as shown in FIG. 4C.
Figure 4B:
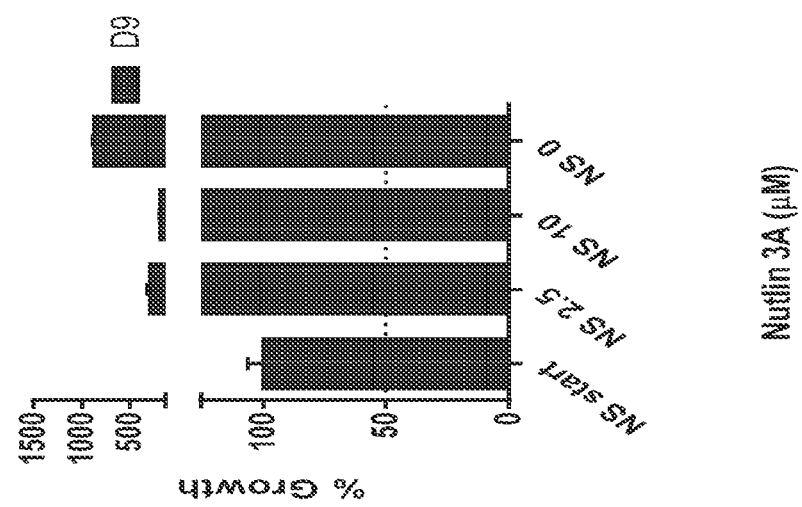
Figure 4A:
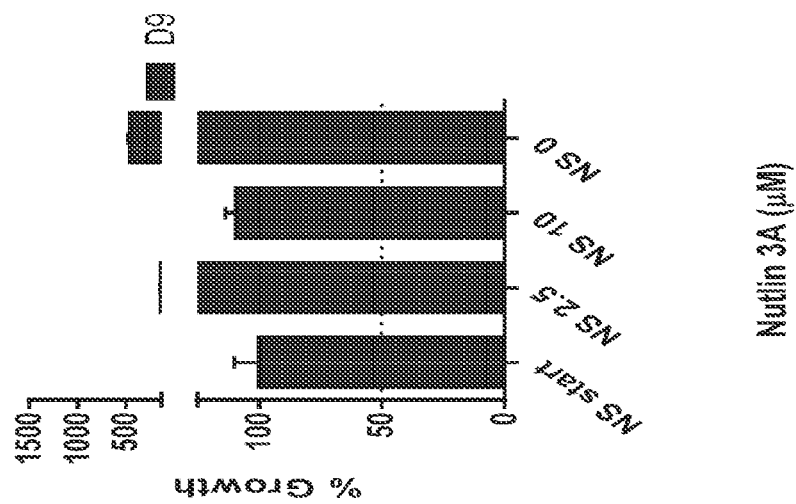

Non-senescent foreskin fibroblasts (HCA2), lung fibroblasts (IMR90), and mouse embryonic fibroblasts (MEF) were treated with varying concentrations (0, 2.5 µM, and 10 µM) of Nutlin-3a for a period of 9 days to assess Nutlin-3a toxicity. Cell counts were taken at the start (NS start) and end of Nutlin-3a treatment. The difference between counts of cells not treated with Nutlin-3a on day 9 (NS 0) and cell counts determined at day zero (NS start) reflects the cell growth over the indicated time period. The results are shown in FIGS. 4A-C, which show that Nutlin-3a treatment reduces proliferation but is non-toxic to non-senescent cells. Nutlin-3a treatment did not decrease the number of cells below the starting level, indicating an absence of toxicity. Decrease in apparent survival between NS 0 and NS 2.5 and between NS 0 and NS 10 reflects a decrease in cell growth. Without wishing to be bound by theory, Nutlin-3a may stabilize p53, leading to cell cycle growth arrest.

Figure 5A:
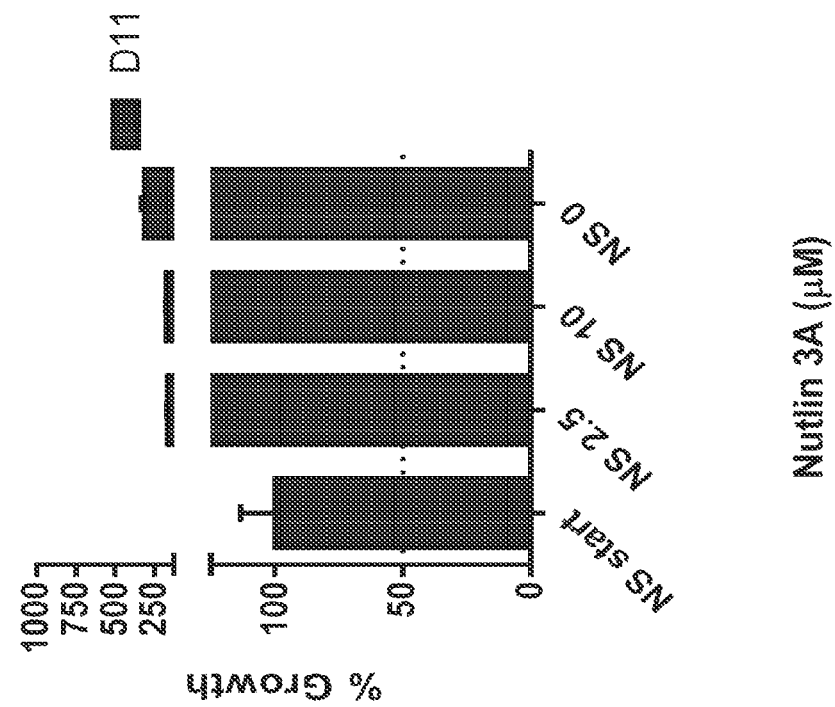
FIGS. 5A-B illustrate percent growth of non-senescent aortic endothelial cells and non-senescent pre-adipocytes treated with Nutlin-3a. Cells were treated with Nutlin-3a for 11 days and percent growth determined (D11).
Figure 5B:
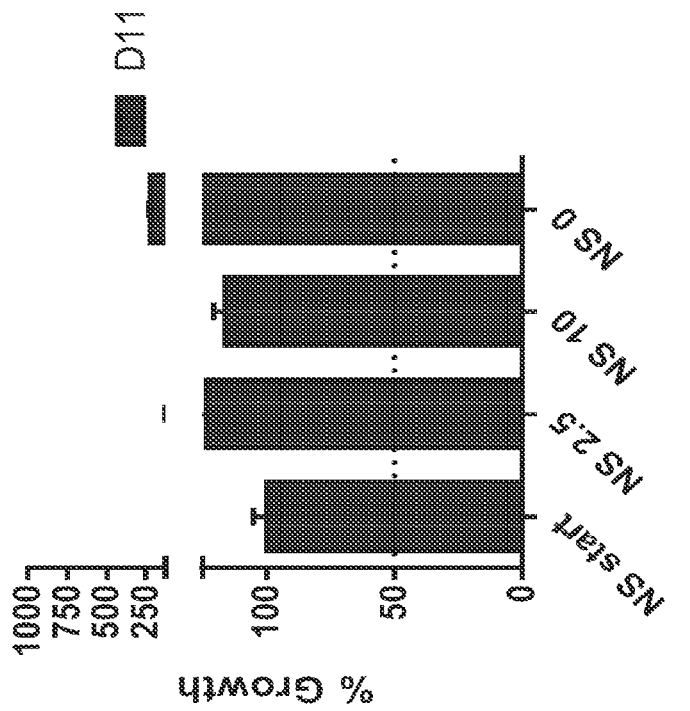

Non-senescent aortic endothelial (Endo Aort) cells and pre-adipocytes (Pread) were also treated with varying concentrations (0, 2.5 µM, and 10 µM) of Nutlin-3a for a period of 11 days to assess Nutlin-3a toxicity, as described above. Cell counts were taken at the start at Day 0 (NS start) and at the end of Nutlin-3a treatment (NS 0). The difference between counts of cells not treated with Nutlin-3a on day 11 (NS 0) and cell counts from NS start reflects the cell growth over the indicated time period. The results are shown in FIGS. 5A-B, illustrating that Nutlin-3a treatment reduces proliferation but is non-toxic to non-senescent cells. As observed with fibroblasts, Nutlin-3a treatment does not decrease the number of cells below the starting level, indicating an absence of toxicity. Decrease in apparent survival between NS 0 and NS 2.5 and between NS 0 and NS 10 reflects a decrease in cell growth.

Example 2

Nutlin-3a Treatment of P16-3MR Transgenic Mice

The capability of Nutlin-3a to remove senescent cells in vivo was determined in transgenic p16-3MR mice (see, e.g., International Application Publication No. WO2013/090645). A schematic of the experimental protocol is provided in FIG. 6. The transgenic mouse comprises a $p16^{Ink4a}$ promoter operatively linked to a trimodal fusion protein for detecting senescent cells and for selective clearance of senescent cells in these transgenic mice, which is illustrated in FIG. 7. The promoter, $p16^{Ink4a}$, which is transcriptionally active in senescent cells but not in non-senescent cells (see, e.g., Wang et al., *J. Biol. Chem.* 276:48655-61 (2001); Baker et al., *Nature* 479:232-36 (2011)), was engineered into a nucleic acid construct. 3MR (tri-modality reporter) is a fusion protein containing functional domains of a synthetic *Renilla luciferase* (LUC), monomeric red fluorescence protein (mRFP), and truncated herpes simplex virus (HSV)-1 thymidine kinase (tTK), which allows killing by ganciclovir (GCV) (see, e.g., Ray et al., *Cancer Res.* 64:1323-30 (2004)). The 3MR cDNA was inserted in frame with p16 in exon 2, creating a fusion protein containing the first 62 amino acids of p16, but not a full-length wild-type p16 protein. Insertion of the 3MR cDNA also resulted in the occurrence of a stop codon in the $p19^{ARF}$ reading frame in exon 2, thereby preventing full-length $p19^{ARF}$ expression from the BAC as well. The $p16^{Ink4a}$ gene promoter (approximately 100 kilobase pairs) was introduced upstream of a nucleotide sequence encoding a trimodal reporter fusion protein. Alternatively, a truncated $p16^{Ink4a}$ promoter may be used (see, e.g., Baker et al., *Nature*, supra; International Application Publication No. WO2012/177927; Wang et al., supra). Thus, the expression of 3MR is driven by the $p16^{Ink4a}$ promoter in senescent cells only. The detectable markers, LUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57B16 background, were established and bred using known procedures for introducing transgenes into animals (see, e.g., Baker et al., *Nature* 479:232-36 (2011)).

Figure 6:
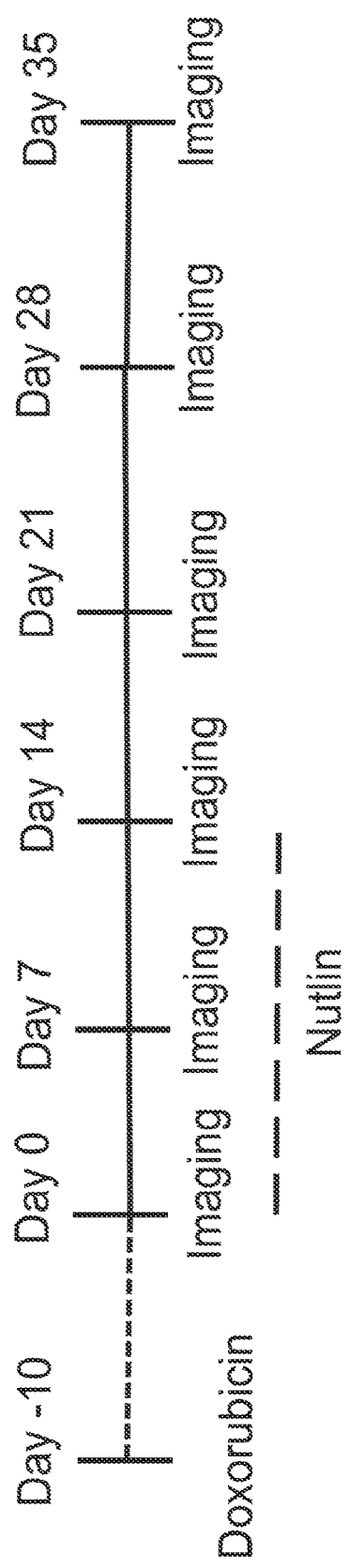
FIG. 6 presents a schematic of a timeline for treatment and imaging analysis of p16-3MR mice with Nutlin-3a. On day 35, the mice were sacrificed and fat and skin were collected for RNA, and lungs were collected and flash frozen for immunomicroscopy. RNA was analyzed for expression of SASP factors (mmp3, IL-6) and senescence markers (p21, p16, and p53). Frozen lung tissue was analyzed for DNA damage marker (γH2AX).
Figure 7:
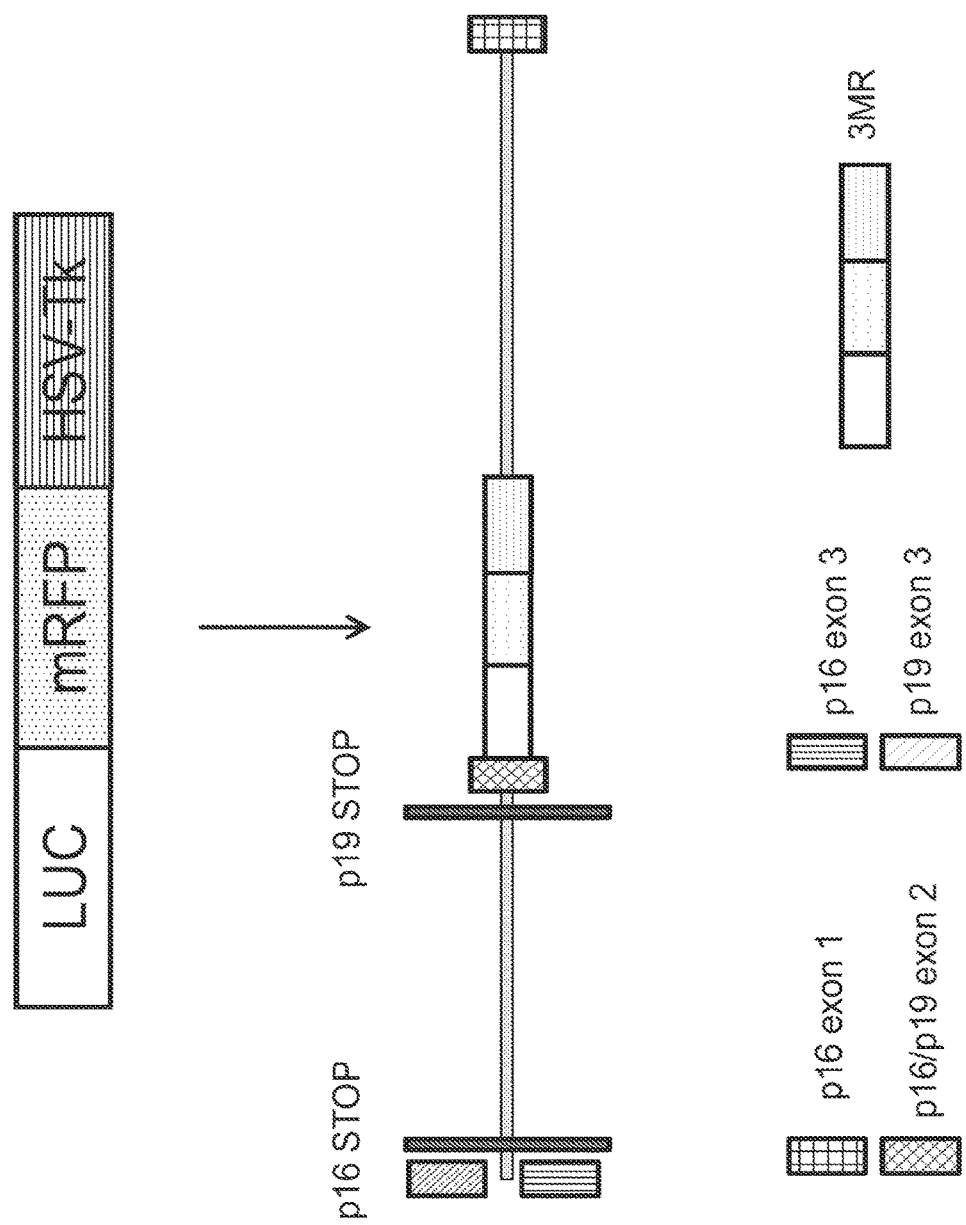
FIG. 7 shows a schematic of p16-3MR transgene insertion. 3MR (tri-modality reporter) is a fusion protein containing functional domains of a synthetic *Renilla luciferase* (LUC), monomeric red fluorescence protein (mRFP), and truncated herpes simplex virus (HSV)-1 thymidine kinase (tTK), which allows killing by ganciclovir (GCV). The 3MR cDNA was inserted in frame with p16 in exon 2, creating a fusion protein containing the first 62 amino acids of p16, but does not include the full-length wild-type p16 protein. Insertion of the 3MR cDNA also introduced a stop codon in the $p19^{ARF}$ reading frame in exon 2.

Female C57/BL6 p16-3MR mice were randomized into doxorubicin+Nutlin-3a treated or doxorubicin only treated groups (see FIG. 6). Senescence was induced by intraperitoneal administration of doxorubicin at 10 mg/kg to the mice ten days prior to administration of Nutlin-3a (Day −10). Nutlin-3a (25 mg/kg) was administered intraperitoneally daily from day 10 to day 24 post-doxorubicin treatment (Group=9 mice). Control mice (doxorubicin treated) were injected with equal volumes of PBS (Group=3 mice). Luminescence imaging (Xenogen Imaging system) was performed at Day 0 (i.e., 10 days post-doxorubicin treatment) as a baseline for each mouse (100% intensity).

Figure 8:
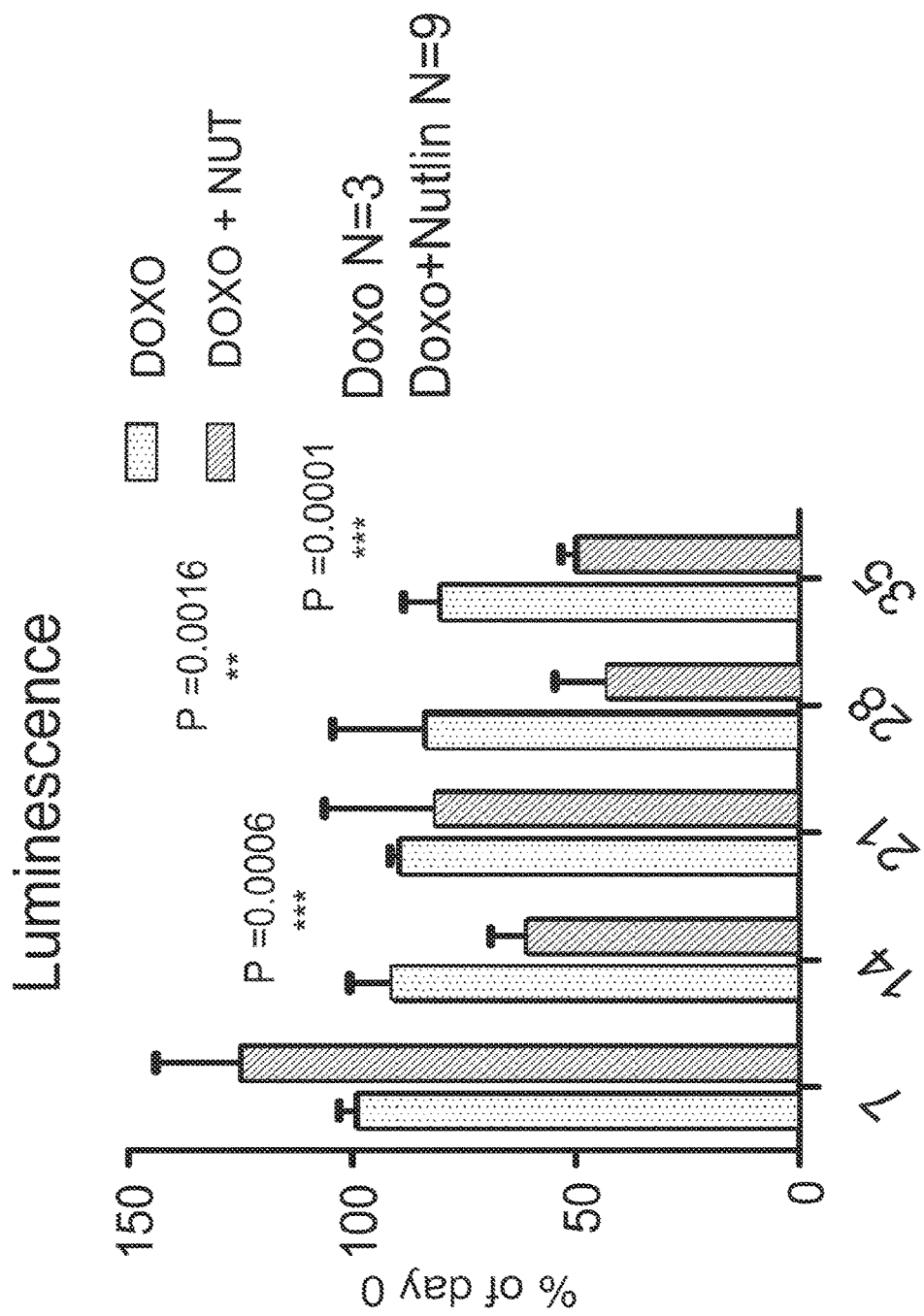
FIG. 8 illustrates the reduction of luminescence intensity of doxorubicin-induced senescence in mice. Female C57/Bl6 p16-3MR mice were treated with doxorubicin (DOXO). Luminescence was measured 10 days later and used as baseline for each mouse (100% intensity). Nutlin-3a (NUT) was administered intraperitoneally daily from day 10 to day 24 post-doxorubicin treatment (N=9). Luminescence was then measured at day 7, 14, 21, 28, 35 post-Nutlin-3a treatments, and final values calculated as % of the baseline values. Control animals (DOXO) were injected with equal volume of PBS (N=3).

Luminescence imaging of the mice was performed on day 7, 14, 21, 28, and 35 following the initiation of Nutlin-3a treatment. Reduction of luminescence (L) was calculated as: L=(Imaging post-Nutlin-3a treatment)/(Baseline Imaging) %. If L is greater than or equal to 100%, the number of senescent cells was not reduced. If L is less than 100%, then the number of senescent cells was reduced. Every mouse was calculated independently, and background was subtracted from each sample. The results are presented in FIG. 8, which suggest that treatment with Nutlin-3a reduced luminescence associated with doxorubicin-induced senescence. A statistically significant decrease in luminescence was observed at day 14, day 28, and day 35 in Nutlin-3a treated animals.

Experiments were performed to determine the effect of Nutlin-3a treatment on expression of genes associated with senescence. Groups of female C57/BL6 p16-3MR were treated as described above. Three weeks after the end of Nutlin-3a treatment (day 35), the doxorubicin treated mice (control) (N=3) and doxorubicin+Nutlin-3a-treated mice (N=6) were sacrificed. Skin and fat biopsies were collected for RNA extraction; fat biopsies were collected for detection of senescence-associated β-galactosidase; and lungs were flash frozen in cryoprotectant OCT media for cryostat sectioning.

RNA was analyzed for mRNA levels of endogenous senescence markers (p21, p16$^{INK4a}$ (p16), and p53) and SASP factors (mmp-3 and IL-6) relative to actin mRNA (control for cDNA quantity) using the Roche Universal Probe Library for real-time PCR assay. The results are presented in FIGS. 9A-E, which suggest Nutlin-3a treatment reduced expression of SASP factors and senescence markers associated with doxorubicin-induced senescence. Values represent fold of induction of the respective mRNA over untreated control animals.

The frozen lung tissue were sectioned to 10 μM thickness and stained with primary rabbit polyclonal antibody against γH2AX (Novus Biologicals, LLC), which is a marker for double-strand breaks in cells (DNA damage). The sections were then stained with ALEXA FLUOR® dye-labeled secondary goat anti-rabbit antibody (Life Technologies) and counterstained with 4',6-diamidino-2-phenylindole (DAPI) (Life Technologies). The number of positive cells was calculated using ImageJ image processing program (National Institutes of Health, see Internet at imagej.nih.gov/ij/index.html) and represented as a percentage of the total number of cells. The results are presented in FIG. 10A-B, which show that nutlin-3A treatment reduced the number of cells with DNA damage induced by doxorubicin. FIG. 10A shows reduced γH2AX staining in doxorubicin+Nutlin-3a treated cells compared with cells treated with doxorubicin alone. FIG. 10B shows a reduction in the percent γH2AX positive cells in doxorubicinC+Nutlin-3a treated cells as compared to cells treated with doxorubicin alone.

Figure 11:
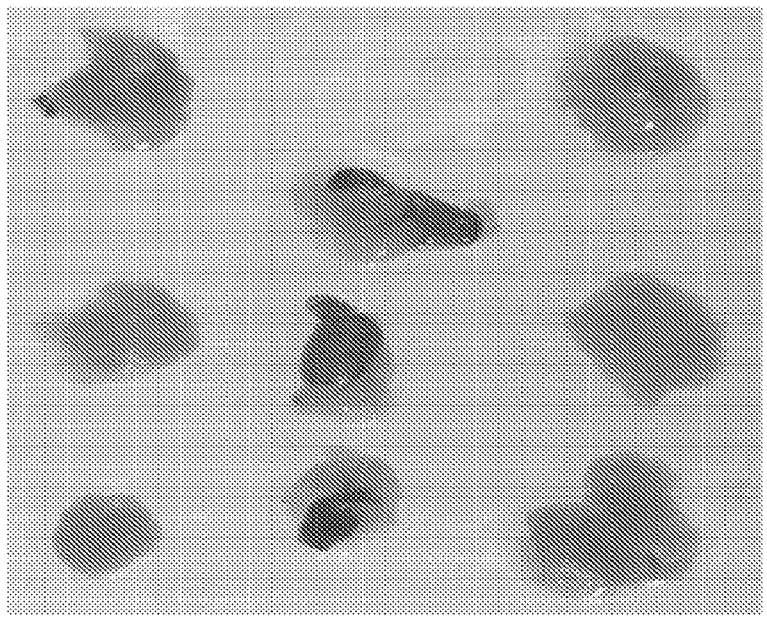
FIG. 11 shows that Nutlin-3a treatment reduced senescence-associated (SA) β-galactosidase (β-gal) intensity of fat biopsies from animals first treated with doxorubicin. Female C57/BL6 p16-3MR mice were treated with doxorubicin. A portion of the doxorubicin treated animals received Nutlin-3a (NUT) or PBS (DOXO) daily from day 10 to day 24 post-doxorubicin treatment. Three weeks after the Nutlin-3a treatment, mice were sacrificed and fat biopsies immediately fixed and stained with a solution containing X-Gal. Untreated animals were used as negative control (CTRL).

Upon collection, fat biopsies were immediately fixed in 4% formalin and then stained with a solution containing X-gal to detect the presence of senescence-associated β-galactosidase (β-gal). Fat biopsies were incubated overnight at 37° C. in X-gal solution and were photographed the next day. Fat biopsies from untreated animals were used as a negative control (CTRL). The results are presented in FIG. 11, which show that Nutlin-3a treatment reduced senescence-associated β-gal intensity in fat biopsies from animals with doxorubicin-induced senescence similar to untreated negative controls, as compared to mice treated with doxorubicin alone.

Example 3

MDM2 Inhibitor Removes Senescent Cells with Established SASP

Figure 12A:
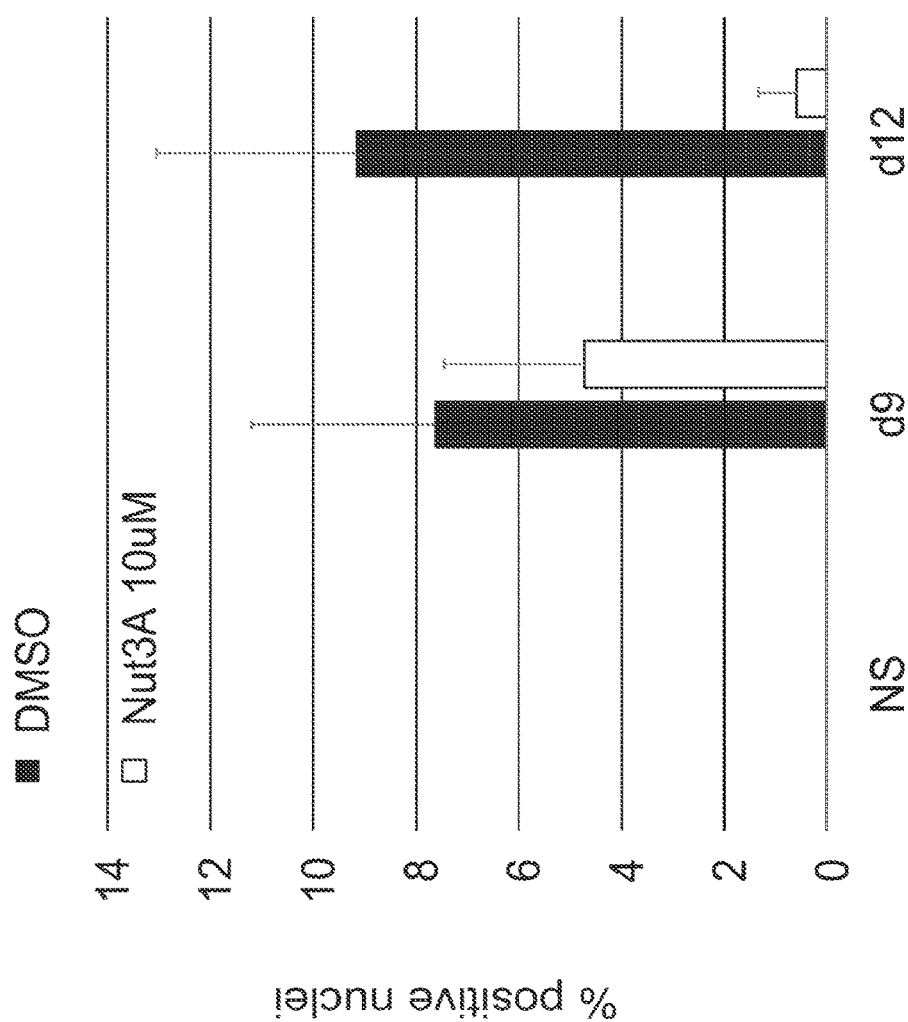
FIGS. 12A-12C show detection of IL-6 production in nuclei of non-senescent (NS) cells and irradiated (IR) senescent cells treated with Nutlin-3a. Primary human fibroblast (IMR90) cells were irradiated at Day −6 and treated with 10 µM Nutlin-3a or DMSO (vehicle control) in media from Day 0 to Day 9. Cells were cultured for an additional 6 days in media without Nutlin-3a or DMSO (Day 12 and Day 15). IL-6 was detected with an anti-IL-6 antibody in nuclei of cells at Day 9 and at Day 12. The percent IL-6 positive nuclei in each of irradiated Nutlin-3a treated cells and DMSO treated cells is illustrated in FIG. 12A. Immunofluorescence of cells expressing IL-6 detected with an anti-IL-6 antibody is illustrated in FIG. 12B.
Figure 12B:
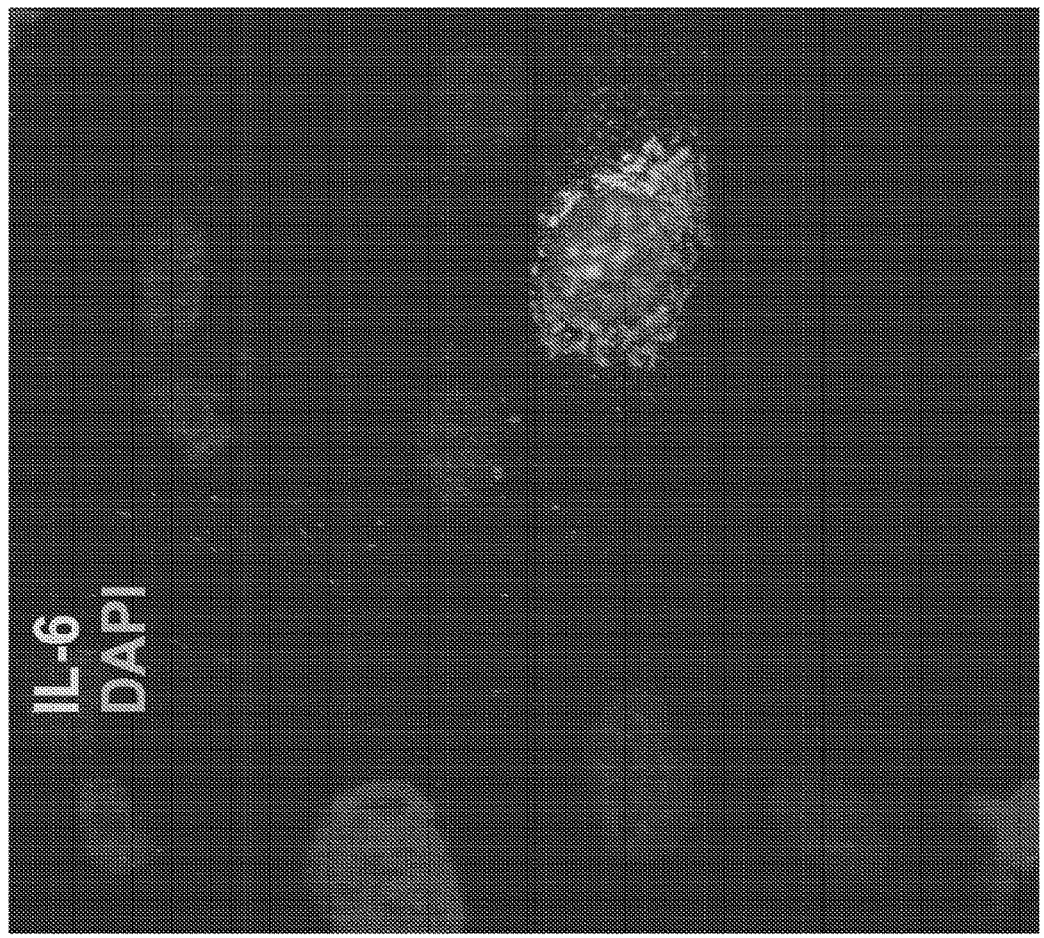
Figure 12C:
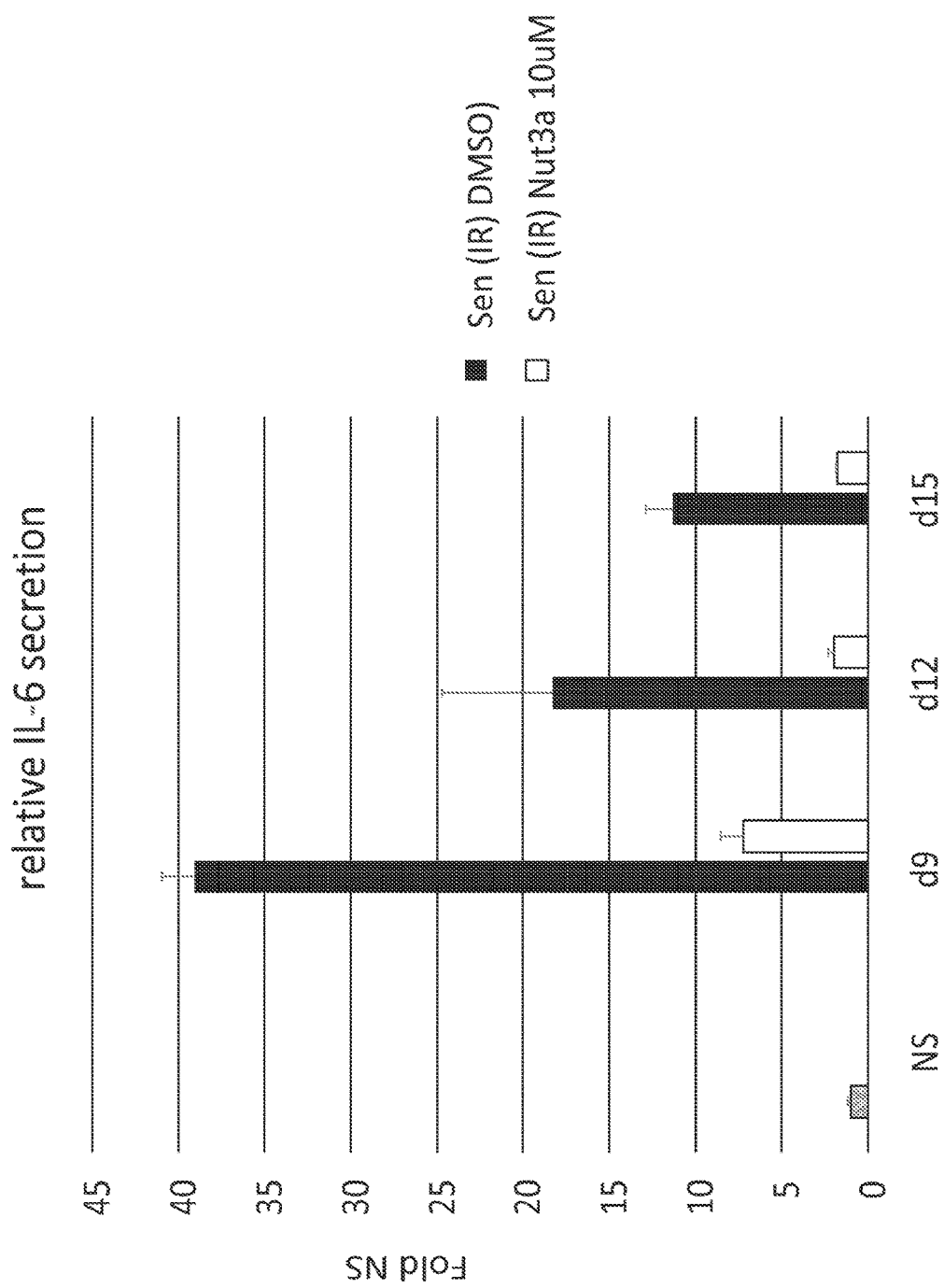
Figure 13A:
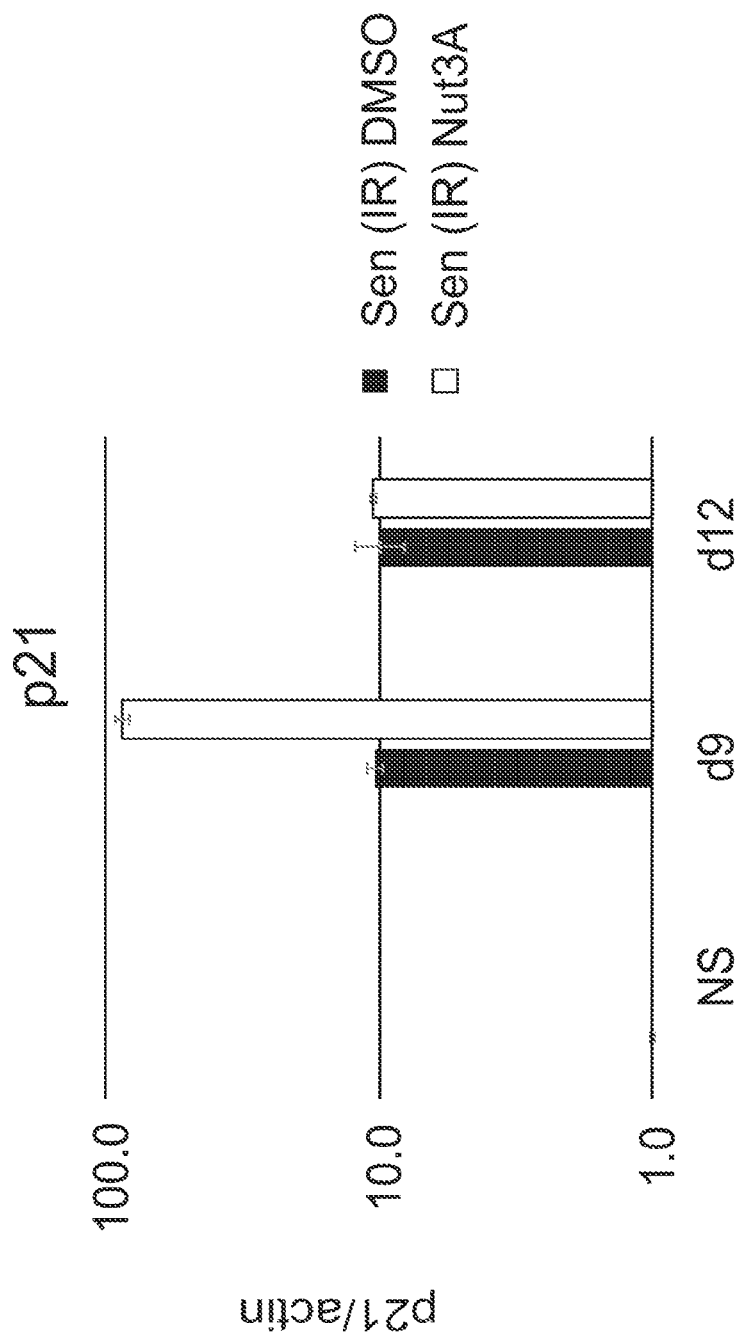
FIGS. 13A-13F illustrate the level of senescence associated proteins (p21, p16, and IL-1a) and SASP factors (CXCL-1, IL-6, and IL-8) expressed by non-senescent (NS) cells and irradiated senescent cells treated with Nutlin-3a. IMR90 cells were irradiated at Day −6 and treated with 10 µM Nutlin-3a or DMSO (vehicle control) in media from Day 0 to Day 9. Cells were cultured for an additional 6 days (Day 12 and Day 15) in media without Nutlin-3a or DMSO, changing media at Day 12. Quantitative PCR was performed, and the levels of p21 (FIG. 13A, p21/actin y-axis on log scale); p16 (FIG. 13B); IL-1a (FIG. 13C); CXCL-1 (FIG. 13D); IL-6 (FIG. 13E); and IL-8 (FIG. 13F) expression were detected in non-senescent cells (NS (i.e., Day −7)) and at Day 9 (d9) and Day 12 (d12) in senescent cells treated with Nutlin-3a (Sen (IR) Nut3A) or vehicle (Sen (IR) DMSO). The data are presented relative to expression of actin.
Figure 13B:
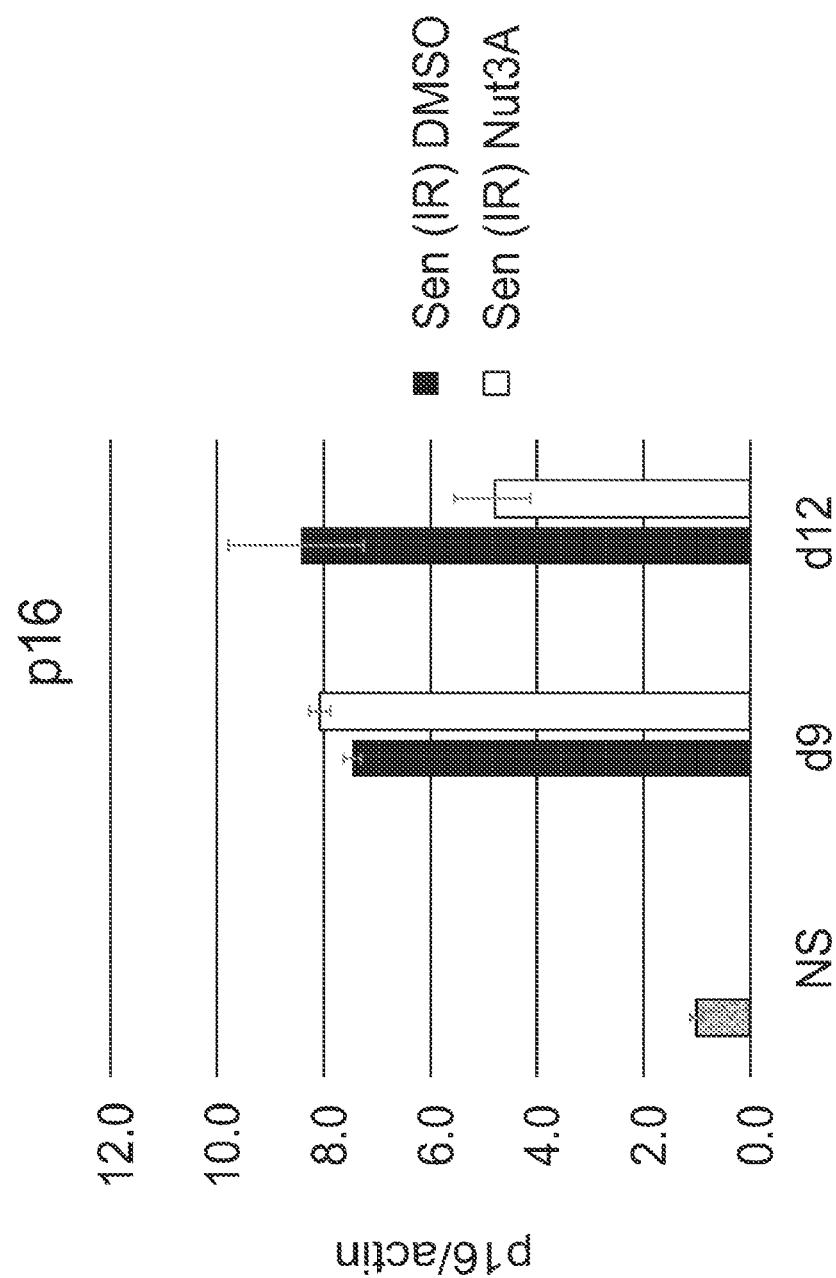
Figure 13C:
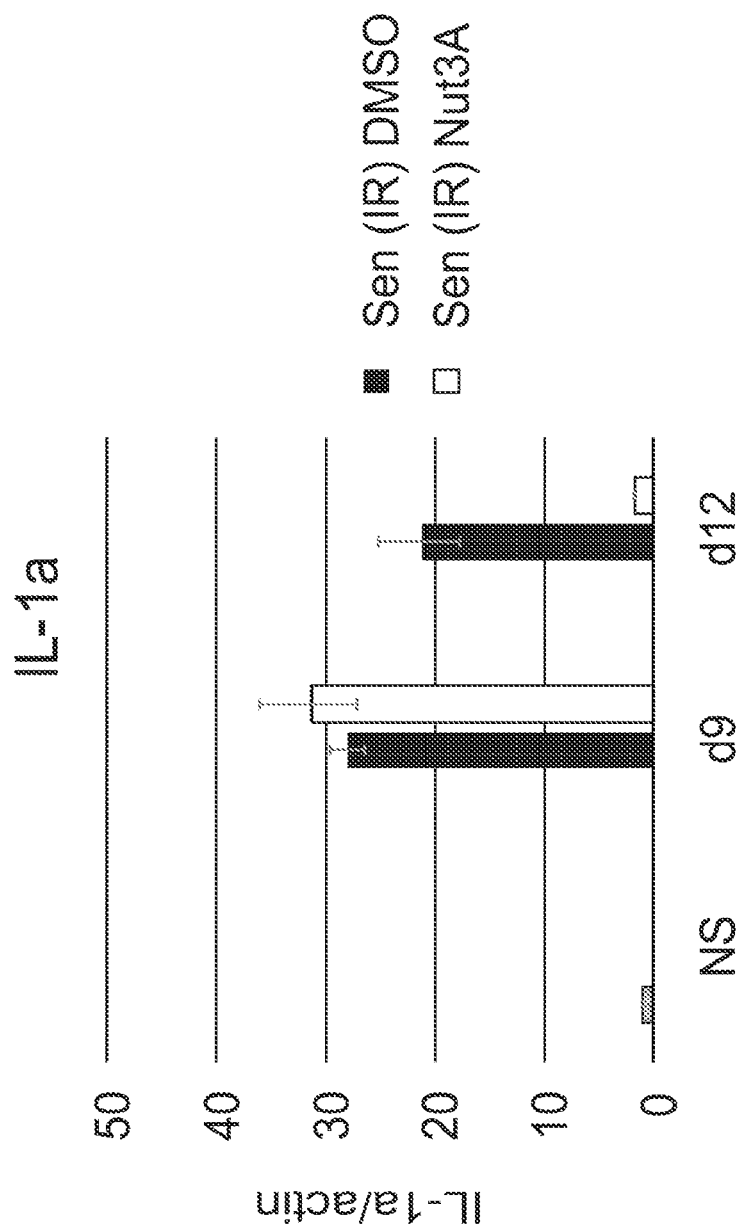
Figure 13D:
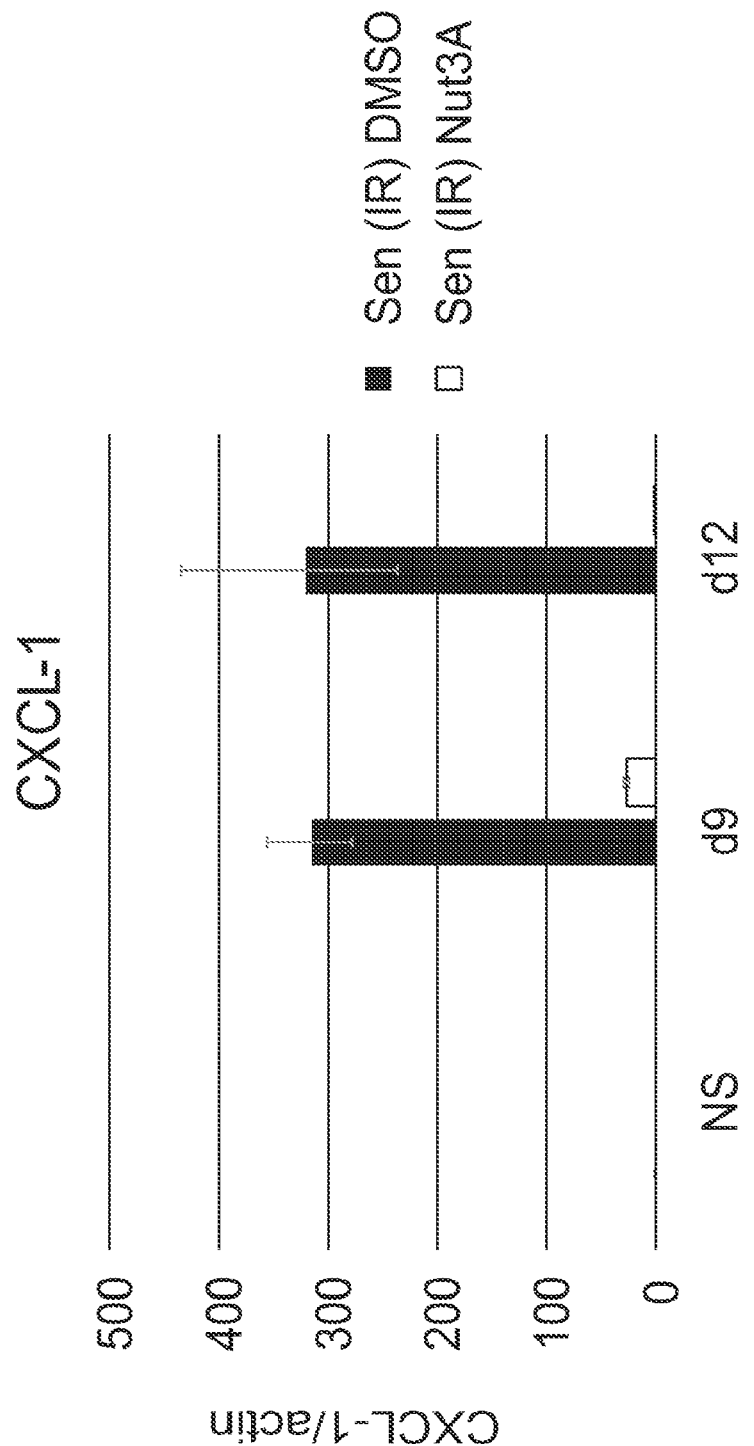
Figure 13E:
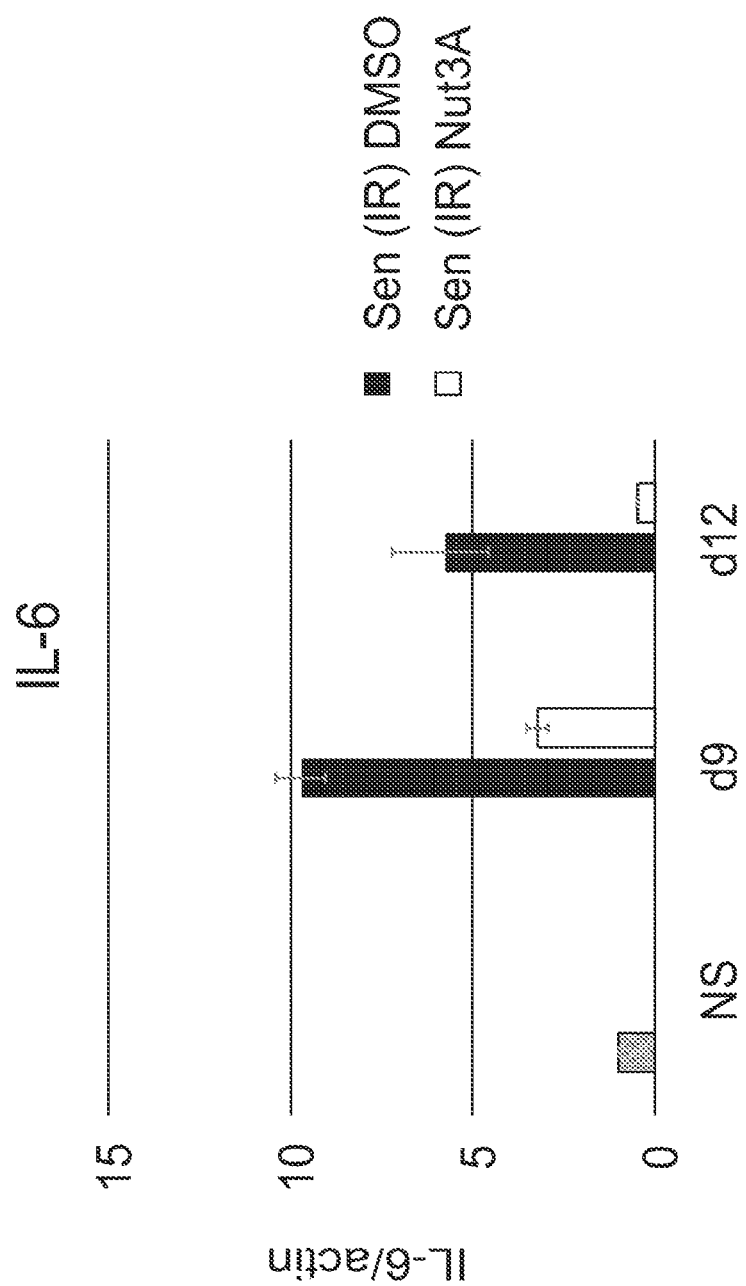
Figure 13F:
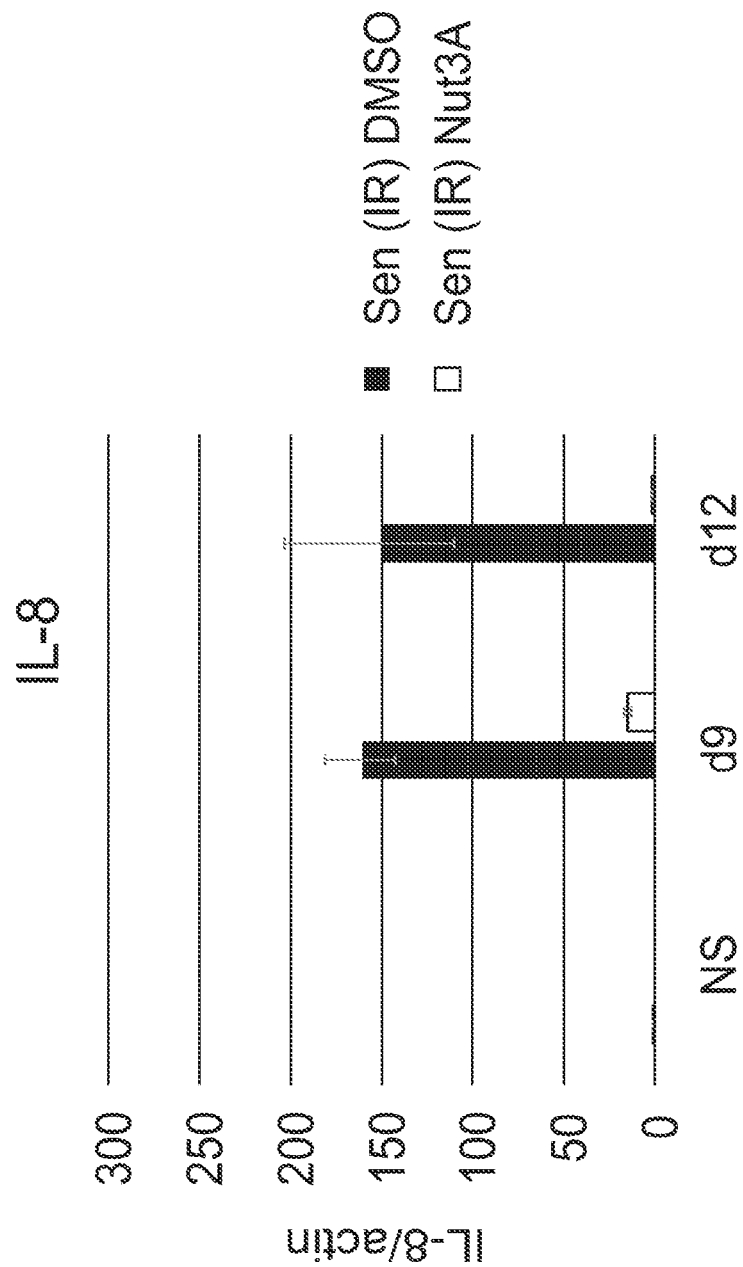

Primary human fibroblast (IMR90) cells were induced to senesce by applying 10 Gy of irradiation. Seven days after irradiation (Day 0), cells were treated with 10 μM Nutlin-3a or vehicle (DMSO) for nine days (Day 9). The drug or vehicle was refreshed every three days. Drug/vehicle was removed at Day 9 and the cells were cultured for an additional three days (Day 12). Cells were then fixed with 4% paraformaldehyde and stained by immunofluorescence with a specific anti-IL-6 antibody (R&D, AF-206-NA). Cells were counterstained with DAPI for nuclear visualization. The percent IL-6 positive cells is illustrated in FIG. 12A. An example of IL-6 positive cell immunofluorescence is shown in FIG. 12B. IL-6 positive cells were determined in an unbiased manner using CellProfiler software. Three different cultures were assessed. Non-senescent cells had no detectable cells IL-6 production while senescent cells were about 8% positive at day 9 after vehicle (DMSO) treatment (16 days after irradiation). Nutlin-3a treatment decreased the percent IL-6 positive cells to a level below 5%. At day 12, 3 days after Nutlin-3a was removed and 19 days after irradiation, IL-6 positive cells in the vehicle control were about 9% and Nutlin3a treated cells were less than 1% positive for IL-6.

Figure 22:
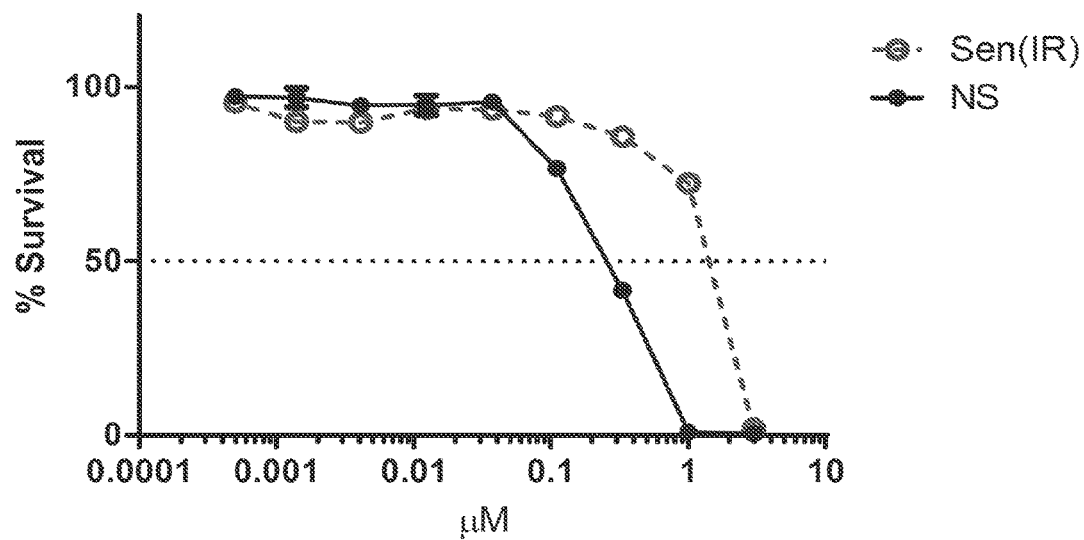
FIG. 22 illustrates a graph showing the effect of ABT-263 treatment in non-senescent and senescent lung fibroblast cells (IMR90).

In another experiment, IMR90 cells were induced to senesce by irradiation (10 Gy). Seven days after irradiation, cells were treated with 10 μM Nutlin-3a or vehicle (DMSO) for nine days (Day 9). The drug or vehicle was refreshed every three days. Drug/vehicle was removed at Day 9 and the cells were cultured for an additional six days. Conditioned media from the treated cells was collected, and IL-6 measurement by ELISA was performed (Perkin Elmer, AL223F). IL-6 levels in culture media were determined by ELISA using a kit according to manufacturer's instructions (AL223F, Perkin Elmer). Cells were fixed with 4% paraformaldehyde and stained by immunofluorescence with a specific anti-IL-6 antibody (R&D, AF-206-NA). The IL-6 level determined by ELISA was normalized to the number of cells in each well. The data are presented in FIG. 22C as a relative level of IL-6 in the treated cells compared to the level in non-senescent cells (NS). The data are presented as an average of three different cell samples.

The level of IL-6 in senescent cells was between 10-40 fold higher than in non-senescent cells. Nutlin-3a treated senescent cells have a level of IL-6 that is 5-9 fold lower than DMSO treated cells. Cells that survive after Nutlin-3a treatment have a lower IL-6 secretion and by extrapolation, a lower SASP, suggesting that Nutlin-3a preferably kills senescent cells with a well-established SASP.

Example 4

MDM2 Inhibitor Removes Senescent Cells with Established SASP: SASP Factor Expression

Primary human fibroblast (IMR90) cells were induced to senesce by applying 10 Gy of irradiation. Seven days after irradiation (Day 0), cells were treated with 10 μM Nutlin-3a or vehicle (DMSO) for nine days (Day 9). The drug or vehicle was refreshed every three days. Drug/vehicle was removed at Day 9 and the cells were cultured for an additional three days (Day 12) in media without drug or DMSO. Cells were then collected, mRNA extracted, and cDNA prepared. Quantitative PCR (qPCR) was then performed to detect expression of various genes. Cells were also collected at Day 12 after drug/vehicle had been removed for three days. The data are presented as an average of three samples. Data were normalized to actin and depicted as a ratio to non-senescent cells. The data are presented in FIGS. 13A-13F.

The level of p21 was approximately 10-fold greater in senescent cells, and was higher (approximately 90 fold) when cells were treated with Nutlin-3a. Nutlin-3a stabilizes p53, and p53 is a transcription factor activating the expression of the cyclin dependent kinase inhibitor p21. At day 12, the level of p21 in the DMSO treated cells was comparable to the level at day 9, which was also comparable to the level in the Nutlin-3a treated cells at day 12. These data suggest the acute effect of Nutlin-3a on cells is abrogated after three days after removal of drug exposure. The level of P16, another senescence marker, increased in irradiated cells and did not change in the presence of Nutlin-3a. Three days after the drug has been removed (Day 12), a decrease in p16 level was observed. The level of IL-1a, a regulator of the SASP, decreased only after Nutlin-3a had been removed. CXCL-1, IL-6 and IL-8 are three other SASP factors. The levels of all three were reduced when Nutlin-3a was present and remained lower after drug removal. These data show that cells surviving Nutlin-3a treatment have a lower p16 level, suggesting that Nutlin-3a preferably kills cells that are high p16 expressers. Similarly, SASP factors were reduced in surviving cells, also suggesting that Nutlin-3a preferably kills cells with a higher SASP.

Example 5

MDM2 Inhibitor Removes Senescent Cells with Elevated DNA Damage Response

Figure 14:
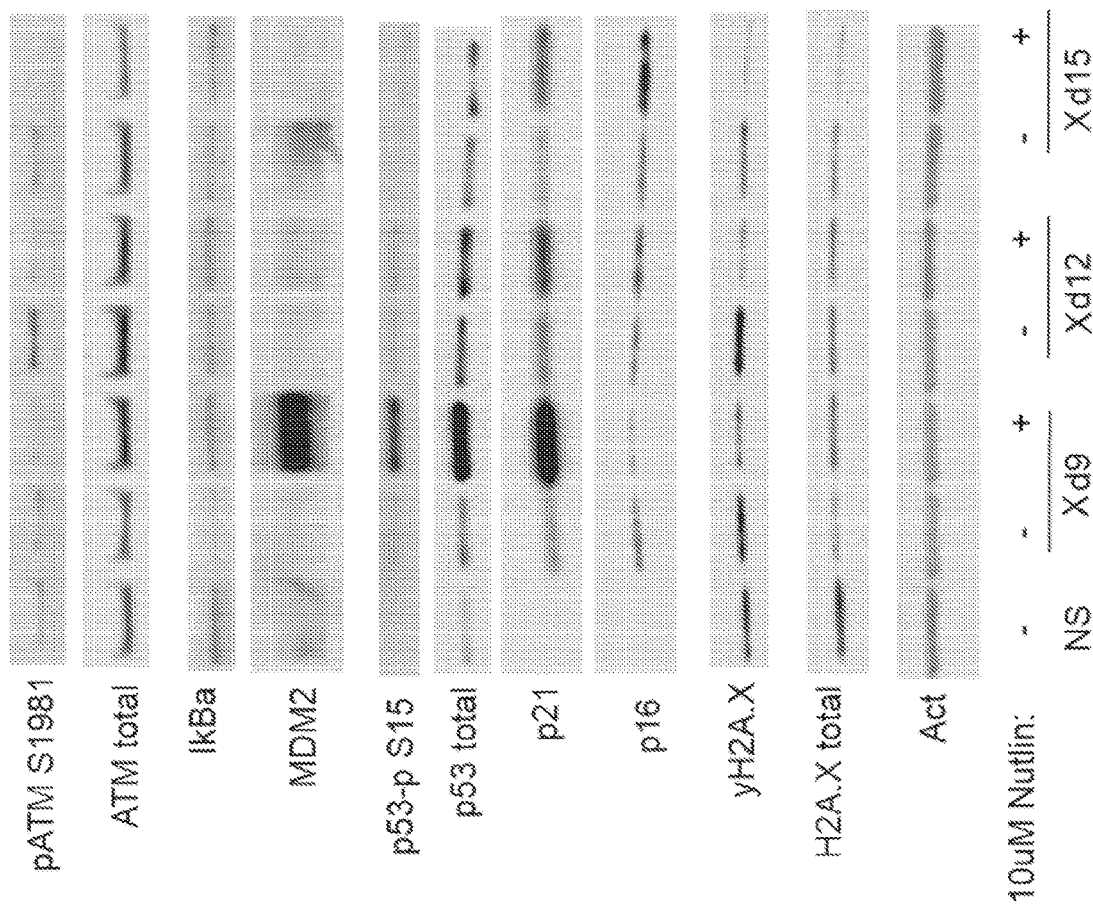
FIG. 14 presents an immunoblot detecting production of proteins in senescent cells treated with Nutlin-3a. IMR90 cells were irradiated at Day −6 and treated with Nutlin-3a or DMSO (vehicle control) in media from Day 0 to Day 9. Cells were cultured for an additional 6 days (Day 12 and Day 15) in media without Nutlin-3a or DMSO, changing media at Day 12. The levels of each protein were detected using commercially available antibodies. The data are shown for non-senescent cells (NS) and for senescent cells at days 9, 12, and 15 (Xd9, Xd12, and Xd15, respectively) cultured in 10 µM Nutlin-3a (+) or vehicle (−).

Primary human fibroblast (IMR90) cells were induced to senesce by applying 10 Gy of irradiation. Seven days after irradiation (Day 0), cells were treated with 10 μM Nutlin-3a or vehicle (DMSO) for nine days (Day 9). The drug or vehicle was refreshed every three days. Drug/vehicle was removed at Day 9 and the cells were cultured for an additional six days in media without drug or DMSO, changing media every three days. Cells were collected at Day 0 (non-senescent cells), Day 9, Day 12, and Day 15, and protein extracted and processed for immunoblotting (Western blotting). Two samples were processed at each time point; the results are provided for one sample in FIG. 14.

The data show that phosphorylation of the kinase ATM is lower in cells that have been treated with Nutlin-3a even when the drug has been removed (see pATM S1981). Similarly, the substrate of ATM, H2AX, had declining levels of phosphorylation (see γH2AX) after Nutlin 3A treatment and also after drug removal. In senescent cells, IkBa gets degraded as the NF-kB pathway is activated, which leads to SASP. The data show that after drug is removed, the level of IkBa in Nutlin-3a treated cells approaches the level of IkBa in non-senescent cells. The levels of each of MDM2, p53 and p21 were elevated in the Nutlin-3a treated samples and decreased when the drug was removed.

These data also support that Nutlin-3a preferentially kills cells with a higher SASP. In addition, because a lower level of activated ATM is produced in surviving cells after drug treatment, these data suggest that DNA damage response-activated senescent cells are the cells that are sensitive to Nutlin-3a.

Example 6

Selective Toxicity of ABT-263 for Senescent Cells Using a Cell Counting Assay

To determine whether ABT-263 is selectively toxic to senescent cells compared to non-senescent cells, a cell counting assay was used to determine cell survival following treatment with ABT-263. The general timelines and procedures for the cell counting assay are shown in FIG. 15. IMR90 cells (human primary lung fibroblasts (IMR90) (IMR-90 (ATCC® CCL-186™, Mannassas, Va.) were seeded in six well plates, and cells were induced to senescence with 10 Gy of ionizing radiation (IR) (Day 0). The media was refreshed every 3 days. The senescent phenotype is allowed to develop for 7 days at which point a cell count was made to determine the baseline number of cells. In the senescent cells (irradiated) and the non-senescent cells (the non-radiated cells), 3 μM ABT-263 was introduced into the media. Some cells were administered a media that did not contain any ABT-263 as a control to account for any ABT-263 toxicity. Each condition was seeded in three wells and counted independently. Cells were counted after a 24 hour exposure to ABT-263 (or control culture).

Figures 16, 17:
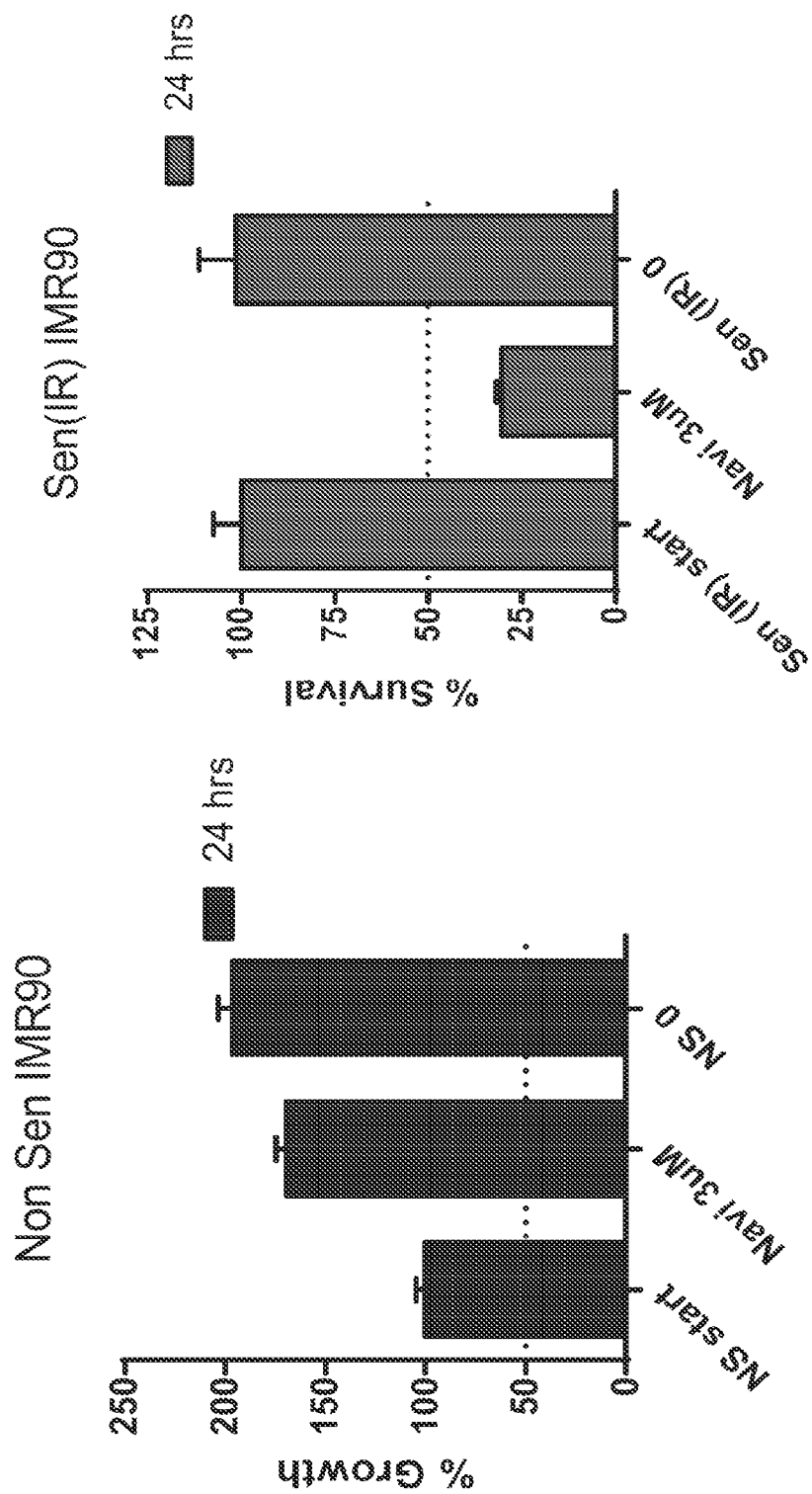
FIG. 16 depicts a graph showing the effect of ABT-263 ("Navi") treatment on non-senescent IMR90 cells (Non Sen IMR90).
FIG. 17 depicts a graph showing the effect of ABT-263 treatment on senescent IMR90 cells (Sen(IR) IMR90).

FIG. 16 demonstrates the effect of ABT-263 on non-senescent cells as measured as a percentage of survival of cells after 24 hours. The addition of ABT-263 to non-senescent (middle bar) did not decrease the cell growth below the starting level (left-most bar) indicating an absence of toxicity in non-senescent cells. Non-ABT-263 treated cells are shown as a control at the far-most right.

FIG. 17 demonstrates the effect of ABT-263 on senescent cells as measured as a percentage of survival of cells after 24 hours. The addition of ABT-263 to senescent cells (middle bar) had decreased cell growth below that of the starting level number of cells (left most bar). The ABT-263 treated cells had 28% of the cell counts before ABT-263 treatment. Non-ABT-263 treated cells are shown as a control at the far-most right.

Example 7

Selective Toxicity of ABT-263 for Senescent Cells Using a CellTiter-Glo® Cell Viability Assay

Figure 18:
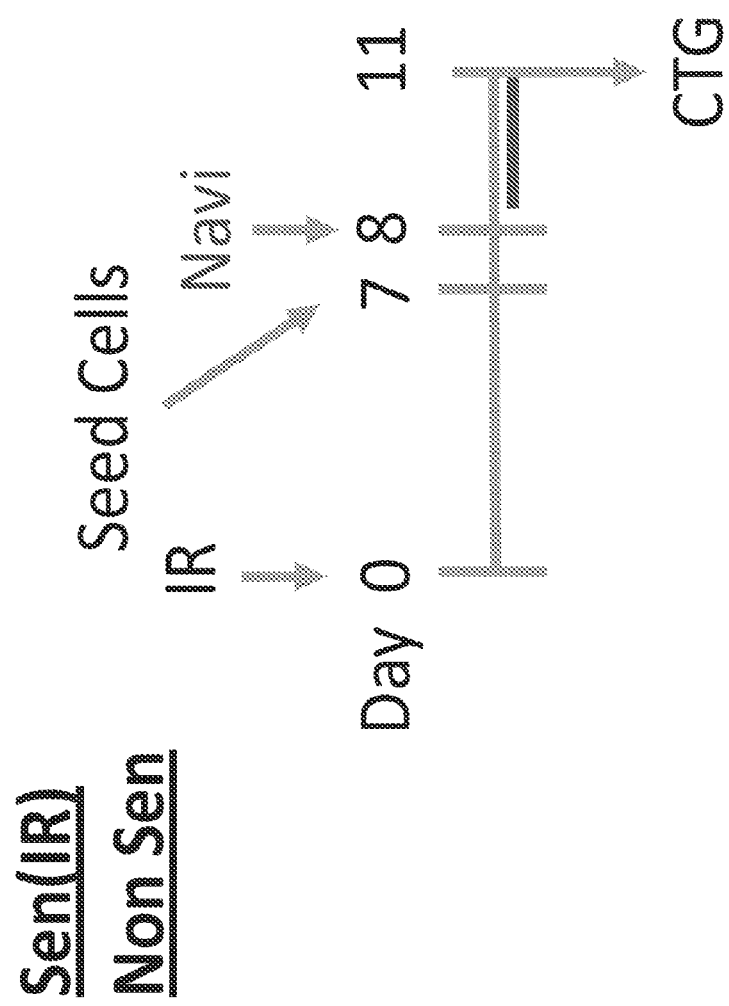
FIG. 18 depicts an exemplary timeline and treatment protocol in senescent (irradiated cells) and non-senescent cells (non-radiated cells) in a cell viability assay (CellTiter-Glo® (CTG)).

To determine whether ABT-263 is selectively toxic to senescent cells compared to non-senescent cells, a cell viability assay was used to assess cell survival following treatment with ABT-263. The general timelines and procedures for the cell counting assay are shown in FIG. 18. IMR90 cells (human primary lung fibroblasts (IMR90)

(IMR-90 (ATCC® CCL-186™, Mannassas, Va.) were seeded in six well plates, and cells were induced to senescence with 10 Gy of ionizing radiation (IR) (Day 0). The media was refreshed every 3 days. The senescent phenotype is allowed to develop for 7 days at which point a cell count was made to determine the baseline number of cells followed by seeding into 96-well plates. On day 8, the senescent cells (irradiated) and the non-senescent cells (the non-radiated cells), were exposed to serial dilutions of ABT-263 for a period of 3 days. ABT-263 concentrations ranged from 0.5 nM to 3 µM. Each condition was seeded in triplicate.

After three days of treatment (Day 11), cells were assayed for cell survival using the commercially available CellTiter-Glo® (CTG) Luminescent Cell Viability Assay (Promega Corporation, Madison, Wis.). The assay determines the number of viable cells in culture based on the quantitation of ATP present which is an indicator of metabolically active cells.

Figure 19:
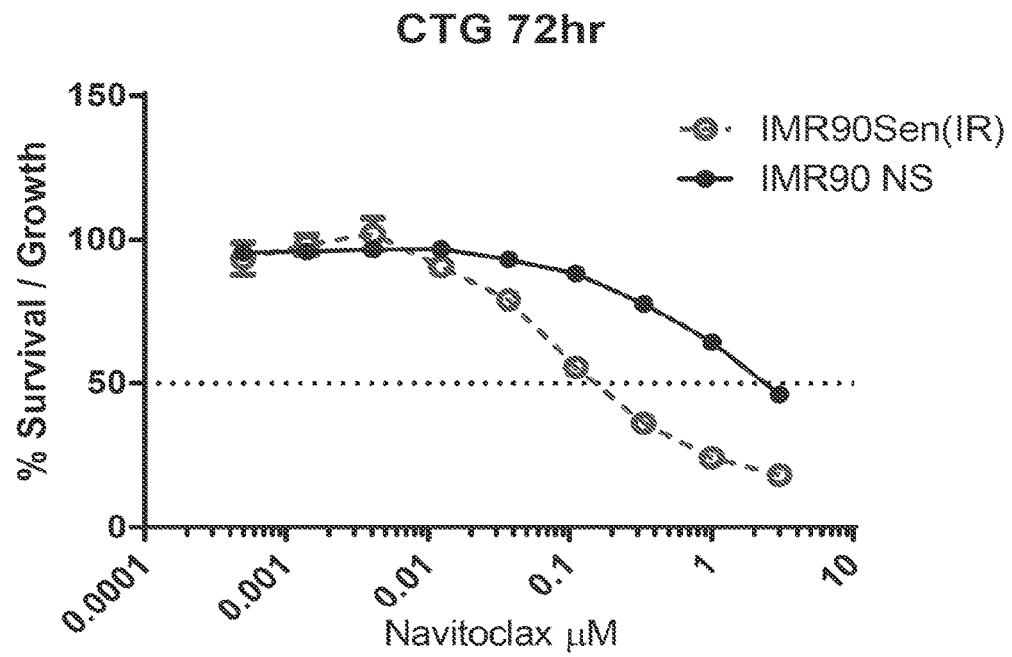
FIG. 19 illustrates a graph showing the effect of ABT-263 treatment on non-senescent and senescent IMR90 cells.

FIG. 19 shows IC50 curves of ABT-263 in senescent cells, and in non-senescent cells. The IC50 curve is a plot of the percentage of cell survival following treatment of ABT-263 as determined by the cell viability assay. The plot shows the effect of the various concentration levels of ABT-263 on cell survival. The IC50 of ABT-263 on non-senescent cells was 2.4 µM compared to an IC50 value of 140 nM on senescent cells, demonstrating the selective toxicity of ABT-263 for senescent cells. An in vitro theoretical therapeutic index of 17 was observed.

Example 8

Figure 23:
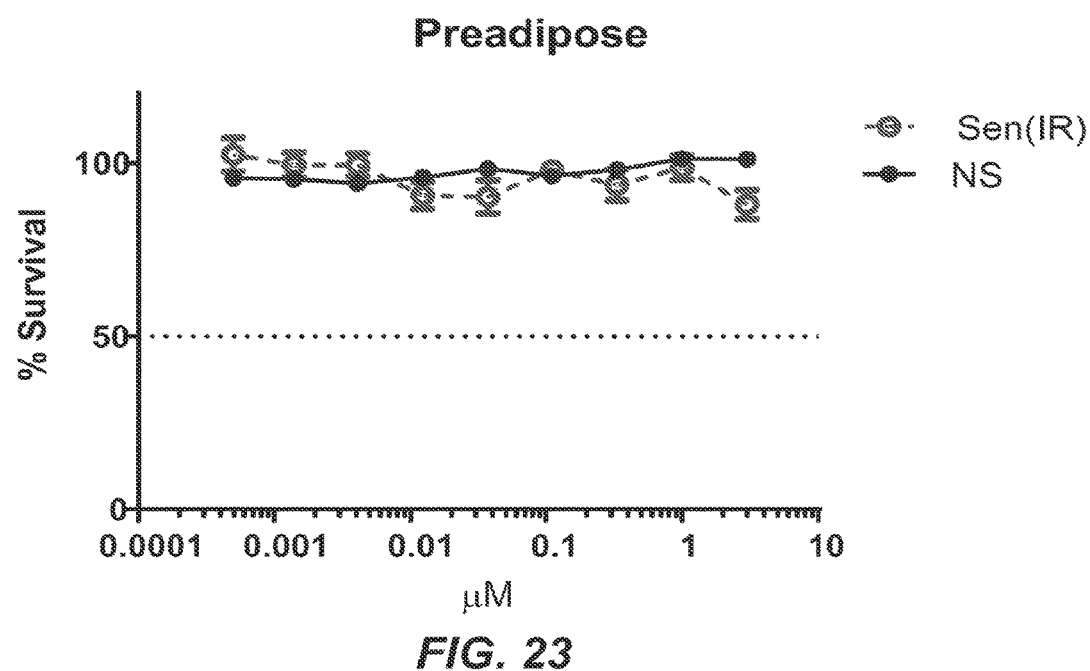
FIG. 23 illustrates a graph showing the effect of ABT-263 treatment in non-senescent and senescent pre-adipose cells.
Figure 24:
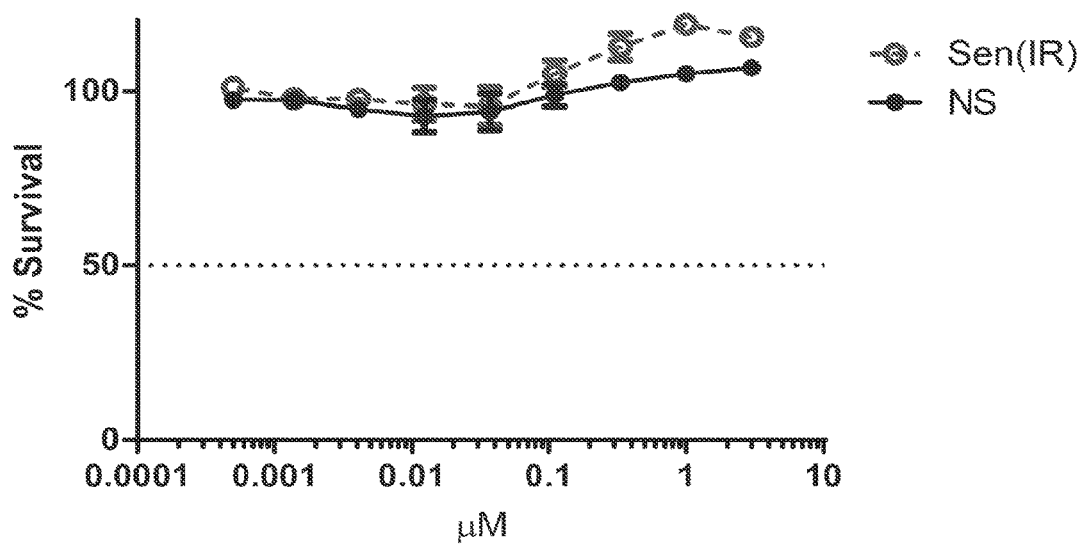
FIG. 24 illustrates a graph showing the effect of ABT-263 treatment in non-senescent and senescent mouse embryonic fibroblasts (MEF) cells.
Figure 25:
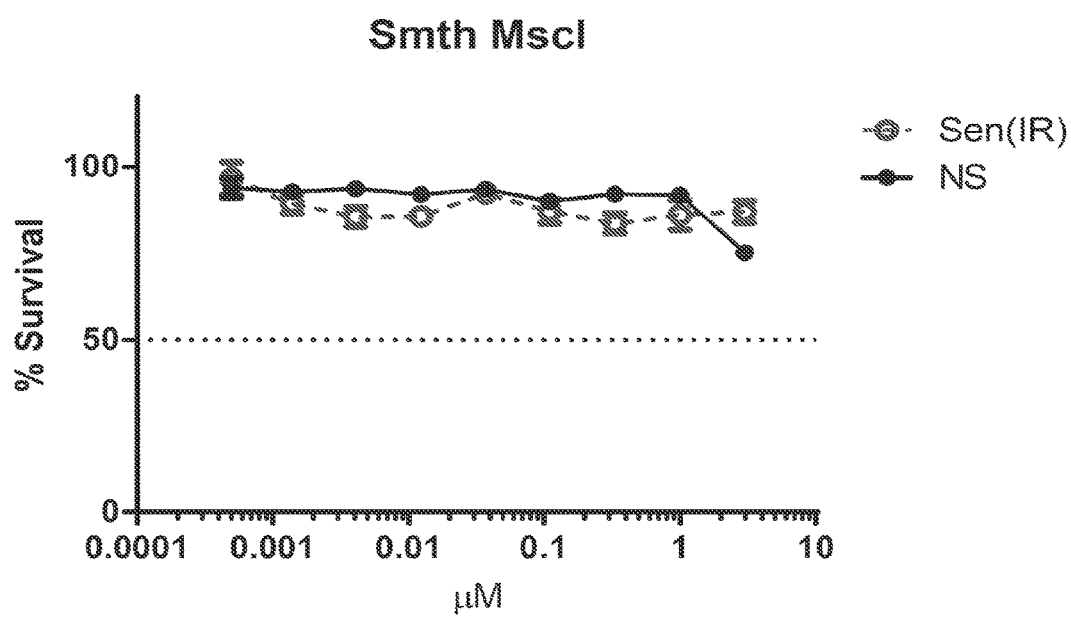
FIG. 25 illustrates a graph showing the effect of ABT-263 treatment in non-senescent and senescent smooth muscle cells (Smth Mscl).

Assessment of Selective Toxicity of ABT-263 for Senescent Cells of Various Cell Types The methods of Example 7 were repeated in other cell strains. Cell strains included Primary Renal Cortical Cells, ATCC Cat# PCS-400-011 (FIG. 20), HCA2 foreskin fibroblast cells (FIG. 21), Primary Small Airway Epithelial Cells, ATCC Cat# PCS-301-010 (lung) (FIG. 22), human pooled Preadipocyte from patients (Pread) (FIG. 23), Mouse embryonic fibroblast extracted from C571316 mice (MEF) (FIG. 24), Primary Coronary Artery Smooth Muscle, ATCC Cat# PCS-100-021 (Smth Mscl) (FIG. 25).

Figure 20:
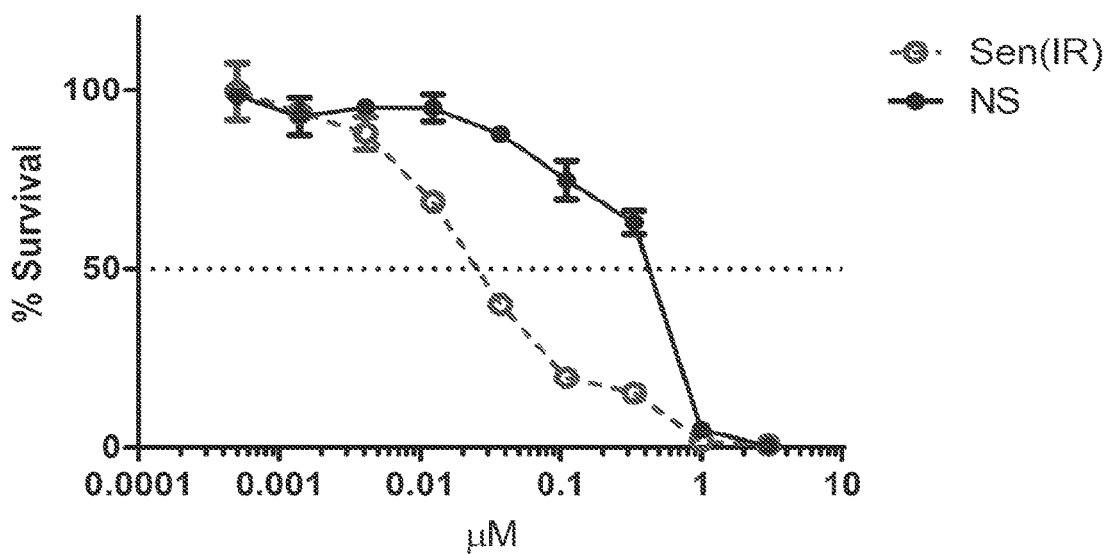
FIG. 20 illustrates a graph showing the effect of ABT-263 treatment in non-senescent and senescent renal epithelial cells.

The experiments performed in these other cell strains were performed essentially as described in Example 7. As shown in FIG. 20, the IC50 of ABT-263 on non-senescent cells was 430 nM compared to an IC50 value of 25 nM on senescent cells, demonstrating the selective toxicity of ABT-263 for senescent cells in renal epithelial cells.

Figure 21:
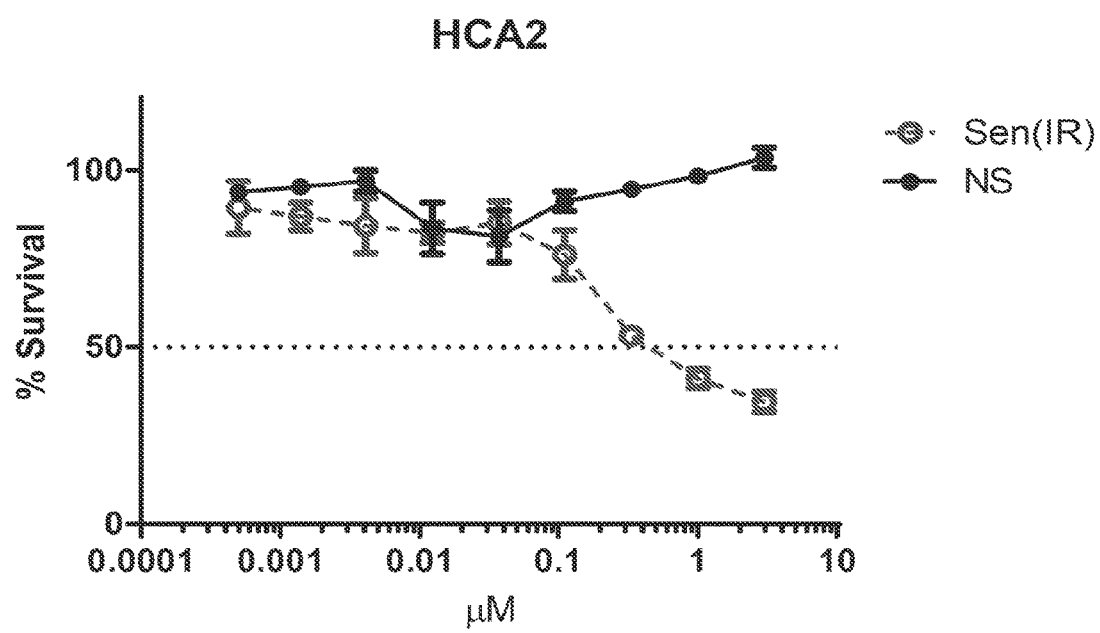
FIG. 21 illustrates a graph showing the effect of ABT-263 treatment in non-senescent and senescent foreskin fibroblasts (HCA2) cells.

As shown in FIG. 21, the IC50 of ABT-263 on non-senescent cells was not toxic as up to 3 µM compared to an IC50 value of 410 nM on senescent cells, demonstrating the selective toxicity of ABT-263 for senescent cells in HCA2 cells.

Example 9

Assessment of Selective Toxicity of ABT-263 and Other BCL-2 Inhibitors for Senescent Human Primary Lung Fibroblasts To determine whether other Bcl-2 inhibitors demonstrate selective toxicity for senescent cells over non-senescent cells, cells were treated with ABT-199 (Selleckem Cat# S8048, Houston, Tex.) or Obatoclax (Selleckem Cat# S1057). ABT-199 and Obatoclax are known Bcl-2 inhibitors.

Figure 26:
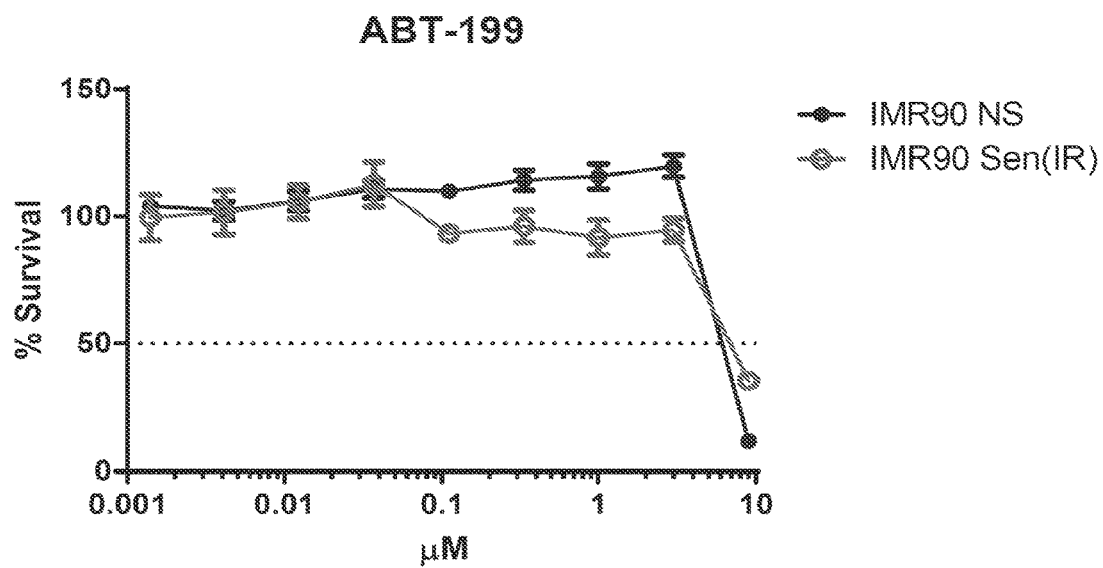
FIG. 26 illustrates a graph showing the effect of ABT-199 treatment in non-senescent and senescent IMR90 cells.
Figure 27:
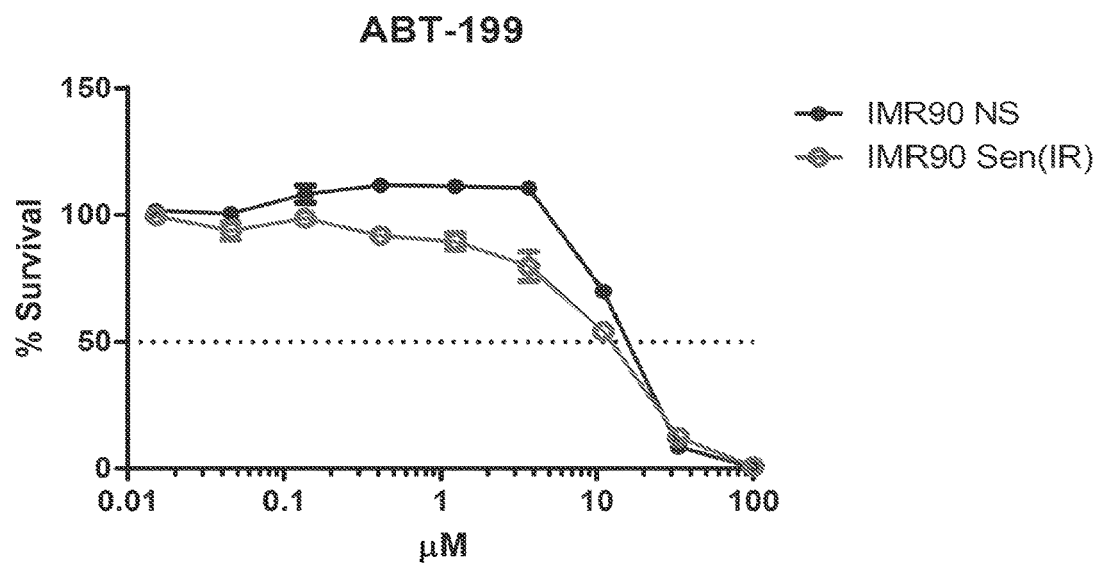
FIG. 27 illustrates a graph showing the effect of ABT-199 treatment in non-senescent and senescent IMR90 cells.
Figure 28:
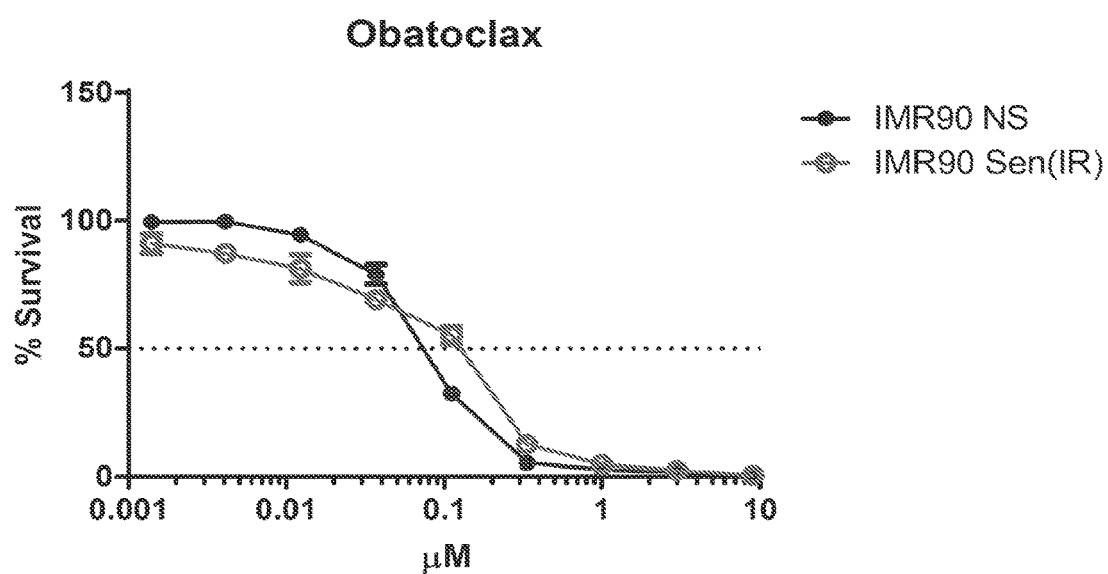
FIG. 28 illustrates a graph showing the effect of Obatoclax treatment in non-senescent and senescent IMR90 cells.

The experiments performed for assessing the effect of these other Bcl-2 inhibitors were performed essentially as described in Example 7. Cells were exposed to ABT-199 at serial dilution concentrations ranging from 15 nM to 100 µM (FIGS. 26 and 27). Cells were exposed to Obatoclax at concentrations ranging from 1.4 nM to 9 µM (FIG. 28).

As shown in FIGS. 26-27, ABT-199 had an IC50 value of 6 µM-15.8 µM in non-senescent cells compared to an IC50 value of 6.9 µM-12.4 µM in senescent cells. As shown in FIG. 28, Obatoclax had an IC50 value of 75 nM in non-senescent cells compared to an IC50 value of 125 nM in senescent cells. FIG. 26-28 demonstrate the inability of ABT-199 and Obatoclax to selectively target senescent cells over non-senescent cells.

A compound specific for Bcl-2A1 also did not selectively kill senescent cells. IMR90 cells were induced to senescence by irradiation as described in Example 7. The irradiated IMR90 cells and non-senescent IMR90 cells were then exposed to a compound called ML214 that is a Bcl-2A1 specific inhibitor. The level of killing of senescent cells was comparable to the level of killing of non-senescent cells.

Example 10

Selective Toxicity for Senescent Cells of the Akt Inhibitor, MK-2206 Alone and in Combination with ABT-263

The effect of ABT-263 in combination with the Akt inhibitor MK-2206 was tested for selective toxicity of senescent cells compared to non-senescent cells in IMR90 cells. The methods of Example 7 were repeated except that cell cultures were exposed to 10 nM MK-2206 (Selleckem, Cat# S1078) in addition to serial dilutions of ABT-263.

Figure 29A:
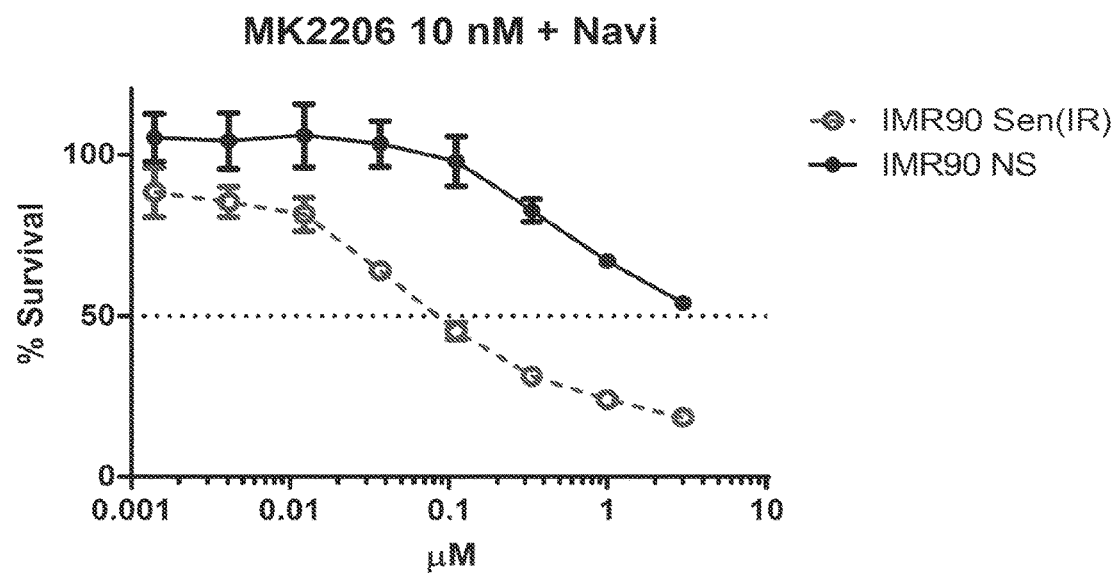
FIG. 29A and FIG. 29B.

FIG. 29A shows the dose dependence plots of ABT-263 treatment in combination with 10 nM MK-2206 on senescent cells and non-senescent cells. ABT-263+MK-2206-treated senescent cells had an IC50 value of 0.083 µM, whereas ABT-263+MK-2206 cells in non-senescent cells had an IC50 value >3 µM, yielding a selectivity index of >36 for senescent cells.

Figure 29B:
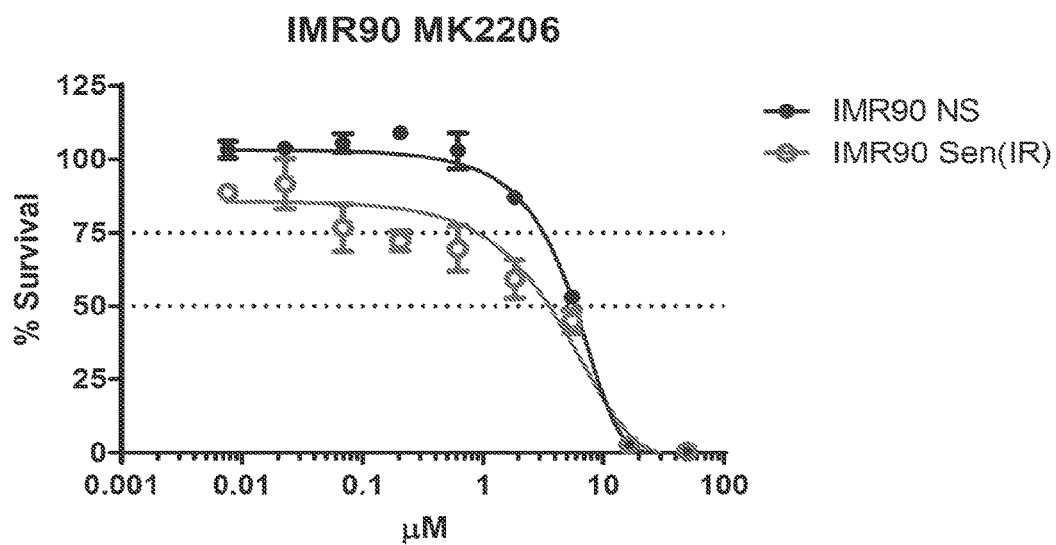

The senolytic effect of MK-2206 alone was determined by exposing senescent IMR90 cells and non-senescent IMR90 cells (see procedures in Example 7) and to serial dilutions of MK-2206. The percent survival was determined, and the results are present in FIG. 29B.

Example 11

An Animal Study for Determining the Senolytic Effect of ABT-263 in Mice

The senolytic effect of senolytic agents, e.g., ABT-263, can be assessed in animal models of senescence. An example of such an animal study is described here. Senescence in animals can be induced through the administration of doxorubicin followed by treatment of a senolytic agent. On day 35, mice are sacrificed, and fat and skin are collected for RNA analysis, while lungs are collected and flash frozen for immunomicroscopy analysis. RNA is analyzed for expression of SASP factors (mmp3, IL-6) and senescence markers (p21, p16, and p53). Frozen lung tissue is analyzed for DNA damage marker ($\gamma$H2AX).

The mice to be tested contain a transgene insertion of p16-3MR. 3MR (tri-modality reporter) is a fusion protein containing functional domains of a synthetic *Renilla luciferase* (LUC), monomeric red fluorescence protein (mRFP), and truncated herpes simplex virus (HSV)-1 thymidine kinase (tTK), which allows killing by ganciclovir (GCV). The 3MR cDNA is inserted in frame with p16 in exon 2, creating a fusion protein containing the first 62 amino acids of p16, but does not include the full-length wild-type p16 protein. Insertion of the 3MR cDNA also introduces a stop codon in the p19$^{ARF}$ reading frame in exon 2.

The effect of ABT-263 is analyzed by the reduction of luminescence intensity. Female C57/Bl6 p16-3MR mice are treated with Doxorubicin. Luminescence is measured 10 days later and used as baseline for each mouse (100% intensity). ABT-263 is administered intraperitoneally daily from day 10 to day 24 post-doxorubicin treatment. Luminescence is then measured at day 7, 14, 21, 28, 35 post-ABT-263 treatments, and final values calculated as % of the baseline values. Control animals (DOXO) are injected with equal volume of PBS.

The level of mRNA of endogenous mmp-3, IL-6, p21, p16, and p53 in the skin and fat from animals after treatment with doxorubicin alone (DOXO) or doxorubicin plus ABT-263 is plotted. The values represent the fold induction of the particular mRNA compared with untreated control animals.

Immunofluorescence microscopy of lung sections from doxorubicin treated animals (DOXO) and doxorubicin and ABT-263 can be detected by binding to a primary rabbit polyclonal antibody specific for γH2AX followed by incubation with a secondary goat anti-rabbit antibody, and then counterstained with DAPI. The percent positive cells from immunofluorescence microscopy are calculated and can be represented as percentage of the total number of cells. Data can be obtained from doxorubicin-treated mice (Doxo), and doxorubicin+ABT-263-treated mice).

ABT-263 can be analyzed for reduced senescence-associated (SA) β-galactosidase (β-gal) intensity of fat biopsies from animals first treated with doxorubicin. Female C57/BL6 p16-3MR mice are treated with doxorubicin. A portion of the doxorubicin treated animals receive ABT-263 or PBS (DOXO) daily from day 10 to day 24 post-doxorubicin treatment. Three weeks after the ABT-263 treatment, mice are sacrificed and fat biopsies immediately fixed and stained with a solution containing X-Gal. Untreated animals are used as negative control (CTRL).

Example 12

In Vitro Cell Assays for Determining Senolytic Activity of WEHI-539

Lung fibroblast cell line IMR90 (human primary lung fibroblasts, ATCC® CCL-186™, Manassas, Va.) and a renal cell line (Primary Renal Cortical Cells, ATCC Cat. No. PCS-400-011) were seeded in six-well plates and induced to senesce with 10 Gy of ionizing radiation (IR). Senescent phenotype was allowed to develop for at least 7 days.

After senescence phenotype had developed, cells were re-seeded into 96 well plates, and senescent cells (irradiated) and non-senescent cells (the non-radiated cells), were exposed to three-fold serial dilutions of WEHI-539 for a period of 3 days. WEHI-539 concentrations ranged from 0.0075 µM to 15 µM. After the three days, cell survival was determined using the commercially available CellTiter-Glo® Luminescent Cell Viability Assay (Promega Corporation, Madison, Wis.). The assay determines the number of viable cells in culture based on the quantitation of ATP present which is an indicator of metabolically active cells.

Figure 30A:
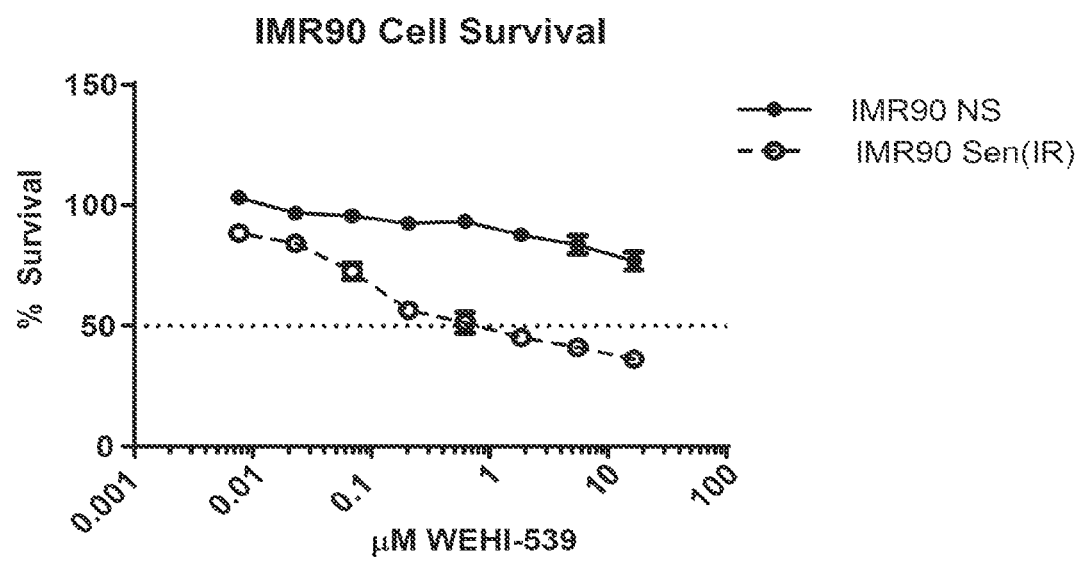
FIGS. 30A-B illustrate the effect of WEHI-539 on percent survival of senescent irradiated lung fibroblasts (Sen(IR) IMR90)) (FIG. 30A) and percent survival of irradiated renal cells (Sen(IR)) (FIG. 30B). NS=Non-senescent cells, which were not exposed to radiation.
Figure 30B:
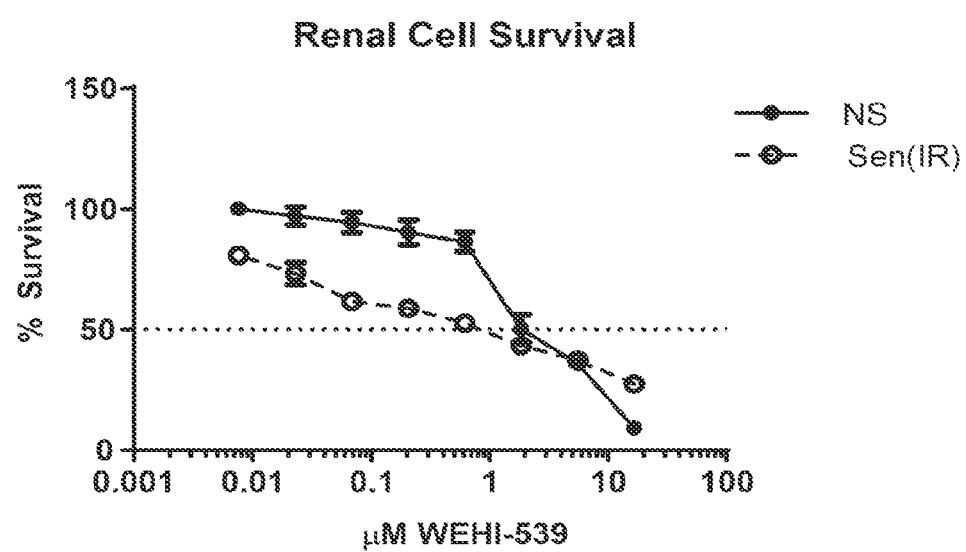

FIG. 30 presents the IMR90 cell survival (see FIG. 30A) and renal cell survival (see FIG. 30B).

Example 13

WEHI-539 Treatment of p16-3MR Transgenic Mice

This example describes an animal model useful for determining the capability of a senolytic agent to selectively kill senescent cells in vivo. The capability of WEHI-539 or another senolytic agent to remove senescent cells in vivo is determined in transgenic p16-3MR mice (see, e.g., International Application Publication No. WO2013/090645). An experiment is performed in a similar manner to the procedure illustration in the schematic provided in FIG. 6. The transgenic mouse comprises a p16$^{Ink4a}$ promoter operatively linked to a trimodal fusion protein for detecting senescent cells and for selective clearance of senescent cells in these transgenic mice, which is illustrated in FIG. 7. The promoter, p16$^{Ink4a}$, which is transcriptionally active in senescent cells but not in non-senescent cells (see, e.g., Wang et al., *J. Biol. Chem.* 276:48655-61 (2001); Baker et al., *Nature* 479:232-36 (2011)), was engineered into a nucleic acid construct. 3MR (tri-modality reporter) is a fusion protein containing functional domains of a synthetic *Renilla luciferase* (LUC), monomeric red fluorescence protein (mRFP), and truncated herpes simplex virus (HSV)-1 thymidine kinase (tTK), which allows killing by ganciclovir (GCV) (see, e.g., Ray et al., *Cancer Res.* 64:1323-30 (2004)). The 3MR cDNA was inserted in frame with p16 in exon 2, creating a fusion protein containing the first 62 amino acids of p16, but not a full-length wild-type p16 protein. Insertion of the 3MR cDNA also resulted in the occurrence of a stop codon in the p19$^{ARF}$ reading frame in exon 2, thereby preventing full-length p19$^{ARF}$ expression from the BAC as well. The p16$^{Ink4a}$ gene promoter (approximately 100 kilobase pairs) was introduced upstream of a nucleotide sequence encoding a trimodal reporter fusion protein. Alternatively, a truncated p16$^{Ink4a}$ promoter may be used (see, e.g., Baker et al., *Nature*, supra; International Application Publication No. WO2012/177927; Wang et al., supra). Thus, the expression of 3MR is driven by the p16$^{Ink4a}$ promoter in senescent cells only. The detectable markers, LUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57B16 background, were established and bred using known procedures for introducing transgenes into animals (see, e.g., Baker et al., *Nature* 479:232-36 (2011)).

To determine the senolytic activity of an agent, such as WEHI-539, female C57/BL6 p16-3MR mice are randomized into doxorubicin+WEHI-539 treated or doxorubicin only treated groups. Senescence is induced by intraperitoneal administration of doxorubicin at 10 mg/kg to the mice ten days prior to administration of WEHI-539 (Day −10). WEHI-539 is administered intraperitoneally daily from day 10 to day 24 post-doxorubicin treatment (Group=9 mice). Control mice (doxorubicin treated) are injected with equal volumes of PBS (Group=3 mice). Luminescence imaging (Xenogen Imaging system) is performed at Day 0 (i.e., 10 days post-doxorubicin treatment) as a baseline for each mouse (100% intensity).

Luminescence imaging of the mice is performed on day 7, 14, 21, 28, and 35 following the initiation of WEHI-539 treatment. Reduction of luminescence (L) is calculated as: L=(Imaging post-WEHI-539 treatment)/(Baseline Imaging) %. If L is greater than or equal to 100%, the number of senescent cells was not reduced. If L is less than 100%, then the number of senescent cells was reduced. Every mouse is calculated independently, and background is subtracted from each sample.

Experiments are performed to determine the effect of WEHI-539 treatment on expression of genes associated with senescence. Groups of female C57/BL6 p16-3MR are treated as described above. Three weeks after the end of WEHI-539 treatment (day 35), the doxorubicin treated mice (control) (N=3) and doxorubicin+WEHI-539-treated mice (N=6) are sacrificed. Skin and fat biopsies are collected for RNA extraction; fat biopsies are collected for detection of senescence-associated β-galactosidase; and lungs are flash frozen in cryoprotectant OCT media for cryostat sectioning.

RNA is analyzed for mRNA levels of endogenous senescence markers (e.g., p21, p16$^{INK4a}$ (p16), and p53) and SASP factors (e.g., mmp-3 and IL-6) relative to actin mRNA (control for cDNA quantity) using the Roche Universal Probe Library for real-time PCR assay.

The frozen lung tissue is sectioned to 10 µM thickness and stained with primary rabbit polyclonal antibody against γH2AX (Novus Biologicals, LLC), which is a marker for double-strand breaks in cells (DNA damage). The sections are then stained with ALEXA FLUOR® dye-labeled secondary goat anti-rabbit antibody (Life Technologies) and counterstained with 4',6-diamidino-2-phenylindole (DAPI) (Life Technologies). The number of positive cells is calculated using ImageJ image processing program (National Institutes of Health, see Internet at imagej.nih.gov/ij/index.html) and represented as a percentage of the total number of cells.

Upon collection, fat biopsies are immediately fixed in 4% formalin and then stained with a solution containing X-gal to detect the presence of senescence-associated β-galactosidase (β-gal). Fat biopsies are incubated overnight at 37° C. in X-gal solution and are photographed the next day. Fat biopsies from untreated animals are used as a negative control (CTRL).

Example 14

Capability of BCL-XL Inhibitor to Remove Senescent Cells with Established SASP

This example describes a method for determining the effect of a senolytic agent on killing of senescent cells that have established SASP. Primary human fibroblast (IMR90) cells are induced to senesce by applying 10 Gy of irradiation. Seven days after irradiation (Day 0), cells are treated with 10 µM of a BCL-XL inhibitor (e.g., WEHI-539) or a BCL-2/BCL-XL inhibitor or vehicle (DMSO) for nine days (Day 9). The drug or vehicle is refreshed every three days. Drug/vehicle is removed at Day 9 and the cells are cultured for an additional three days (Day 12). Cells are then fixed with 4% paraformaldehyde and stained by immunofluorescence with a specific anti-IL-6 antibody (R&D, AF-206-NA). Cells are counterstained with DAPI for nuclear visualization. IL-6 positive cells are determined in an unbiased manner using CellProfiler software.

In another experiment, IMR90 cells are induced to senesce by irradiation (10 Gy). Seven days after irradiation, cells are treated with senolytic agent (e.g., a BCL-XL inhibitor (e.g., WEHI-539) or a BCL-2/BCL-XL inhibitor; MDM2 inhibitor; Akt inhibitor) or vehicle (DMSO) for nine days (Day 9). The drug or vehicle is refreshed every three days. Drug/vehicle is removed at Day 9 and the cells are cultured for an additional six days. Conditioned media from the treated cells is collected, and IL-6 measurement by ELISA is performed (Perkin Elmer, AL223F). IL-6 levels in culture media are determined by ELISA using a kit according to manufacturer's instructions (AL223F, Perkin Elmer). Cells are fixed with 4% paraformaldehyde and stained by immunofluorescence with a specific anti-IL-6 antibody (R&D, AF-206-NA). The IL-6 level determined by ELISA is normalized to the number of cells in each well.

Example 15

Capability of a Senolytic Agent to Remove Senescent Cells with Established SASP: SASP Factor Expression This example describes a method for determining the effect of a senolytic agent on SASP factor expression. Primary human fibroblast (IMR90) cells are induced to senesce by applying 10 Gy of irradiation. Seven days after irradiation (Day 0), cells are treated with a senolytic agent (e.g., a BCL-XL inhibitor (e.g., WEHI-539) or a BCL-2/BCL-XL inhibitor; MDM2 inhibitor; Akt inhibitor) or vehicle (DMSO) for nine days. The drug or vehicle is refreshed every three days. After drug/vehicle is removed prior to evaluation of SASP expression at Day 9, the cells are cultured for an additional three days in media without drug or DMSO. Cells are then collected, mRNA extracted, and cDNA prepared. Quantitative PCR (qPCR) is then performed to detect expression of various genes. Cells are also collected at Day 12 after drug/vehicle had been removed for three days. Data are normalized to actin and depicted as a ratio to non-senescent cells.

Example 16

Capability of a Senolytic Agent to Remove Senescent Cells with Elevated DNA Damage Response This example describes a method for determining the effect of a senolytic agent on selectively killing senescent that that have an elevated DNA damage response. Primary human fibroblast (IMR90) cells are induced to senesce by applying 10 Gy of irradiation. Seven days after irradiation (Day 0), cells are treated with a senolytic agent (for example, a BCL-XL inhibitor (e.g., WEHI-539) or a BCL-2/BCL-XL inhibitor, MDM2 inhibitor; Akt inhibitor) or vehicle (DMSO) for nine days (Day 9). The drug or vehicle is refreshed every three days. Drug/vehicle is removed at Day 9 and the cells are cultured for an additional six days in media without drug or DMSO, changing media every three days. Cells are collected at Day 0 (non-senescent cells), Day 9, Day 12, and Day 15, and protein extracted and processed for immunoblotting (Western blotting). Two samples are processed at each time point.

Example 17

BCL-XL Selective Inhibitor Kills Senescent Cells Via Apoptosis

Figure 31:
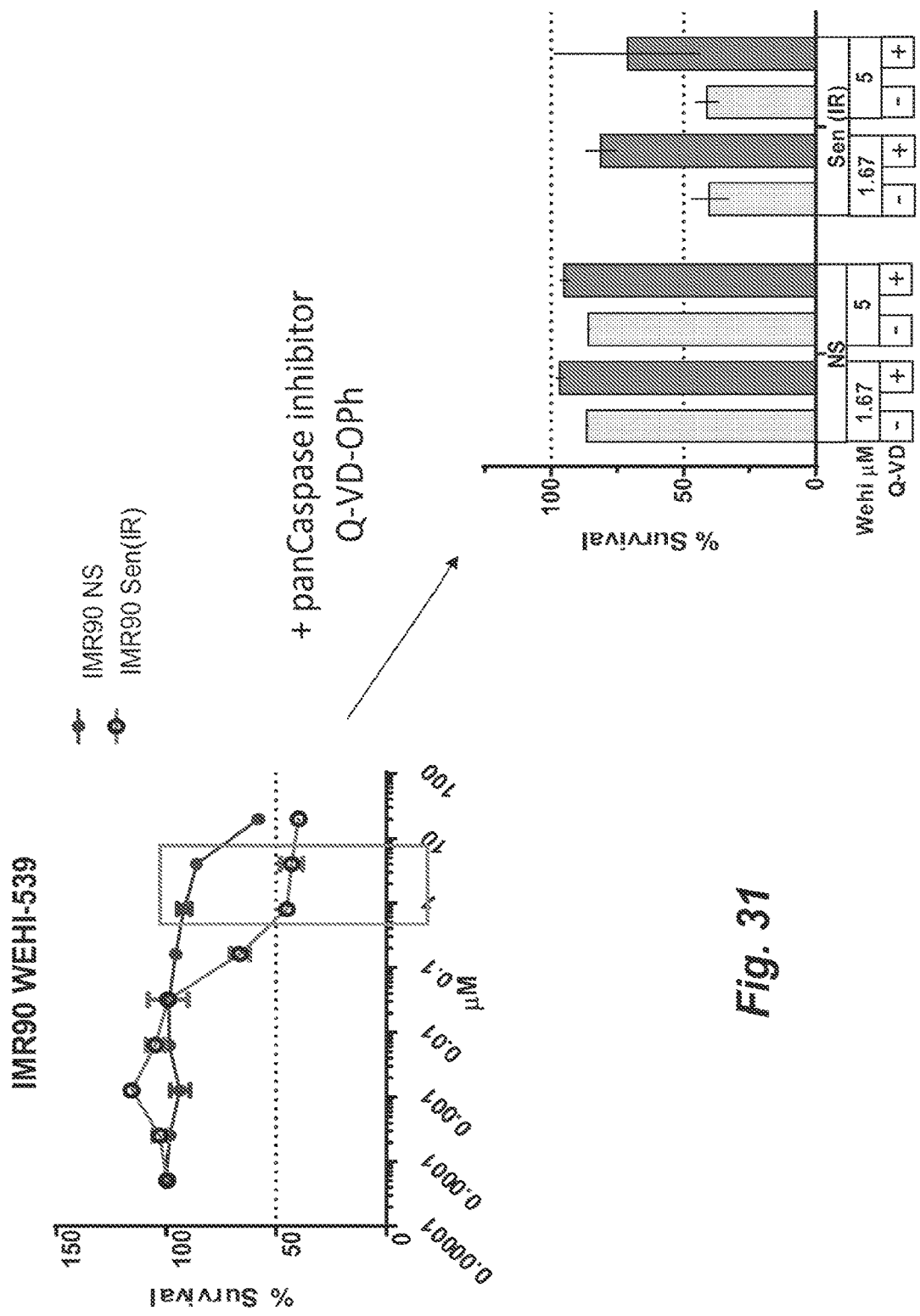
FIG. 31 illustrates that in the presence of a caspase inhibitor (panCaspase inhibitor, Q-VD-OPh) the senolytic activity of WEHI-539 is inhibited. The left side of FIG. 31 illustrates the effect of WEHI-539 on killing senescent cells (IMR90 Sen(IR)). The data points within the boxed area depict killing of senescent cells at the WEHI-539 concentrations of 1.67 µM and 5 µM of to which non-senescent cells (NS) and senescent cells (Sen (IR)) were exposed in the presence or absence of Q-VC-OPh. The percent survival of non-senescent cells and senescent cells in the presence and absence of the pan-Caspase inhibitor (Q-VD in the figure) is illustrated in the figure on the bottom right.

Lung fibroblast cell line IMR90 (human primary lung fibroblasts, ATCC® CCL-186™, Manassas, Va.) were seeded in six-well plates and induced to senesce with 10 Gy of ionizing radiation (IR) as described in Example 12. After senescence was established, cells were re-seeded into 96 well plates. The pan-caspase inhibitor Q-VD-OPh (20 µM) was added to wells of senescent cells (irradiated) (IMR90 Sen(IR)) and to wells containing non-senescent cells (the non-radiated cells) (IMR90 NS). Four hours later, the senescent and non-senescent cells were each exposed for a period of 3 days to 1.67 or 5 µM WEHI-539. At the end of the assay time period, cells were counted. Each condition was seeded in three plate wells and counted independently. Initial cell count served as a control to determine the induction of senescence, as compared to the last day count without WEHI-539 treatment. Initial non-senescent cell count serves as a proxy to determine WEHI-539 toxicity. Cell survival was determined using the commercially available CellTiter-Glo® Luminescent Cell Viability Assay (Promega Corporation, Madison, Wis.). The assay determines the number of viable cells in culture based on the quantitation of ATP present which is an indicator of metabolically active cells. FIG. 31 (left side) is an illustration that WEHI-539 selectively kills senescent cells (see Example 12) and illustrates the WEHI-539 concentrations used in this experiment. In the presence of the pan-caspase inhibitor, the percent of surviving senescent cells increased (FIG. 31, right side).

Example 18

Effective Killing of Senescent Cells by Inhibiting BCL-XL

This example demonstrates that BCL-XL is the BCL-2 anti-apoptotic family member important for apoptosis of senescent cells. Short hairpin RNAs (shRNA) comprising sequences specific for BCL-2, BCL-XL (also called BCL2L1), and BCL-w (also called BCL2L2) were prepared and introduced into lentiviral vectors. Four different shRNAs for each of BCL-XL and BCL-w and three for BCL-2 were synthesized by the Broad Institute of MIT and Harvard (Cambridge, Mass.). Lentiviral vectors comprising each respective shRNA were purchased from Sigma Aldrich (St. Louis, Mo.). The shRNA sequences and the target sequences are provided in the table below. The nucleotide sequence of each protein can be readily obtained from public databases (see, e.g., Bcl-xL at GenBank NM_001191.2 and NM_138578.1 (BCL2-like 1 (BCL2L1)); Bcl-w at GenBank NM_004050.3 (BCL2-like 2 (BCL2L2)); and Bcl-2 at NM_000633.2, NM_000657 (B-cell CLL/lymphoma 2 (BCL2)).

Triplicate samples of senescent cells and non-senescent cells were transduced with each of the different lentiviral vectors and with two control vectors according to methods practiced in the art. Control samples include senescent and non-senescent cells that were not transduced (NT) with a lentivirus. IMR90 cells were induced to senesce by exposure to 10 Gy of ionizing radiation (IR) as described in Example 12. After senescence phenotype had developed, cells were re-seeded into 96 well plates, and shRNA was added. After 24 hrs, the shRNA was removed and media was refreshed. Media was again refreshed after 3 days. After the last media refresh (6 days after shRNA removal), survival was measured with CellTiter-Glo® Luminescent Cell Viability Assay.

TABLE shRNA Sequences

| SYMBOL | Protein Encoded | shRNA Sequence | Target Sequence |
|---|---|---|---|
| BCL2 | Bcl-2 | CCGGCCGGGAGATAG TGATGAAGTACTCGA GTACTTCATCACTAT CTCCCGGTTTTTG (SEQ ID NO: 1) | CCGGGAGATAGT GATGAAGTA (SEQ ID NO: 2) |
| BCL2 | Bcl-2 | CCGGGTGATGAAGTA CATCCATTATCTCGA GATAATGGATGTACT TCATCACTTTTTG (SEQ ID NO: 3) | GTGATGAAGTACA TCCATTAT (SEQ ID NO: 4) |
| BCL2 | Bcl-2 | CCGGGTGATGAAGTA CATCCATTATCTCGA GATAATGGATGTACT TCATCACTTTTTG (SEQ ID NO: 3) | GTGATGAAGTACA TCCATTAT (SEQ ID NO: 4) |
| BCL2 | Bcl-2 | CCGGAGAGTGACAGT GGATTGCATTCTCGA GAATGCAATCCACTG TCACTCTTTTTG (SEQ ID NO: 5) | AGAGTGACAGTG GATTGCATT (SEQ ID NO: 6) |
| BCL2L1 | Bcl-xL | CCGGGCTCACTCTTC AGTCGGAAATCTCGA GATTTCCGACTGAAG AGTGAGCTTTTTG (SEQ ID NO: 7) | GCTCACTCTTCAG TCGAA (SEQ ID NO: 8) |
| BCL2L1 | Bcl-xL | CCGGGTGGAACTCTA TGGGAACAATCTCGA GATTGTTCCCATAGA GTTCCACTTTTTG (SEQ ID NO: 9) | GTGGAACTCTATG GGAACA (SEQ ID NO: 10) |
| BCL2L1 | Bcl-xL | CCGGGTTTAGTGATG TGGAAGAGAACTCGA GTTCTCTTCCACATC ACTAAACTTTTTG (SEQ ID NO: 11) | GTTTAGTGATGTG GAAGAG (SEQ ID NO: 12) |
| BCL2L1 | Bcl-xL | CCGGGCTCACTCTTC AGTCGGAAATCTCGA GATTTCCGACTGAAG AGTGAGCTTTTTG (SEQ ID NO: 13) | GCTCACTCTTCAG TCGGAAAT (SEQ ID NO: 14) |
| BCL2L2 | Bcl-w | CCGGTGGCAGACTTT GTAGGTTATACTCGA GTATAACCTACAAAG TCTGCCATTTTTG (SEQ ID NO: 15) | TGGCAGACTTTGT AGGTTA (SEQ ID NO: 16) |
| BCL2L2 | Bcl-w | CCGGGTCAACAAGGA GATGGAACCACTCGA GTGGTTCCATCTCCT TGTTGACTTTTTG (SEQ ID NO: 17) | GTCAACAAGGAG ATGGAAC (SEQ ID NO: 18) |
| BCL2L2 | Bcl-w | CCGGCAGAAGGGTTA TGTCTGTGGACTCGA GTCCACAGACATAAC CCTTCTGTTTTTG (SEQ ID NO: 19) | CAGAAGGGTTAT GTCTGTG (SEQ ID NO: 20) |
| BCL2L2 | Bcl-w | CCGGCCATTAGATGA GTGGGATTACTCGA GTAAATCCCACTCAT CTAATGGTTTTTG (SEQ ID NO: 21) | CCATTAGATGAGT GGGATTTA (SEQ ID NO: 22) |

Figure 32:
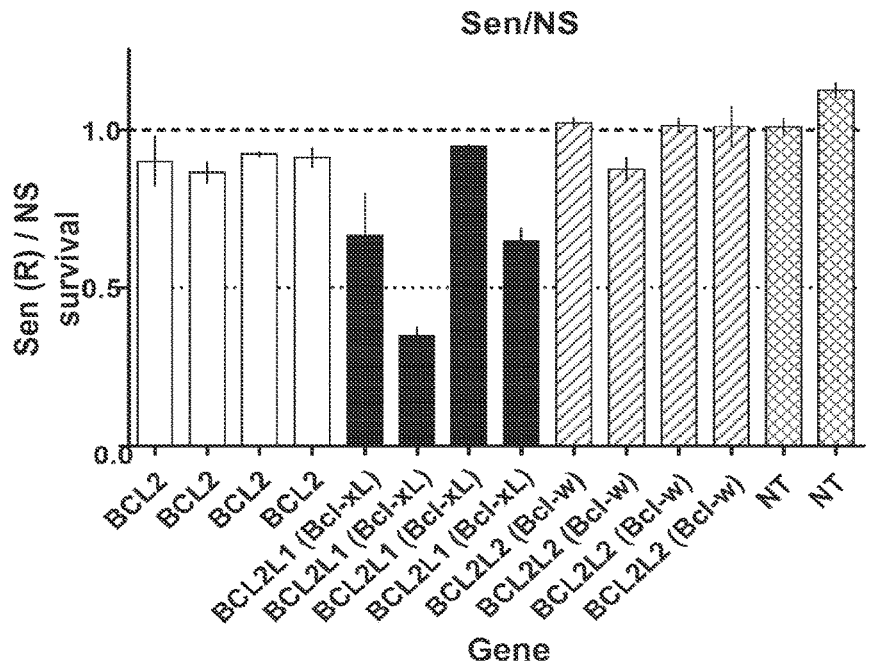
FIG. 32 shows the effect of specific shRNA molecules on survival of senescent cells. Senescent cells and non-senescent IMR90 cells were transduced with lentiviral vectors comprising shRNA molecules specific for each of BCL-2, BCL-xL, and BCL-w encoding polynucleotides. The ratio of senescent cell survival to non-senescent cell survival for each shRNA is shown. Each bar represents the average of triplicates. The shRNA sequences introduced into the cells are as follows from left to right: BCL-2: SEQ ID NO:1, 3, 3, 5; BCL-XL: SEQ ID NO: 7, 9, 11, 13; BCL-w: SEQ ID NO:15, 17, 19, 21; two non-transduced (NT) samples.

Survival of senescent cells and non-senescent cells was then determined in triplicate for each shRNA tested. The shRNAs as listed in order in the table are represented in the figure from left to right. The second and third shRNA sequences specific for BCL-2 are identical. The ratio of senescent cell survival to non-senescent cell survival is presented for each shRNA in FIG. 32. A ratio of 1.0 indicates no difference in the proportion of survival of senescent cells compared with non-senescent cells. Introduction of three of the four BCL-XL specific shRNA molecules into senescent cells resulted in significant senescent cell death compared with senescent cells into which Bcl-w or BCL-2 specific shRNAs were introduced. The data illustrate that BCL-XL expression is important to survival of senescent cells.

Example 19

Effective Killing of Senescent Cells by Inhibiting BCL-2 Anti-Apoptotic Protein Family Members To determine whether other Bcl-2/Bcl-xL/Bcl-w inhibitors are selectively toxic to senescent cells compared to non-senescent cells, a cell viability assay was used to assess cell survival following treatment with ABT-737. The general timelines and procedures for the cell counting assay are shown in FIG. 18 and described in Example 7. IMR90 cells (human primary lung fibroblasts) were seeded in six well plates, and cells were induced to senescence with 10 Gy of ionizing radiation (IR) (Day 0). The media was refreshed every 3 days. The senescent phenotype is allowed to develop for 7 days at which point a cell count was made to determine the baseline number of cells followed by seeding into 96-well plates. On day 8, the senescent cells (irradiated) and the non-senescent cells (the non-radiated cells), were exposed to serial dilutions of ABT-737 for a period of 3 days. ABT-737 concentrations were serially diluted starting at 50 µM. Each condition was seeded in triplicate.

After three days of treatment (Day 11), cells were assayed for cell survival using CellTiter-Glo® (CTG) Luminescent Cell Viability Assay. The assay determines the number of viable cells in culture based on the quantitation of ATP present, which is an indicator of metabolically active cells.

Figure 33:
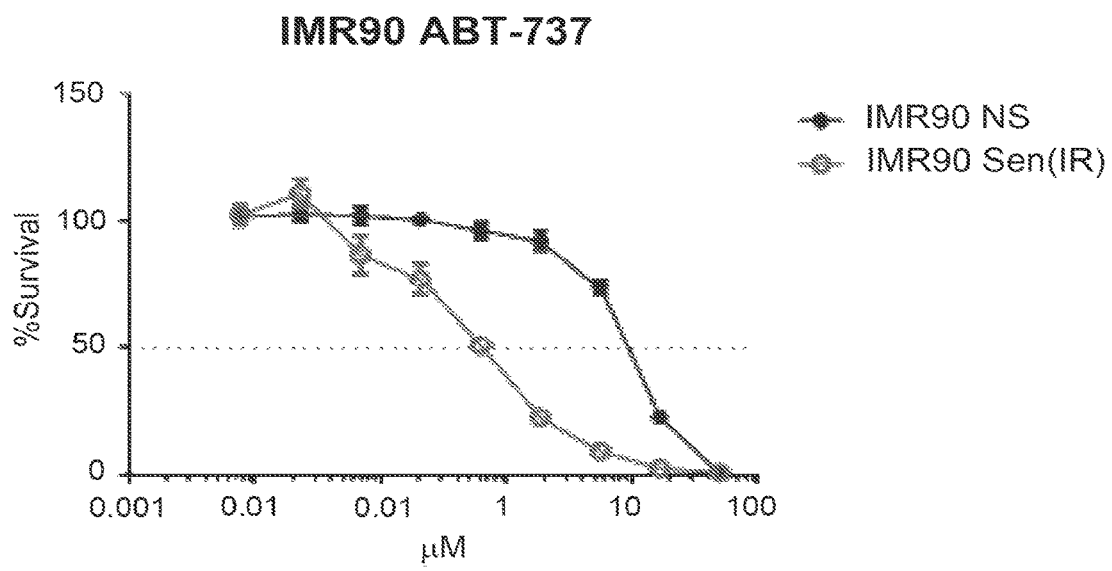
FIG. 33 illustrates the effect of ABT-737 on viability of non-senescent lung fibroblast cells (IMR90) (IMR90 NS) and senescent lung fibroblast cells (IMR90) (IMR90 Sen (IR)).

FIG. 33 shows IC50 curves of ABT-737 in senescent cells and in non-senescent cells. The IC50 curve is a plot of the percentage of cell survival following treatment of ABT-737 as determined by the cell viability assay. The plot shows the effect of the various concentration levels of ABT-737 on cell survival.

Example 20

BCL-2/BCL-xL/BCL-w Inhibitor Kills Senescent Cells Via Apoptosis

Figure 34:
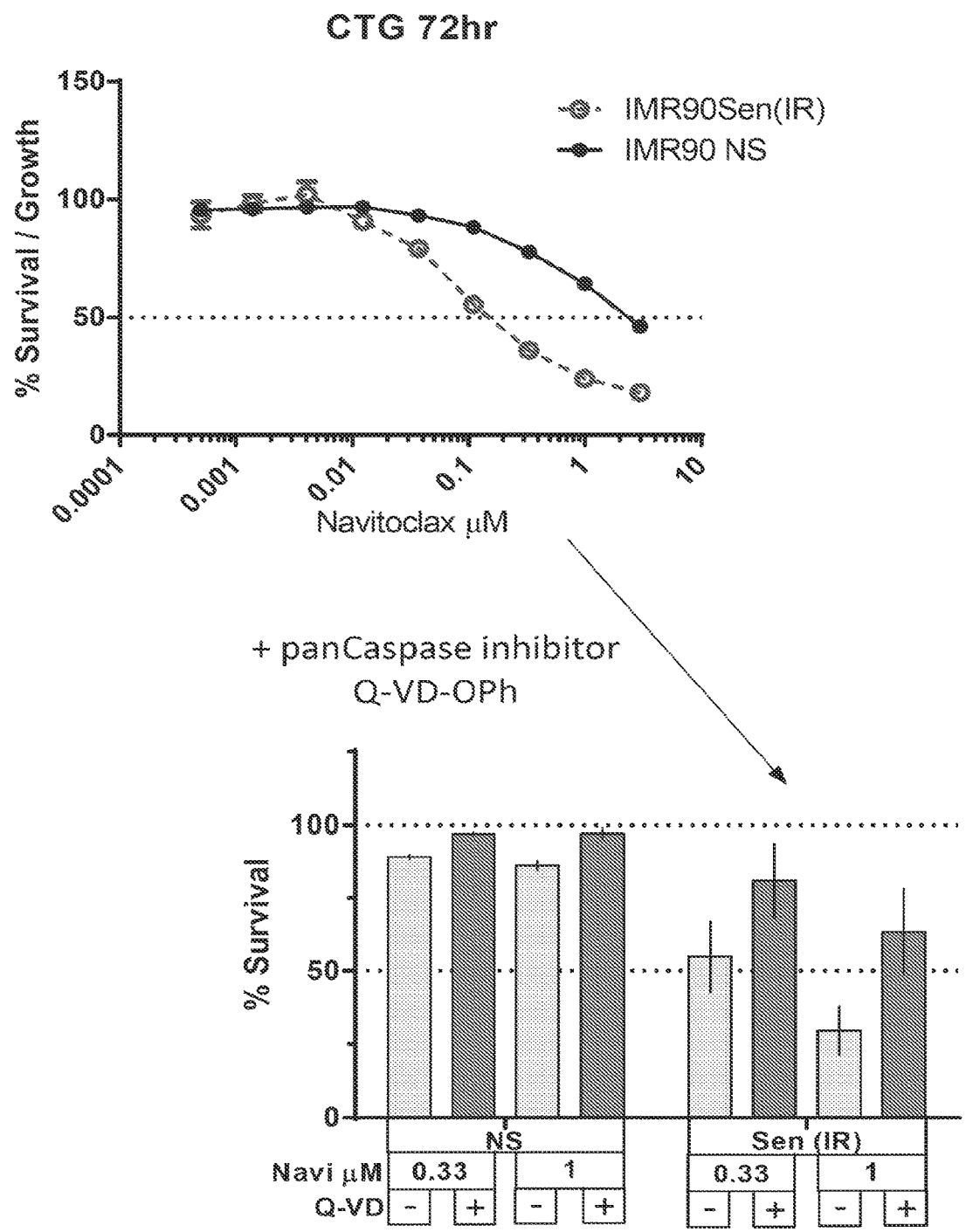
FIG. 34 illustrates that in the presence of a caspase inhibitor (panCaspase inhibitor, Q-VD-OPh) the senolytic activity of ABT-263 is inhibited. The top left side of FIG. 34 illustrates the effect of ABT-263 on killing senescent cells (IMR90 Sen(IR)). Non-senescent cells (NS) and senescent cells (Sen (IR)) were exposed to ABT-263 at concentrations of 0.33 µM and 1 µM in the presence or absence of the pan-Caspase inhibitor, Q-VC-OPh. The percent survival of non-senescent cells and senescent cells in the presence and absence of the pan-Caspase inhibitor (Q-VD in the figure) is illustrated in the FIG. 34 on the bottom right.

An experiment as described in Example 17 was performed to determine whether other inhibitors of one or more BCL-2 anti-apoptotic family members kill senescent cells by apoptosis. Lung fibroblast cell line IMR90 (human primary lung fibroblasts, ATCC® CCL-186™, Manassas, Va.) were seeded in six-well plates and induced to senesce with 10 Gy of ionizing radiation (IR) as described in Example 12. After senescence was established, cells were re-seeded into 96 well plates. The pan-caspase inhibitor Q-VD-OPh (20 µM) was added to wells of senescent cells (irradiated) (IMR90 Sen(IR)) and to wells containing non-senescent cells (the non-radiated cells) (IMR90 NS). Four hours later, the senescent and non-senescent cells were each exposed for a period of 3 days to 0.33 or 1 µM ABT-263 (Navitoclax). At the end of the assay time period, cells were counted. Each condition was seeded in three plate wells and counted independently. Initial cell count served as a control to determine the induction of senescence, as compared to the last day count without ABT-263 treatment. Initial non-senescent cell count serves as a proxy to determine ABT-263 toxicity. Cell survival was determined using CellTiter-Glo® Luminescent Cell Viability Assay (Promega Corporation, Madison, Wis.). The assay determines the number of viable cells in culture based on the quantitation of ATP present which is an indicator of metabolically active cells. FIG. 34 (top graphic) is an illustration that ABT-263 selectively kills senescent cells and illustrates the ABT-263 concentrations used in this experiment. In the presence of the pan-caspase inhibitor, the percent of surviving senescent cells increased (FIG. 34, lower graphic).

Example 21

Effect of Removal of Senescent Cells in Animal Model of Osteoarthritis

Figure 36:
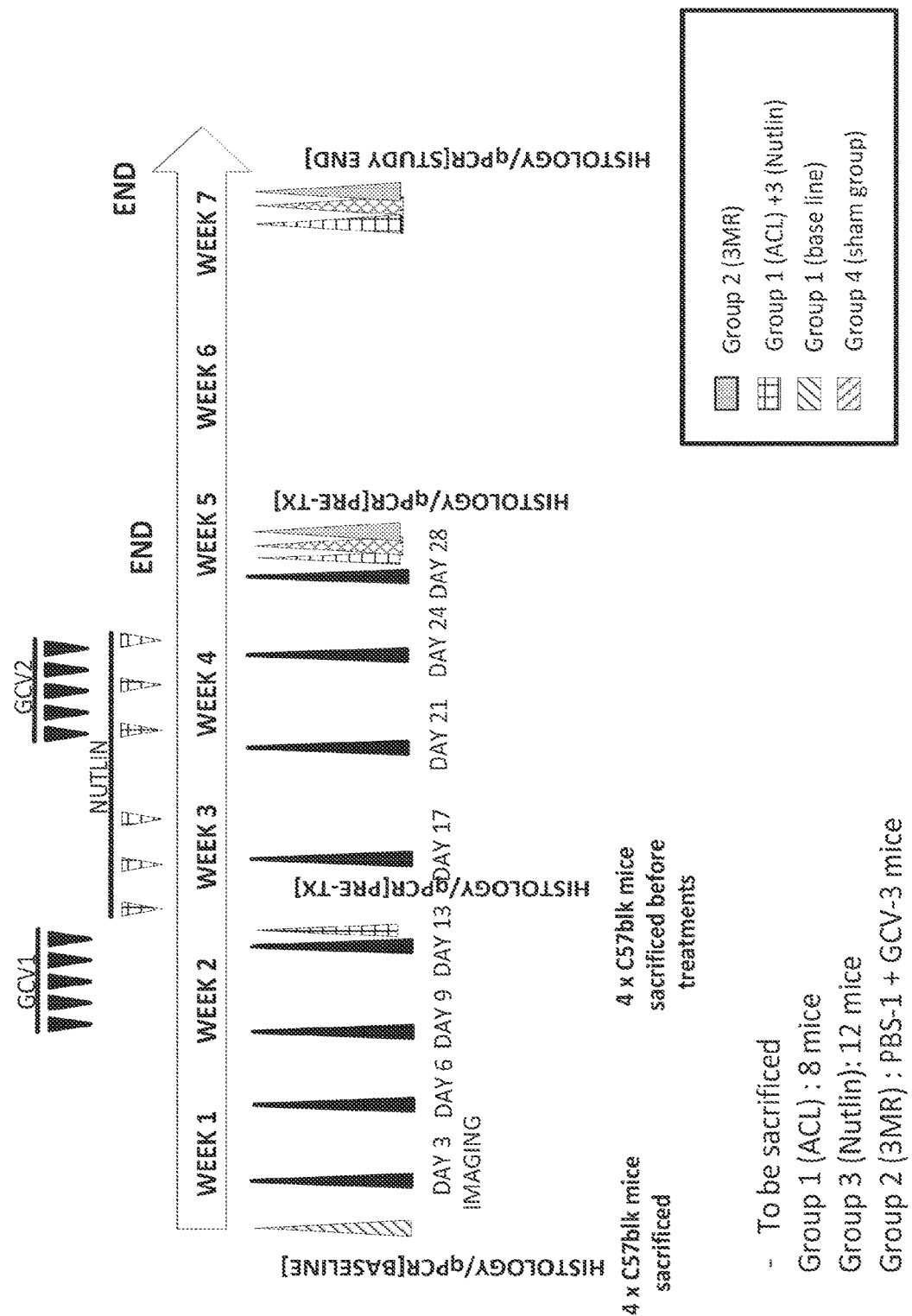
FIG. 36 depicts a timeline for the animal study designs described in FIG. 35.

A table and schematic of two osteoarthritis mouse model study designs are presented in FIGS. 35 and 36, respectively. The two treatment studies were designed to determine the effect of removing senescent cells in an animal model of osteoarthritis.

Parallel studies were performed. One study investigated the effect of eliminating senescent cells with ganciclovir (GCV) in 3MR mice. Mice underwent surgery to cut the anterior cruciate ligament of one rear limb to induce osteoarthritis in the joint of that limb. During week 2 post-surgery, 3MR mice received 2.5 µg GCV to the operated knee by intra-articular injection, qd for 5 days, with a $2^{nd}$ treatment (2.5 µg GCV qd for 5 days) during week 4 post-surgery. At the end of 4 weeks post-surgery, operated joints of the mice were monitored for presence of senescent cells, assessed for function, monitored for markers of inflammation, and underwent histological assessment.

In a parallel study, C57BL/6J mice underwent surgery to cut the anterior cruciate ligament of one rear limb to induce osteoarthritis in the joint of that limb. During week 3 and week 4 post-surgery, the mice were treated with 5.8 µg of Nutlin-3A (n=7) per operated knee by intra-articular injection, qod for 2 weeks. At the end of 4 weeks post-surgery, joints of the mice were monitored for presence of senescent cells, assessed for function, monitored for markers of inflammation, and underwent histological assessment.

Two control groups of mice were included in the studies performed: one group comprising C57BL/6J or 3MR mice that had undergone a sham surgery (n=3) (i.e., surgical procedures followed except for cutting the ACL) and intra-articular injections of vehicle parallel to the GCV-treated group; and one group comprising C57BL/6J or 3MR mice that had undergone an ACL surgery and received intra-articular injections of vehicle (n=5) parallel to the GCV-treated group.

Figure 37C:
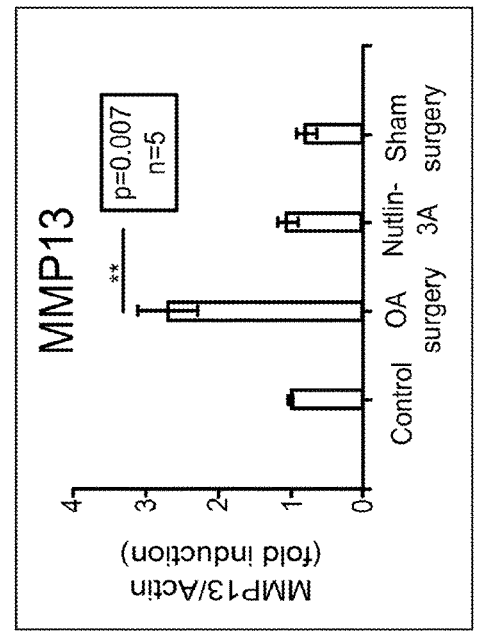
FIGS. 37A-C illustrate the level of senescence associated proteins (p16) and SASP factors (IL-6 and MMP13) expressed by cells from joints of mice that had osteoarthritis surgery (OA surgery), joints of mice that had OA surgery and received Nutlin-3A treatment (Nutlin-3A), joints that received sham surgery, and joints of control mice that did not receive any surgery (control). Quantitative PCR was performed, and the levels of p16 (FIG. 37A); IL-6 (FIG. 37B); and MMP13 (FIG. 37C) expression were detected in cells extracted from the joints of mice with OA surgery, mice with OA surgery and Nutlin-3A treatment, sham surgery, and control (no surgery). The data are presented relative to expression of actin. The data shows that Nutlin-3A treatment clears senescent cells from the joint.
Figure 37A:
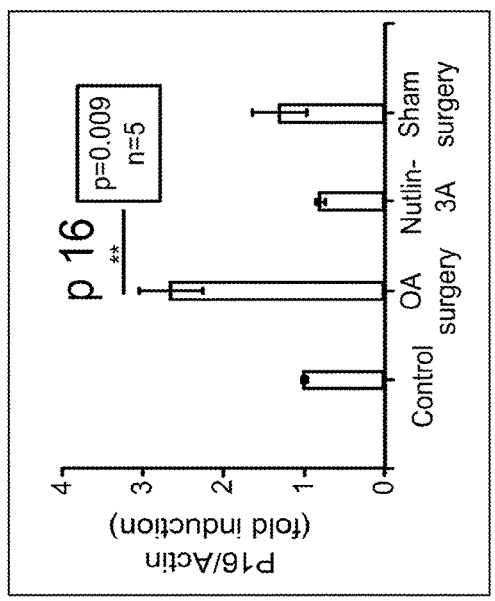
Figure 37B:
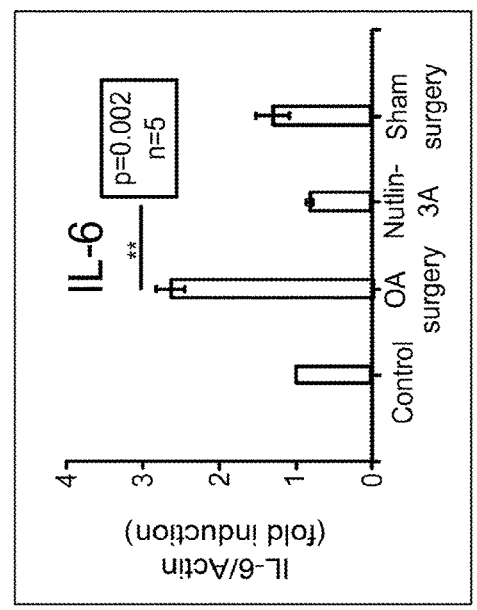
Figure 38:
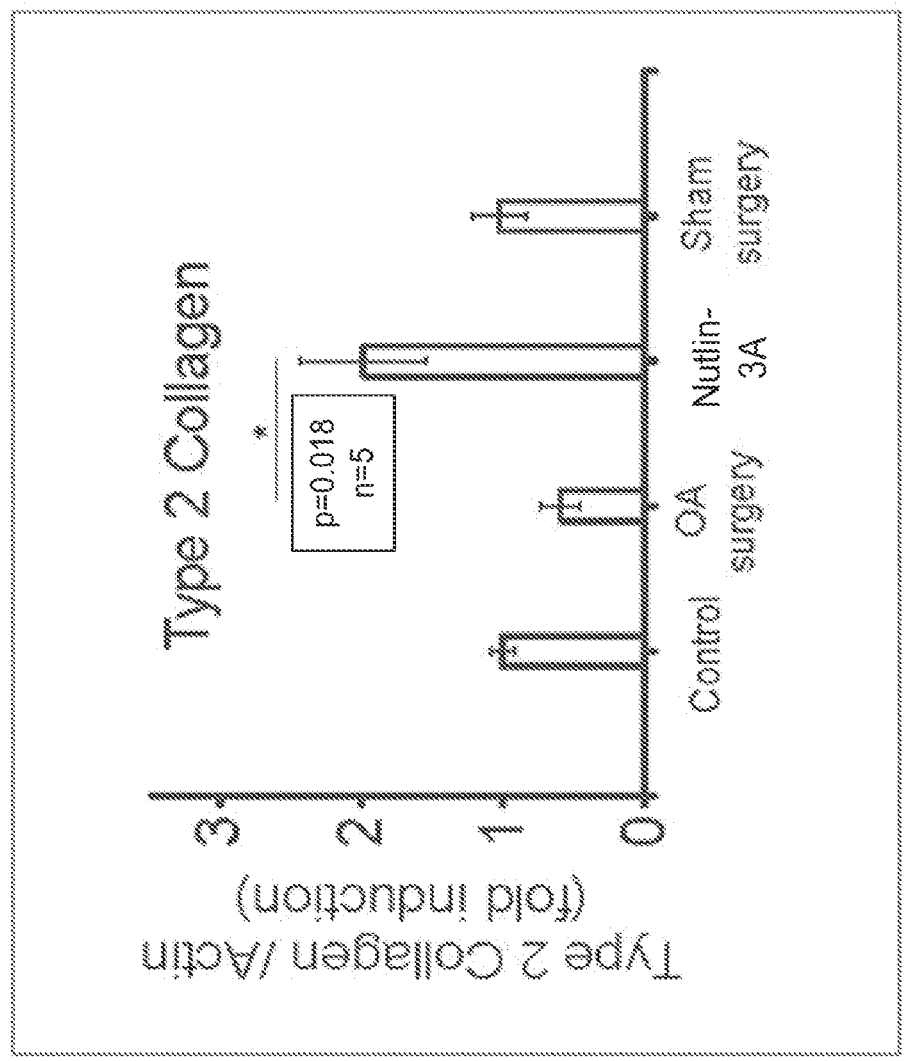
FIG. 38 illustrates the level of type 2 collagen expressed by cells from joints of mice that had osteoarthritis surgery (OA surgery), joints of mice that had OA surgery and received Nutlin-3A treatment (Nutlin-3A), joints that received sham surgery, and joints of control mice that did not receive any surgery. Quantitative PCR was performed, and the levels of type 2 collagen was detected in cells extracted from the joints of mice with OA surgery, mice with OA surgery and Nutlin-3A treatment, sham surgery, and control (no surgery). The data are presented relative to expression of actin. The data shows that Nutlin-3A treatment drives ab initio collagen production in OA joints.

RNA from the operated joints of mice from the Nutlin-3A treated mice was analyzed for expression of SASP factors (mmp3, IL-6) and senescence markers (p16). qRT-PCR was performed to detect mRNA levels. As shown in FIGS. 37A-C, treatment with Nutlin-3A clears senescent cells from the joint. RNA from the operated joints of mice was also analyzed for expression of type 2 collagen and compared with expression of actin as a control. As shown in FIG. 38, treatment with Nutlin-3A in mice that have undergone osteoarthritis surgery drives collagen production as compared to untreated mice.

Figure 39:
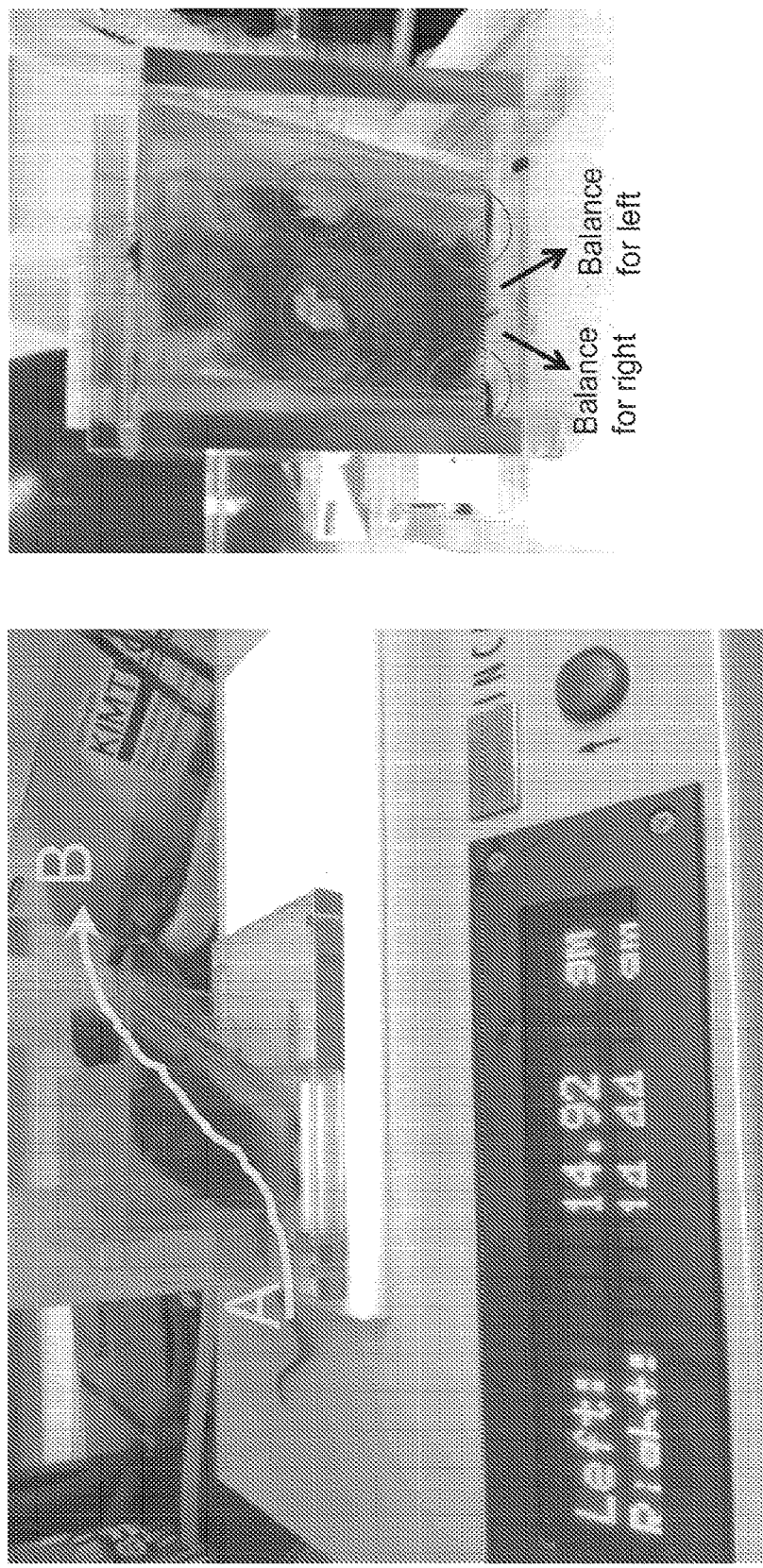
FIG. 39 illustrates incapacitance measurements 4 weeks after osteoarthritis surgery as measured by a weight bearing test to detect which leg mice favored. The mice were placed in a chamber, standing with 1 hind paw on each scale. The weight that was placed on each hind limb was then measured over a 3-second period. At least 3 separate measurements were made for each animal at each time point, and the result was expressed as the percentage of the weight placed on the operated limb/the contralateral unoperated limb.
Figure 40:
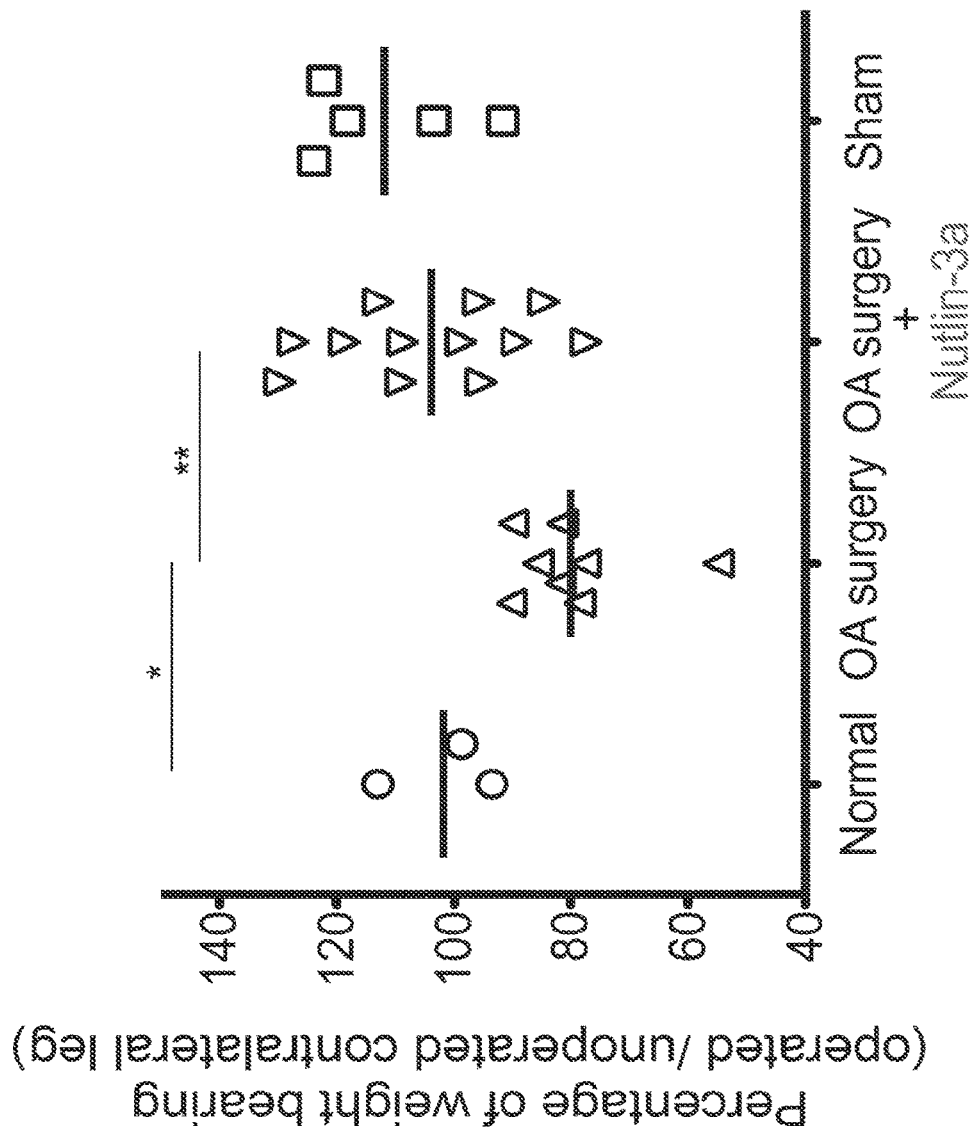
FIG. 40 depicts the results of the weight bearing test shown in FIG. 39. Osteoarthritis causes mice to favor the unoperated leg over the operated leg (Δ). Clearing senescent with Nutlin-3A abrogates this effect (∇).

Function of the limbs was assessed 4 weeks post-surgery by a weight bearing test to determine which leg the mice favored (FIG. 39). The mice were allowed to acclimate to the chamber on at least 3 occasions prior to taking measurements. Mice were maneuvered inside the chamber to stand with 1 hind paw on each scale. The weight that was placed on each hind limb was measured over a 3-second period. At least 3 separate measurements were made for each animal at each time point. The results were expressed as the percentage of the weight placed on the operated limb versus the contralateral unoperated limb. As shown in FIG. 40, untreated mice that have undergone osteoarthritis surgery favor the unoperated hind limb over the operated hind limb (Δ). However, clearing senescent cells with Nutlin-3A abrogates this effect in mice that have undergone surgery (∇).

Figure 41:
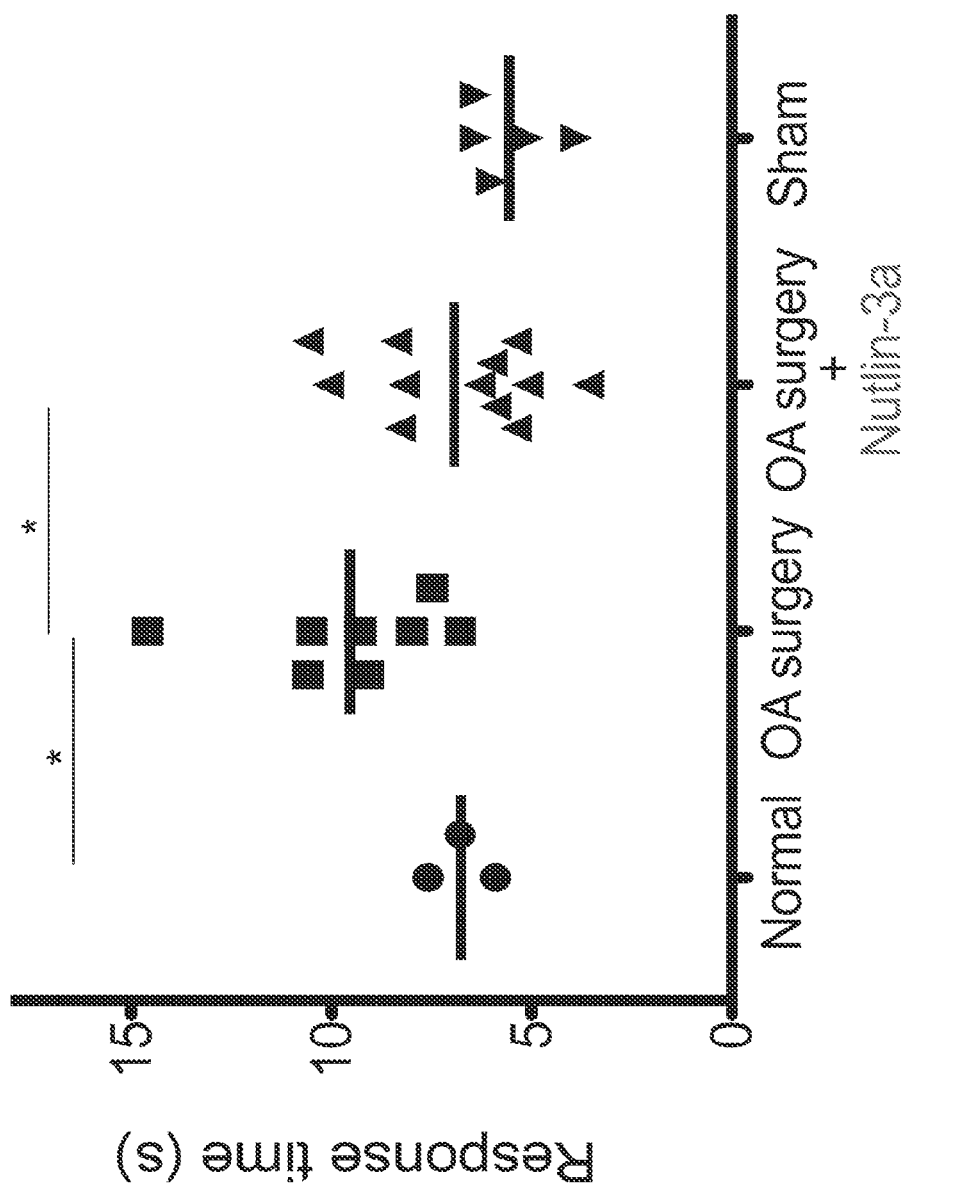
FIG. 41 depicts the results of a hotplate analysis to provide an assessment of sensitivity and reaction to pain stimulus. Paw-lick response time for the operated hind limb (measured in seconds) due to attainment of pain threshold after placement onto a 55° C. platform was measured 4 weeks after osteoarthritis (OA) surgery. The data shows that Nutlin-3A treatment reduces response time in OA surgery mice (▲) as compared to untreated OA surgery mice (■).

The function of the limbs was also assessed at 4 weeks post-surgery by hotplate analysis to show sensitivity and reaction to pain stimulus. In brief, a mouse was placed on a hotplate at 55° C. When placed on the hot surface of the plate, mice will lift their paws and lick them (paw-lick response) due to attainment of pain threshold. The latency period for the hind limb response (paw-lick response) is recorded as response time. As shown in FIG. 41, untreated mice that have undergone osteoarthritis surgery have an increased response time as compared to normal mice that have not been surgically altered (■). However, treatment of mice that have undergone osteoarthritis surgery with Nutlin-3A decreases the response time in a significant manner (▲).

Histopathology of osteoarthritis induced by ACL surgery illustrated that the proteoglycan layer was destroyed. Clearing of senescent cells with Nutlin-3A completely abrogated this effect. Clearing of senescent cells from the 3MR mice treated with GCV, which kills senescent cells, had the same impact on pathophysiology of osteoarthritis as Nutlin-3A. See FIG. 42.

Example 22

Effect of Removal of Senescent Cells in Animal Models of Atherosclerosis

Schematics of two atherosclerosis mouse models are presented in FIGS. 43A-B. The study illustrated in FIG. 43A assessed the extent to which clearance of senescent cells from plaques in LDLR$^{-/-}$ mice with Nutlin-3A reduces plaque load. Two groups of LDLR$^{-/-}$ mice (10 weeks) are fed a high fat diet (HFD) (Harlan Teklad TD.88137) having 42% calories from fat, beginning at Week 0 and throughout the study. Two groups of LDLR$^{-/-}$ mice (10 weeks) are fed normal chow (–HFD). From weeks 0-2, one group of HFD mice and –HFD mice are treated with Nutlin-3A (25 mg/kg, intraperitoneally). One treatment cycle is 14 days treatment, 14 days off. Vehicle is administered to one group of HFD mice and one group of –HFD mice. At week 4 (timepoint 1), one group of mice are sacrificed and to assess presence of senescent cells in the plaques. For the some of the remaining mice, Nutlin-3A and vehicle administration is repeated from weeks 4-6. At week 8 (timepoint 2), the mice are sacrificed and to assess presence of senescent cells in the plaques. The remaining mice are treated with Nutlin-3A or vehicle from weeks 8-10. At week 12 (timepoint 3), the mice are sacrificed and to assess the level of plaque and the number of senescent cells in the plaques.

Plasma lipid levels were measured in LDLR$^{-/-}$ mice fed a HFD and treated with Nutlin-3A or vehicle at timepoint 1 as compared with mice fed a –HFD (n=3 per group). Plasma was collected mid-afternoon and analyzed for circulating lipids and lipoproteins. The data are shown in FIG. 44A-D.

At the end of timepoint 1, LDLR$^{-/-}$ mice fed a HFD and treated with Nutlin-3A or vehicle were sacrificed (n=3, all groups), and the aortic arches were dissected for RT-PCR analysis of SASP factors and senescent cell markers. Values were normalized to GAPDH and expressed as fold-change versus age-matched, vehicle-treated LDLR$^{-/-}$ mice on a normal diet. The data show that clearance of senescent cells with Nutlin-3A in LDLR$^{-/-}$ mice fed a HFD reduced expression of several SASP factors and senescent cell markers, MMP3, MMP13, PAI1, p21, IGFBP2, IL-1A, and IL-1B after 1 treatment cycle (see FIGS. 45A-D).

At the end of timepoint 2, LDLR$^{-/-}$ mice fed a HFD and treated with Nutlin-3A or vehicle (n=3 for all groups) were sacrificed, and aortic arches were dissected for RT-PCR analysis of SASP factors and senescent cell markers. Values were normalized to GAPDH and expressed as fold-change versus age-matched, vehicle-treated LDLR$^{-/-}$ mice on a normal diet. The data show expression of some SASP factors and senescent cell markers in the aortic arch within HFD mice (FIGS. 46A-C). Clearance of senescent cells with multiple treatment cycles of Nutlin-3A in LDLR$^{-/-}$ mice fed a HFD reduced expression of most markers (FIGS. 46A-B).

At the end of timepoint 3, LDLR$^{-/-}$ mice fed a HFD and treated with Nutlin-3A or vehicle (n=3 for all groups) were sacrificed, and aortas were dissected and stained with Sudan IV to detect the presence of lipid. Body composition of the mice was analyzed by MRI, and circulating blood cells were counted by Hemavet. The data show that treatment with Nutlin-3A reduces plaques in the descending aorta by ~45% (FIGS. 47A-C). As shown in FIGS. 48A-B, the platelet and lymphocyte counts were equivalent between the Nutlin-3A and vehicle treated mice. As shown in FIGS. 49A-B, treatment with Nutlin-3A also decreased mass and body fat composition in mice fed a HFD.

The study illustrated in FIG. 43B assessed the extent to which acyclovir based clearance of senescent cells from LDLR$^{-/-}$/3MR double transgenic mice improves pre-existing atherogenic disease. LDLR$^{-/-}$/3MR double transgenic mice (10 weeks) and LDLR$^{-/-}$ single transgenic mice (10 weeks) are fed a high fat diet beginning at Week 0 until Week 12. Gancyclovir is administered to both groups of mice (25 mg/kg intraperitoneally) from weeks 12-13 and weeks 14-15. At week 16, the level of plaque and the number of senescent cells in the plaques are determined. As shown in FIG. 50, clearance of senescent cells with GCV in LDLR$^{-/-}$/3MR double transgenic mice fed a HFD (n=10) reduces the % of the aorta covered with plaque as compared to LDLR$^{-/-}$ mice/HFD controls (n=9). As shown in FIG. 51, clearance of senescent cells with GCV also reduced the plaque cross-sectional area in LDLR$^{-/-}$/3MR double transgenic mice fed a HFD (n=3) as compared to LDLR$^{-/-}$ mice/HFD controls (n=5).

Example 23

Senescent Cell Clearance Sustains Cardiac Stress Resistance with Aging

To study the impact of senescent cell clearance on health and lifespan, cohorts of INK-ATTAC transgenic mice on FVB×129Sv/E×C57BL/6 mixed or C57BL/6 pure genetic backgrounds were established. At 12 months age, one half of each cohort was injected three times/week with AP20187 to induce apoptosis of p16-positive senescent cells (0.2 mg/kg and 2 mg/kg AP20187 for the mixed and the pure C57BL/6 cohorts, respectively), while the other half of each cohort received vehicle. At 18 months, subsets of male and female mice from each cohort were subjected to a cardiac stress test, in which mice were injected with a lethal dose of isoproterenol (680 mg/kg) and the time to cardiac arrest was recorded. While 18-month-old untreated (vehicle) mice consistently showed a marked acceleration of cardiac arrest compared to 12-month-old control mice, AP20187-treated mice sustained youthful cardio-protection against isoproterenol, regardless of gender and genetic background (see FIG. 52).

Cardio-protective signaling pathways are known to provide tolerance to metabolic stresses such as ischemia and hypoxia decline (Granfeldt et al., 2009, *Cardiovasc. Res.* 83:234-246). However, cardio-protective signaling deteriorates with aging, thus decreasing the functional and adaptive reserve capacity of the heart (Ogawa et al., 1992, *Circulation* 86:494-503; Wiebe et al., 1998, *Clin. J. Sport Med.* 8:272-279). ATP-dependent K channels (KATP) play a central role in cardio-protective signaling (Gross and Auchampach, 1992, *Cardiovasc. Res.* 26:1011-1016). These KATP channels are composed of the pore-forming subunit Kir6.2/Kir6.1, the regulatory subunit Sur2a, and additional accessory proteins. KATP channels are thought to decline with aging due to decreased expression of Sur2a (Du et al., 2006, *FASEB J.* 20:1131-1141; Jovanovic and Jovanovic, 2009, *Curr. Opin. Pharmacol.* 9:189-193; Ranki et al., 2002, *Mech. Ageing Dev.* 123:695-705). Elevated expression of Sur2a, either through diet alteration (Sukhodub et al., 2011, *J. Cell. Mol. Med.* 15:1703-1712) or transgenic approaches (Sudhir et al., 2011, *Biogerentology* 12:147-155), has been shown to sustain cardiac stress resistance in aged mice. Thus, the contribution of senescent cells to the age-related decline in Sur2a expression was examined in 18 month old AP20187-treated and vehicle treated mice from subjected to the cardiac stress test previously described. Indeed, youthful performance in the isoproterenol stress test of 18-month-old female AP20187-treated animals consistently correlated with sustained Sur2a expression (see FIG. 53). Taken together, these experiments indicate that the presence of senescent cells with aging negatively impacts KATP channel function, and senescent cell clearance is an effective therapy to counteract this deterioration. Sustained cardiac performance could contribute to the median lifespan extension observed in AP20187-treated INK-ATTAC mice.

Example 24

Clearance of Senescent Cells Ameliorates Atherosclerosis in LDLR$^{-/-}$/3MR Mice The impact of clearance of senescent cells on the stability and size of mature atherosclerotic plaques was studied in LDLR$^{-/-}$/3MR double transgenic mice. From 10 weeks of age, LDLR$^{-/-}$/3MR double transgenic mice (10 weeks) and LDLR$^{-/-}$ single transgenic mice (control) were fed a high fat diet (Harlan Teklad TD.88137) having 42% calories from fat beginning at Week 0 until Week 12.5, when the mice were switched to normal chow diet. Both groups of mice were treated with ganciclovir from week 12.5 over the next 100 days, with each treatment cycle comprising 5 days of ganciclovir (25 mg/kg intraperitoneally daily) and 14 days off. At the end of the 100 day treatment period, the mice were sacrificed, plasma and tissues were collected, and atherosclerosis was quantitated.

Descending aortas were dissected and stained with Sudan IV to visualize the plaque lipids. As shown in FIGS. 54A-B, ganciclovir-treated LDLR$^{-/-}$/3MR double transgenic mice had fewer atherosclerotic plaques with less intense staining than the LDLR$^{-/-}$ control mice fed a HFD. The % of the aorta covered in plaques as measured by area of Sudan IV staining was also significantly lower in the ganciclovir-treated LDLR$^{-/-}$/3MR mice as compared to the LDLR$^{-/-}$ control mice (see FIG. 54C).

Plaques from ganciclovir-treated LDLR$^{-/-}$ control and LDLR$^{-/-}$/3MR mice (see dashed circled plaques in FIGS. 55A-B, respectively) were harvested and cut into cross-sections and stained with to characterize the general architecture of the atherosclerotic plaques. "#" indicates fat located on the outside of the aorta (see FIG. 55A). The plaques marked with an "*" and "**" in FIGS. 55A and B, respectively, are shown as stained cross-sections in FIGS. 55B and D, respectively. As illustrated in FIGS. 55B and D, clearance of senescent cells in ganciclovir-treated LDLR$^{-/-}$/3MR mice has an effect on plaque morphology as compared to LDLR$^{-/-}$ control mice. The plaque from the control mice has identifiable "lipid pockets" accumulating within. The plaque from the ganciclovir treated LDLR$^{-/-}$/3MR mice shows the presence of a thick fibrin cap and the absence of lipid pockets. Disruption or tear in the cap of a lipid-rich plaque is a trigger for coronary events through exposure of plaque thrombogenic components to platelets and clotting components of the blood. Plaques that grow more rapidly as a result of rapid lipid deposition and have thin fibrin caps are prone to rupture. Slowly growing plaques with mature fibrin caps tend to stabilize and are not prone to rupture. Taken together, these experiments indicate that removal of senescent cells may affect atherosclerotic plaque architecture and have a stabilizing effect.

Tissue sections of atherosclerotic aortas were prepared and stained to detect SA-$\beta$-GAL. X-GAL crystals were located in the lysosomes of lipid-bearing macrophage foam cells and smooth muscle foam cells (see FIGS. 56-58).

Example 25

Effect of Clearance of Senescent Cells in Pulmonary Disease Models

One animal model study assessed the effect of clearance of senescence cells in the transgenic mouse strain 3MR that has bleomycin induced lung injury. In the bleomycin injury model for idiopathic pulmonary fibrosis, mice develop lung fibrosis within 7-14 days after bleomycin treatment (see, e.g., Limjunyawong et al., 2014, *Physiological Reports* 2:e00249; Daniels et al., 2004, *J. Clin. Invest.* 114:1308-1316). Bleomycin was administered to anesthetized 6-8 week old 3MR mice by intratracheal aspiration (2.5 U/kg of bleomycin in 50 µl PBS) using a microsprayer syringe (Penn-Century, Inc.) as described in Daniels et al. (2004, *J. Clin. Invest.* 114:1308-1316). Control mice were administered saline. The day following bleomycin treatment, ganciclovir (GCV) (25 mg/kg in PBS) was administered. 3MR mice were treated via intraperitoneal injection with ganciclovir for 5 consecutive days, followed by 5 days of rest, followed by a second treatment cycle of 5 consecutive days. Untreated mice received an equal volume of vehicle. At 7, 14, and 21 days post-bleomycin treatment, lung function was assessed by monitoring oxygen saturation using the MouseSTAT PhysioSuite pulse oximeter (Kent Scientific). Animals were anesthetized with isoflurane (1.5%) and a toe clip was applied. Mice were monitored for 30 seconds and the average peripheral capillary oxygen saturation (SpO$_2$) measurement over this duration was calculated. As shown in FIG. 59, bleomycin administration significantly reduced $SpO_2$ levels in vehicle treated mice, and removal of senescent cells resulted in higher $SpO_2$ levels, which approached normal levels at 21 days post bleomycin administration. At 21 days post-bleomycin treatment, airway hyper-reactivity (AHR) of mice was examined. AHR of mice was measured by methacholine challenge while other parameters of lung function (airway mechanics, lung volume and lung compliance) were determined using a SCIREQ flexiVent ventilator. While under ketamine/xylazine anesthesia and subjected to cannulation of the trachea via a tracheostomy (19 Fr blunt Luer cannula), airway resistance (elastance) and compliance of mice were assessed at baseline and in response to increasing concentrations of methacholine (0 to 50 mg/ml in PBS) delivered via nebulization (AeroNeb) as described in Aravamudan et al. (*Am. J. Physiol. Lung Cell. Mol. Physiol.* (2012) 303:L669-L681). Animals were maintained at 37° C., and while under muscle paralysis (pancuronium); airway function was measured by using the FlexiVent™ ventilator and lung mechanics system (SCIREQ, Montreal, Quebec, Canada), which was housed on Stabile 8. As shown in FIG. 60A, in vehicle treated mice, bleomycin administration increased lung elastance, whereas ganciclovir treatment reduced lung elastance. As shown in FIGS. 60B-C, bleomycin administration reduced static compliance and (dynamic) compliance in vehicle treated mice. Clearance of senescent cells with ganciclovir in bleomycin exposed mice improved compliance values significantly (FIGS. 60B-C). Although not statistically significant because the animal group size was too small, data suggested that clearance of senescent cells with a senolytic agent (Nutlin-3A) also reduced lung elastance and increased lung compliance in a bleomycin exposed mouse. Mice were euthanized by i.p injection of pentobarbital. Bronchoalveolar lavage (BAL) fluids and lungs is obtained and analyzed. Hydroxyproline content of lungs is measured as described in Christensen et al. (1999, *Am. J. Pathol.* 155:1773-1779), and quantitative histopathology is performed. RNA is extracted from lung tissue to measure senescence cell markers by qRT-PCR in treated and control mice.

The effect of clearance of senescence cells in the bleomycin induced lung injury model of IPF may also be studied in INK-ATTAC transgenic mice in the study design described above. INK-ATTAC (p16$^{Ink4a}$ apoptosis through targeted activation of caspase) transgenic mice have an FK506-binding protein (FKBP)-caspase 8 (Casp8) fusion polypeptide under the control of the p16$^{Ink4a}$ promoter (see, e.g., Baker et al., *Nature*, supra; Int'l Patent Application Publication No. WO/2012/177927). In the presence of AP20187, a synthetic drug that induces dimerization of a membrane bound myristoylated FKBP-Casp8 fusion protein, senescent cells specifically expressing the FKBP-Casp8 fusion protein via the p16$^{Ink4a}$ promoter undergo programmed cell death (apoptosis) (see, e.g., Baker, *Nature*, supra, FIG. 1 therein).

A second study also assesses the effect of clearance of senescence cells using a senolytic agent in C57BL6/J mice that have bleomycin induced lung injury. Bleomycin is administered to 6 week old C57BL6/J mice as described above. A senolytic agent is administered during the first and third week post-bleomycin treatment. Control mice are treated with vehicle. At 21 days post-bleomycin treatment, clearance of senescent cells and lung function/histopathology is assessed.

In a second animal model for pulmonary diseases (e.g., COPD), mice were exposed to cigarette smoke. The effect of a senolytic agent on the mice exposed to smoke is assessed by senescent cell clearance, lung function, and histopathology.

Six week-old 3MR (n=35) or INK-ATTAC (n=35) mice were chronically exposed to cigarette smoke generated from a Teague TE-10 system, an automatically-controlled cigarette smoking machine that produces a combination of side-stream and mainstream cigarette smoke in a chamber, which is transported to a collecting and mixing chamber where varying amounts of air is mixed with the smoke mixture. The COPD protocol was adapted from the COPD core facility at Johns Hopkins University (at Internet site web.jhu.edu/Biswal/exposure_core/copd.html#Cigarette_Smoke) (Rangasamy et al., 2004, *J. Clin. Invest.* 114:1248-1259; Yao et al., 2012, *J. Clin. Invest.* 122:2032-2045). Mice received a total of 6 hours of cigarette smoke exposure per day, 5 days a week for 6 months. Each lighted cigarette (3R4F research cigarettes containing 10.9 mg of total particulate matter (TPM), 9.4 mg of tar, and 0.726 mg of nicotine, and 11.9 mg carbon monoxide per cigarette [University of Kentucky, Lexington, Ky.]) was puffed for 2 seconds and once every minute for a total of 8 puffs, with the flow rate of 1.05 L/min, to provide a standard puff of 35 $cm^3$. The smoke machine was adjusted to produce a mixture of side stream smoke (89%) and mainstream smoke (11%) by smoldering 2 cigarettes at one time. The smoke chamber atmosphere was monitored for total suspended particulates (80-120 mg/$m^3$) and carbon monoxide (350 ppm). Beginning at day 7, (10) INK-ATTAC and (10) 3MR mice were treated with AP20187 (3× per week) or gancyclovir (5 consecutive days of treatment followed by 16 days off drug, repeated until the end of the experiment), respectively. An equal number of mice received the corresponding vehicle. The remaining 30 mice (15 INK-ATTAC and 15 3MR) were evenly split with 5 of each genetically modified strain placed into three different treatment groups. One group (n=10) received Nutlin-3A (25 mg/kg dissolved in 10% DMSO/3% Tween-20 in PBS, treated 14 days consecutively followed by 14 days off drug, repeated until the end of the experiment). One group (n=10) received ABT-263 (Navitoclax) (100 mg/kg dissolved in 15% DMSO/5% Tween-20, treated 7 days consecutively followed by 14 days off drug, repeated until the end of the experiment), and the last group (n=10) received only the vehicle used for ABT-263 (15% DMSO/5% Tween-20), following the same treatment regimen as ABT-263. An additional 70 animals that did not receive exposure to cigarette smoke were used as controls for the experiment.

After two months of cigarette smoke exposure, lung function was assessed by monitoring oxygen saturation using the MouseSTAT PhysioSuite pulse oximeter (Kent Scientific). Animals were anesthetized with isoflurane (1.5%) and the toe clip was applied. Mice were monitored for 30 seconds and the average peripheral capillary oxygen saturation ($SpO_2$) measurement over this duration was calculated. As shown in FIG. 61, clearance of senescent cells via AP20187, ganciclovir, ABT-263 (Navi), or Nutlin-3A resulted in statistically significant increases in $SpO_2$ levels in mice after 2 months of cigarette smoke exposure compared to untreated controls.

At the end of the experimental period, airway hyper-reactivity (AHR) of mice to methacholine challenge using a SCIREQ flexiVent ventilator and lung mechanics system is examined as described above. After AHR measurement, mice are killed by i.p. injection of pentobarbital for in-depth analysis of lung histopathology as previously described (Rangasamy et al., 2004, *J. Clin. Invest.* 114:1248-1259).

Briefly, lungs are inflated with 0.5% low-melting agarose at a constant pressure of 25 cm. Part of the lung tissue is collected for RNA extraction and qRT-PCR analysis of senescent markers. Other parts of lungs are fixed in 10% buffered formalin and embedded in paraffin. Sections (5 μm) are stained with hematoxylin and eosin. Mean alveolar diameter, alveolar length, and mean linear intercepts are determined by computer-assisted morphometry with Image Pro Plus software (Media Cybernetics).

The potential therapeutic effect of clearance of senescent cells after COPD is fully developed may be assessed in 3MR or INK-ATTAC mice. Six week-old 3MR or INK-ATTAC mice are chronically exposed to cigarette smoke for 6 months as described above. At 6 months following the start of smoke exposure, 3MR or INK-ATTAC mice are treated with ganciclovir (5 consecutive days of treatment followed by 16 days off drug) or AP20187 (3x/week), respectively, until 9 months following the start of smoke exposure, when assessment of senescent cell clearance, lung function, and histopathology is performed.

Example 26

In Vitro Cell Assays for Determining Senolytic Activity of MDM2 Inhibitor RG-7112

Lung fibroblast cell line IMR90 (human primary lung fibroblasts, ATCC® CCL-186™, Manassas, Va.) was seeded in six-well plates and induced to senesce with 10 Gy of ionizing radiation (IR). Senescent phenotype was allowed to develop for at least 7 days.

After senescence phenotype had developed, cells were re-seeded into 96 well plates, and senescent cells (irradiated) and non-senescent cells (the non-radiated cells), were exposed to eight two-fold serial dilutions starting at 100 μM of the MDM2 inhibitor RG-7112 (see structure in FIG. 62A) for a period of 3 or 6 days. After the three days, cell survival was determined using the commercially available CellTiter-Glo® Luminescent Cell Viability Assay (Promega Corporation, Madison, Wis.). The assay determines the number of viable cells in culture based on the quantitation of ATP present which is an indicator of metabolically active cells. FIG. 62 presents the IMR90 cell survival after 3 days exposure to RG-7112 (see FIG. 62B) and after six days (see FIG. 62C).

Example 27

Effect of Clearance of Senescent Cells by ABT-263 to Reduce Chemotherapy Related Side Effects The capability of a senolytic agent, such as ABT-263, to reduce chemotherapy related side effects, such as fatigue, was examined in p16-3MR transgenic mice. In addition to doxorubicin, paclitaxel also induces cellular senescence when administered to animals. See Example 2 for a description of the p16-3MR transgenic mouse model.

Paclitaxel induces senescence and SASP in p16-3MR transgenic mice. Groups of mice (n=4) were treated three times every two days with 20 mg/kg paclitaxel or vehicle. Senescence was observed as shown by luminescence in mice treated with paclitaxel (see FIG. 63A). The level of mRNA in skin was determined for each of the target genes: p16, 3MR transgene, and IL-6. As shown in FIG. 63B, the levels of mRNA for each of p16, 3MR, and IL-6 increased in paclitaxel treated animals compared with vehicle treated animals.

a schematic of the experiment is presented in FIG. 64. In this experiment, paclitaxel was administered to groups of p16-3mr mice (n=4) three times, every two days. Two days after the third dose of paclitaxel, ganciclovir was administered daily for three days (days 1, 2, and 3) intraperitoneally at 25 mg/kg. ABT-263 (100 mg/kg) was administered intraperitoneally daily for seven days after paclitaxel administration. Two days after the last dose of ABT-263, all groups of animals were housed in metabolic cages (promethion, sable systems international, Las Vegas, Nev.) to monitor voluntary exercise as determined by wheel counts. Data were collected and analyzed two days later. The data are shown in FIG. 64 (left hand side). Clearance of senescent cells by ABT-263 and ganciclovir restored approximately 70% of wheel count reduction caused by chemotherapy treatment.

Example 28

Chemotherapy Drugs that Induce Senescence

To examine senescence induced by different chemotherapeutic drugs, groups of p16-3MR animals (n=4) were treated with thalidomide (100 mg/kg; 7 daily injections); romidepsin (1 mg/kg; 3 injections); pomalidomide (5 mg/kg; 7 daily injections); lenalidomide (50 mg/kg; 7 daily injections); 5-azacytidine (5 mg/kg; 3 injections) and compared with doxorubicin (10 mg/kg, 2-4 injections over 7 days). The level of luminescence in animals treated with the drugs is shown in FIG. 65. Treatment of animals with omalidomide, lenalidomide, and doxorubicin resulted in significant levels of senescent cells (p<0.05).

Example 29

Senescence Associated Pathways

Proteomic analyses by nano LC MS/MS were performed on lysates on human abdominal subcutaneous preadipocytes that were senescent or non-senescent. Preadipocytes, one of the most abundant cell types in humans susceptible to senescence, were extracted from fat tissues of nine different healthy kidney transplant donors by collagenase digestion. Prior consent from the donors was obtained. Senescence was induced by 10 Gy radiation or by serial subculturing. Bioinformatics methods were used to identify pathways that were susceptible to existing drugs and that could mediate cell death.

Senescence-associated β-galactosidase (SA-β gal) activity was used to assess the percentage of senescent cells present in the irradiated cell cultures. To be considered a senescent culture in this experiment, 75% or more of the cells needed to demonstrate SA-β gal activity. Both whole cell lysates and cellular supernatants were collected. Proteins were separated on 1D SDS-PAGE. Sections of the gels were destained, reduced, alkylated, and trypsin-digested. Extracted peptides were analyzed by nano-LC-MS/MS on a THERMO SCIENTIFIC™ Q Exactive mass spectrometer. LC Progenesis software (Nonlinear Dynamics, UK) was used to identify and quantify proteins. The data were then submitted to Ingenuity, Metacore, Cytoscape, and other software for pathway and protein network analysis. Among the pathways altered during senescence were those involved in cell survival signaling and inflammatory pathways. These pathways include at least PI3K/AKT, Src kinase signaling, insulin/IGF-1 signaling, p38/MAPK, NF-κB signaling, TGFβ signaling, and mTOR/protein translation.

FIG. 66 shows a confirmatory Western immunoblot of proteins involved in these and related pathways at various times (24 hr; 3, 6, 8, 11, 15, 20, and 25 days) after radiation. Phosphorylated polypeptides in the senescent cell samples were detecting using horseradish peroxidase labeled antibodies (Cell Signaling Technology, Danvers, Mass.) specific for the polypeptides indicated in FIG. 66. Senescence is fully established between day 25 to day 30 in these cells.

Example 30

High Fat Feeding-Induced Senescence Reduced by a Senolytic Agent in P16-3MR Mice Groups of p16-3MR mice (n=6) were fed a high fat diet (60% fat) for four months mice or a regular chow diet. The presence of senescence cells was determined by measuring luminescence (i.e., p16 positive cells). As shown in FIG. 67, animals fed a high fat diet have increased numbers of senescence cells compared with the regular chow fed animals.

Animals were then treated with ganciclovir or vehicle to determine if removal of senescent cells reduced the presence of senescent cells in adipose tissue. Groups of animals were treated with ganciclovir or vehicle. Ganciclovir (25 mg/kg) was administered daily for five consecutive days. The presence of senescent cells in perirenal, epididymal, or subcutaneous inguinal adipose tissue was detected by SA-$\beta$-Gal staining. Data were analyzed by ANOVA. The results are presented in FIG. 68. A significant reduction in presence of senescent cells was observed in epididymal fat. $p=<0.004$.

Example 31

Clearance of Senescent Cells Improves Glucose Tolerance and Insulin Sensitivity

Groups of p16-3MR mice (n=9) were fed a high fat diet for four months mice or a regular chow diet. Animals were then treated with ganciclovir (3 rounds of 25 mg/kg ganciclovir administered daily for five consecutive days) or vehicle. A glucose bolus was given at time zero, and blood glucose was monitored at 20, 30, 60, and 120 minutes after delivering glucose to determine glucose disposal (see FIG. 69A). This was also quantified as "area under the curve" (AUC) (see FIGS. 69B and 69C), with a higher AUC value indicating glucose intolerance. AUCs of mice treated with ganciclovir were significantly lower than their vehicle-treated counterparts although not as low as chow-fed animals. Hemoglobin A1c was lower in ganciclovir-treated mice (see FIG. 69C), suggesting that the animals' longer-term glucose handling was also improved.

Insulin sensitivity was also determined (Insulin Tolerance Testing (ITT)). The results are presented in FIG. 70. Ganciclovir-treated mice showed a greater decrease in blood glucose at 0, 14, 30, 60, and 120 minutes after the administration of glucose bolus at time zero (see FIG. 70A), suggesting that senescent cell clearance improved insulin sensitivity. A change in insulin tolerance testing when ganciclovir was administered to wild-type mice was not observed (see FIG. 70B).

Changes in weight, body composition, and food intake were also monitored. Treatment by ganciclovir did not alter body weight, body composition monitored by measuring percent of fat, or food intake (measured in grams per week).

Example 32

Senolytic Activity of a BCL-2/BCL-xL Inhibitor

A cell viability assay was used to assess cell survival following treatment with A-1155463. The general timelines and procedures for the cell counting assay are shown in FIG. 18 and described in Example 7. IMR90 cells (human primary lung fibroblasts) were seeded in six well plates, and cells were induced to senescence with 10 Gy of ionizing radiation (IR) (Day 0). The media was refreshed every 3 days. The senescent phenotype is allowed to develop for 7 days at which point a cell count was made to determine the baseline number of cells followed by seeding into 96-well plates. On day 8, the senescent cells (irradiated) and the non-senescent cells (the non-radiated cells), were exposed to serial dilutions of A-1155463 for a period of 24 hours. Each condition was seeded in triplicate. Cells were assayed for cell survival using CellTiter-Glo® (CTG) Luminescent Cell Viability Assay. The assay determines the number of viable cells in culture based on the quantitation of ATP present, which is an indicator of metabolically active cells.

FIG. 72 shows IC50 curves of A-1155463 in senescent cells and in non-senescent cells. The IC50 curve is a plot of the percentage of cell survival following treatment.

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet, including U.S. Provisional Application Ser. No. 61/932,704, filed Jan. 28, 2014; 61/932,711, filed Jan. 28, 2014; 61/979,911, filed Apr. 15, 2014; 62/002,709, filed May 23, 2014; 62/042,708, filed Aug. 27, 2014; 62/044,664, filed Sep. 2, 2014; 62/057,820, filed Sep. 30, 2014; 62/057,825, filed Sep. 30, 2014; 62/057, 828, filed Sep. 30, 2014; 62/061,627, filed Oct. 8, 2014; and 62/061,629, filed Oct. 8, 2014, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating a disease or disorder that is not a cancer in a target tissue in a subject,
wherein symptoms of the disease or disorder are caused at least in part by senescent cells that are located in or around the target tissue,
wherein the senescent cells are defined as non-cancerous cells that express p16,
the method comprising administering in or around the target tissue a course of therapy with a pharmaceutical composition,
wherein the pharmaceutical composition includes a formulation of an amount of senolytic agent that is less than 10,000 mol. wt., the senolytic agent being a means for binding to Akt kinase, thereby directly inhibiting Akt kinase activity,
wherein the amount of the senolytic agent and the formulation of the composition configure the composition such that upon administration to the target tissue in the subject, the senolytic agent contacts the senescent cells located in or around the target tissue, and selectively removes such senescent cells in preference to adjacent non-senescent cells,
wherein the course of therapy includes a treatment period during which the pharmaceutical composition is administered to the subject in one or a plurality of doses, followed by a therapeutic period of at least two weeks during which the pharmaceutical composition is not administered but one or more signs or symptoms of the disease or disorder in the target tissue are alleviated.

2. The method of claim 1, wherein the means for directly inhibiting Akt kinase is selected from CCT128930, GDC-0068, GSK2110183 (afuresertib), GSK690693, AT7867, Perifosine (KRX-0401), AKTide-2T, GST-anti-Akt1-MTS, PX-316, GSK-2141795, VQD-002 (Triciribine), AZD5363, API-1, and pharmaceutically acceptable salts thereof.

3. The method of claim 1, wherein the means for directly inhibiting Akt kinase is MK-2206 (8-[4-(1-aminocyclobutyl)phenyl]-9-phenyl-2H-[1,2,4]triazolo[3,4-f][1,6]naphthyridin-3-one dihydrochloride), or a pharmaceutically acceptable salt thereof.

4. The method of claim 1, wherein a single dose of the pharmaceutical composition is administered to the subject during the treatment period.

5. The method of claim 1, wherein the therapeutic period during which the composition is not administered lasts at least one month.

6. The method of claim 1, wherein the disease or disorder is osteoarthritis.

7. The method of claim 1, wherein the disease or disorder is a lung disease.

8. The method of claim 1, wherein the disease or disorder is atherosclerosis.

9. The method of claim 1, wherein the disease or disorder is cardiac stress, a side effect of chemotherapy in a cancer patient, or diabetes.

10. A method for treating a disease or disorder that is not a cancer in a target tissue in a subject,
wherein symptoms of the disease or disorder are caused at least in part by senescent cells that are located in or around the target tissue,
wherein the senescent cells are defined as non-cancerous cells that express p16,
the method comprising administering in or around the target tissue a course of therapy with a pharmaceutical composition, and
monitoring senescent cells in or around the target tissue during or following the therapy;
wherein the pharmaceutical composition includes a formulation of an amount of senolytic agent that is less than 10,000 mol. wt., the senolytic agent being a means for binding to Akt kinase, thereby directly inhibiting Akt kinase activity,
wherein the senolytic agent is a means for inhibiting Akt kinase, and
wherein the amount of the senolytic agent and the formulation of the composition configure the composition such that upon administration to the target tissue in the subject, the senolytic agent contacts the senescent cells located in or around the target tissue, and selectively removes such senescent cells from the target tissue in preference to adjacent non-senescent cells.

11. The method of claim 10, wherein the means for directly inhibiting Akt kinase is selected from CCT128930, GDC-0068, GSK2110183 (afuresertib), GSK690693, AT7867, Perifosine (KRX-0401), AKTide-2T, GST-anti-Akt1-MTS, PX-316, GSK-2141795, VQD-002 (Triciribine), AZD5363, API-1, and pharmaceutically acceptable salts thereof.

12. The method of claim 10, wherein the means for directly inhibiting Akt kinase is MK-2206 (8-[4-(1-aminocyclobutyl)phenyl]-9-phenyl-2H-[1,2,4]triazolo[3,4-f][1,6]naphthyridin-3-one dihydrochloride), or a pharmaceutically acceptable salt thereof.

\* \* \* \* \*

SEQUENCE LISTING

<160> NUMBER OF SEQ ID NOS: 22

<210> SEQ ID NO 1
<211> LENGTH: 58
<212> TYPE: DNA

```
<213> ORGANISM: Artificial Sequence
<220> FEATURE:
<223> OTHER INFORMATION: shRNA sequence

<400> SEQUENCE: 1
ccggccggga gatagtgatg aagtactcga gtacttcatc actatctccc ggtttttg     58

<210> SEQ ID NO 2
<211> LENGTH: 21
<212> TYPE: DNA
<213> ORGANISM: Artificial Sequence
<220> FEATURE:
<223> OTHER INFORMATION: shRNA sequence

<400> SEQUENCE: 2
ccgggagata gtgatgaagt a                                             21

<210> SEQ ID NO 3
<211> LENGTH: 58
<212> TYPE: DNA
<213> ORGANISM: Artificial Sequence
<220> FEATURE:
<223> OTHER INFORMATION: shRNA sequence

<400> SEQUENCE: 3
ccgggtgatg aagtacatcc attatctcga gataatggat gtacttcatc acttttg      58

<210> SEQ ID NO 4
<211> LENGTH: 21
<212> TYPE: DNA
<213> ORGANISM: Artificial Sequence
<220> FEATURE:
<223> OTHER INFORMATION: shRNA sequence

<400> SEQUENCE: 4
gtgatgaagt acatccatta t                                             21

<210> SEQ ID NO 5
<211> LENGTH: 58
<212> TYPE: DNA
<213> ORGANISM: Artificial Sequence
<220> FEATURE:
<223> OTHER INFORMATION: shRNA sequence

<400> SEQUENCE: 5
ccggagagtg acagtggatt gcattctcga gaatgcaatc cactgtcact cttttttg     58

<210> SEQ ID NO 6
<211> LENGTH: 21
<212> TYPE: DNA
<213> ORGANISM: Artificial Sequence
<220> FEATURE:
<223> OTHER INFORMATION: shRNA sequence

<400> SEQUENCE: 6
agagtgacag tggattgcat t                                             21

<210> SEQ ID NO 7
<211> LENGTH: 58
<212> TYPE: DNA
<213> ORGANISM: Artificial Sequence
<220> FEATURE:
<223> OTHER INFORMATION: shRNA sequence

<400> SEQUENCE: 7
ccgggctcac tcttcagtcg gaaatctcga gatttccgac tgaagagtga gcttttg      58
```

<210> SEQ ID NO 8
<211> LENGTH: 19
<212> TYPE: DNA
<213> ORGANISM: Artificial Sequence
<220> FEATURE:
<223> OTHER INFORMATION: shRNA sequence

<400> SEQUENCE: 8
gctcactctt cagtcggaa                                                    19

<210> SEQ ID NO 9
<211> LENGTH: 58
<212> TYPE: DNA
<213> ORGANISM: Artificial Sequence
<220> FEATURE:
<223> OTHER INFORMATION: shRNA sequence

<400> SEQUENCE: 9
ccgggtggaa ctctatggga acaatctcga gattgttccc atagagttcc acttttg         58

<210> SEQ ID NO 10
<211> LENGTH: 19
<212> TYPE: DNA
<213> ORGANISM: Artificial Sequence
<220> FEATURE:
<223> OTHER INFORMATION: shRNA sequence

<400> SEQUENCE: 10
gtggaactct atgggaaca                                                    19

<210> SEQ ID NO 11
<211> LENGTH: 58
<212> TYPE: DNA
<213> ORGANISM: Artificial Sequence
<220> FEATURE:
<223> OTHER INFORMATION: shRNA sequence

<400> SEQUENCE: 11
ccgggtttag tgatgtggaa gagaactcga gttctcttcc acatcactaa acttttg         58

<210> SEQ ID NO 12
<211> LENGTH: 19
<212> TYPE: DNA
<213> ORGANISM: Artificial Sequence
<220> FEATURE:
<223> OTHER INFORMATION: shRNA sequence

<400> SEQUENCE: 12
gtttagtgat gtggaagag                                                    19

<210> SEQ ID NO 13
<211> LENGTH: 58
<212> TYPE: DNA
<213> ORGANISM: Artificial Sequence
<220> FEATURE:
<223> OTHER INFORMATION: shRNA sequence

<400> SEQUENCE: 13
ccgggctcac tcttcagtcg gaaatctcga gatttccgac tgaagagtga gcttttg         58

<210> SEQ ID NO 14
<211> LENGTH: 21
<212> TYPE: DNA
<213> ORGANISM: Artificial Sequence
<220> FEATURE:

<223> OTHER INFORMATION: shRNA sequence

<400> SEQUENCE: 14
gctcactctt cagtcggaaa t                                            21

<210> SEQ ID NO 15
<211> LENGTH: 58
<212> TYPE: DNA
<213> ORGANISM: Artificial Sequence
<220> FEATURE:
<223> OTHER INFORMATION: shRNA sequence

<400> SEQUENCE: 15
ccggtggcag actttgtagg ttatactcga gtataaccta caaagtctgc cattttg     58

<210> SEQ ID NO 16
<211> LENGTH: 19
<212> TYPE: DNA
<213> ORGANISM: Artificial Sequence
<220> FEATURE:
<223> OTHER INFORMATION: shRNA sequence

<400> SEQUENCE: 16
tggcagactt tgtaggtta                                               19

<210> SEQ ID NO 17
<211> LENGTH: 58
<212> TYPE: DNA
<213> ORGANISM: Artificial Sequence
<220> FEATURE:
<223> OTHER INFORMATION: shRNA sequence

<400> SEQUENCE: 17
ccgggtcaac aaggagatgg aaccactcga gtggttccat ctccttgttg acttttg     58

<210> SEQ ID NO 18
<211> LENGTH: 19
<212> TYPE: DNA
<213> ORGANISM: Artificial Sequence
<220> FEATURE:
<223> OTHER INFORMATION: shRNA sequence

<400> SEQUENCE: 18
gtcaacaagg agatggaac                                               19

<210> SEQ ID NO 19
<211> LENGTH: 58
<212> TYPE: DNA
<213> ORGANISM: Artificial Sequence
<220> FEATURE:
<223> OTHER INFORMATION: shRNA sequence

<400> SEQUENCE: 19
ccggcagaag ggttatgtct gtggactcga gtccacagac ataacccttc tgttttg     58

<210> SEQ ID NO 20
<211> LENGTH: 19
<212> TYPE: DNA
<213> ORGANISM: Artificial Sequence
<220> FEATURE:
<223> OTHER INFORMATION: shRNA sequence

<400> SEQUENCE: 20
cagaagggtt atgtctgtg                                               19

```
<210> SEQ ID NO 21
<211> LENGTH: 59
<212> TYPE: DNA
<213> ORGANISM: Artificial Sequence
<220> FEATURE:
<223> OTHER INFORMATION: shRNA sequence

<400> SEQUENCE: 21
ccggccatta gatgagtggg atttactcga gtaaatccca ctcatctaat ggttttttg      59

<210> SEQ ID NO 22
<211> LENGTH: 21
<212> TYPE: DNA
<213> ORGANISM: Artificial Sequence
<220> FEATURE:
<223> OTHER INFORMATION: shRNA sequence

<400> SEQUENCE: 22
ccattagatg agtgggattt a                                              21
```